(12) United States Patent
Morris et al.

(10) Patent No.: US 11,129,820 B2
(45) Date of Patent: Sep. 28, 2021

(54) FERROPORTIN-INHIBITOR SALTS

(71) Applicant: Vifor (International) AG, St. Gallen (CH)

(72) Inventors: Collin D. Morris, Grayslake, IL (US); Fritz Blatter, Reinach (CH); Giuseppe Lapadula, Basel (CH); Stefan Reim, St. Gallen (CH); Michael Burgert, Friedrichshafen (DE); Erik Philipp, Arbon (CH)

(73) Assignee: Vifor (International) AG, St. Gallen (CH)

( * ) Notice: Subject to any disclaimer, the term of this patent is extended or adjusted under 35 U.S.C. 154(b) by 0 days.

(21) Appl. No.: 16/603,904

(22) PCT Filed: Apr. 18, 2018

(86) PCT No.: PCT/EP2018/059906
§ 371 (c)(1),
(2) Date: Oct. 9, 2019

(87) PCT Pub. No.: WO2018/192973
PCT Pub. Date: Oct. 25, 2018

(65) Prior Publication Data
US 2020/0113885 A1 Apr. 16, 2020

(30) Foreign Application Priority Data
Apr. 18, 2017 (EP) .................................... 17166907

(51) Int. Cl.
| C07D 417/14 | (2006.01) |
| A61K 31/4436 | (2006.01) |
| A61K 31/4439 | (2006.01) |
| A61P 7/06 | (2006.01) |
| A61K 45/06 | (2006.01) |
| C07D 413/14 | (2006.01) |

(52) U.S. Cl.
CPC .......... *A61K 31/4439* (2013.01); *A61K 45/06* (2013.01); *A61P 7/06* (2018.01); *C07D 413/14* (2013.01); *C07D 417/14* (2013.01)

(58) Field of Classification Search
CPC ................ C07D 417/14; C07D 413/14; A61K 31/4436; A61K 31/4439; A61P 7/00
USPC .................... 546/269.7, 271.4; 514/342, 341
See application file for complete search history.

(56) References Cited

U.S. PATENT DOCUMENTS

| 5,922,761 | A | 7/1999 | Lai |
| 6,723,742 | B2 | 4/2004 | Lattmann et al. |
| 7,365,225 | B2 | 4/2008 | Thomas et al. |
| 8,278,337 | B2 | 10/2012 | Belanger |
| 8,324,265 | B2 | 12/2012 | Kurose et al. |
| 8,338,610 | B2 | 12/2012 | Kuzmich et al. |
| 8,623,859 | B2 | 1/2014 | Madden et al. |
| 9,040,091 | B2 | 5/2015 | Talton |
| 9,586,914 | B2 | 3/2017 | Fairlie et al. |
| 9,896,481 | B2 | 2/2018 | Ganz et al. |
| 10,010,535 | B2 | 7/2018 | Bergeron, Jr. |
| 10,364,239 | B2 | 7/2019 | Dürrenberger et al. |
| 10,441,669 | B2 | 10/2019 | Chong |
| 2003/0109548 | A1 | 6/2003 | Royt et al. |
| 2004/0138268 | A1 | 7/2004 | Boy et al. |
| 2006/0100196 | A1 | 5/2006 | Gailunas et al. |
| 2006/0161007 | A1 | 7/2006 | Martin et al. |
| 2006/0252807 | A1 | 11/2006 | Severance et al. |
| 2008/0234327 | A1 | 9/2008 | Cadieux et al. |
| 2008/0234384 | A1 | 9/2008 | Chafeev et al. |
| 2009/0069408 | A1 | 3/2009 | Chafeev et al. |
| 2009/0118200 | A1 | 5/2009 | Bergman et al. |
| 2010/0093871 | A1 | 4/2010 | Kagehara et al. |
| 2010/0113305 | A1 | 5/2010 | Martin et al. |
| 2010/0240713 | A1 | 9/2010 | Cadieux et al. |
| 2011/0224136 | A1 | 9/2011 | Ting et al. |
| 2012/0040951 | A1 | 2/2012 | Chuaqui et al. |
| 2012/0094974 | A1 | 4/2012 | Chen et al. |
| 2013/0303508 | A1 | 11/2013 | Clark et al. |
| 2016/0243201 | A1 | 8/2016 | Ginzburg |

FOREIGN PATENT DOCUMENTS

| CN | 103508957 A | 1/2014 |
| EP | 1072265 A1 | 1/2001 |
| EP | 1074254 A2 | 2/2001 |
| EP | 1889842 A1 | 2/2008 |
| EP | 2 133 339 A1 | 12/2009 |
| EP | 2 620 142 A1 | 7/2013 |
| GB | 937878 | 9/1963 |
| WO | 98/25887 A2 | 6/1998 |

(Continued)

OTHER PUBLICATIONS

Espacenet Abstract for CN103508957 published Jan. 15, 2014, one page.
International Search Report for corresponding PCT/EP2018/059906 dated Aug. 9, 2018, two pages.
Notification Concerning Transmittal of International Preliminary Report on Patentability dated Oct. 31, 2019, eight pages.
Wang, et al. "Metal ions influx is a double edged sword for the pathogenesis of Alzheimer's disease." Ageing research reviews 35 (2017): pp. 265-290.
Urrutia, et al. "Hepcidin attenuates amyloid beta-induced inflammatory and pro-oxidant responses in astrocytes and microglia." Journal of neurochemistry 142.1 (2017): pp. 140-152.

(Continued)

*Primary Examiner* — Charanjit Aulakh
(74) *Attorney, Agent, or Firm* — Christopher Jan Korff; Rankin Hill & Clark LLP

(57) ABSTRACT

The invention relates to novel salts of compounds of the general formula (I), pharmaceutical compositions comprising them and the use thereof as medicaments, in particular for the use as ferroportin inhibitors, more particularly for the use in the prophylaxis and/or treatment of diseases caused by a lack of hepcidin or iron metabolism disorders, such as particularly iron overload states such as in particular thalassemia, sickle cell disease and hemochromatosis.

26 Claims, 83 Drawing Sheets

(56) References Cited

FOREIGN PATENT DOCUMENTS

| WO | 98/27108 | A2 | 6/1998 | |
|---|---|---|---|---|
| WO | 02/22599 | A2 | 3/2002 | |
| WO | 02/50039 | A1 | 6/2002 | |
| WO | 2005/014576 | A1 | 2/2005 | |
| WO | 2005/051411 | A1 | 6/2005 | |
| WO | 2006/040646 | A1 | 4/2006 | |
| WO | 2006/062224 | A1 | 6/2006 | |
| WO | 2007/022258 | A1 | 2/2007 | |
| WO | 2007/084390 | A2 | 7/2007 | |
| WO | 2010/054398 | A1 | 5/2010 | |
| WO | 2011/023722 | A1 | 3/2011 | |
| WO | 2011/029832 | A1 | 3/2011 | |
| WO | 2015/019325 | A1 | 2/2015 | |
| WO | 2017/068089 | A2 | 4/2017 | |
| WO | WO 2017/068090 | A1 * | 4/2017 | ........... C07D 413/14 |

OTHER PUBLICATIONS

Qian, et al., "Hepcidin and its therapeutic potential in neurodegenerative disorders." Medicinal research reviews 40.2 (2019): pp. 633-653.

Liang, et al. "Brain hepcidin suppresses major pathologies in experimental parkinsonism." Iscience 23.7 (2020): pp. 1-33.

Galaris, et al. "Iron homeostasis and oxidative stress: An intimate relationship." Biochimica et Biophysica Acta (BBA)—Molecular Cell Research 1866.12 (2019): 118535 pp. 1-15.

Arezes, et al. "Hepcidin-induced hypoferremia is a critical host defense mechanism against the siderophilic bacterium Vibrio vulnificus." Cell host & microbe 17.1 (2015): pp. 47-57.

Stefanova, et al., "Endogenous hepcidin and its agonist mediate resistance to selected infections by clearing non-transferrin-bound iron." Blood 130.3 (2017): pp. 245-257.

Stefanova, et al., "Hepcidin protects against lethal *Escherichia coli* sepsis in mice inoculated with isolates from septic patients." Infection and immunity 86.7 (2018): pp. 1-12.

Ramos, et al., "Minihepcidins prevent iron overload in a hepcidin-deficient mouse model of severe hemochromatosis." Blood, The Journal of the American Society of Hematology 120.18 (2012): pp. 3829-3836.

Coates, "Physiology and pathophysiology of iron in hemoglobin-associated diseases." Free Radical Biology and Medicine 72 (2014): pp. 23-40.

Ozkay, et al. "Antimicrobial Activity of a New Series of Benzimidazole Derivatives", Arch. Pharm. Res. vol. 34, No. 9 pp. 1427-1435 (2011).

European Office Action for EP Application No. 16 784 510.6 dated Jul. 24, 2020, 7 pages.

Espacenet bibliographic data for WO9827108 published Jun. 25, 1998, two pages.

Zou et al. "Discovery of pyrazole as C-terminus of selective BACE1 inhibitors," European Journal of Medicinal Chemistry 68 (2013) pp. 270-283.

Tussing-Humphreys, PhD, RD et al. "Rethinking Iron Regulation and Assessment in Iron Deficiency, Anemia of Chronic Disease, and Obesity: Introducing Hepcidin," Journal of the Academy of Nutrition and Dietetics, vol. 112, No. 3, Mar. 2012, pp. 391-400.

Riordan et al. "Bleomycin Analogs, Synthesis and Proton NMR Spectral Assignments of Thiazole Amides Related to Bleomycin A2(1)," J. Heterocyclic Chem., vol. 18, Oct. 1981, pp. 1213-1221.

Sasaki "Synthesis of a Novel Bis(2,4'-Bithiazole) Derivative as a Co(II)-Activated DNA Cleaving Agent," Chem. Pharm. Bull. vol. 42, No. 8, (1994), pp. 1685-1687.

Ballell et al. "Fueling Open-Source Drug Discovery: 177 Small-Molecule Leads against Tuberculosis," ChemMedChem 2013, 8, pp. 313-321.

* cited by examiner

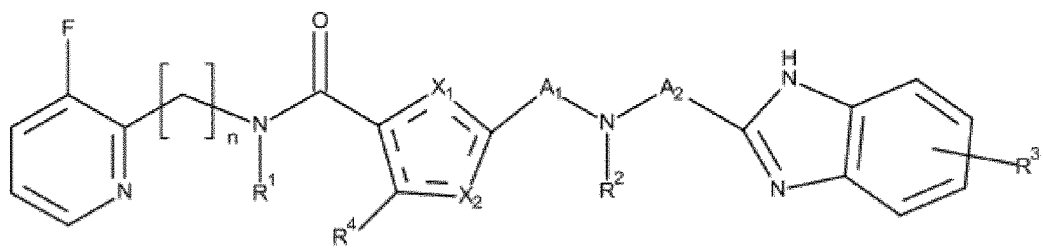
Fig. 1
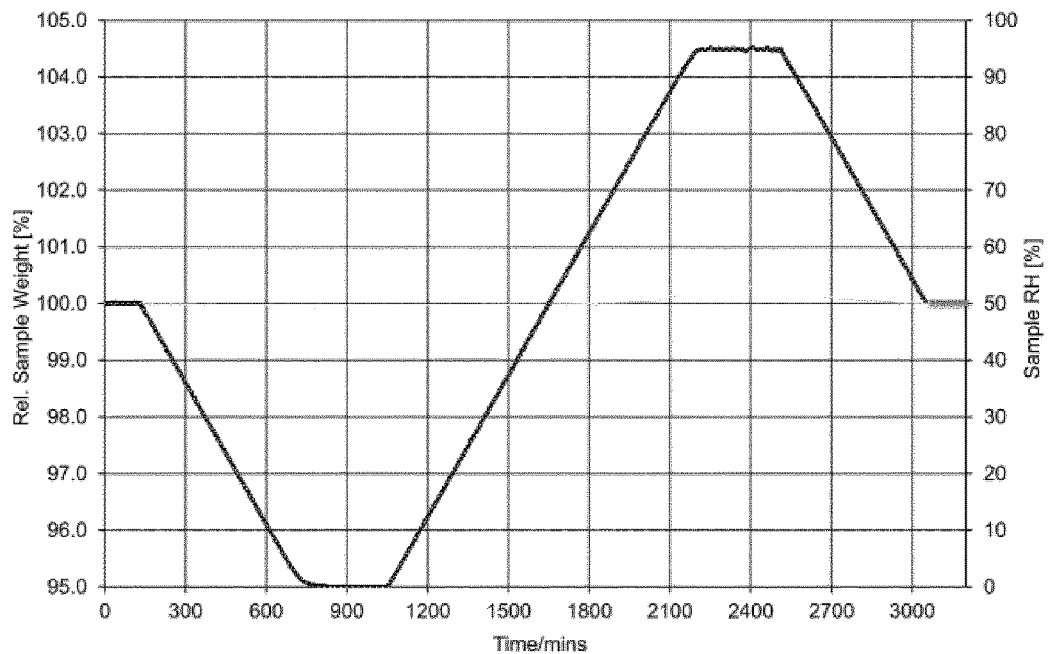
Fig. 2
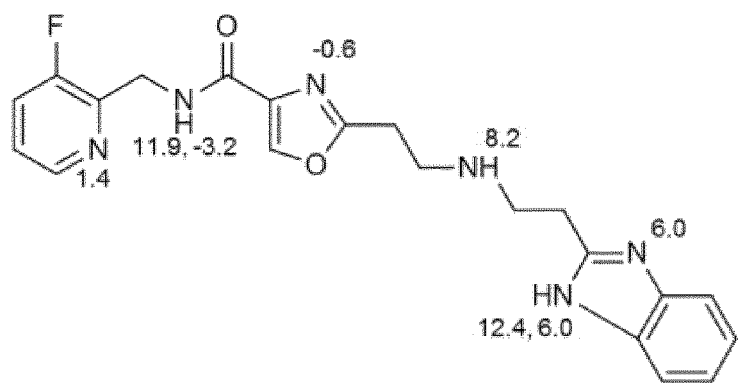
Fig. 3.1

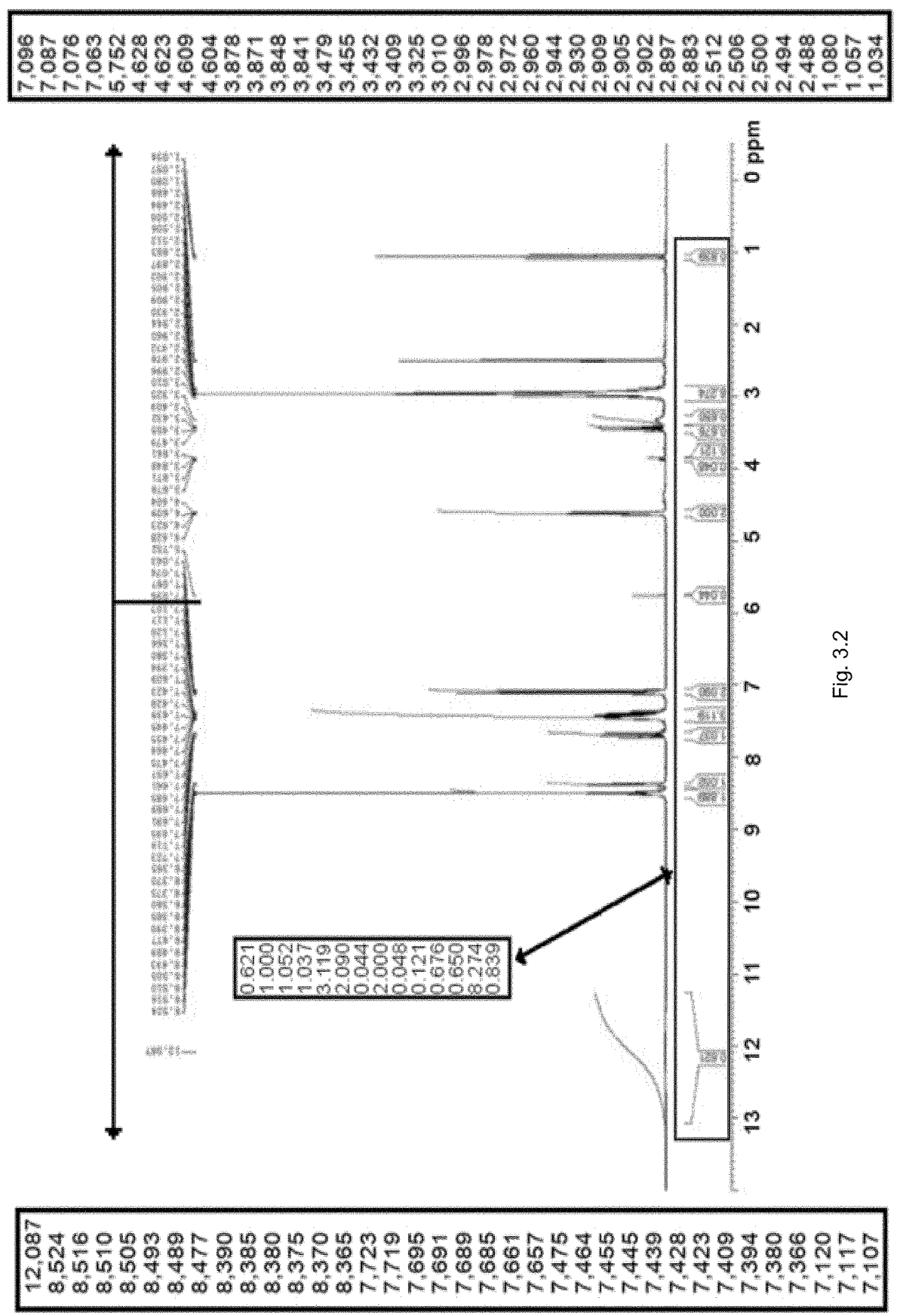
Fig. 3.2

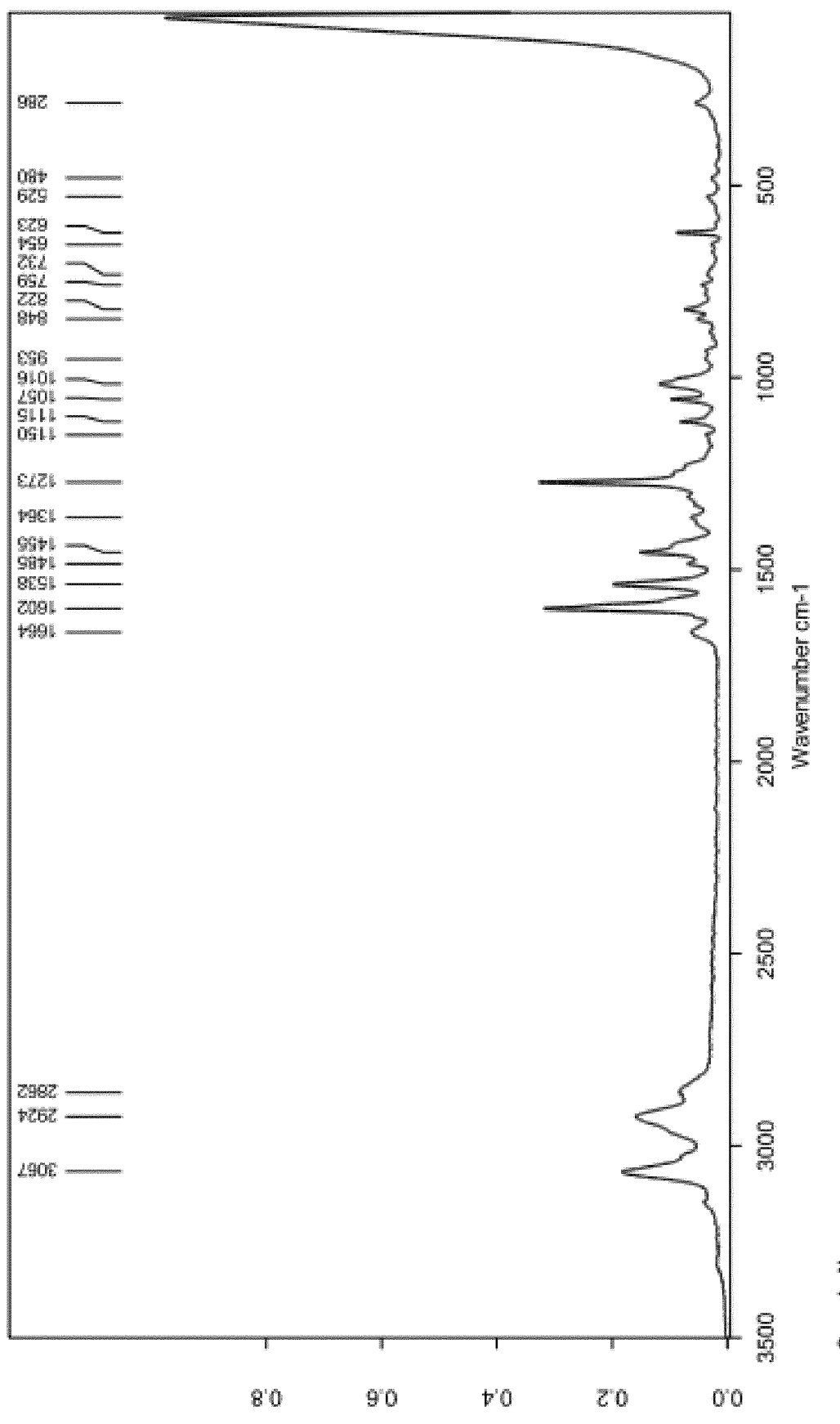
Fig. 3.3

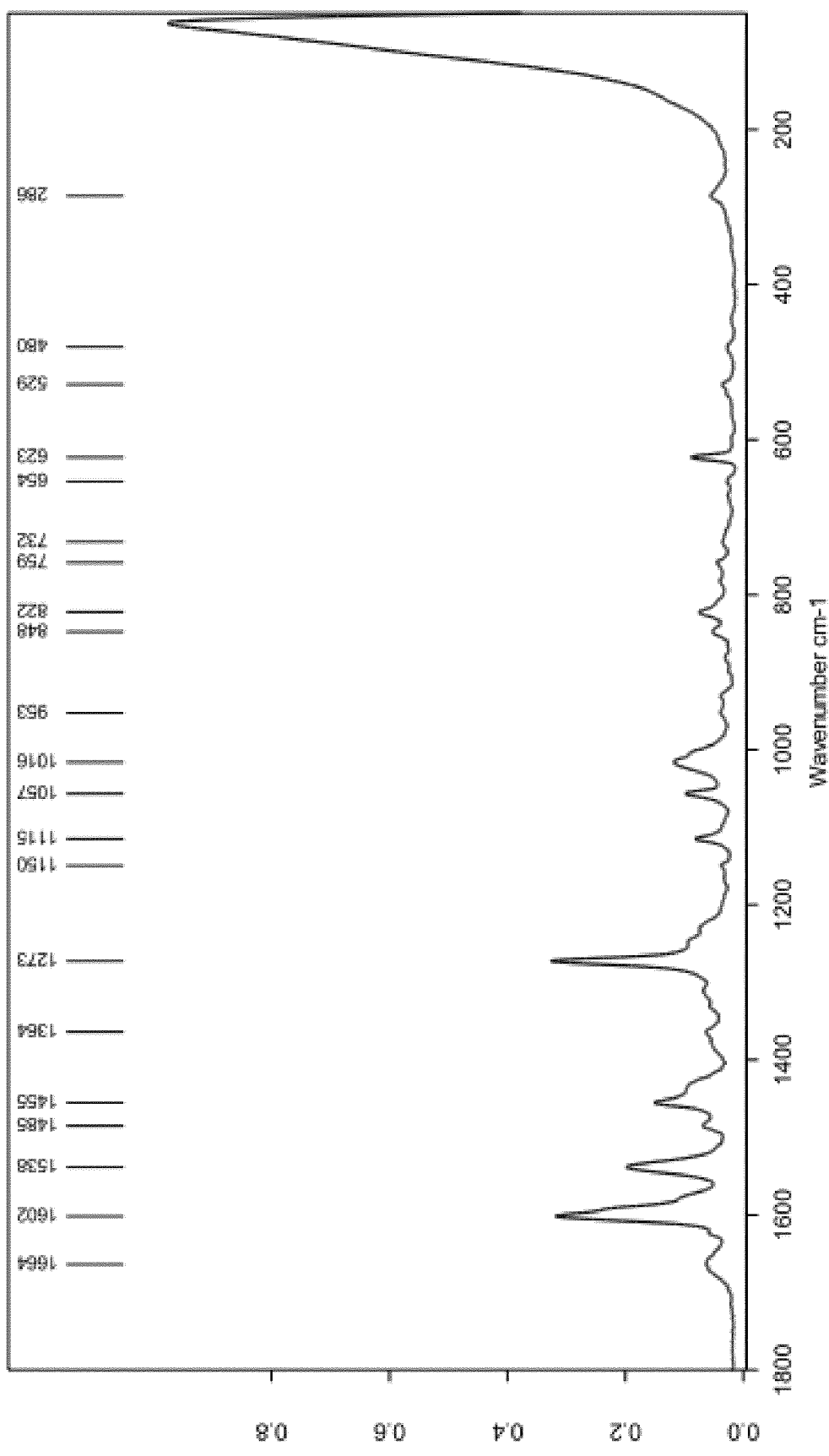
Fig. 3.4

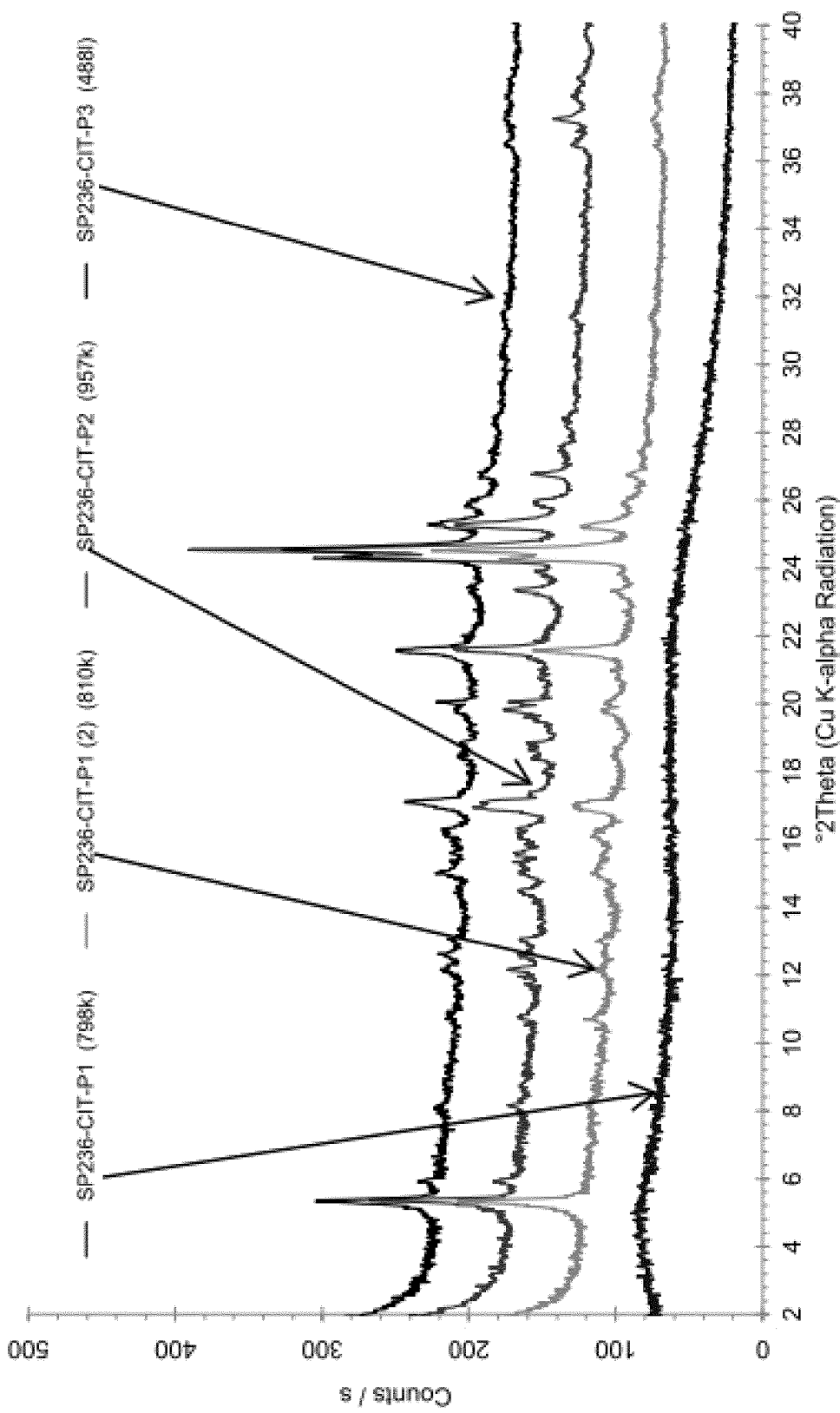
Fig. 5.1

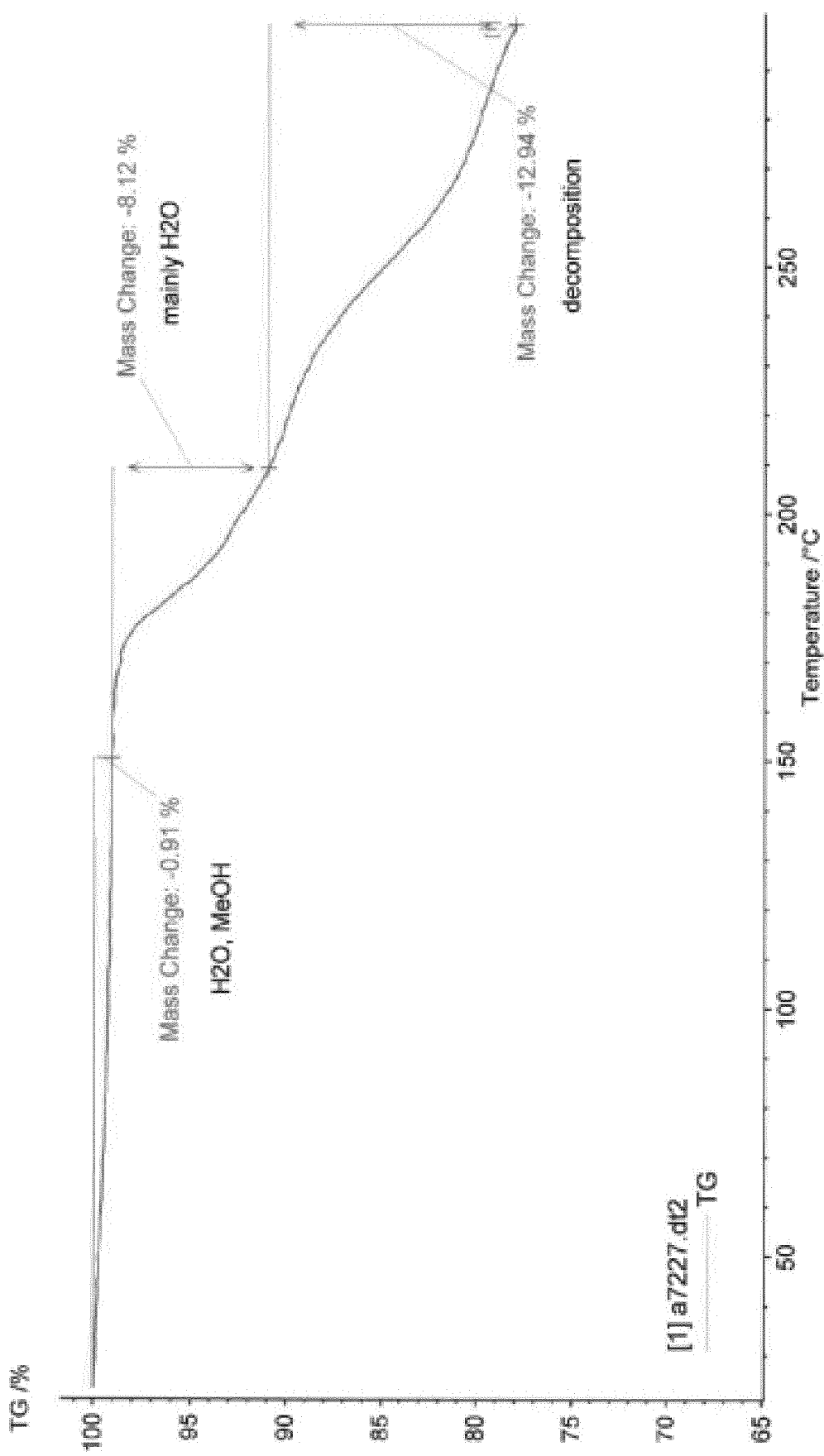
Fig. 5.2

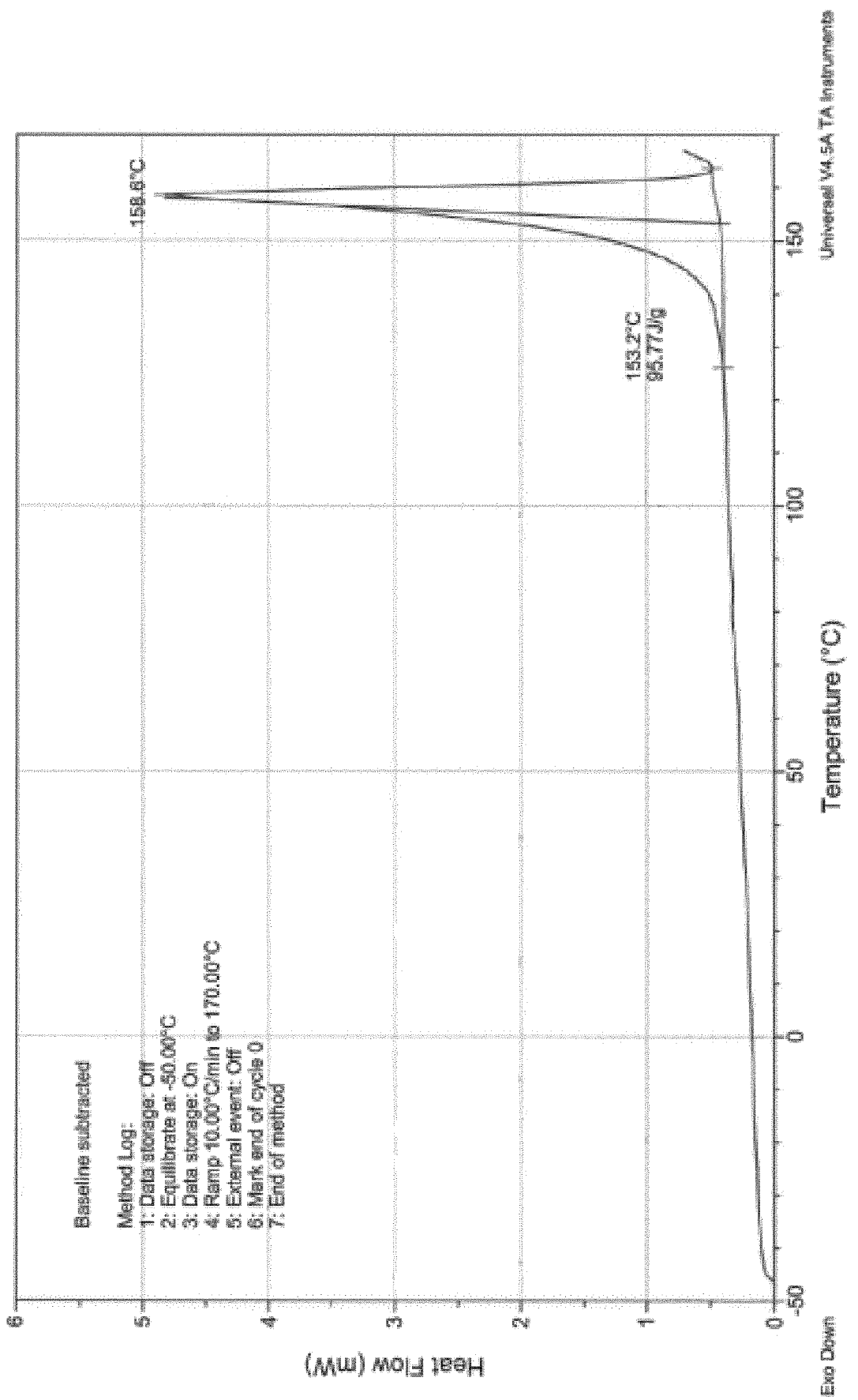
Fig. 5.3

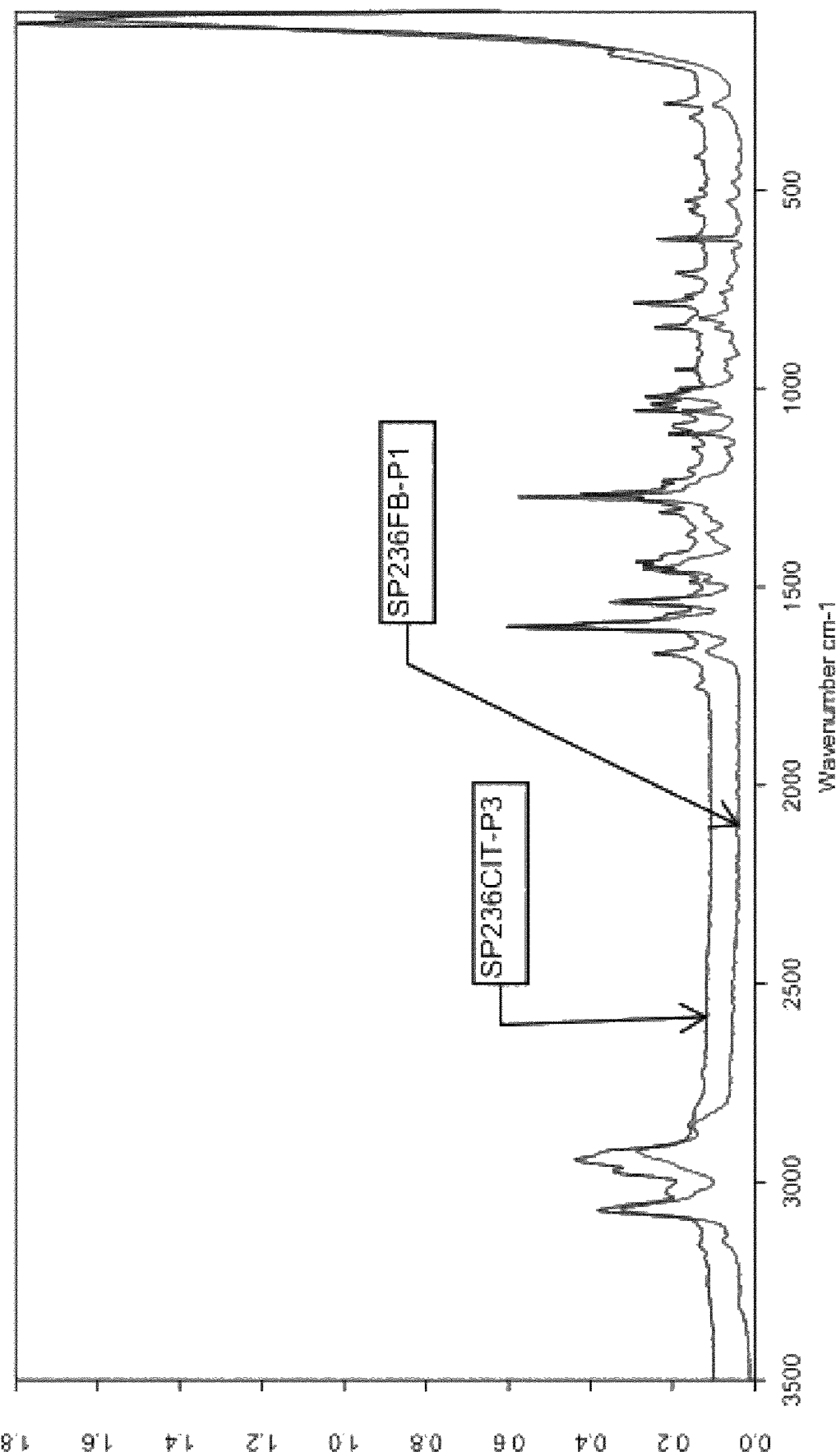
Fig. 5.4

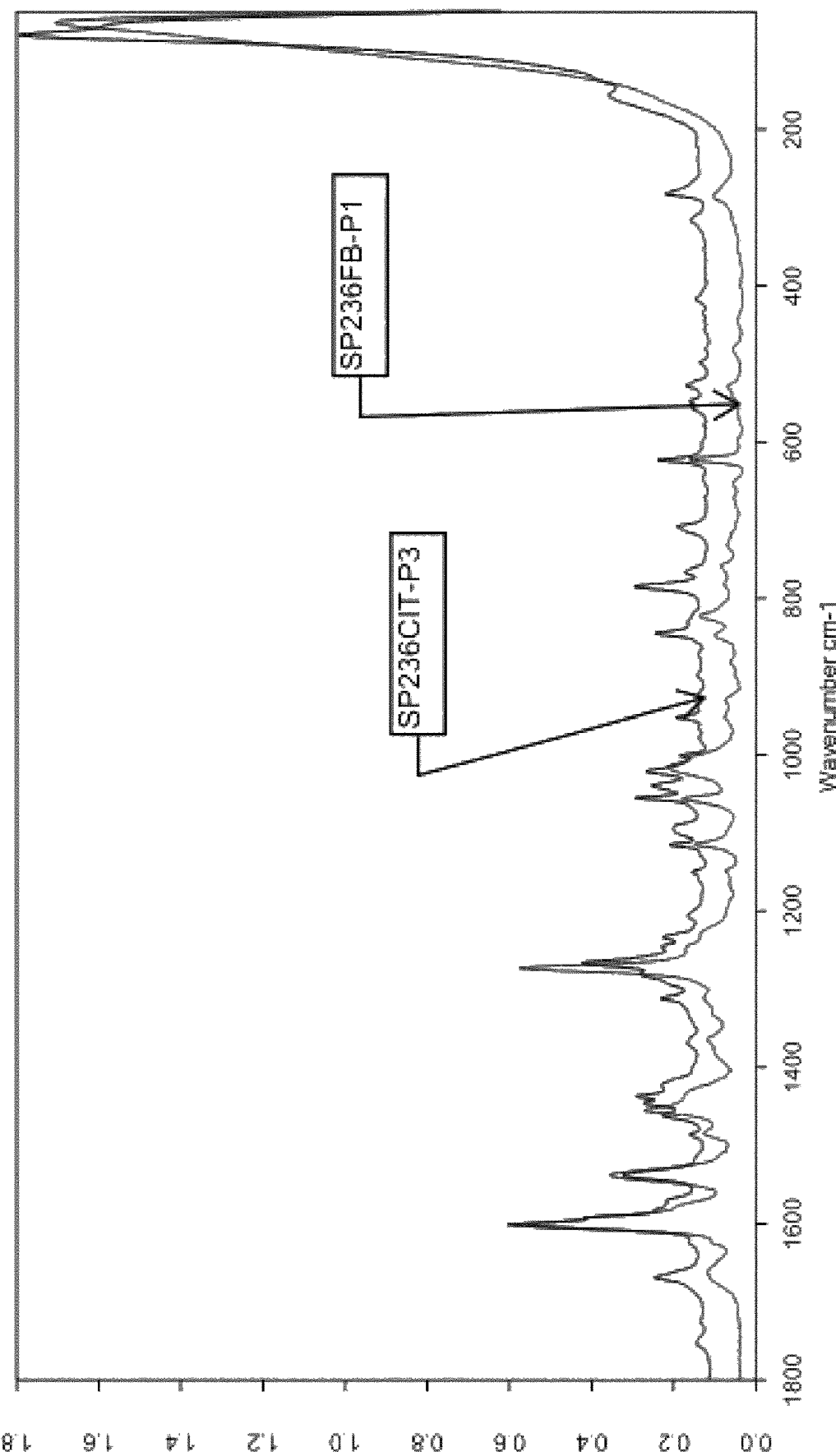
Fig. 5.5

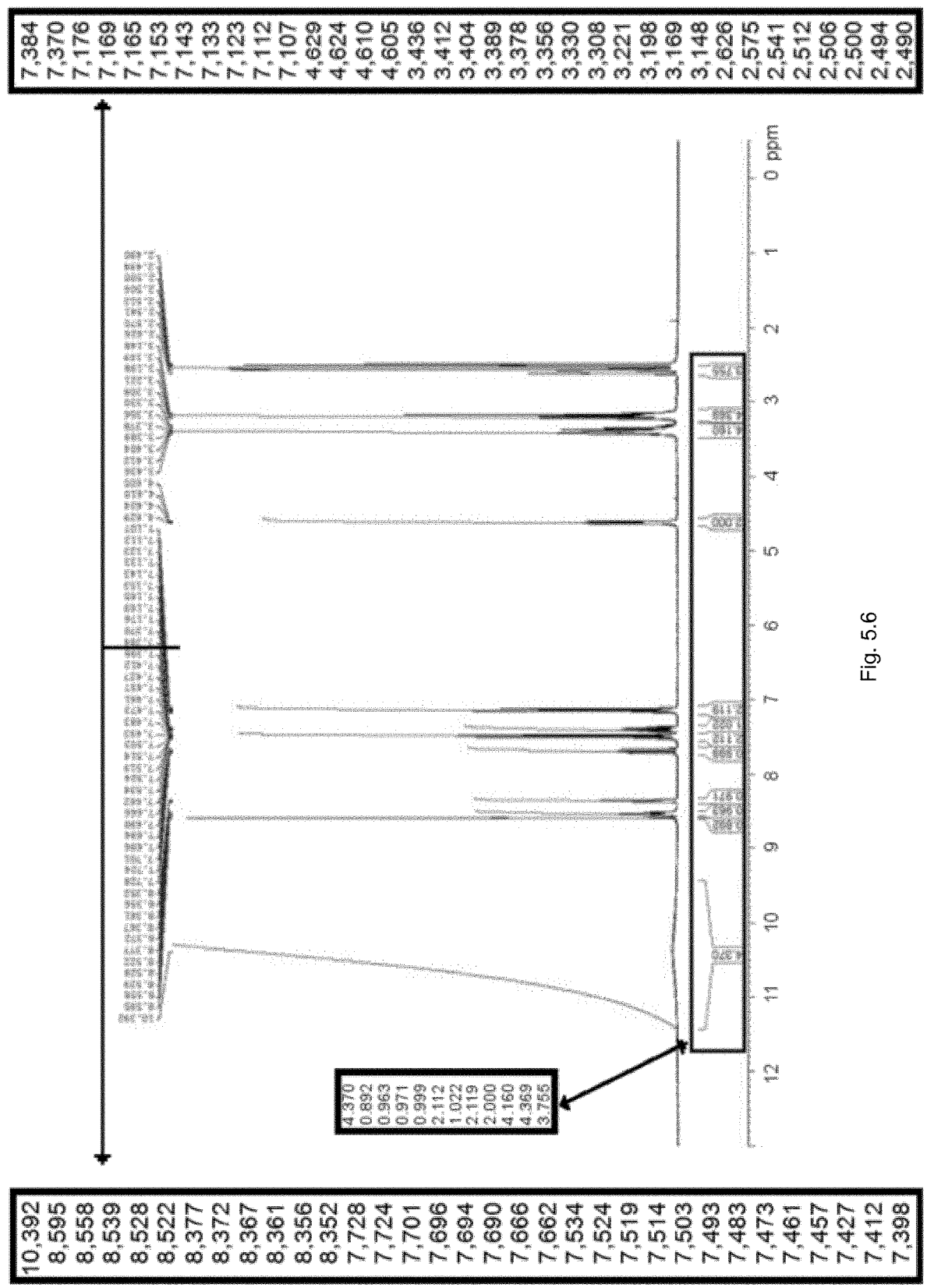
Fig. 5.6

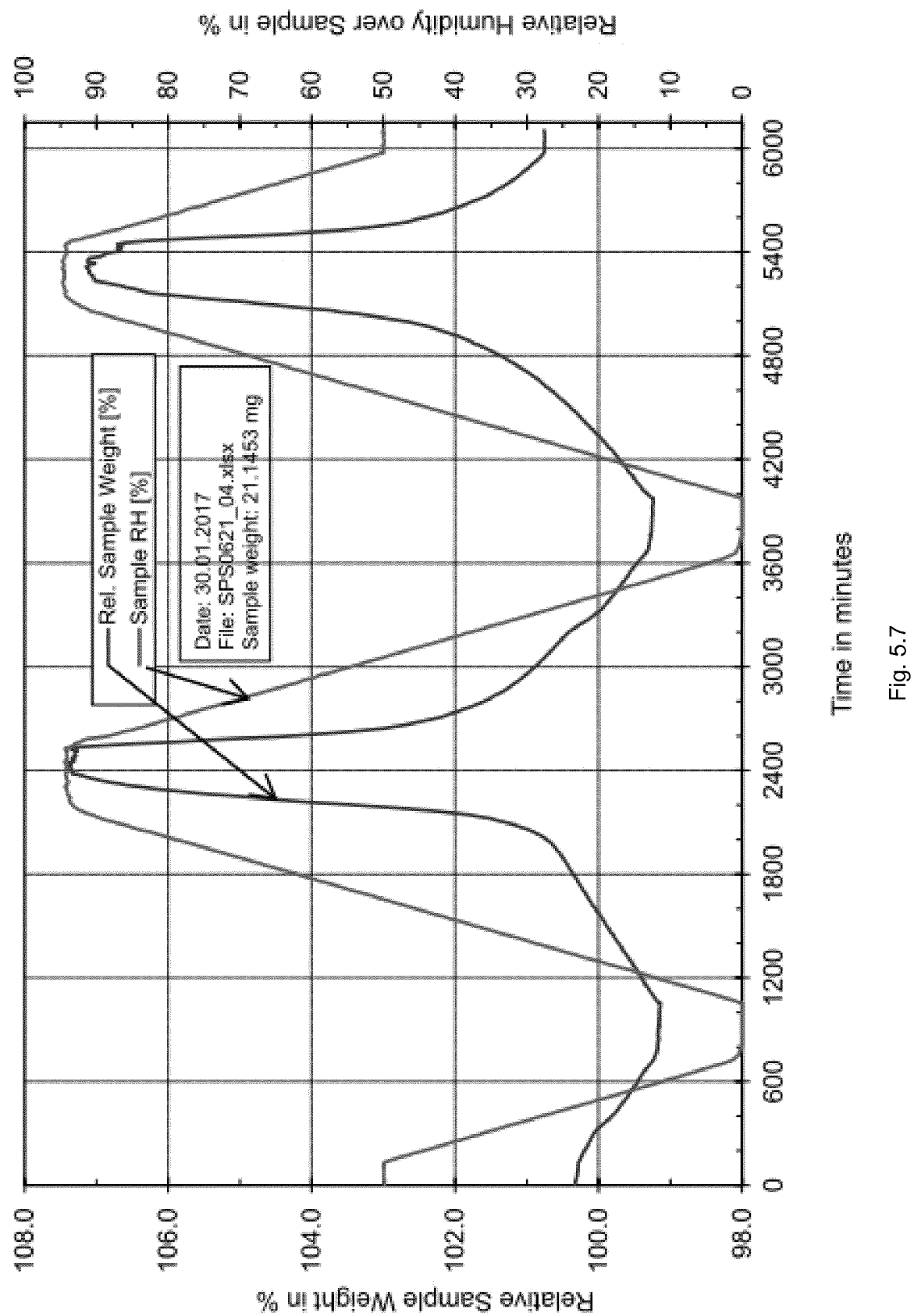
Fig. 5.7

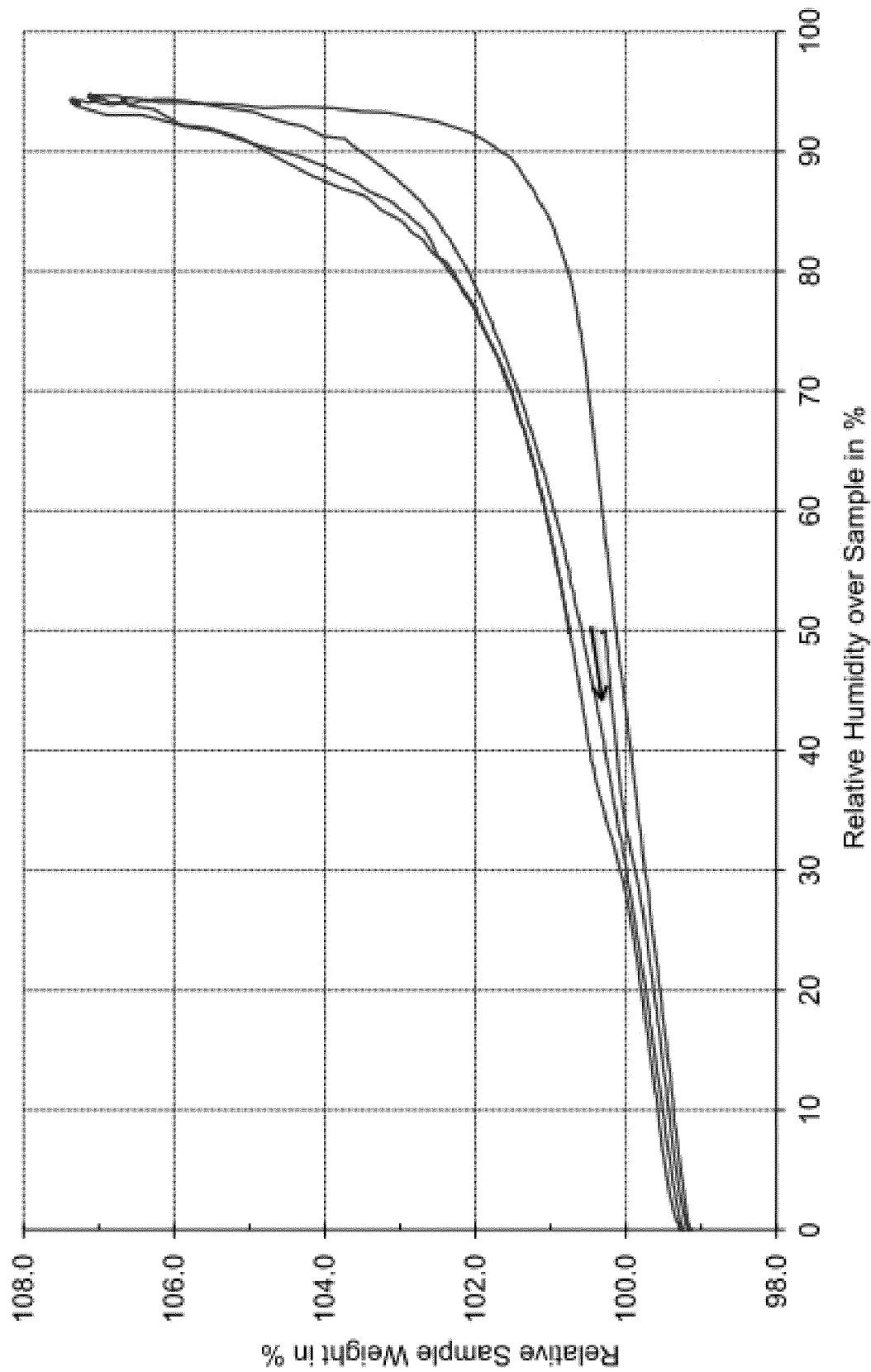
Fig. 5.8

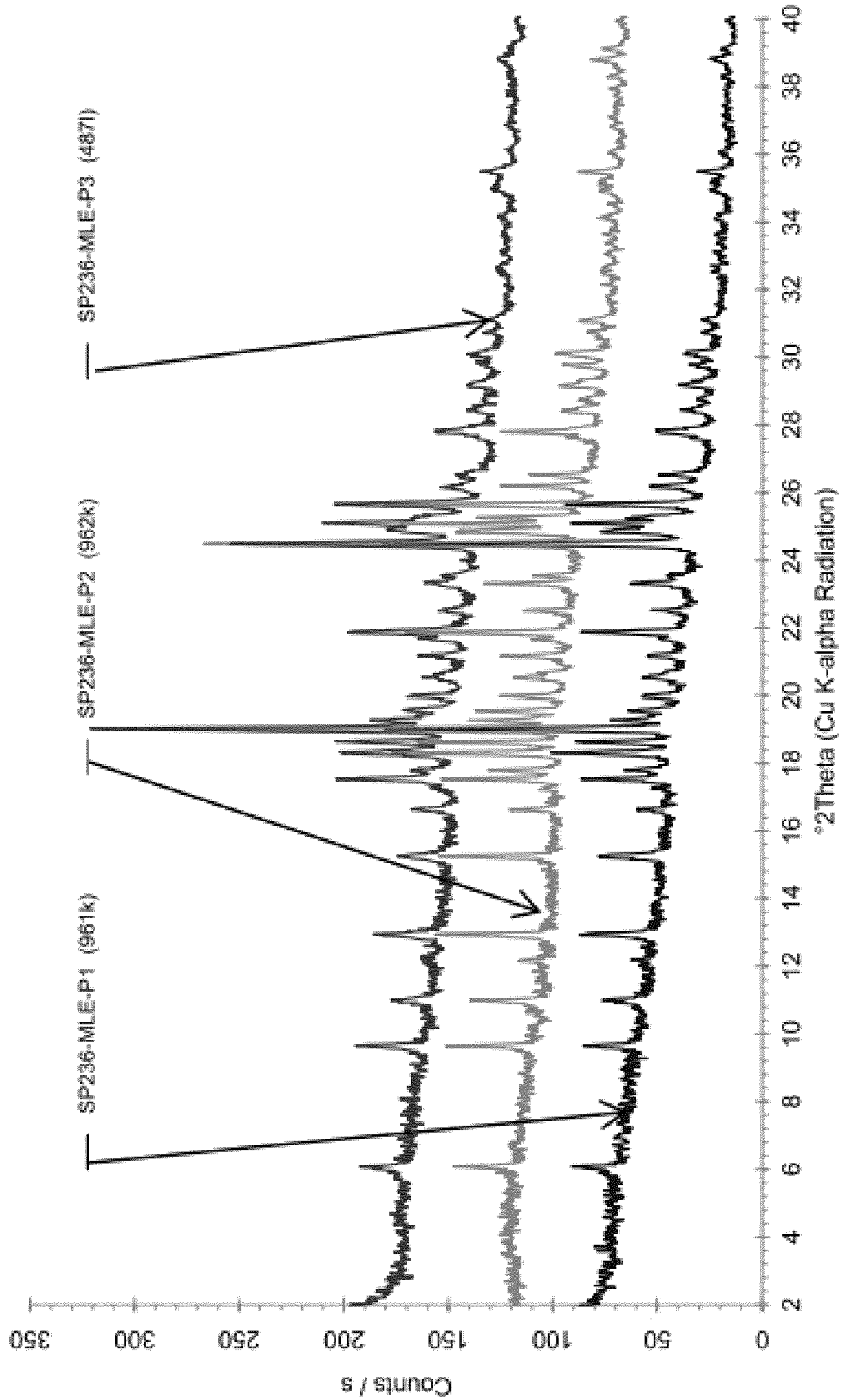
Fig. 5.9

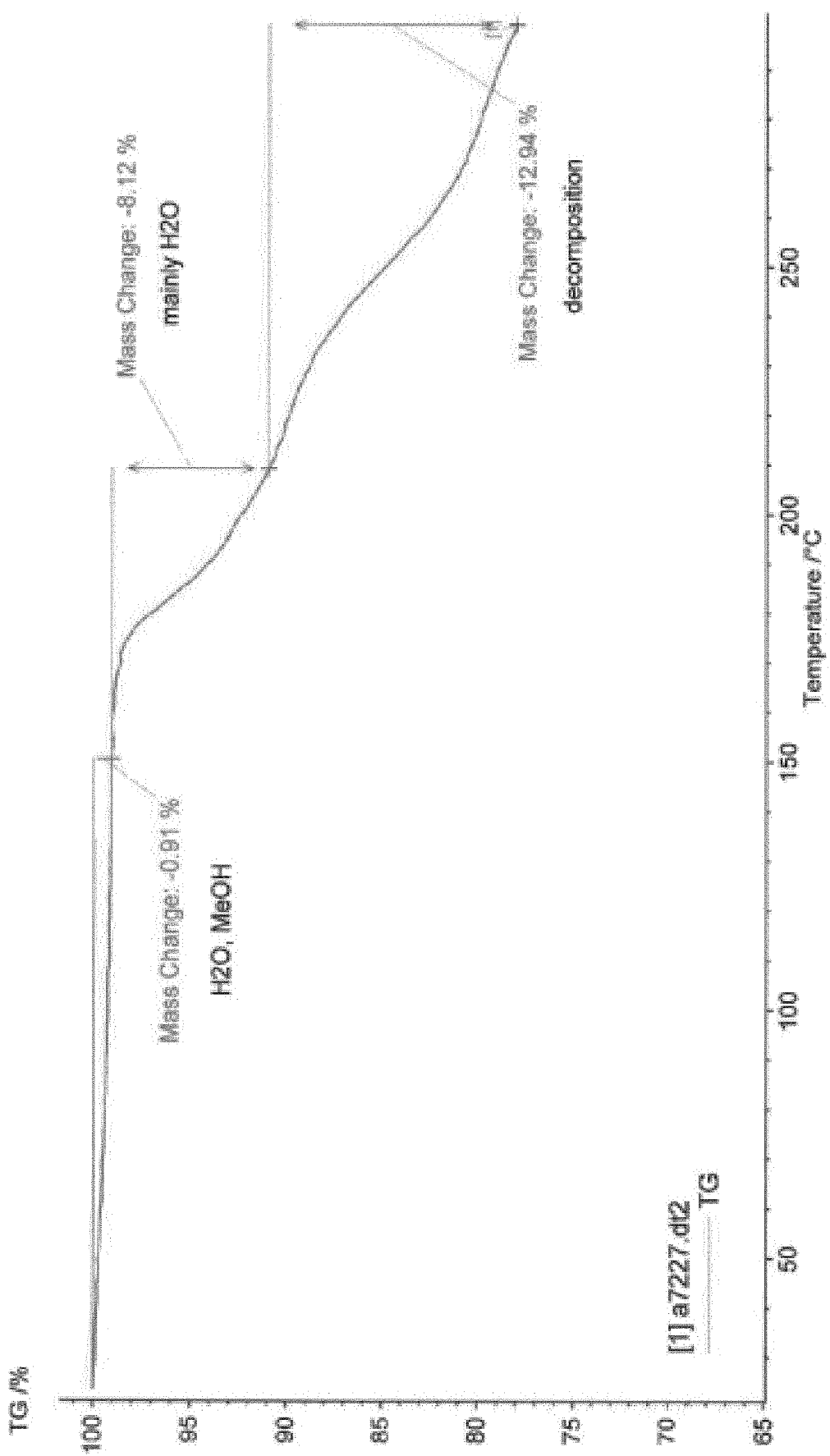
Fig. 5.10

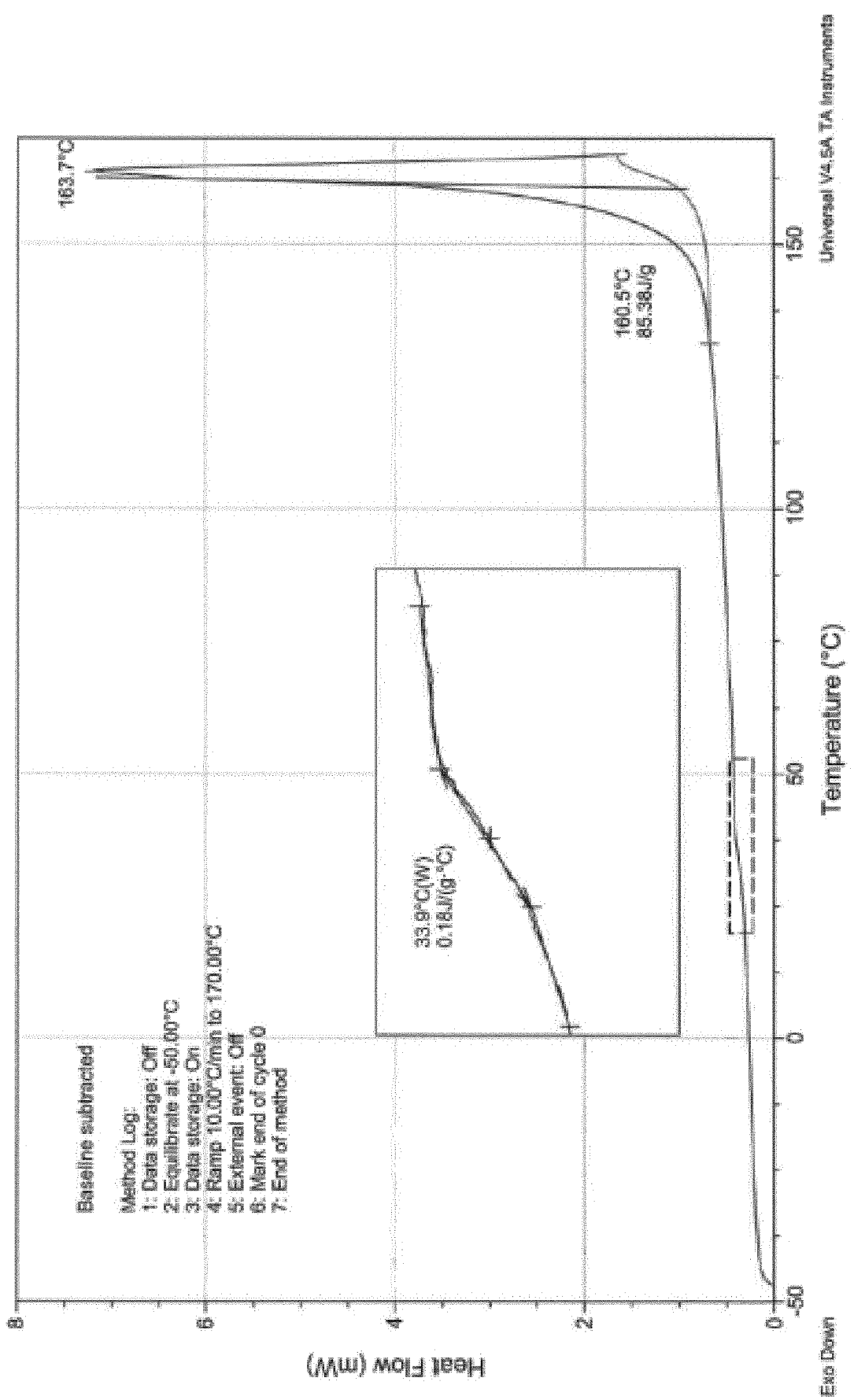
Fig. 5.11

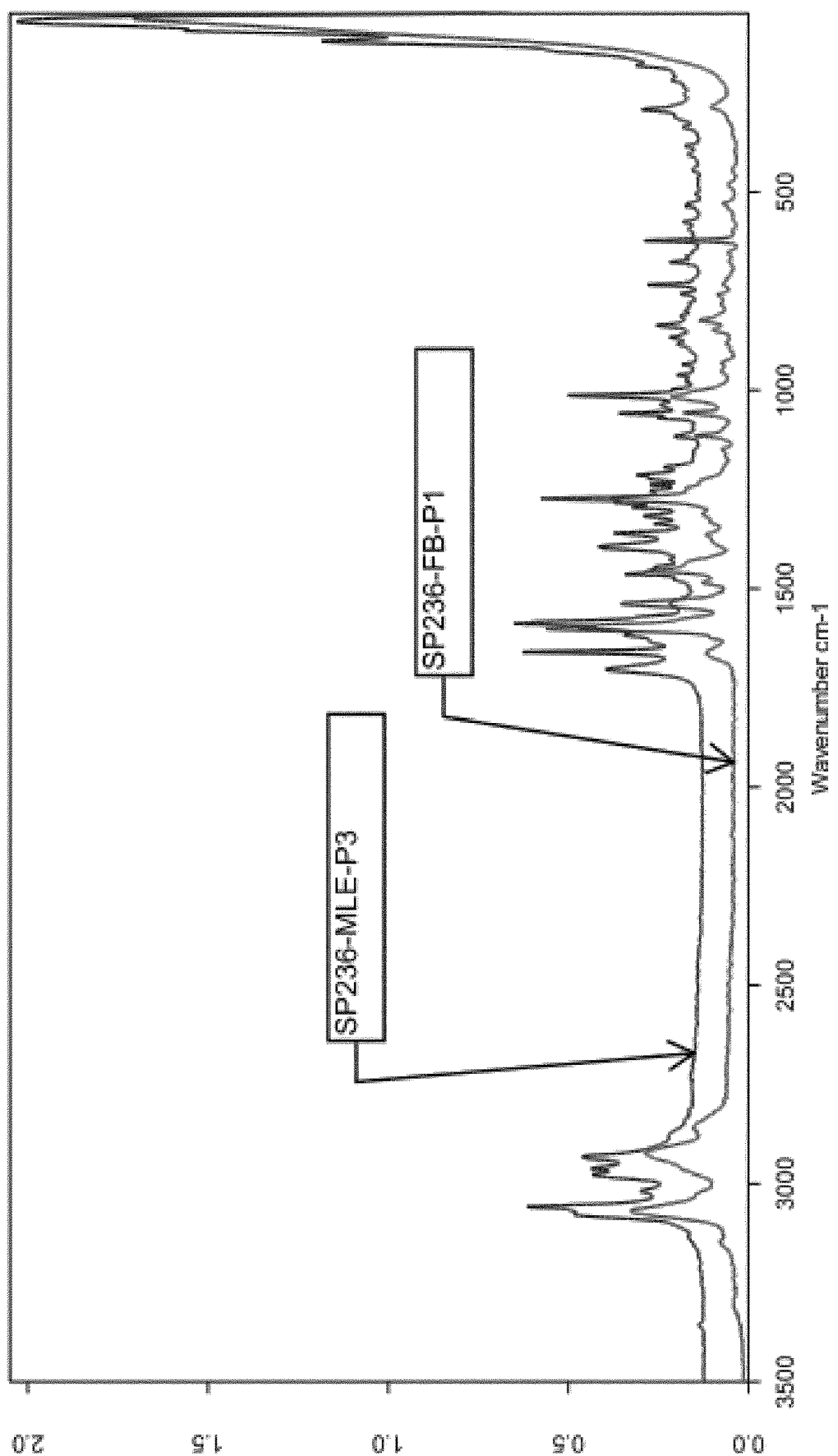
Fig. 5.12

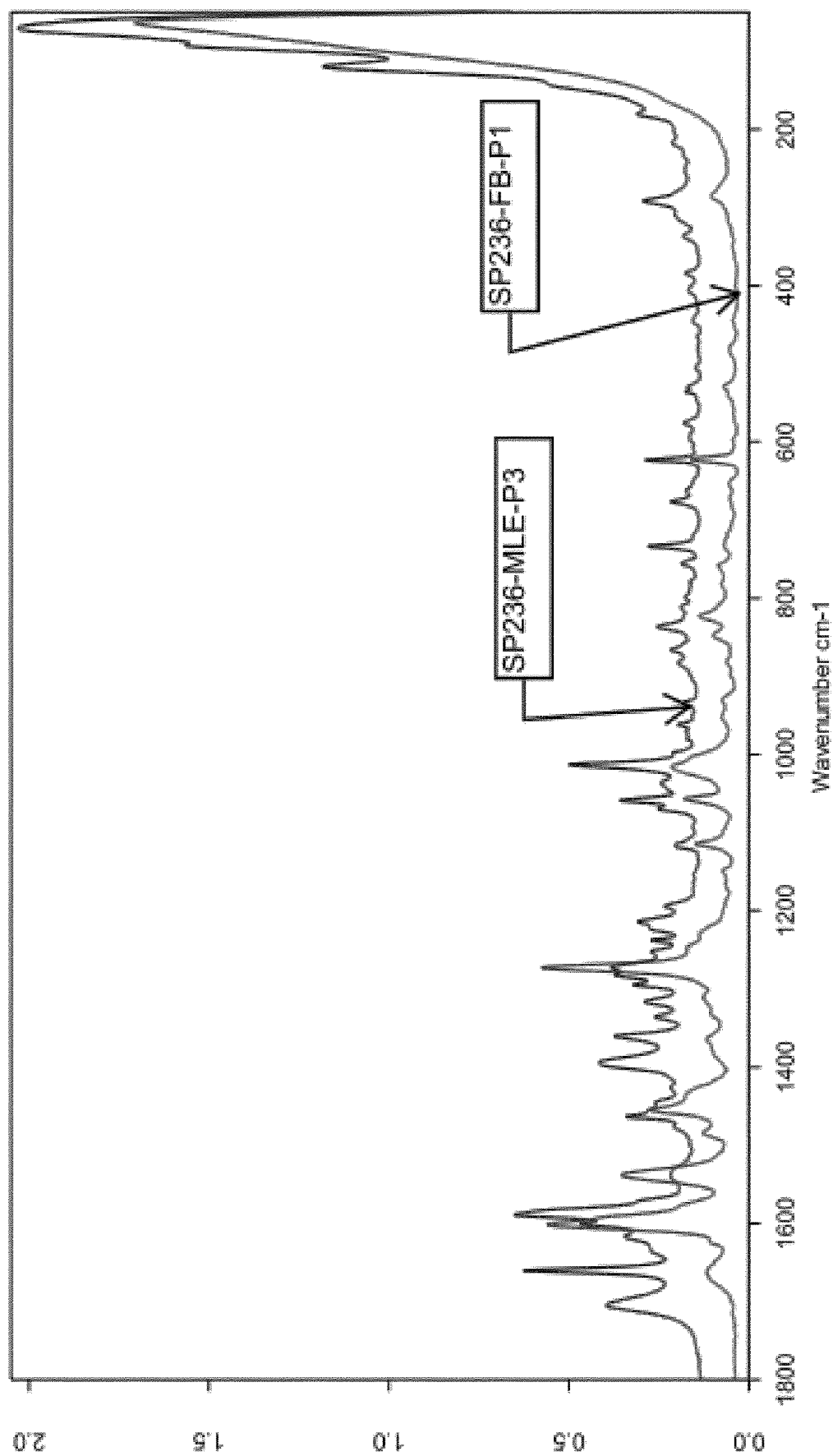
Fig. 5.13

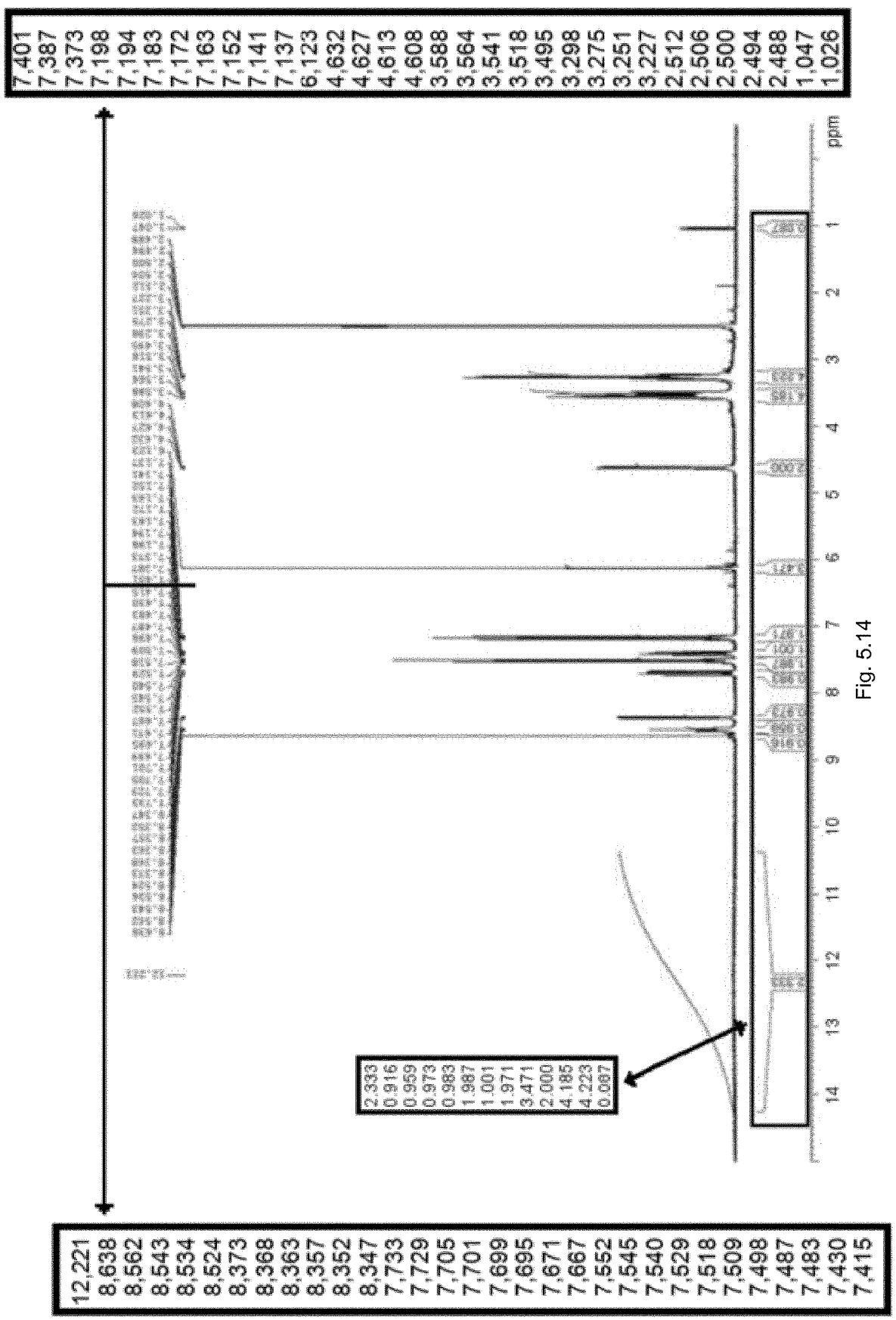
Fig. 5.14

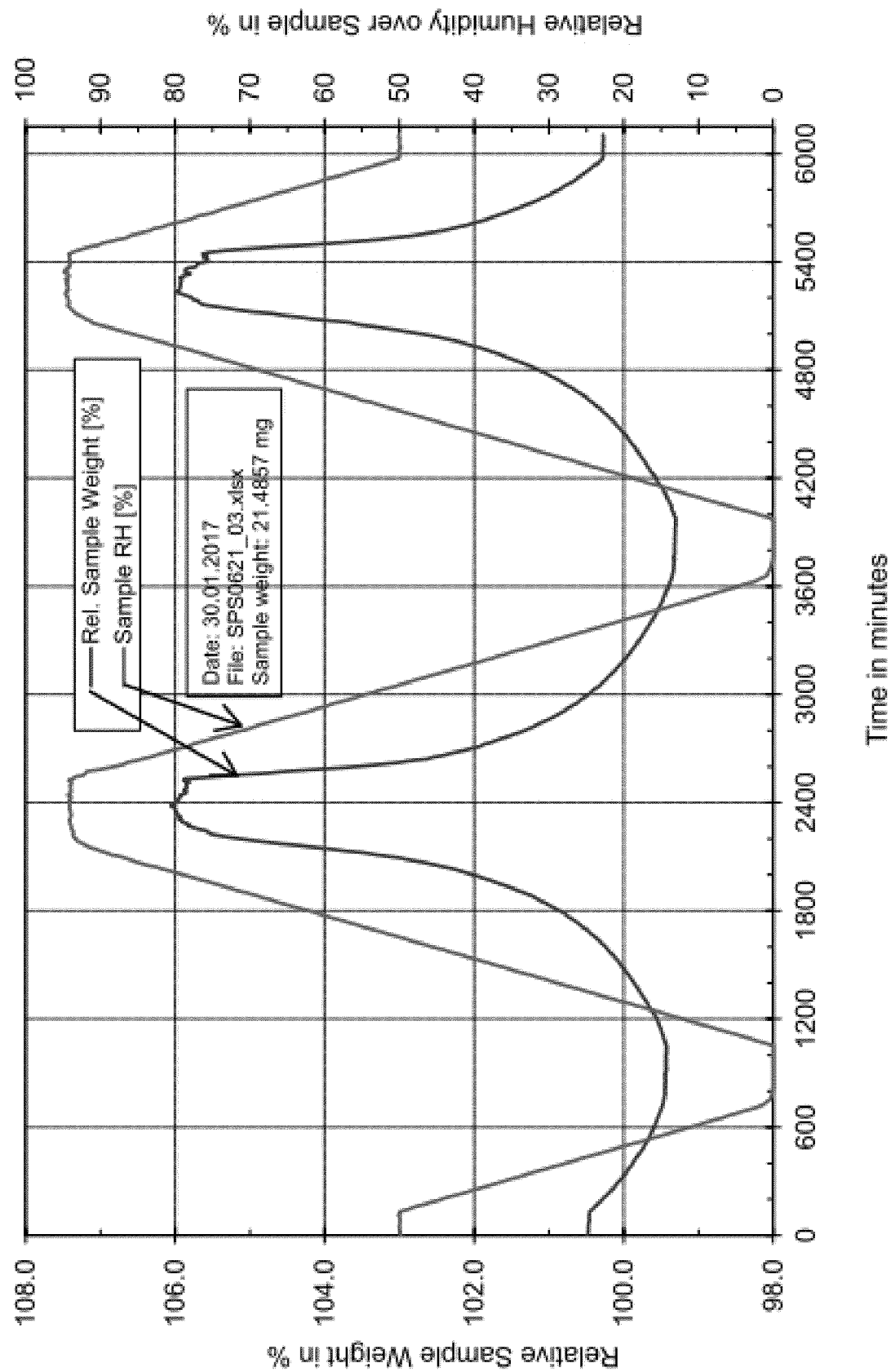
Fig. 5.15

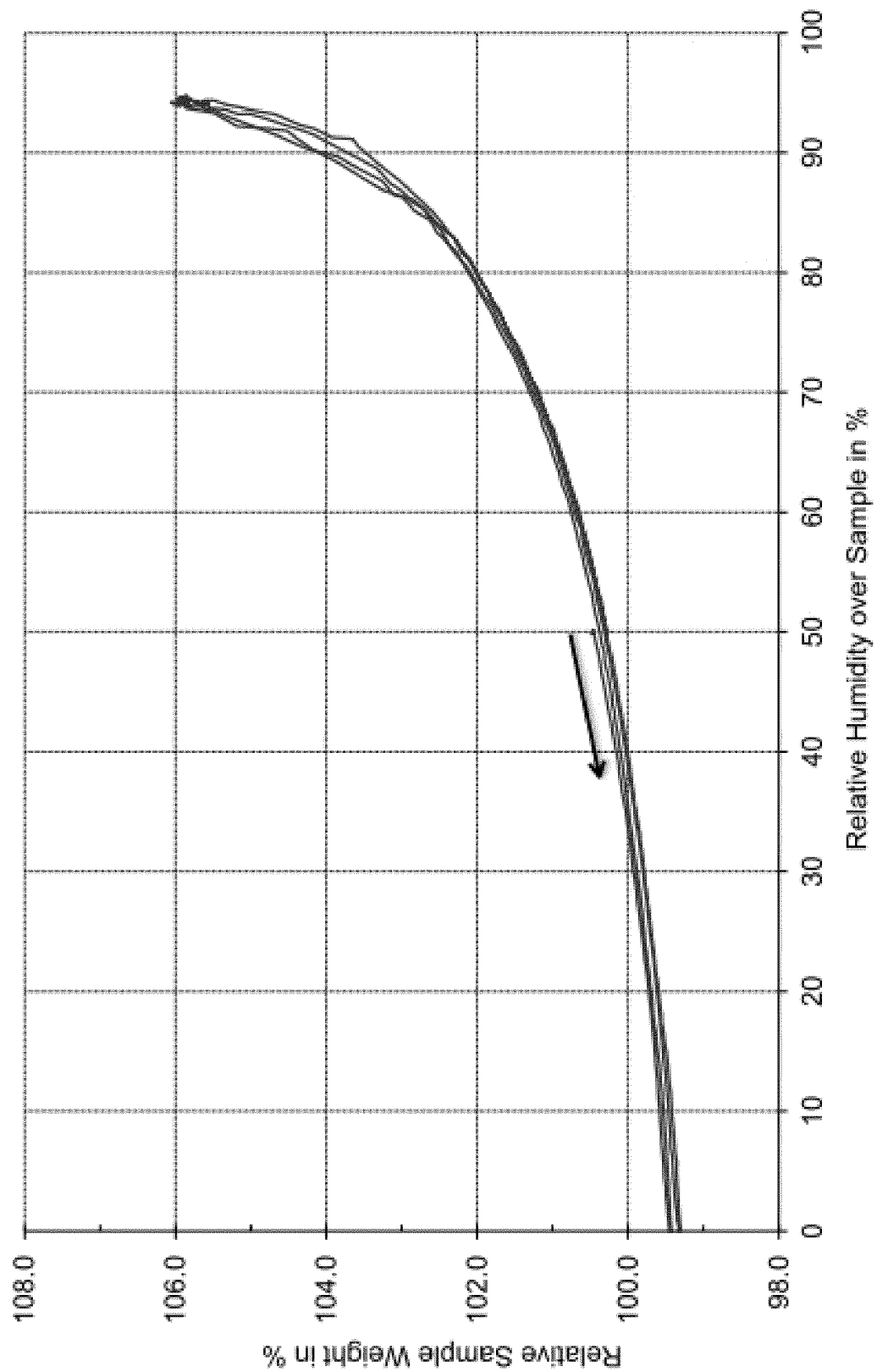
Fig. 5.16

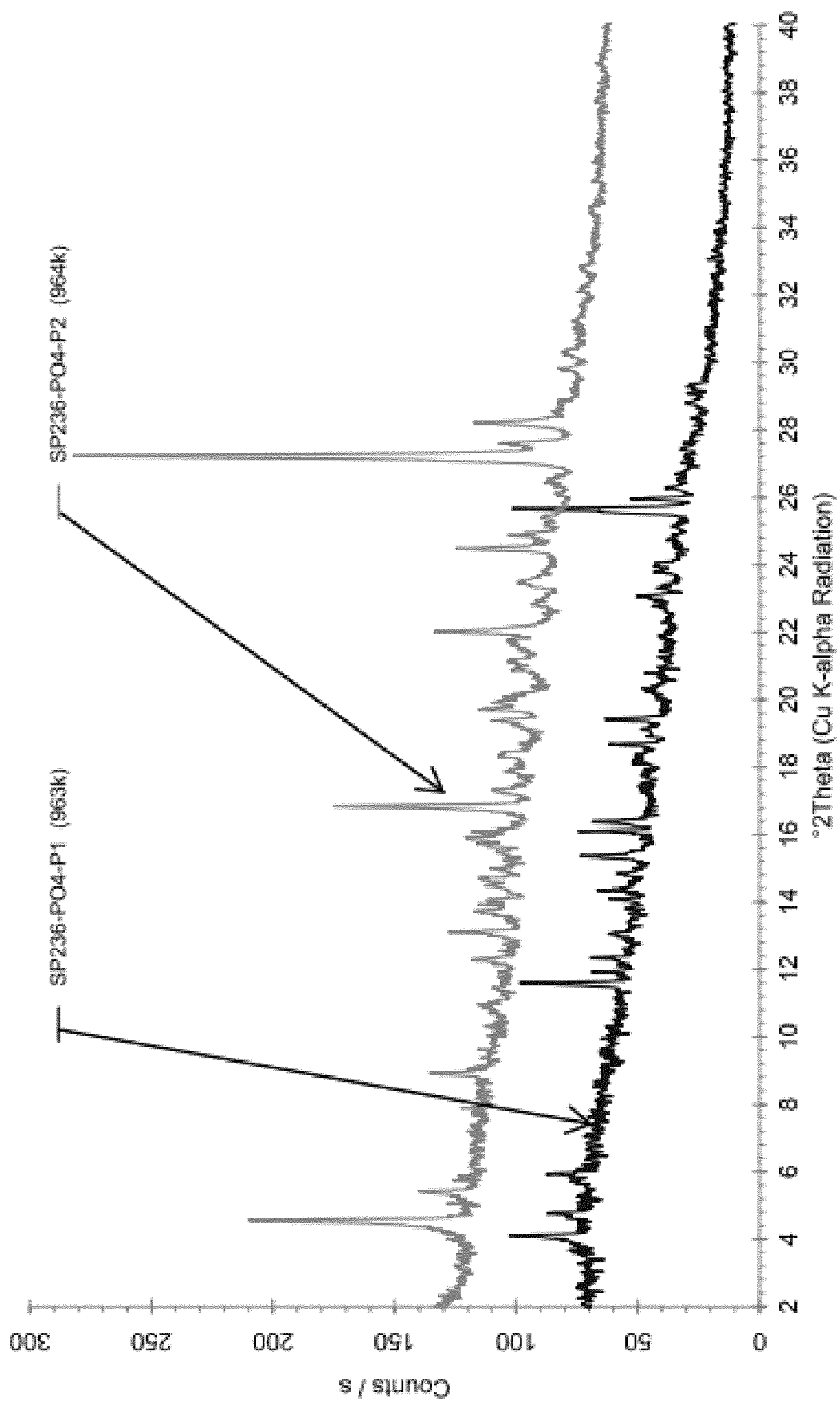
Fig. 5.17

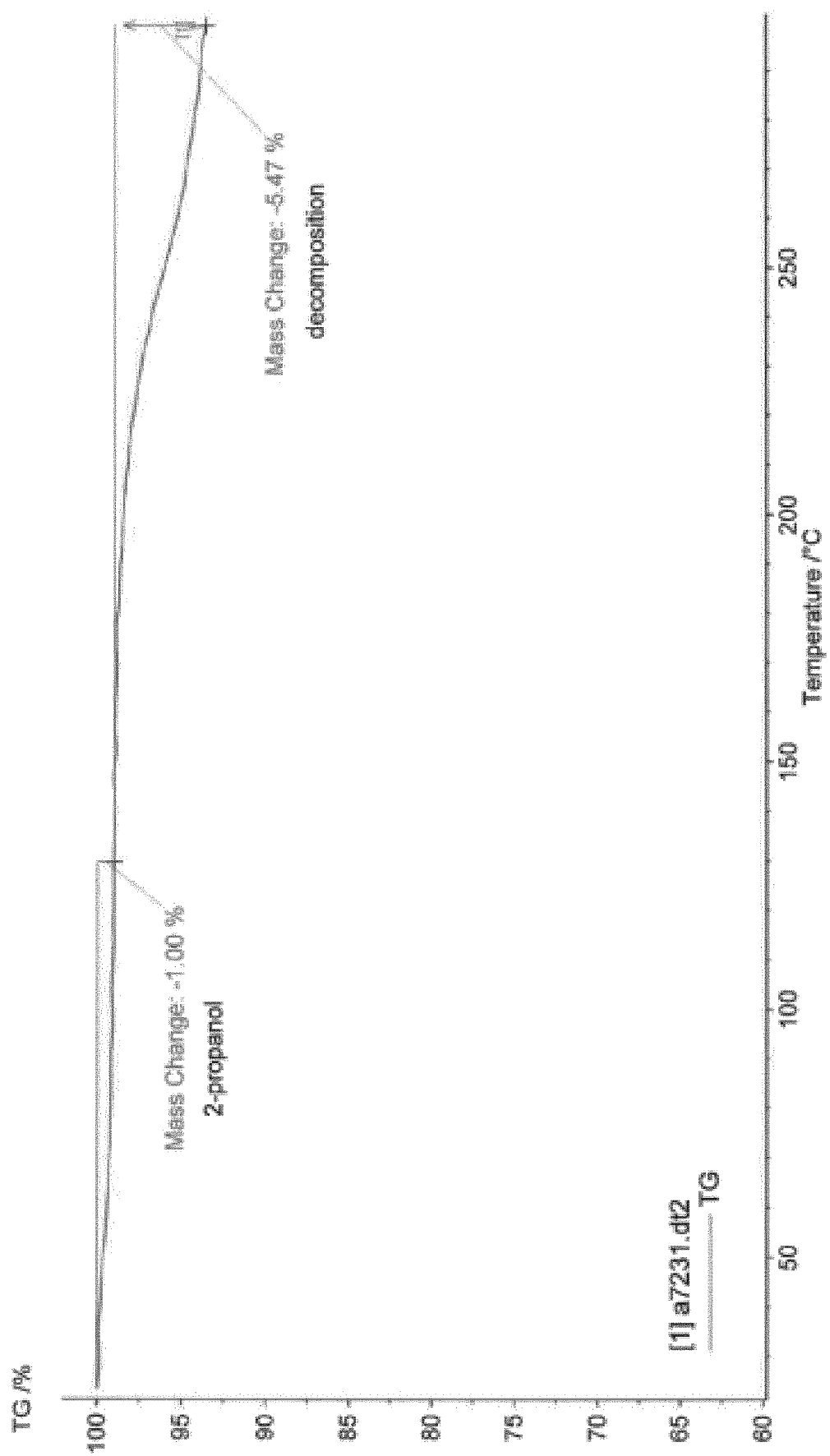
Fig. 5.18

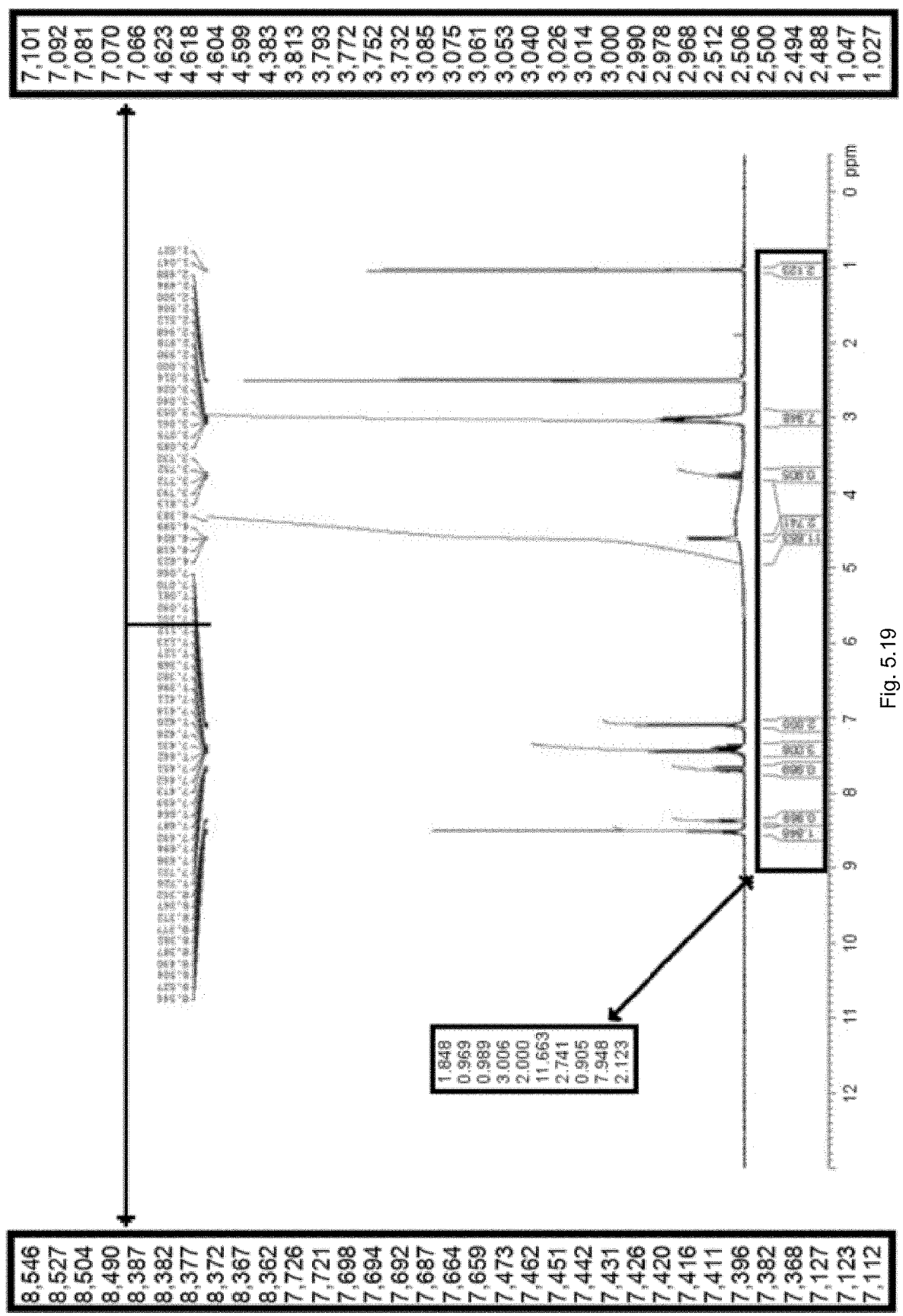
Fig. 5.19

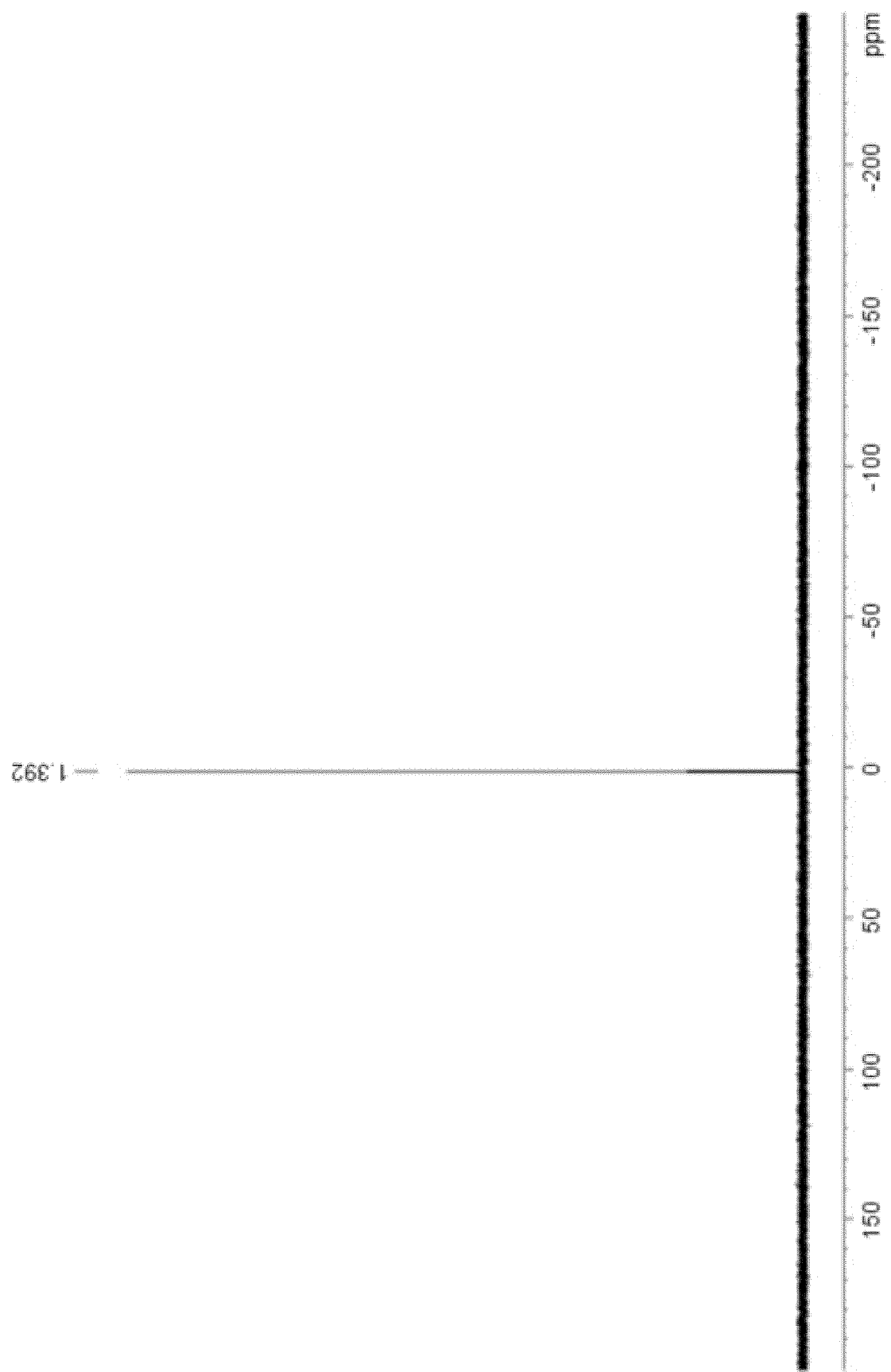
Fig. 5.20

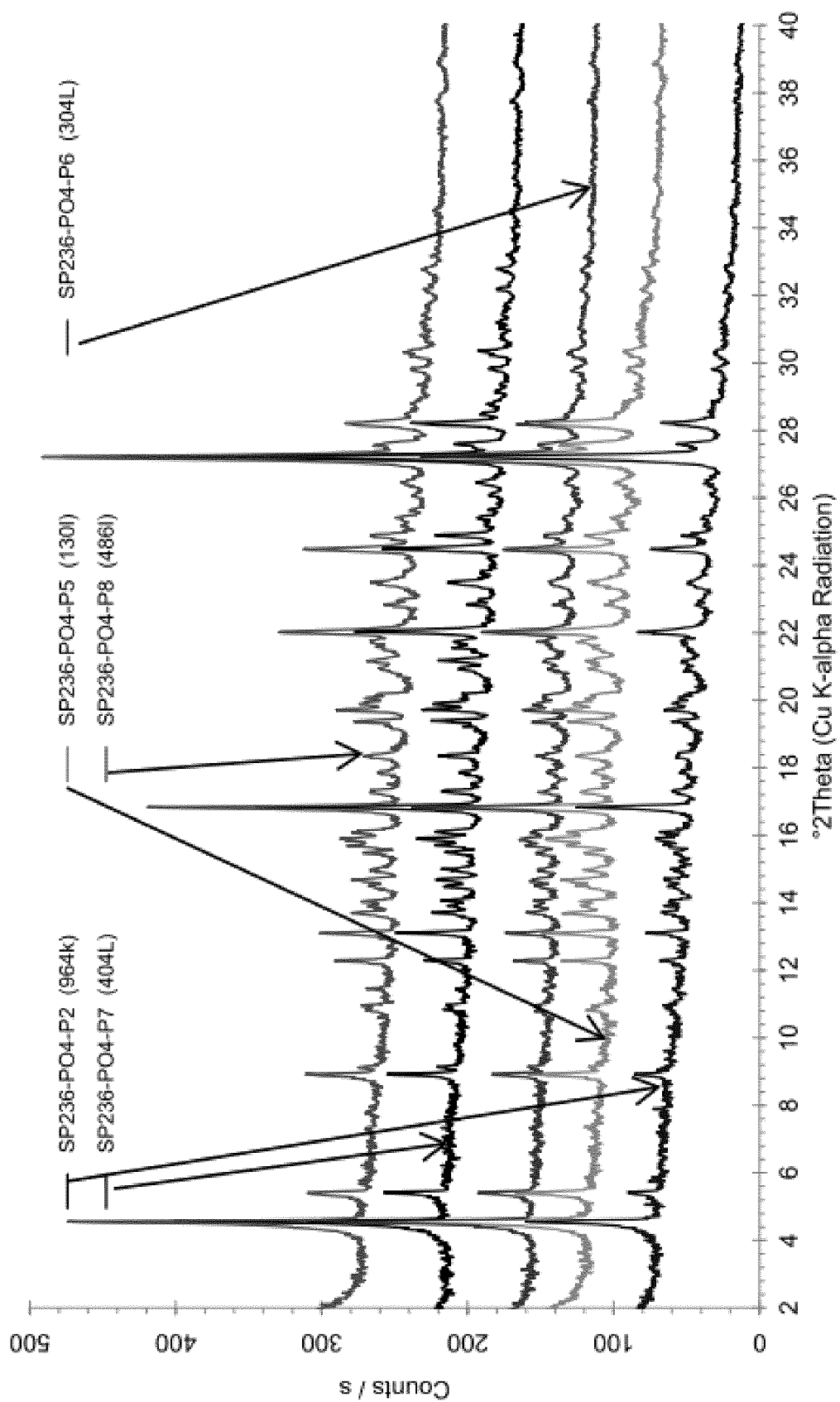
Fig. 5.21

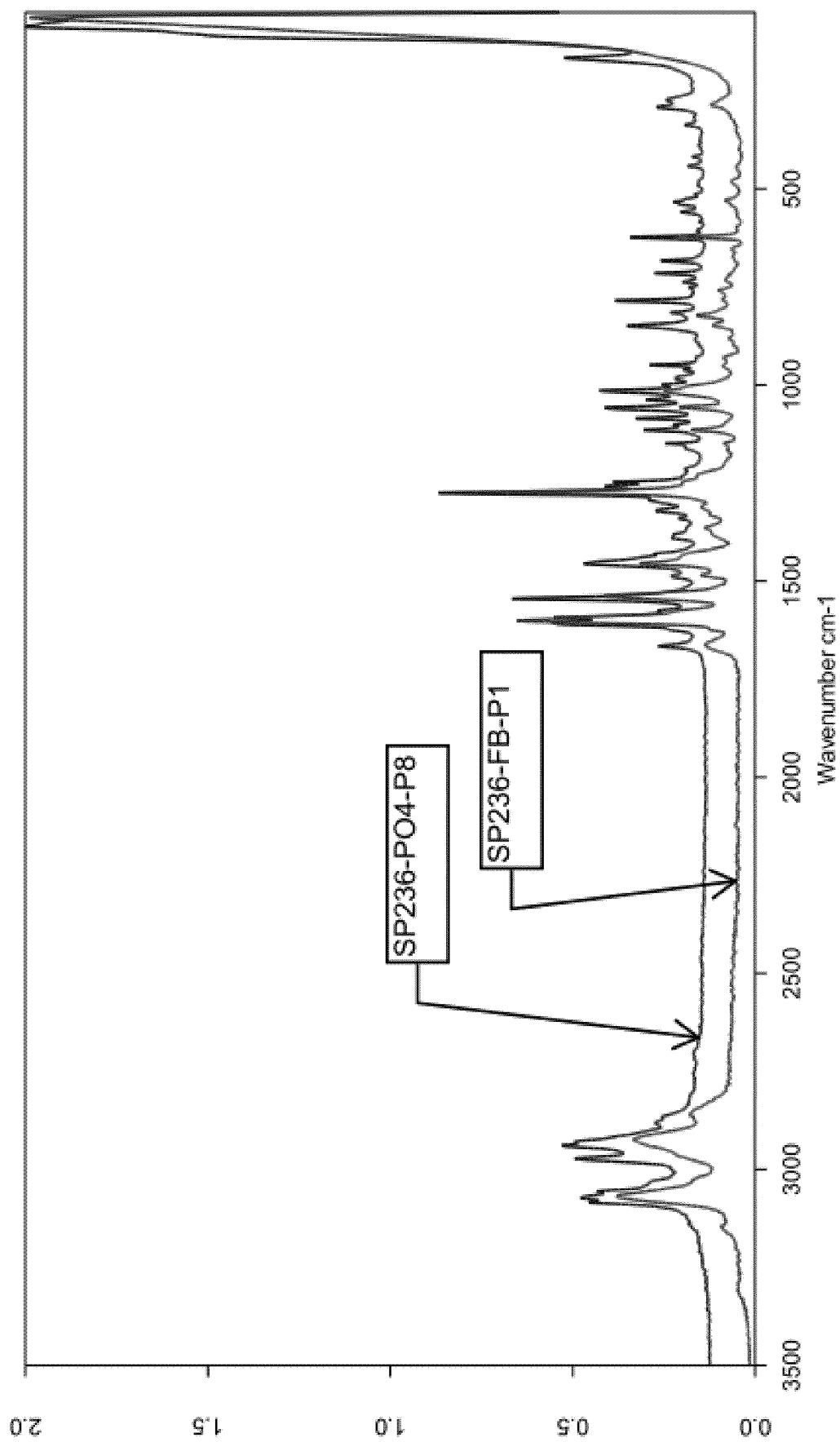
Fig. 5.22

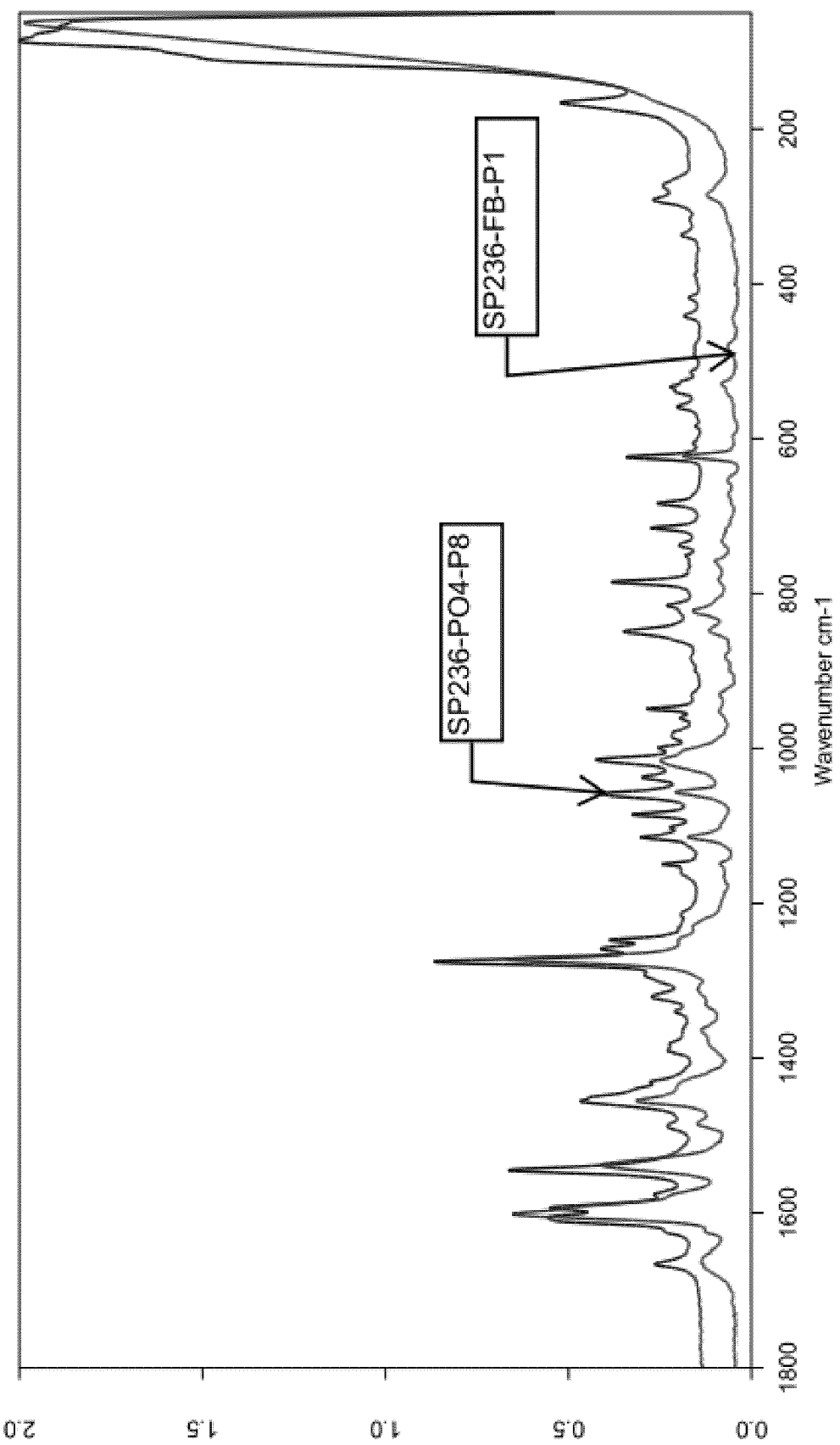
Fig. 5.23

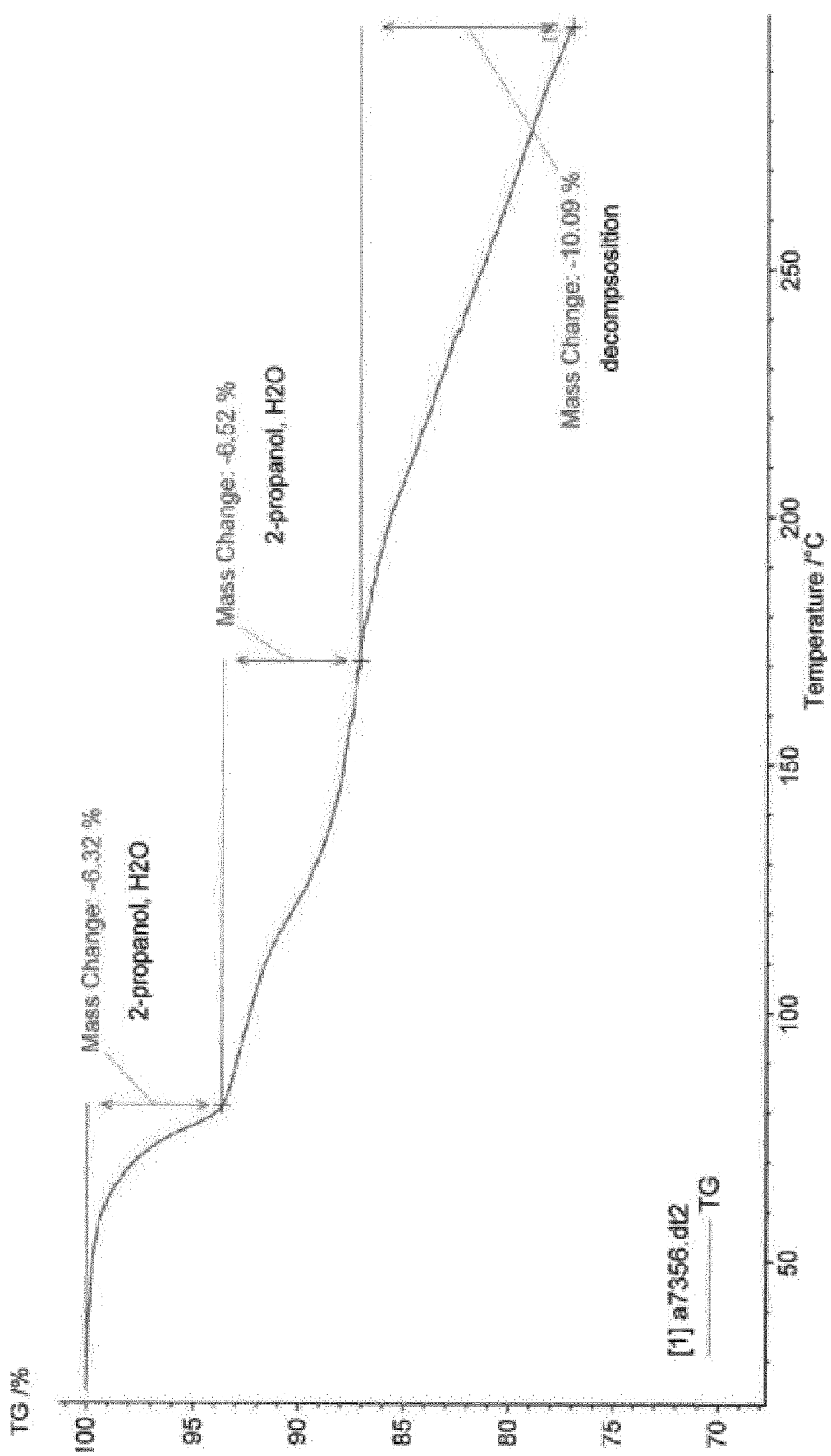
Fig. 5.24

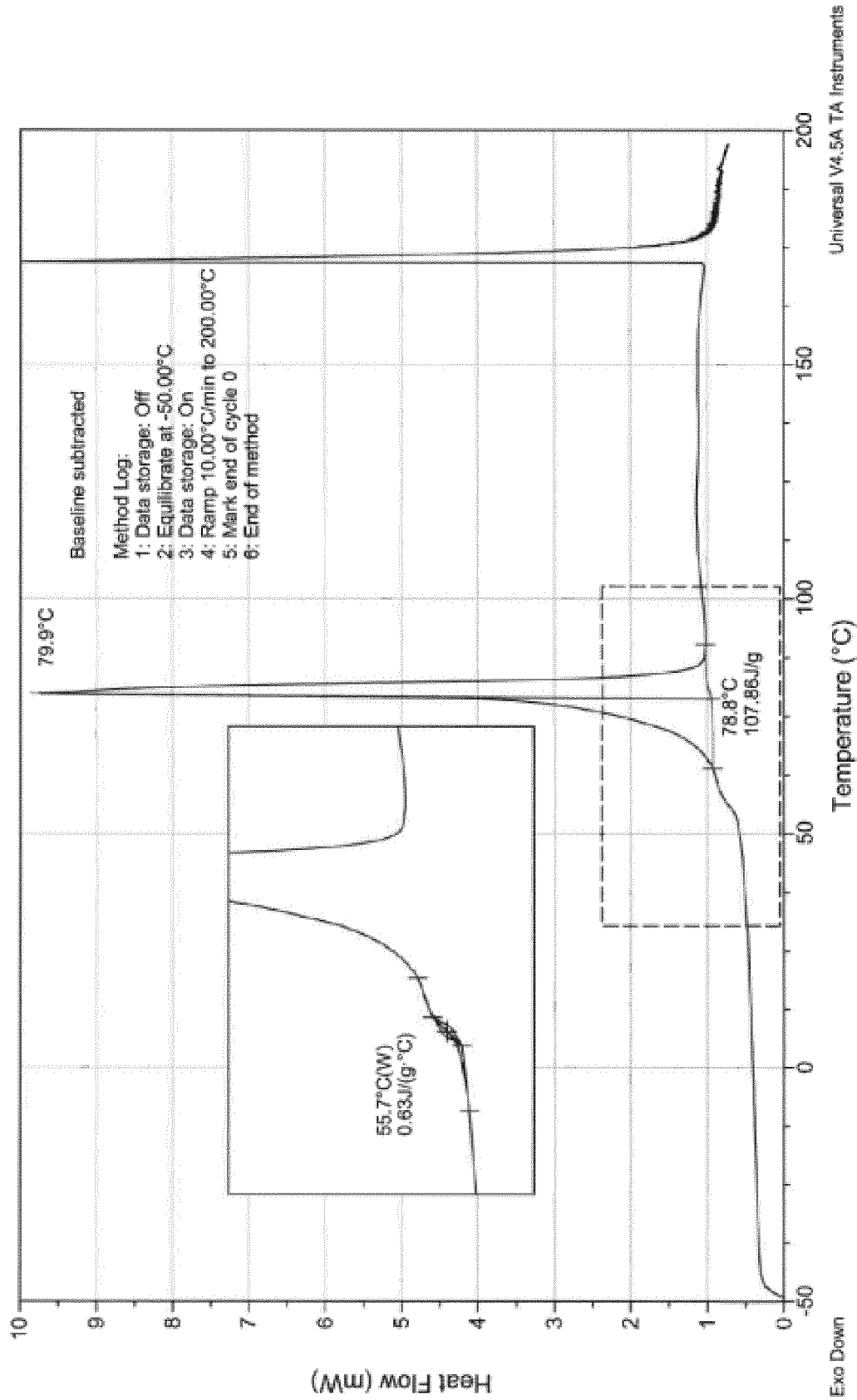
Fig. 5.25

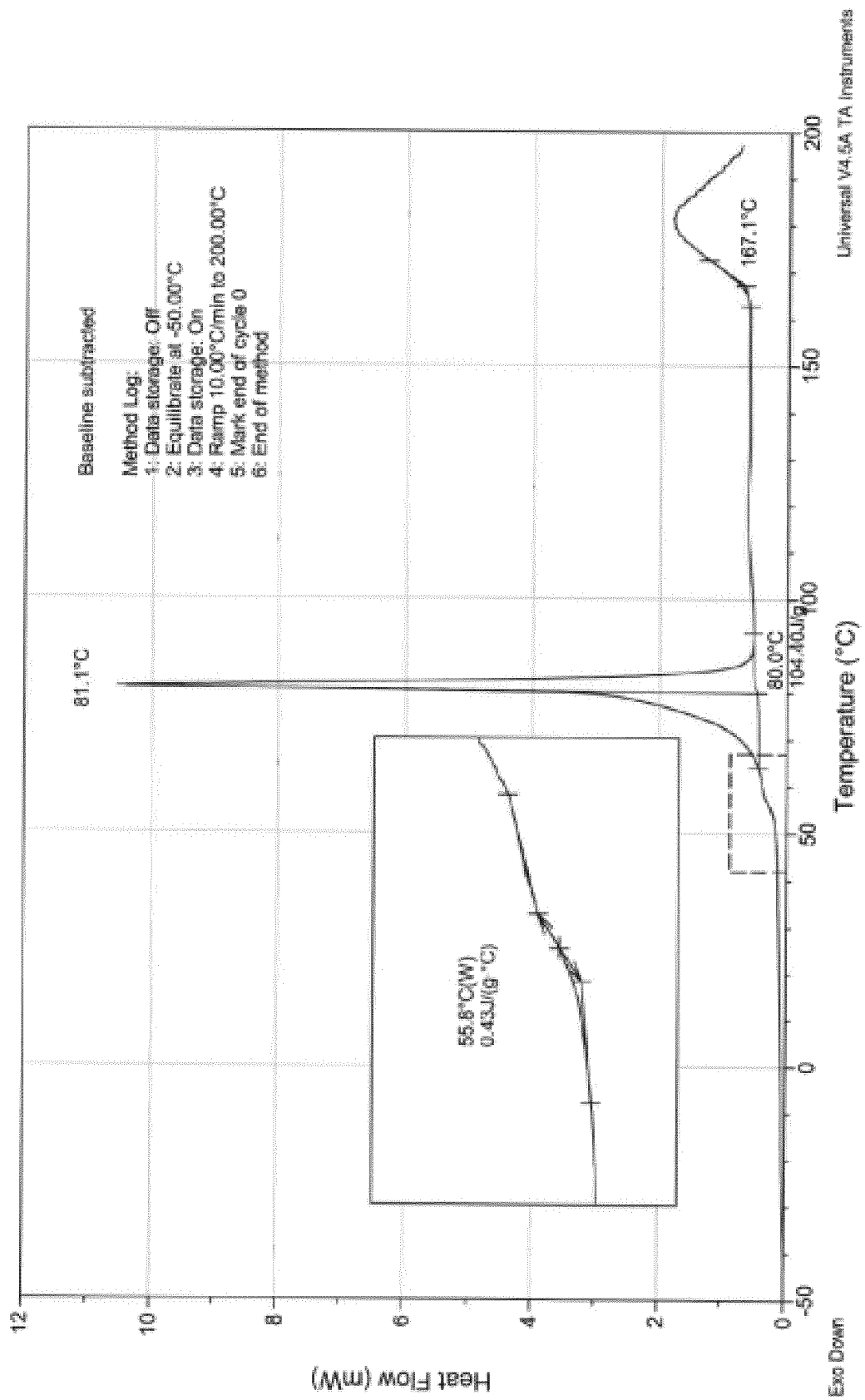
Fig. 5.26

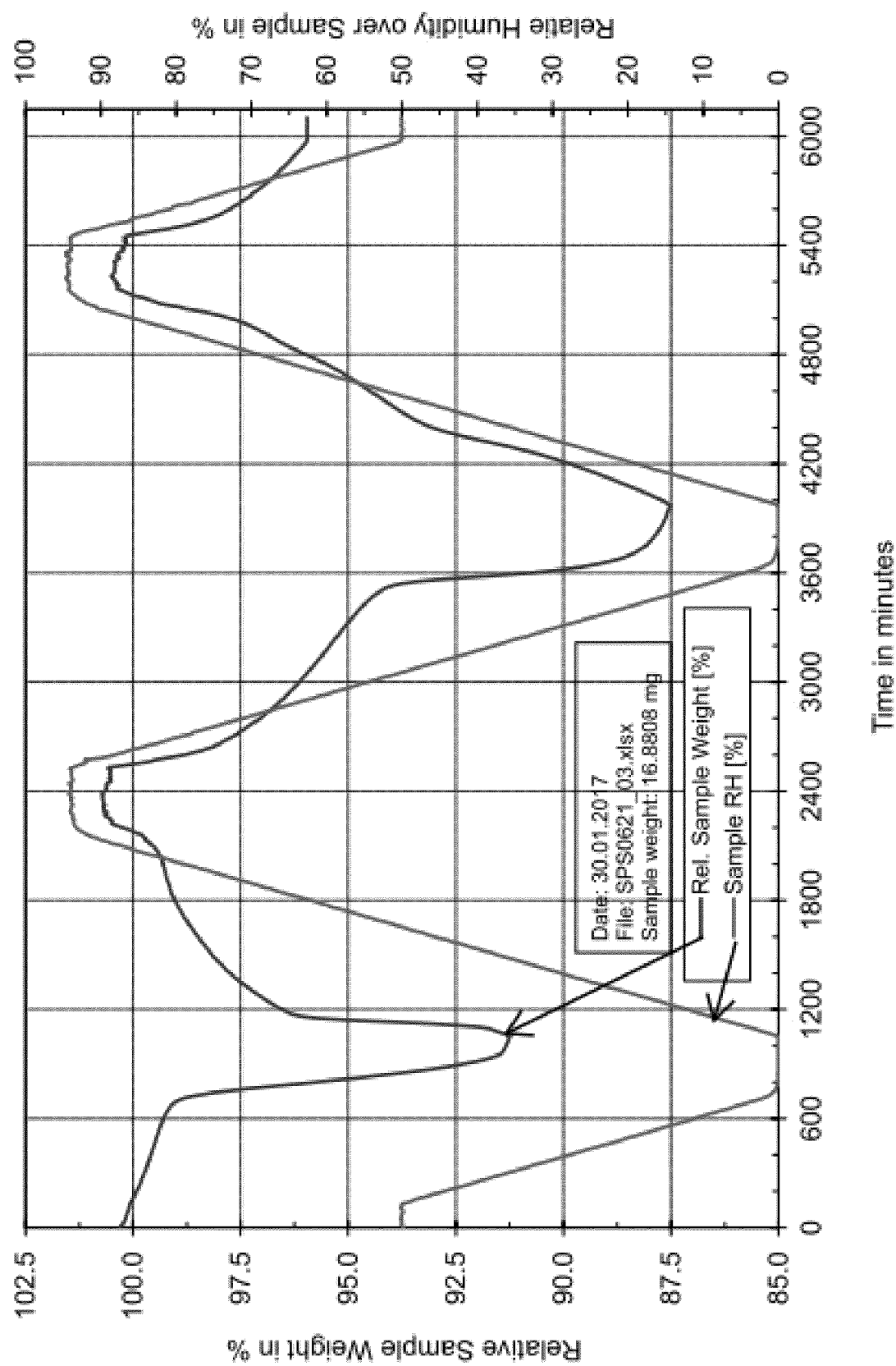
Fig. 5.27

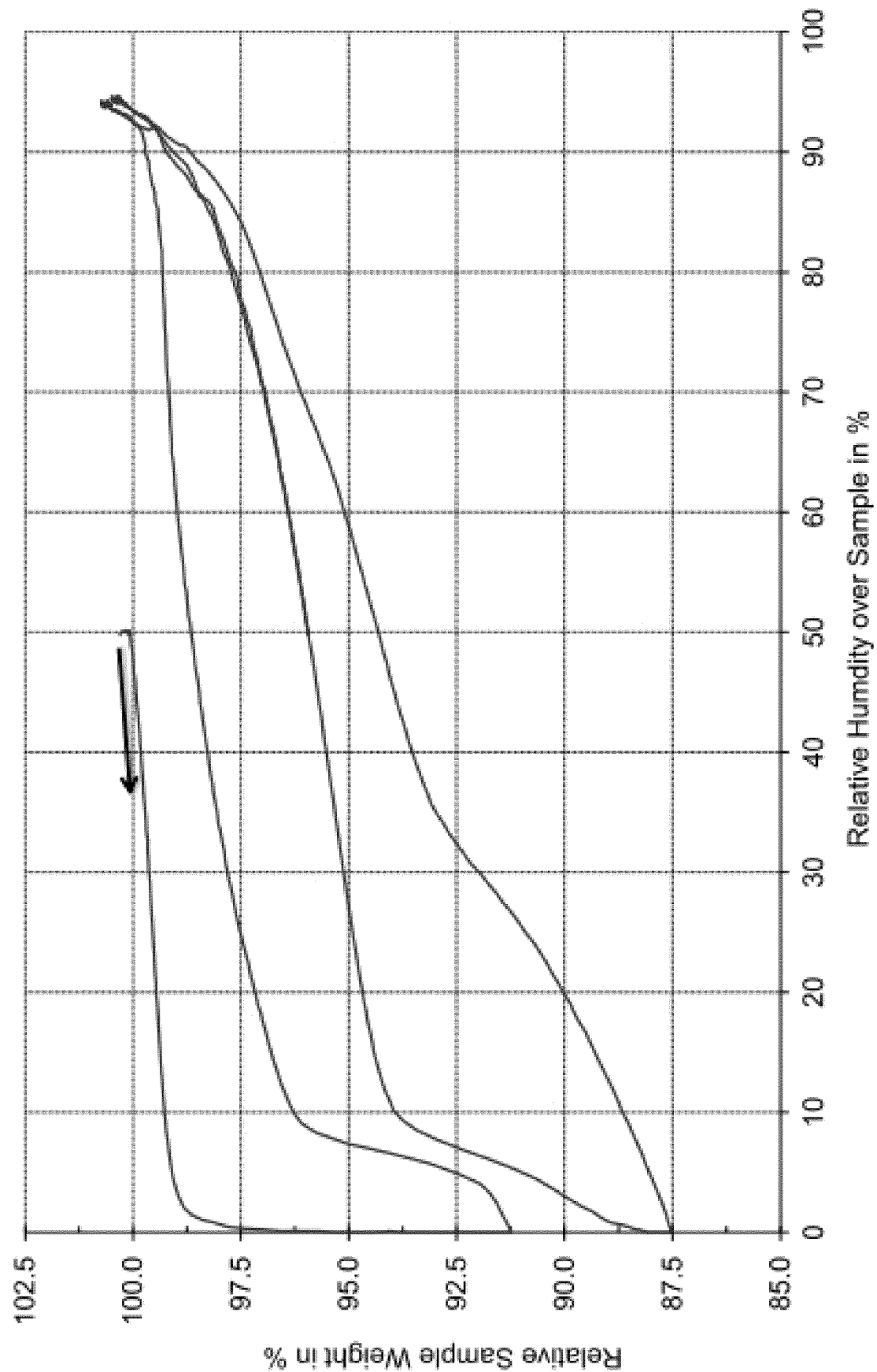
Fig. 5.28

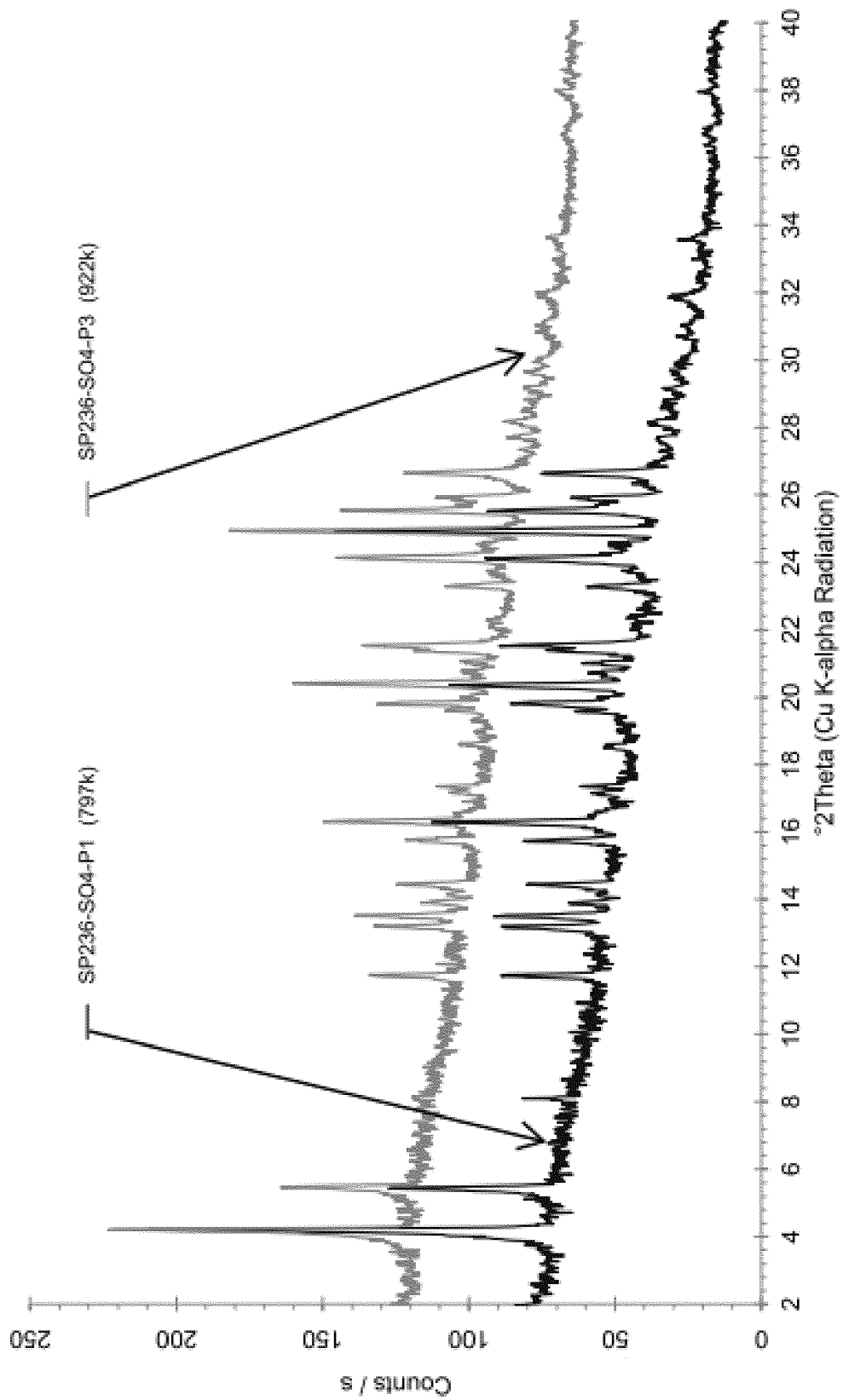
Fig. 5.29

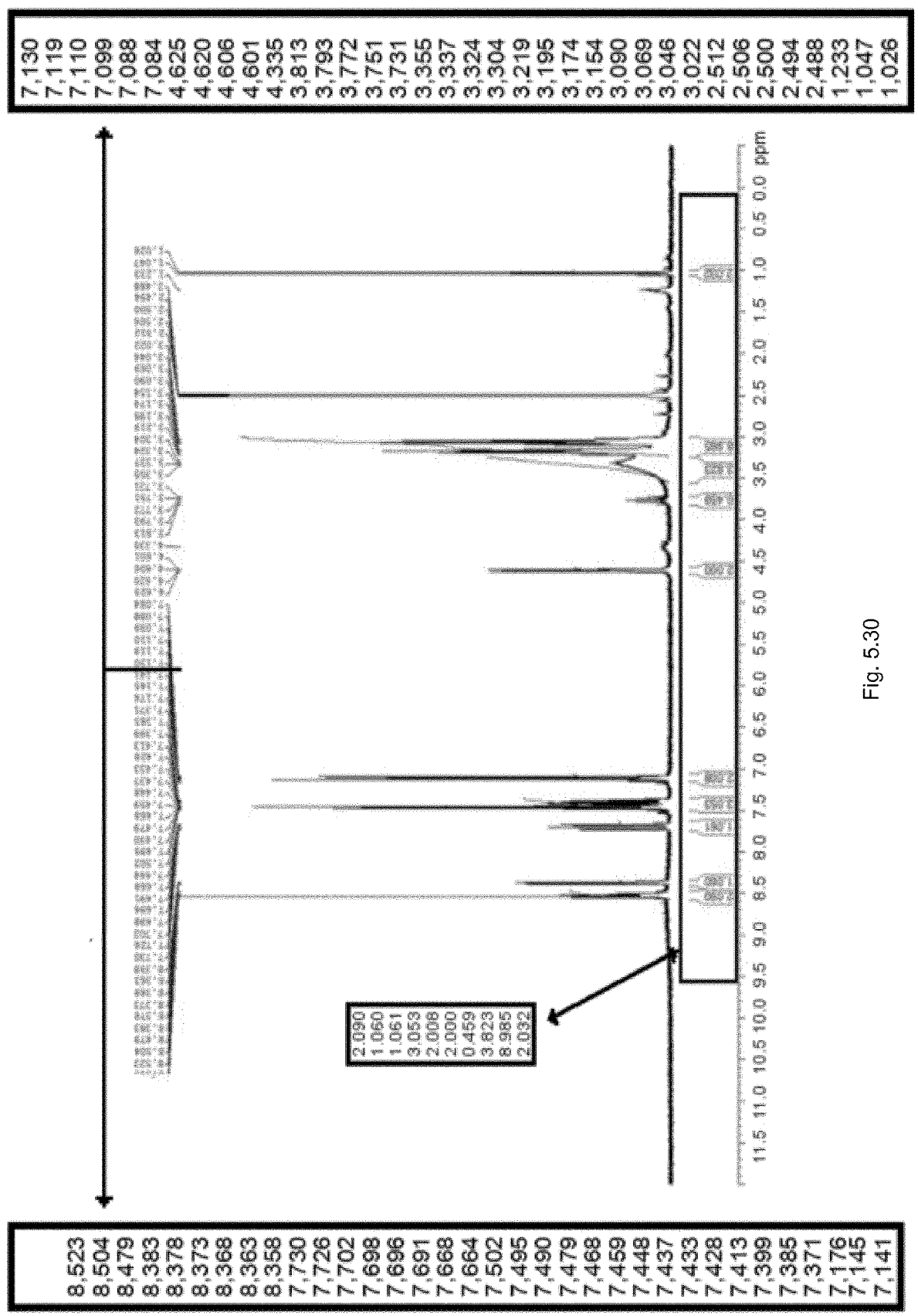
Fig. 5.30

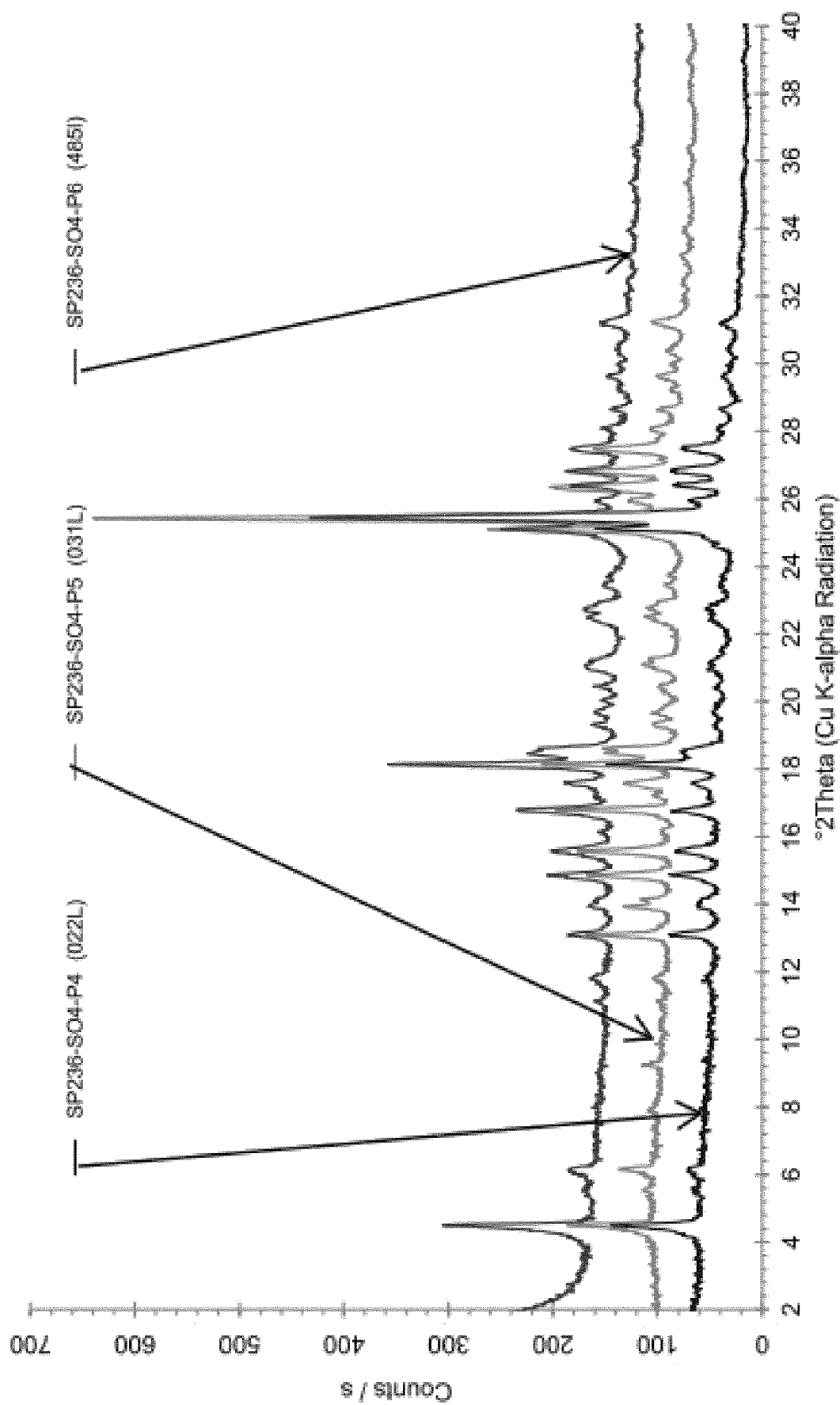
Fig. 5.31

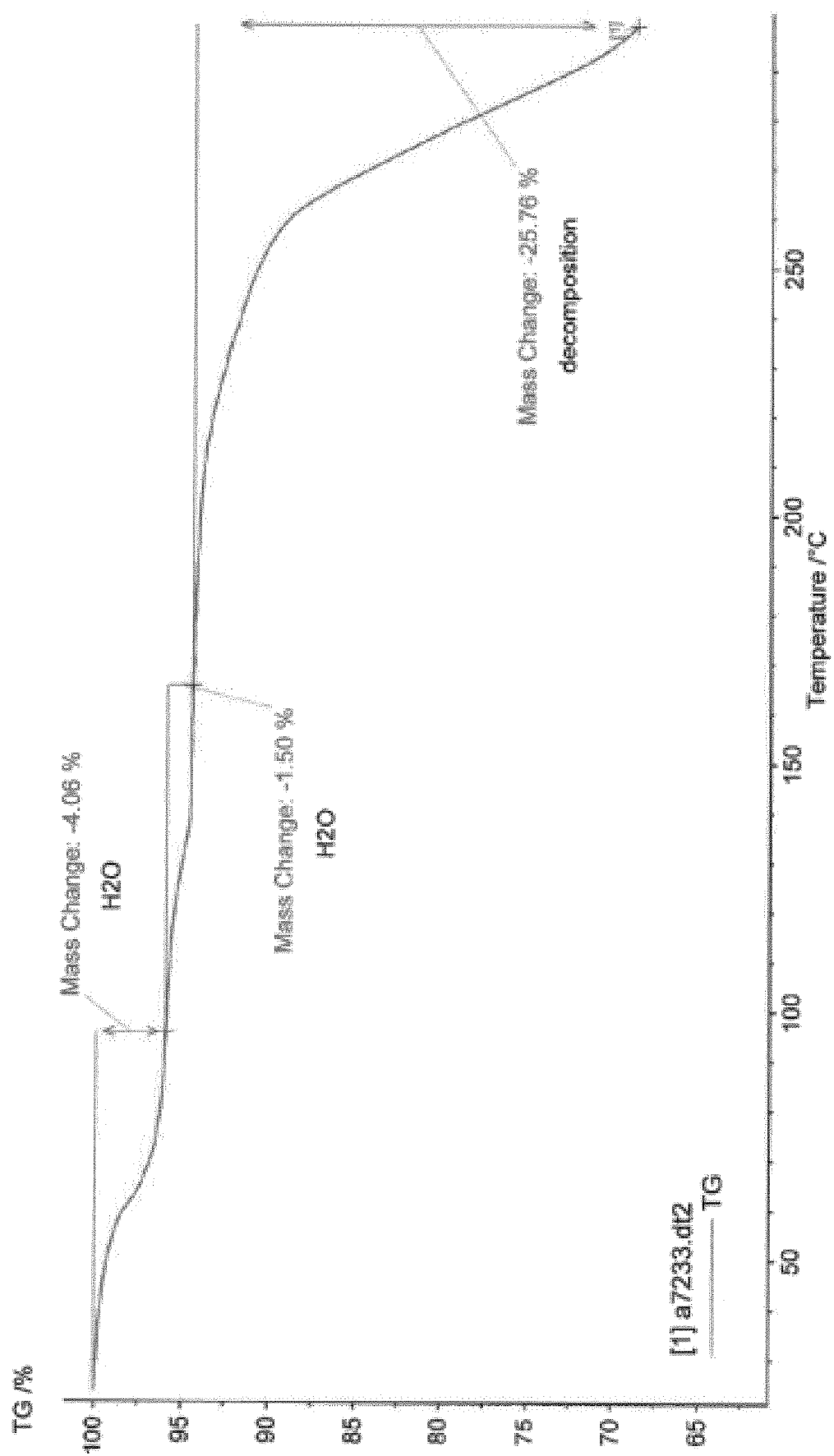
Fig. 5.32

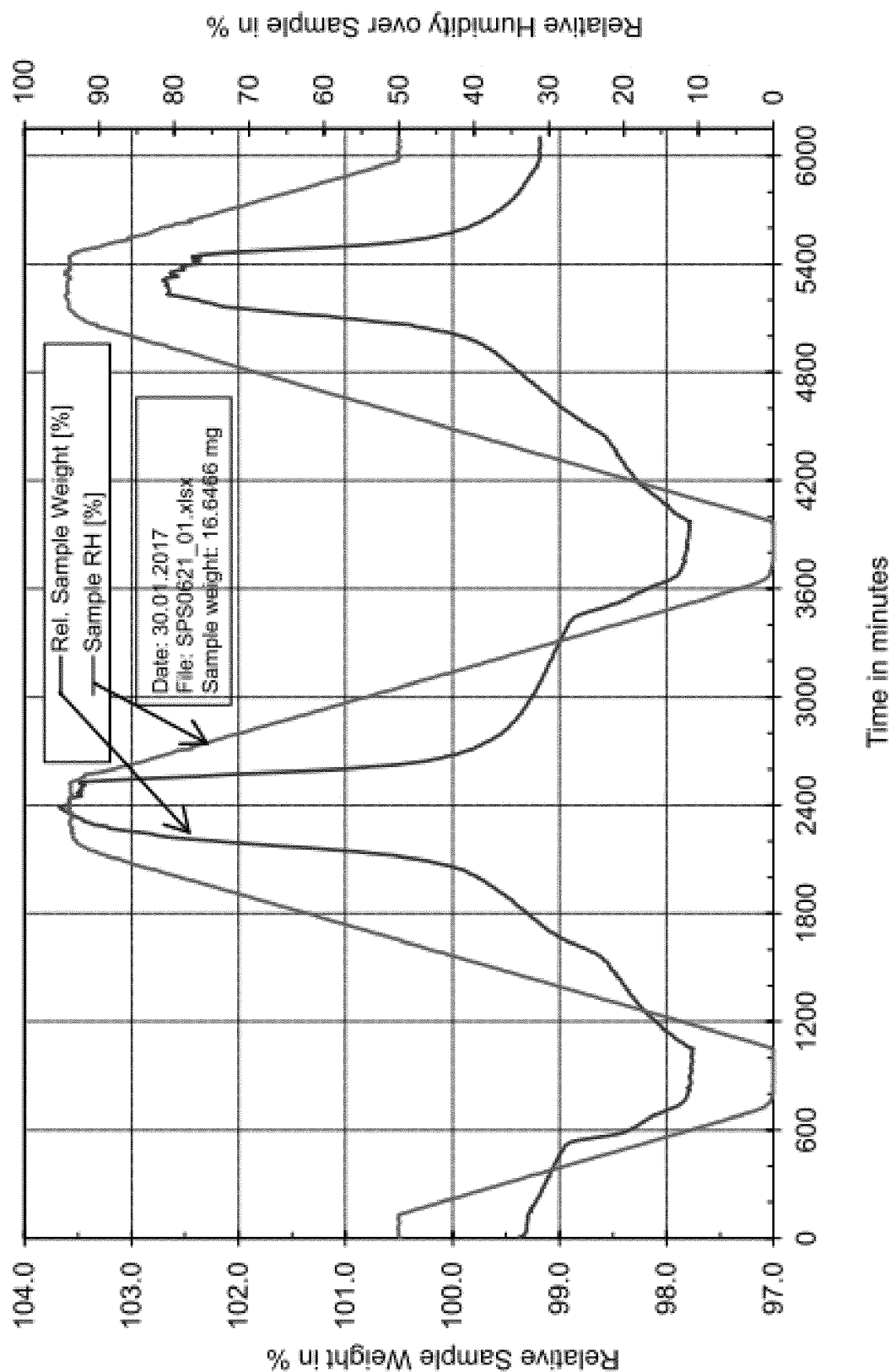
Fig. 5.33

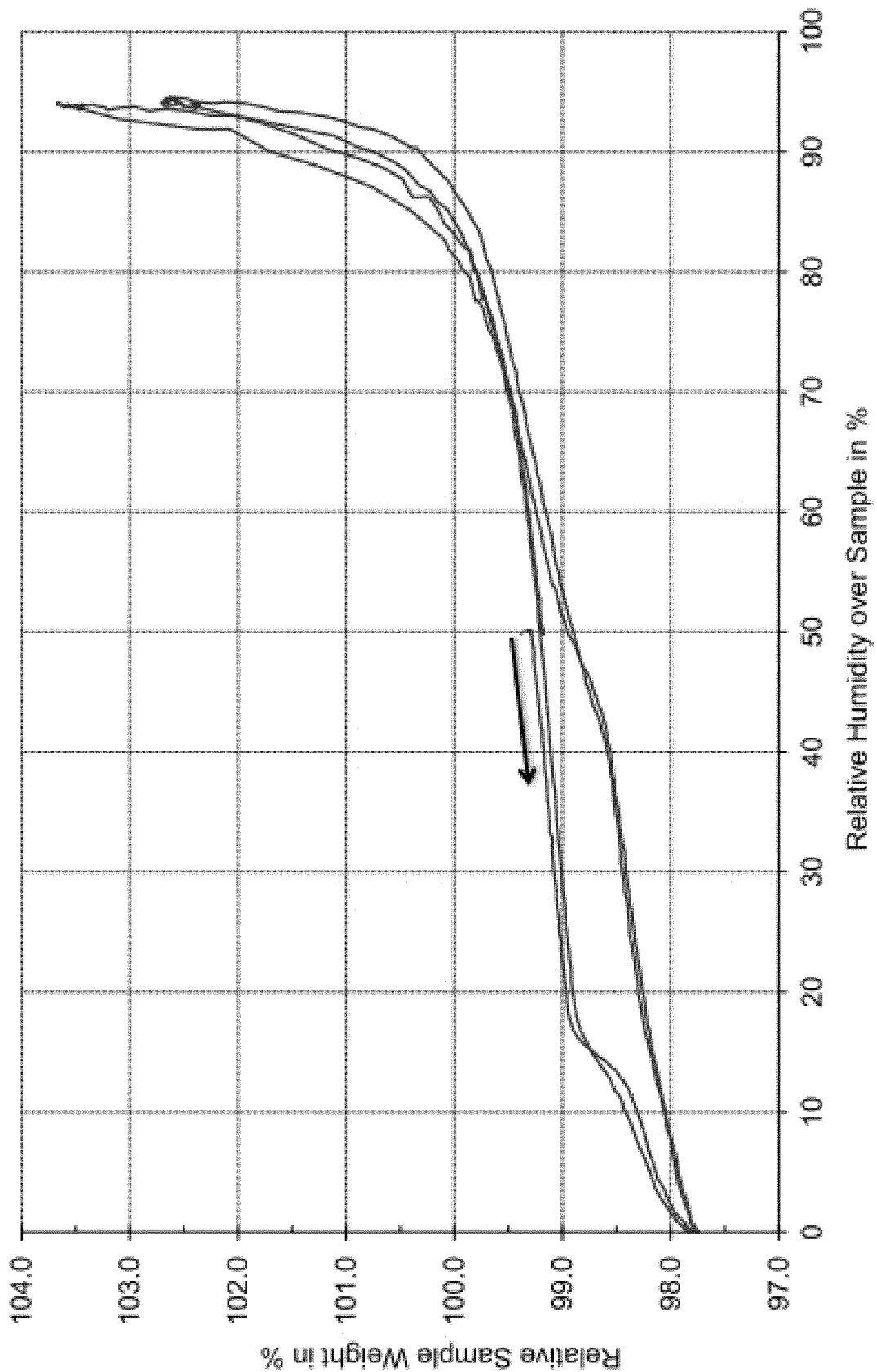
Fig. 5.34

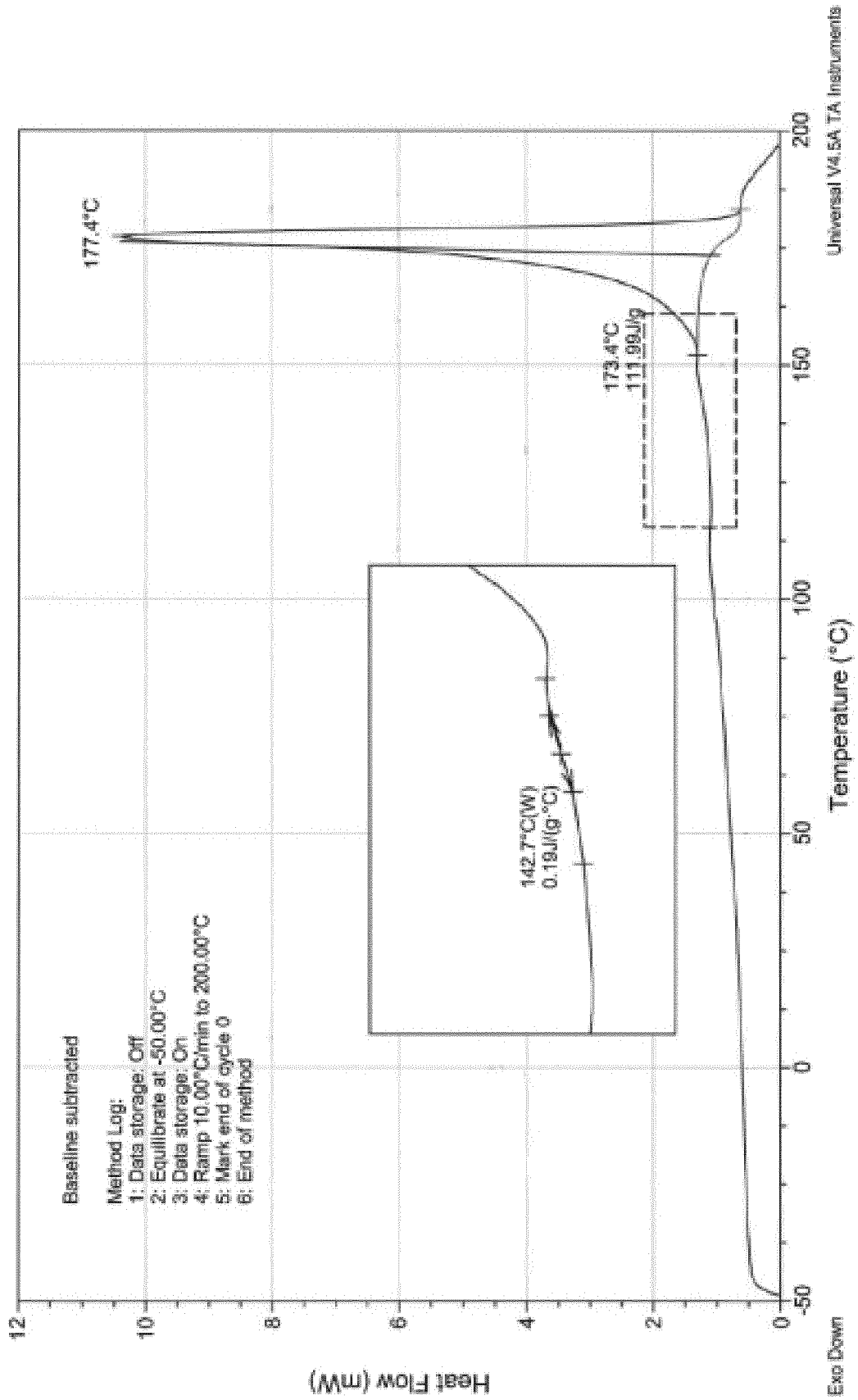
Fig. 5.35

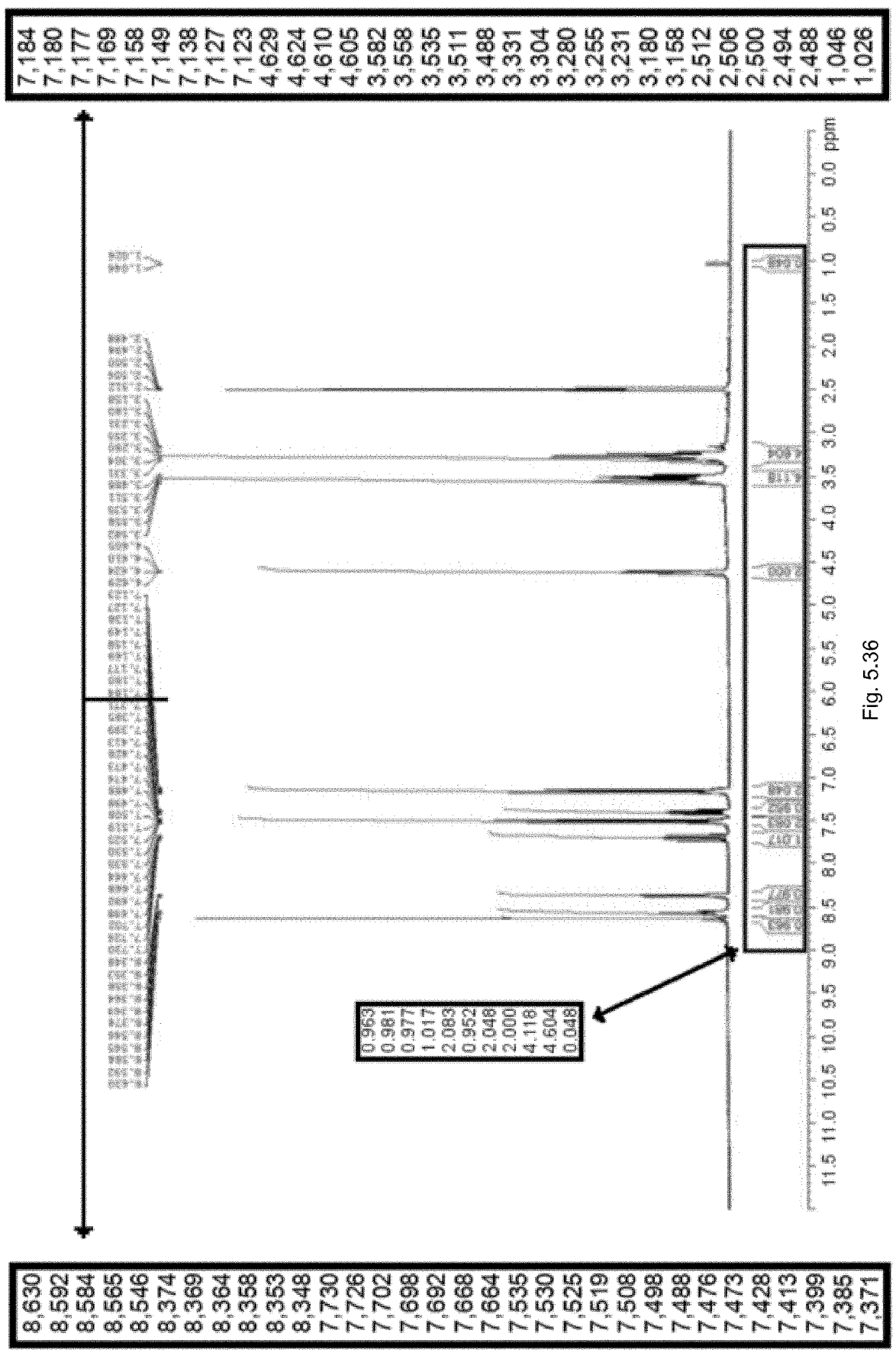
Fig. 5.36

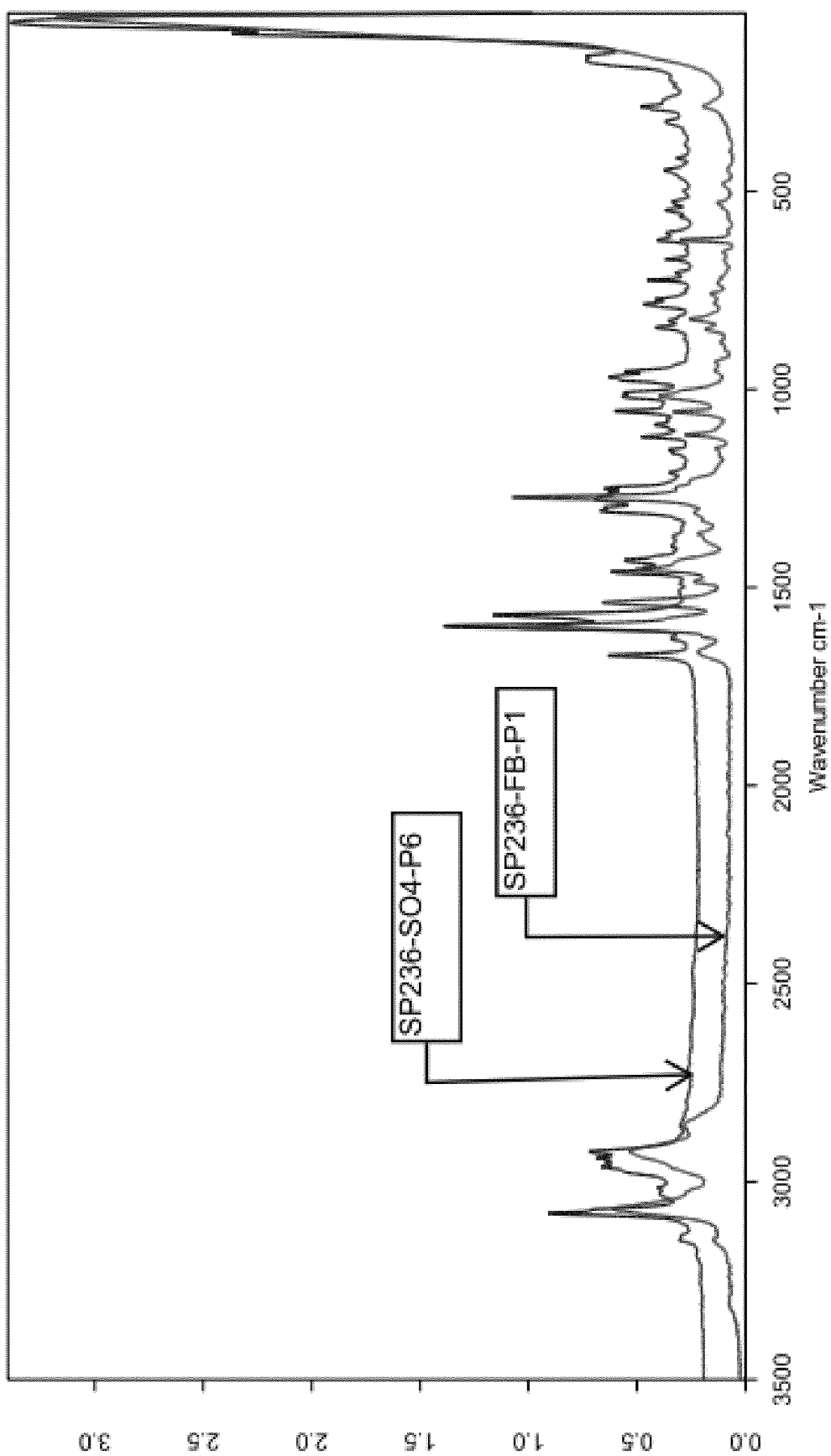
Fig. 5.37

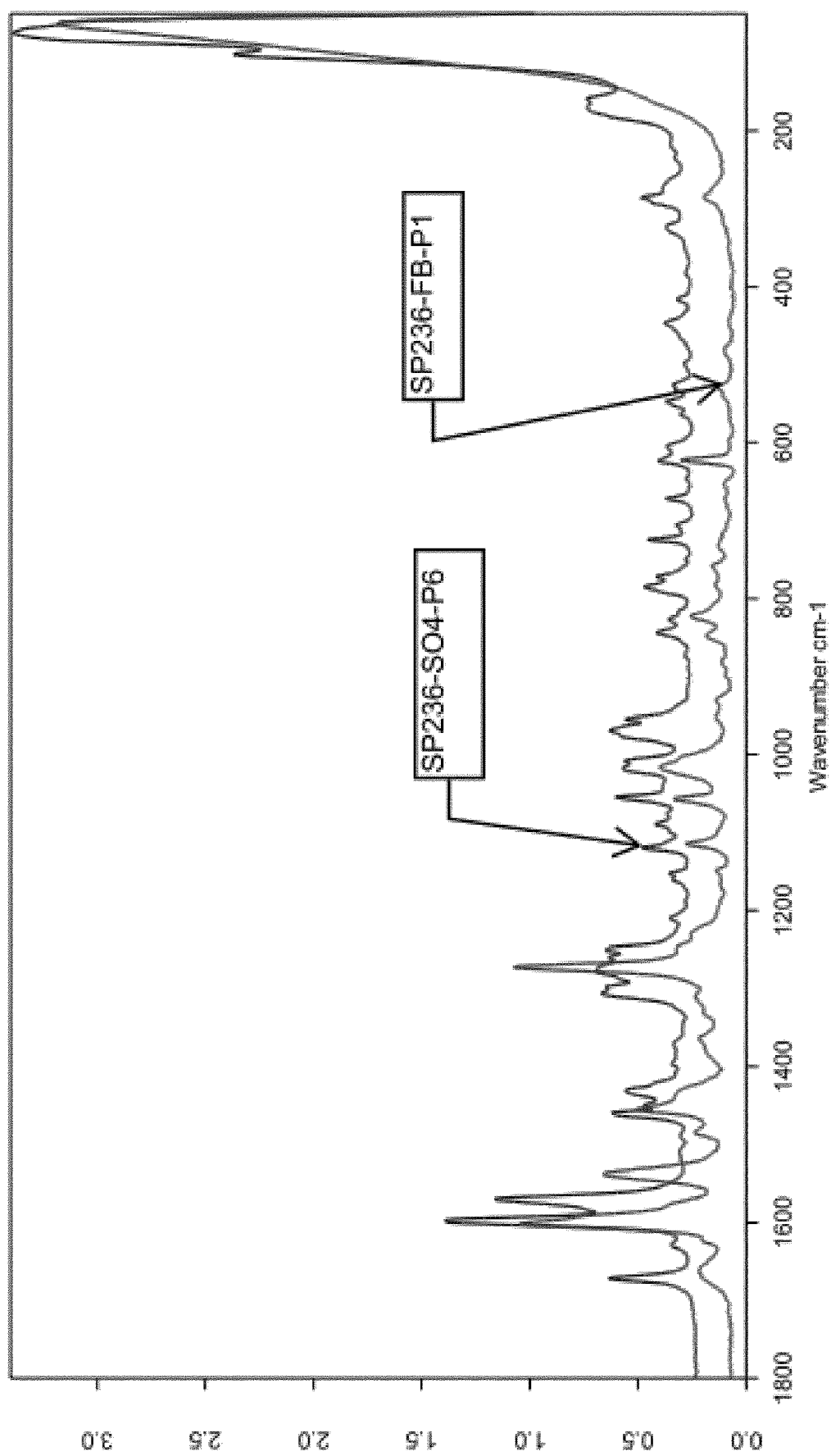
Fig. 5.38

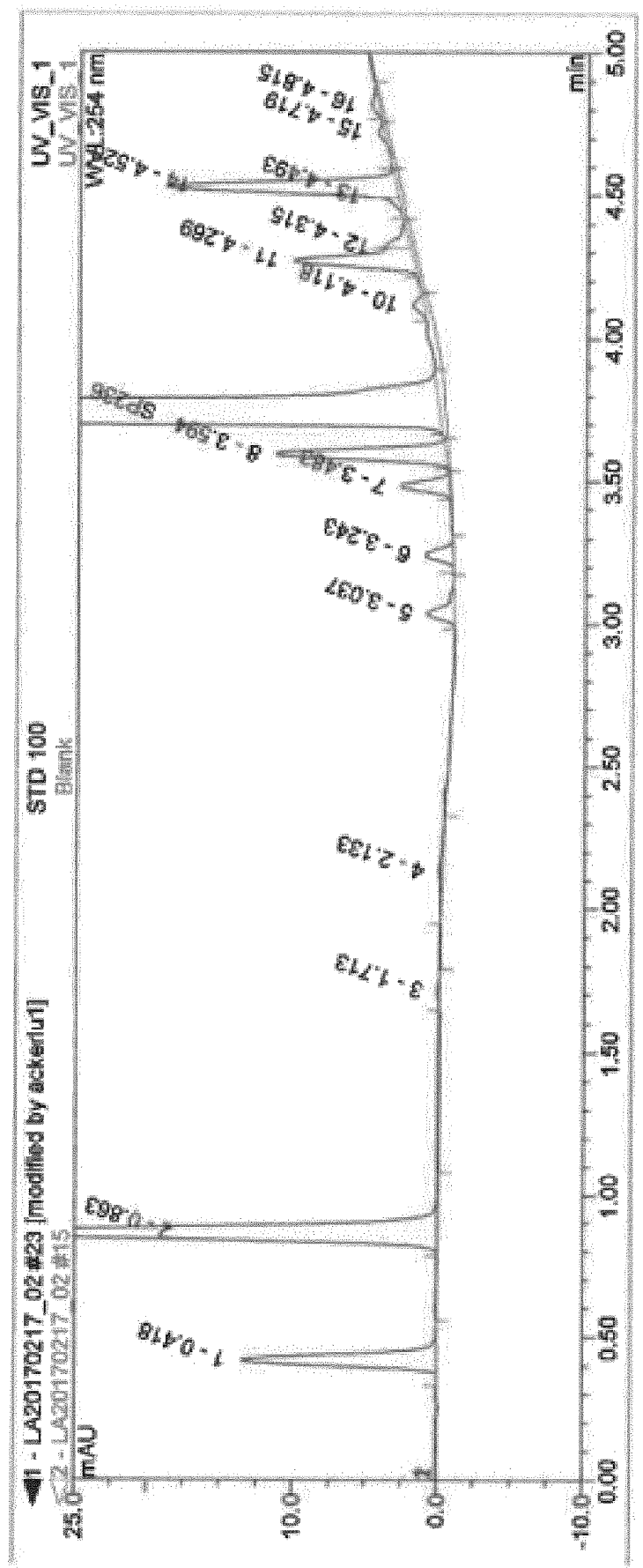
Fig. 5.39

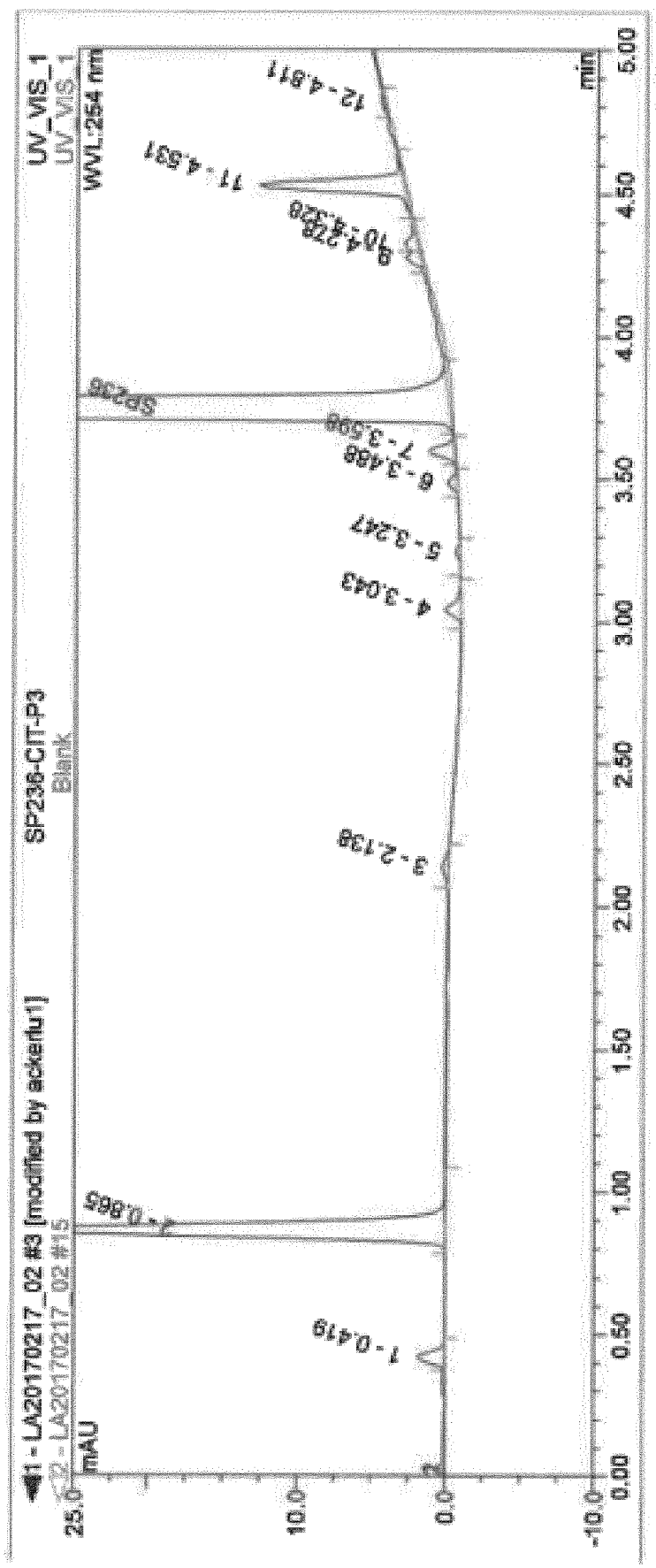
Fig. 5.40

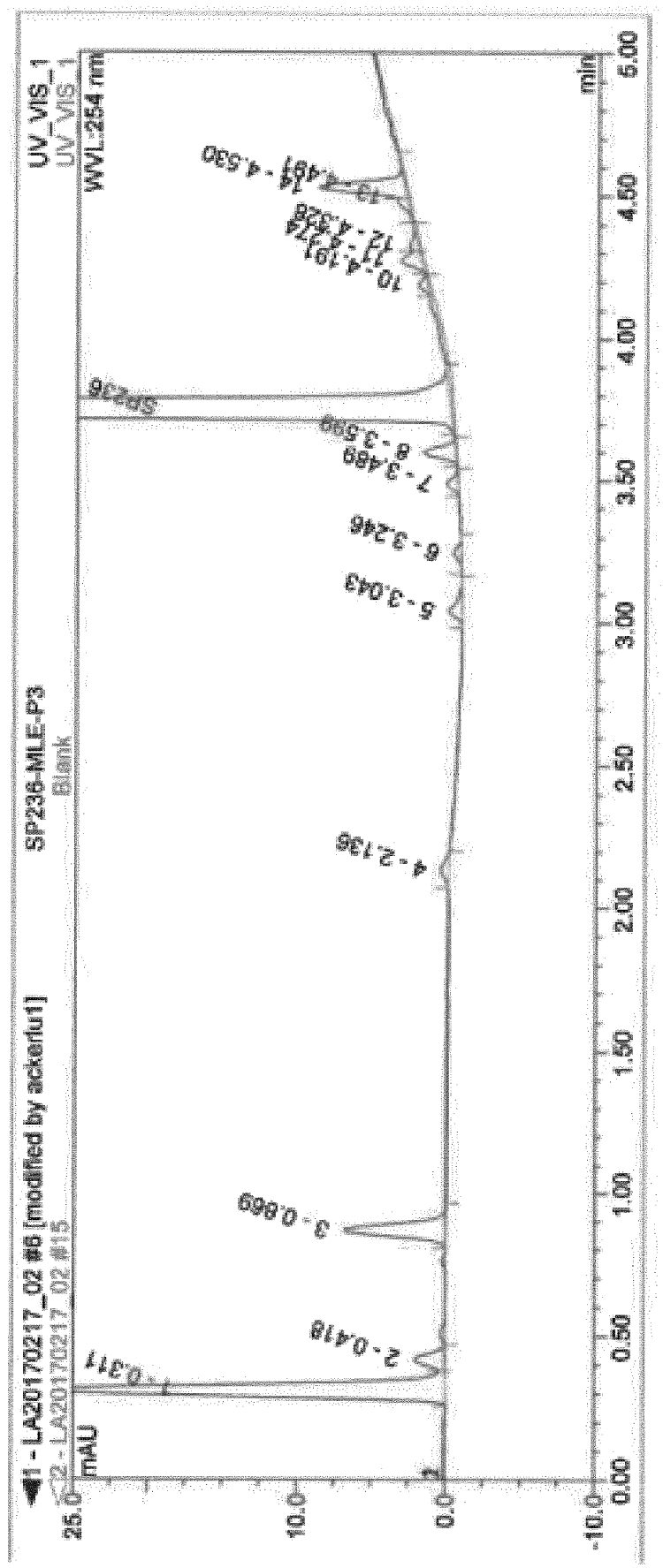
Fig. 5.41

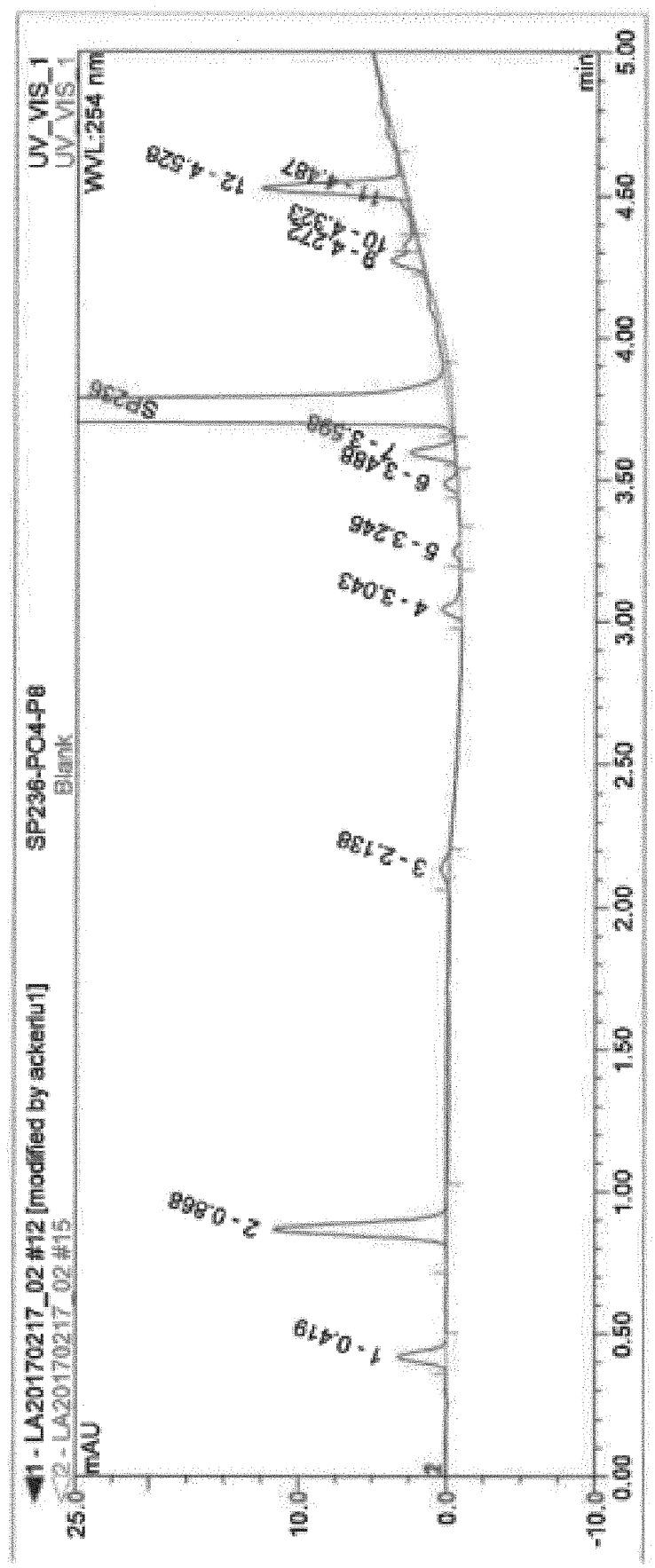
Fig. 5.42

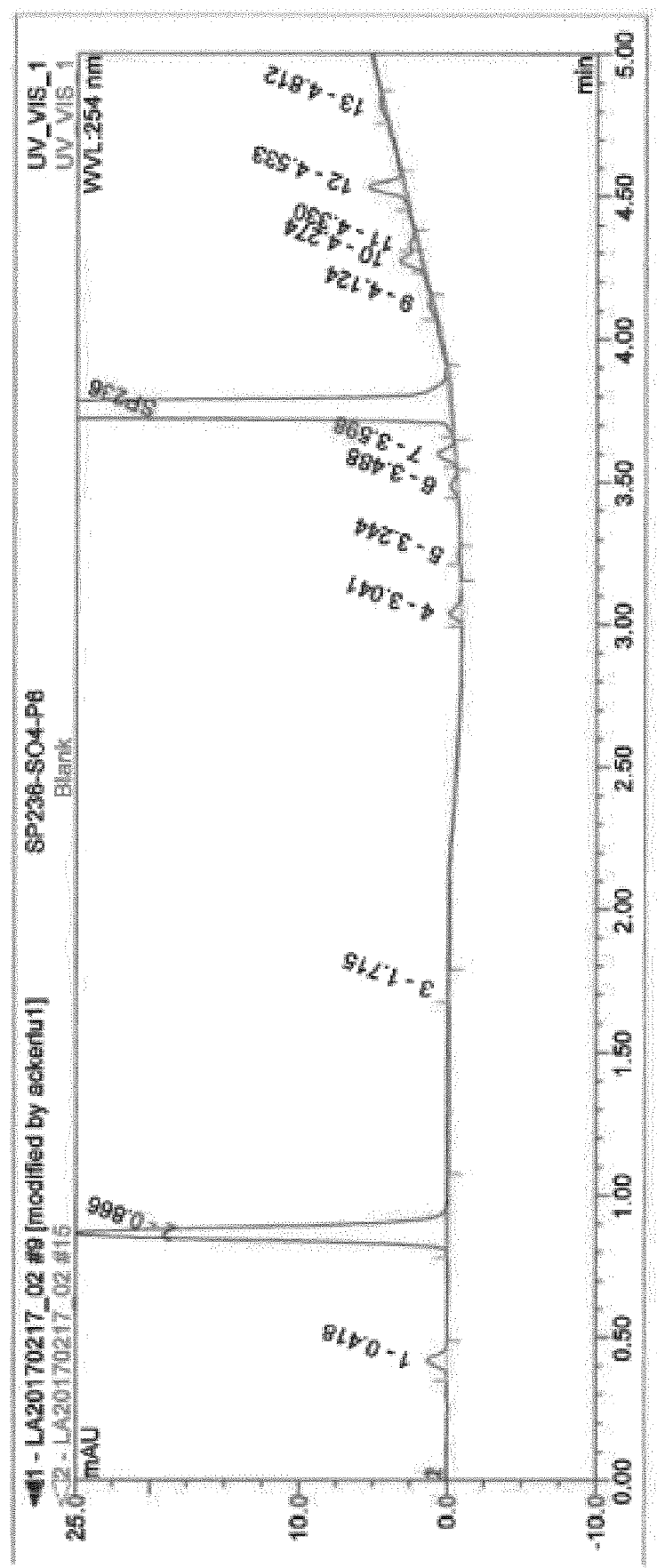
Fig. 5.43

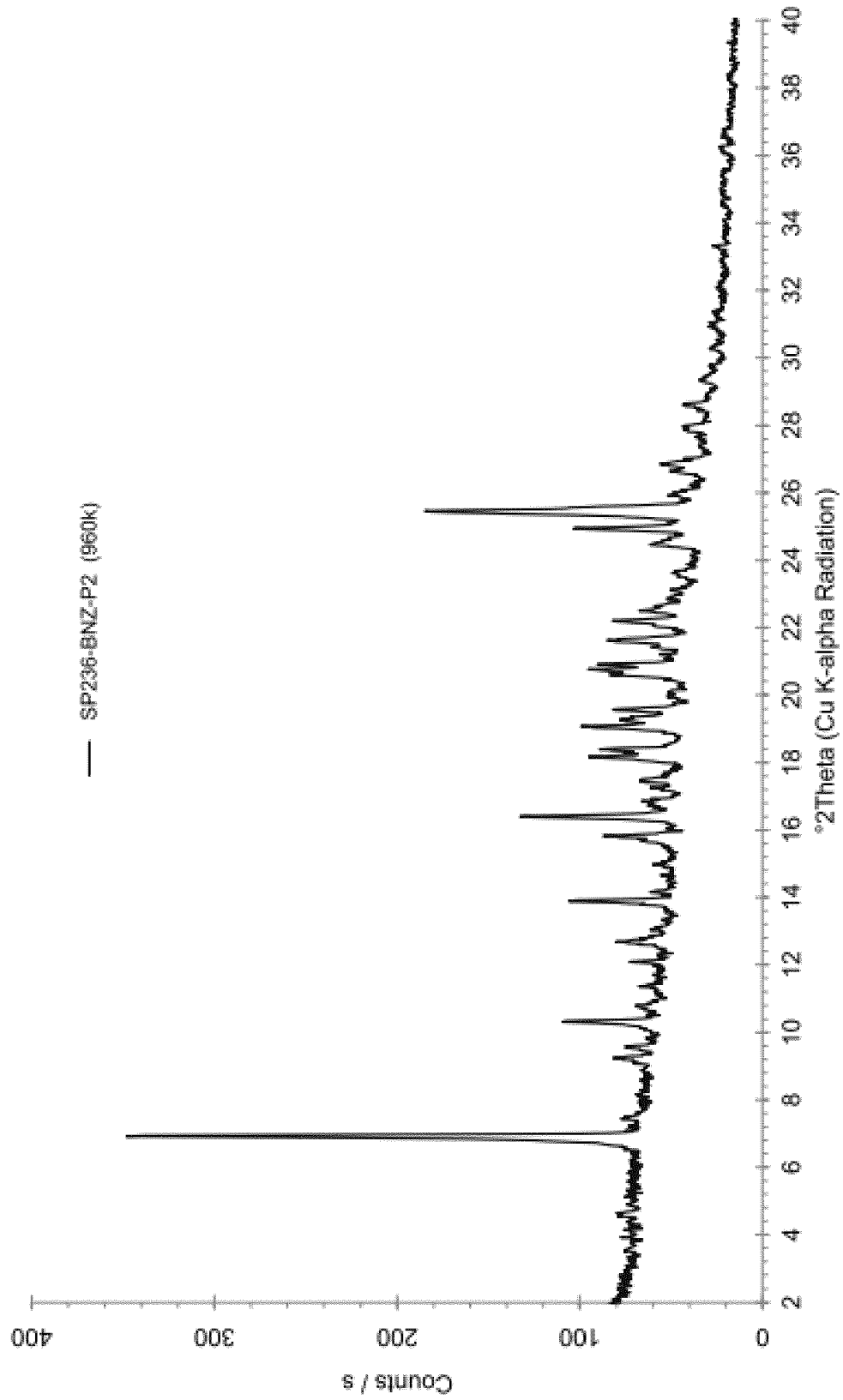
Fig. 6.1

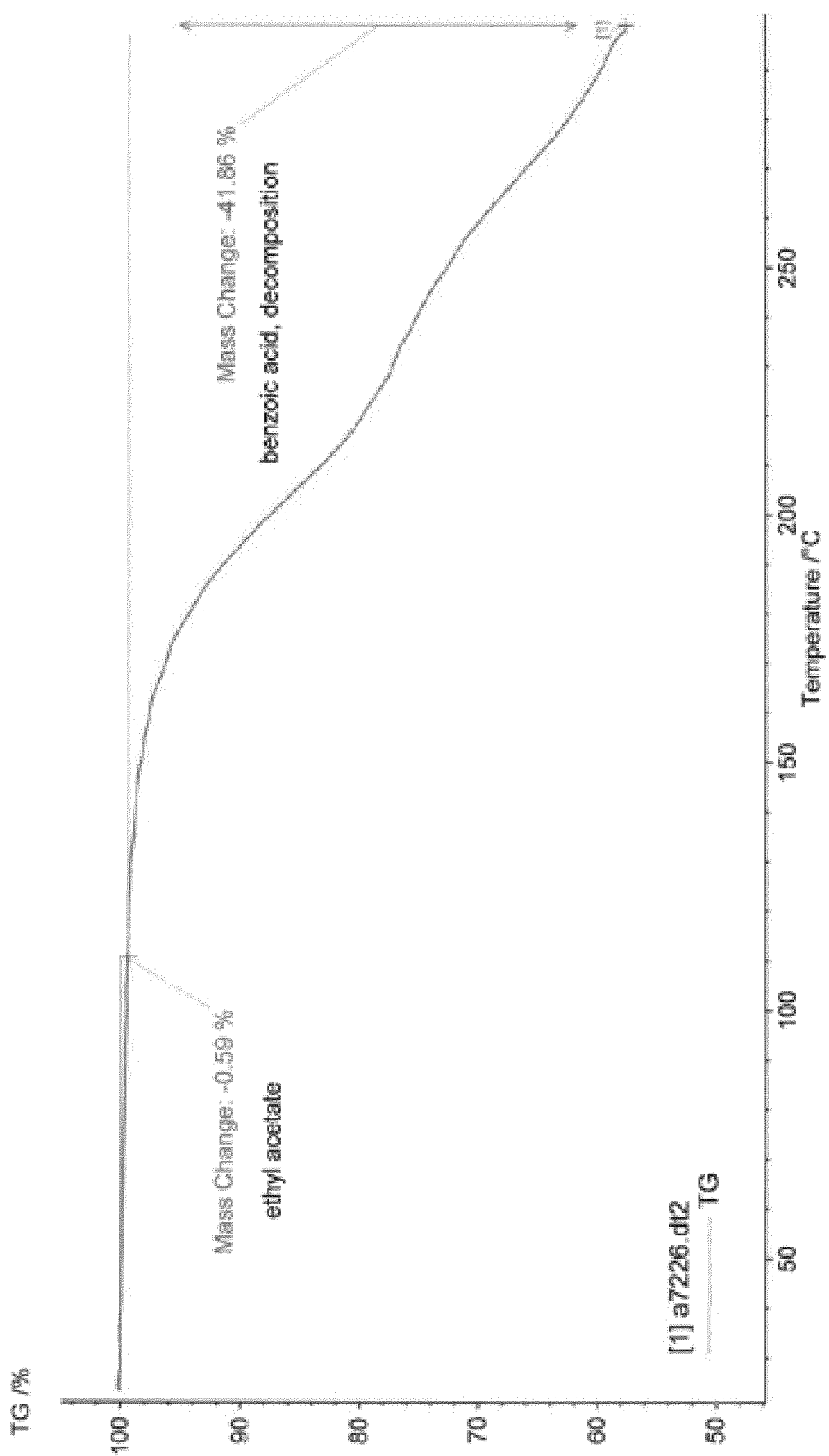
Fig. 6.2

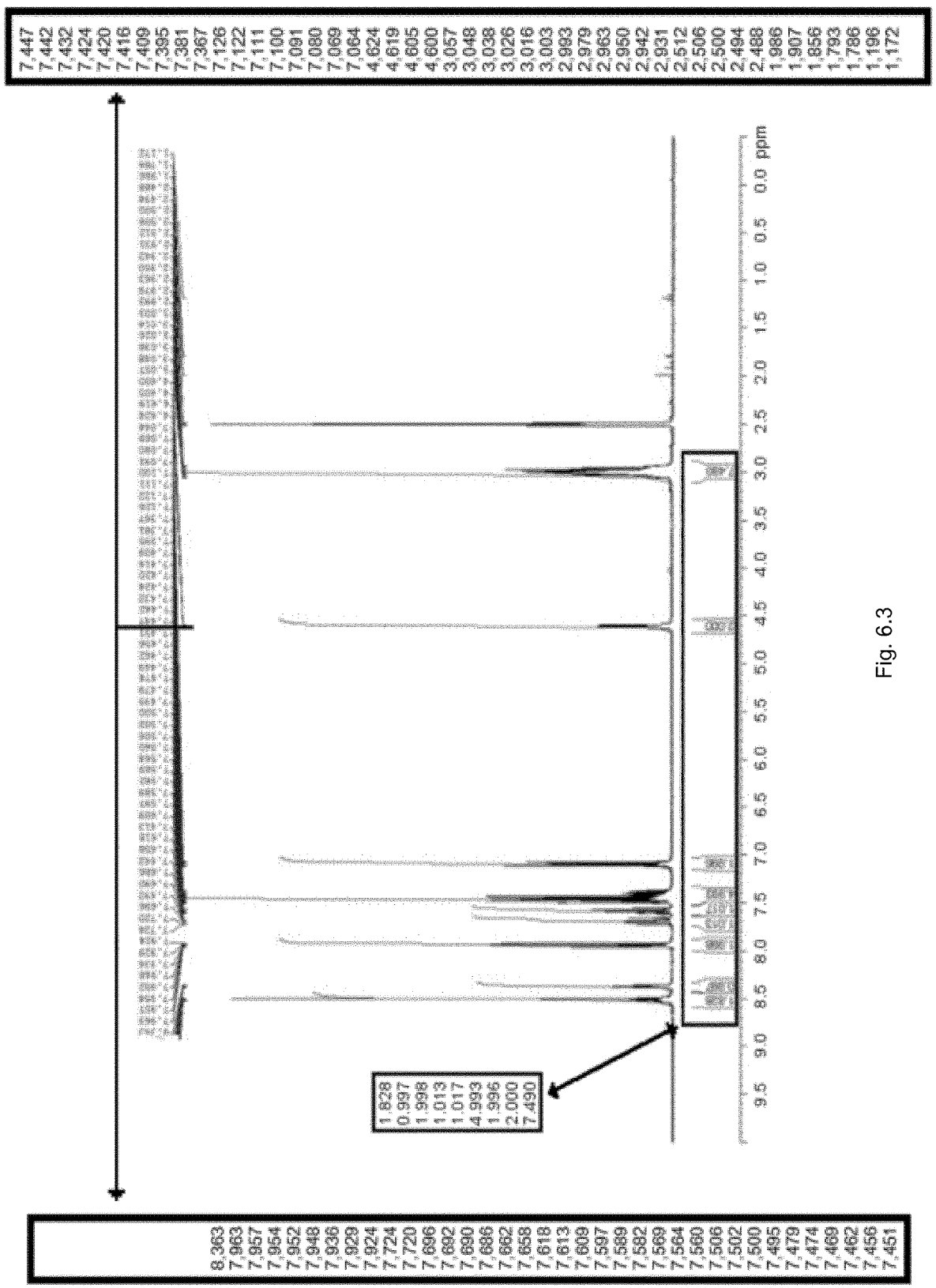
Fig. 6.3

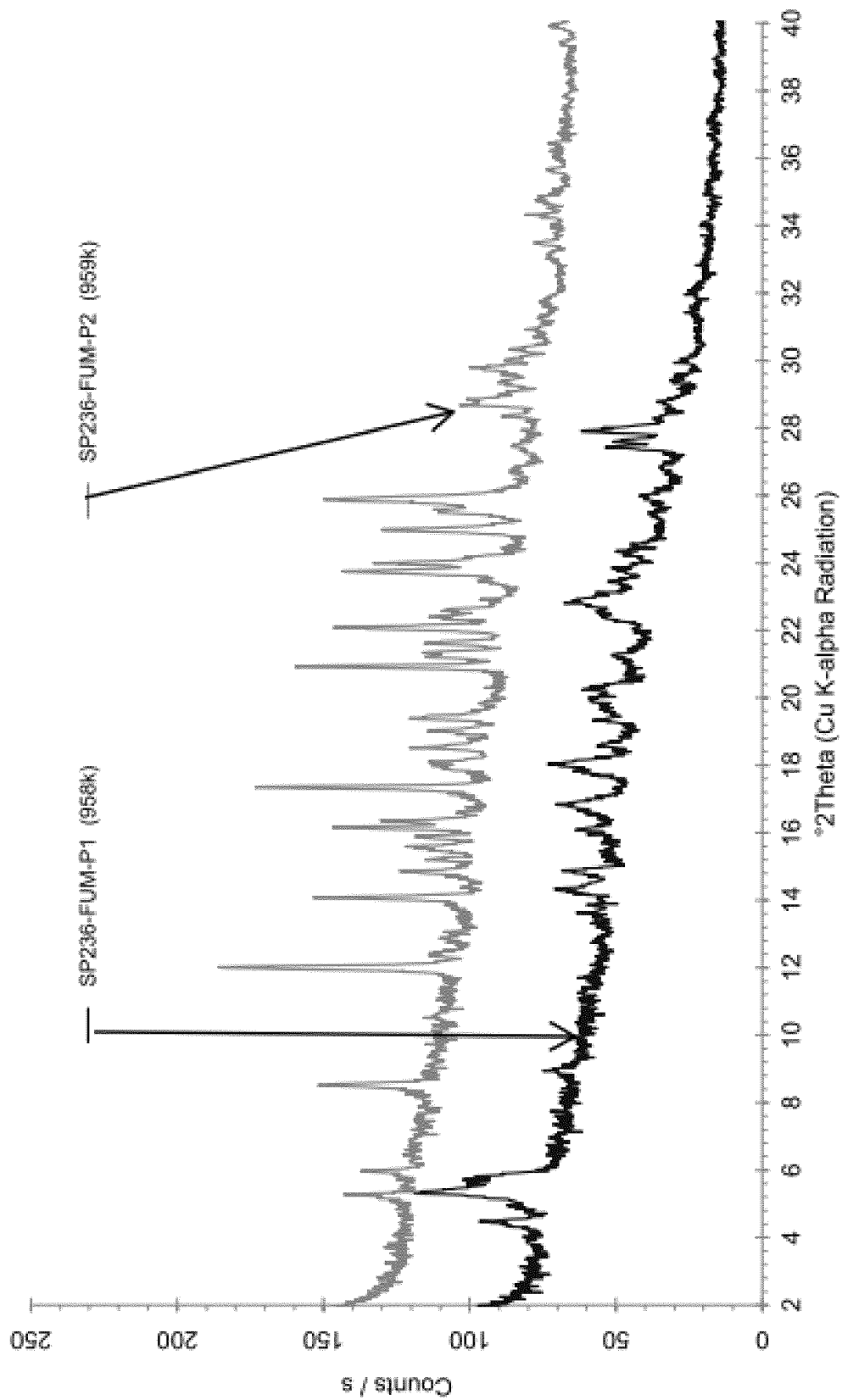
Fig. 6.4

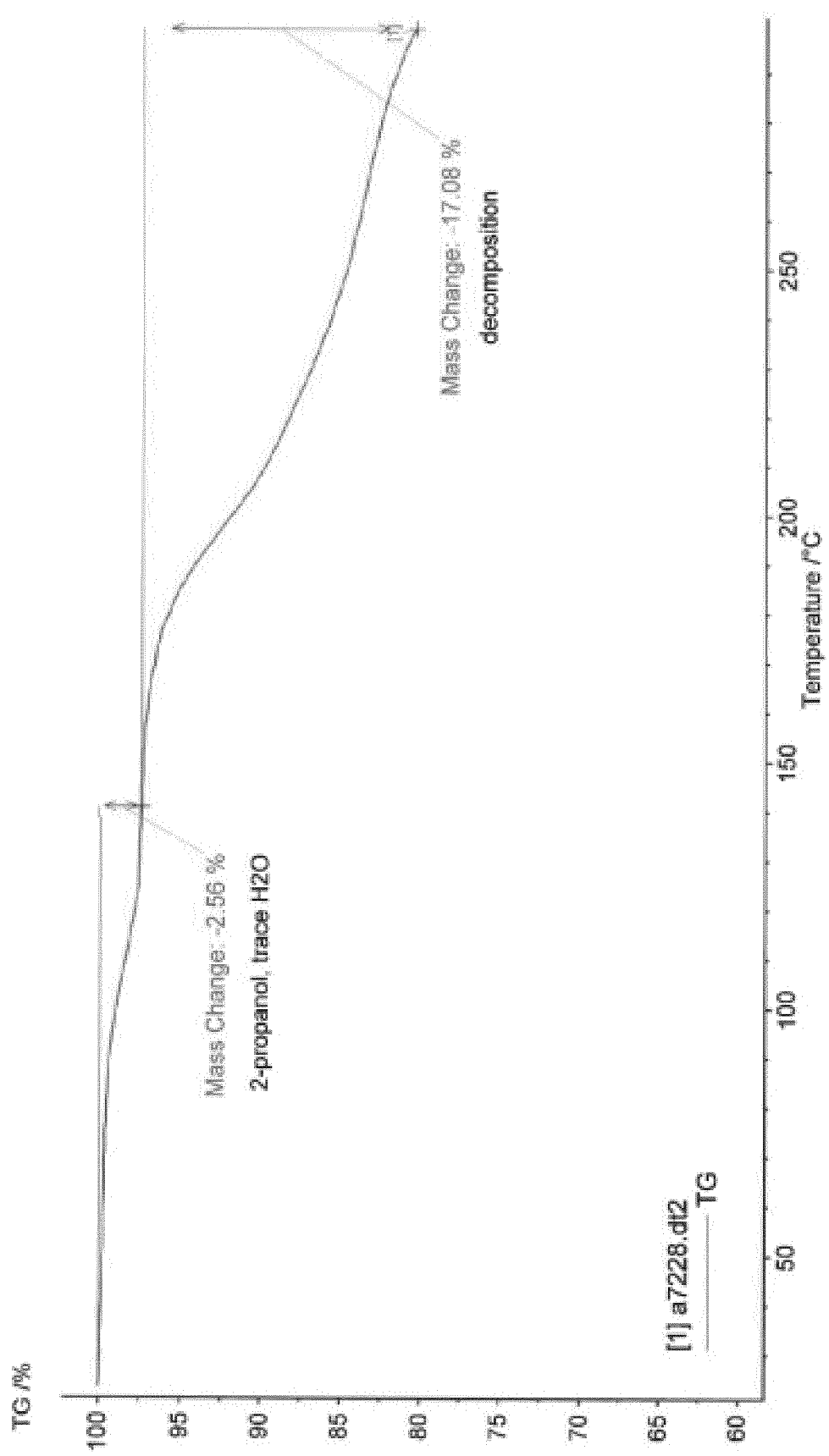
Fig. 6.5

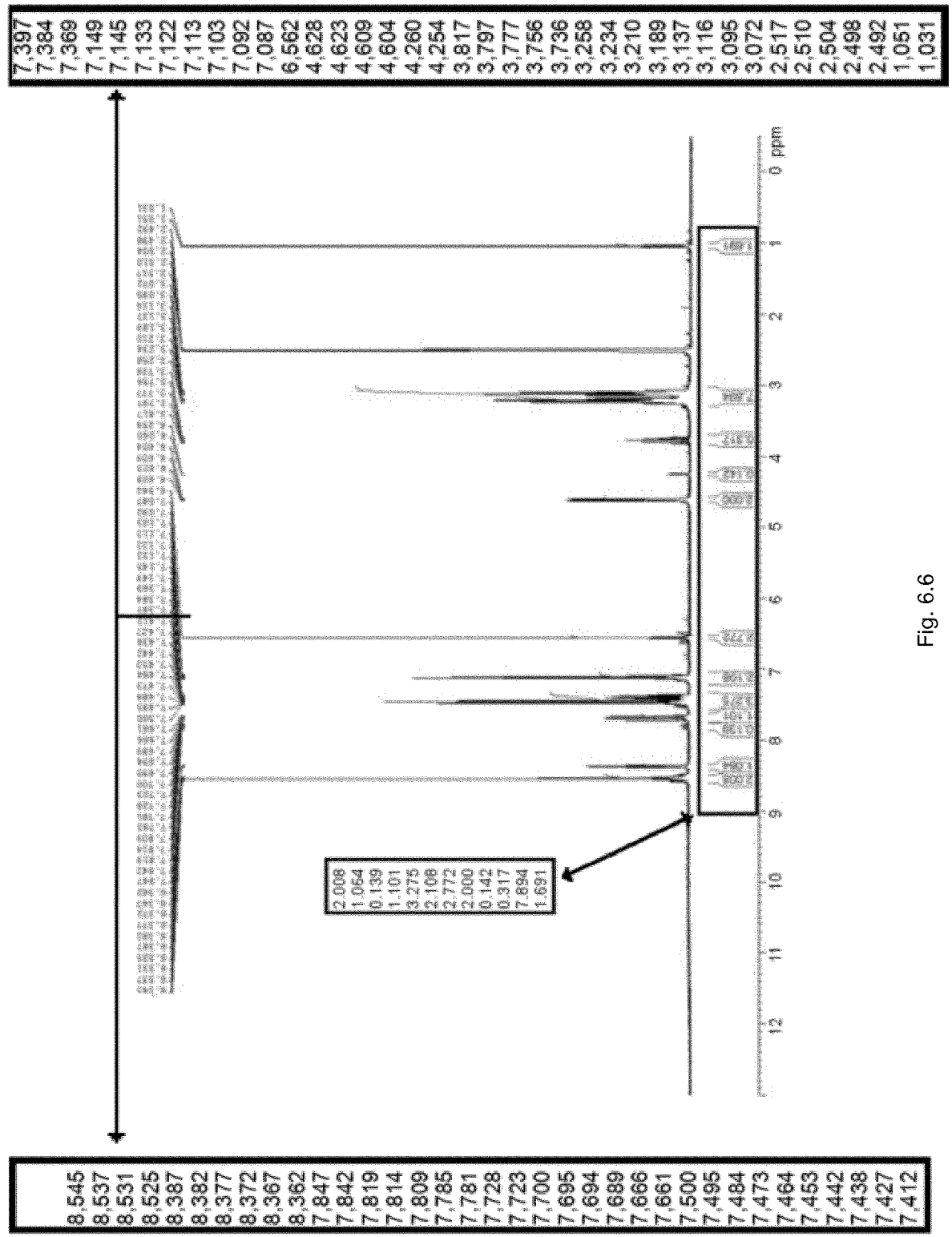
Fig. 6.6

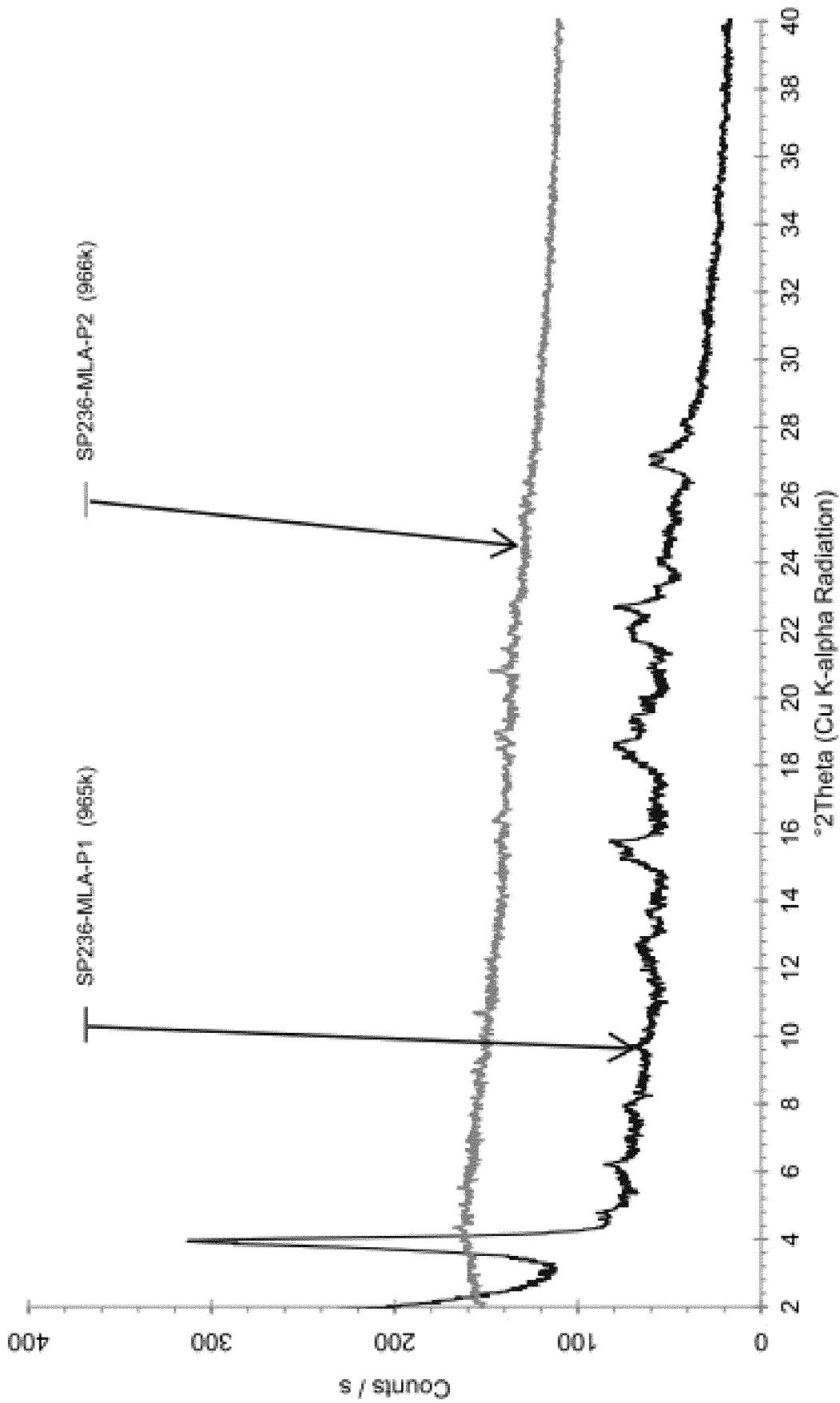
Fig. 6.7

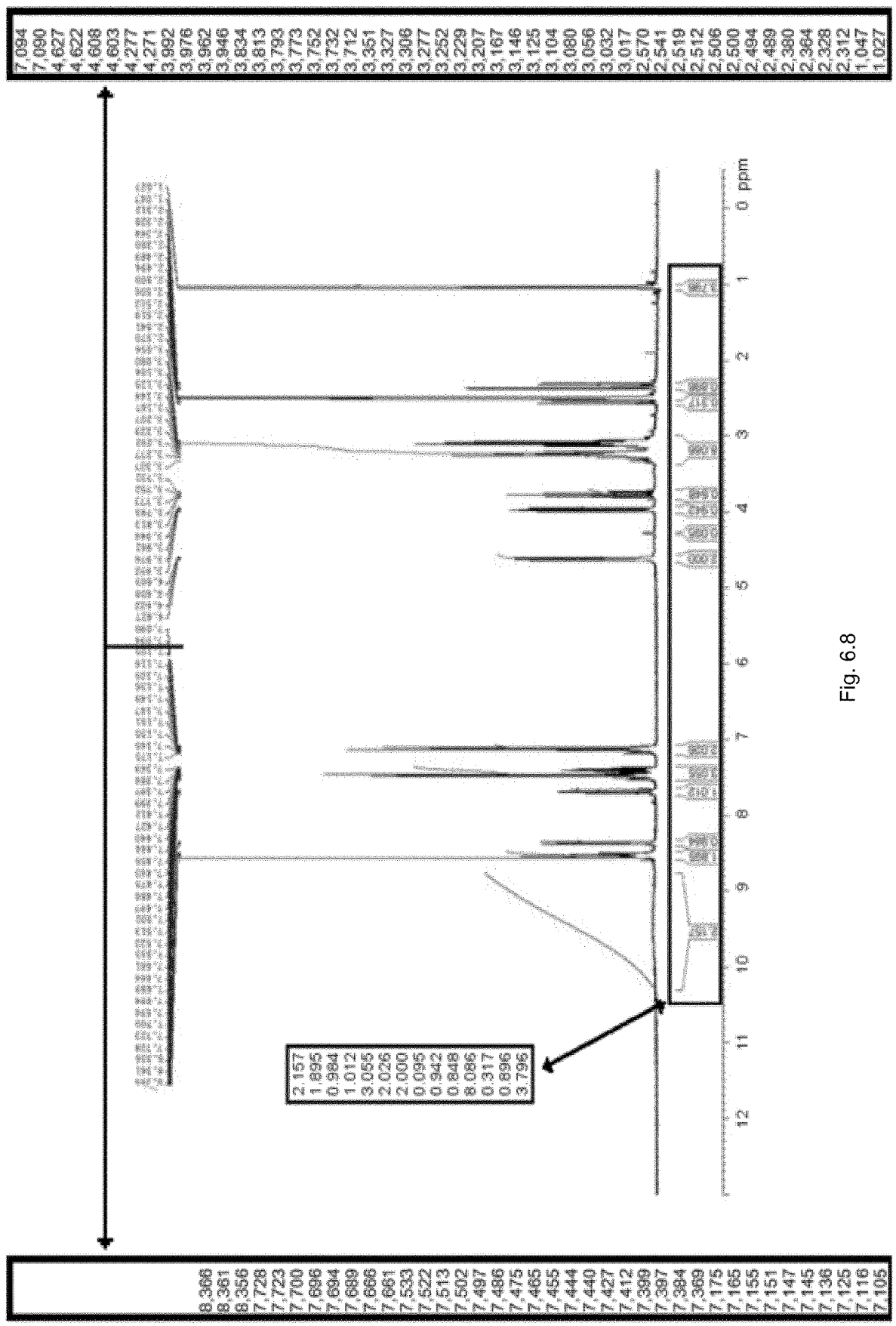
Fig. 6.8

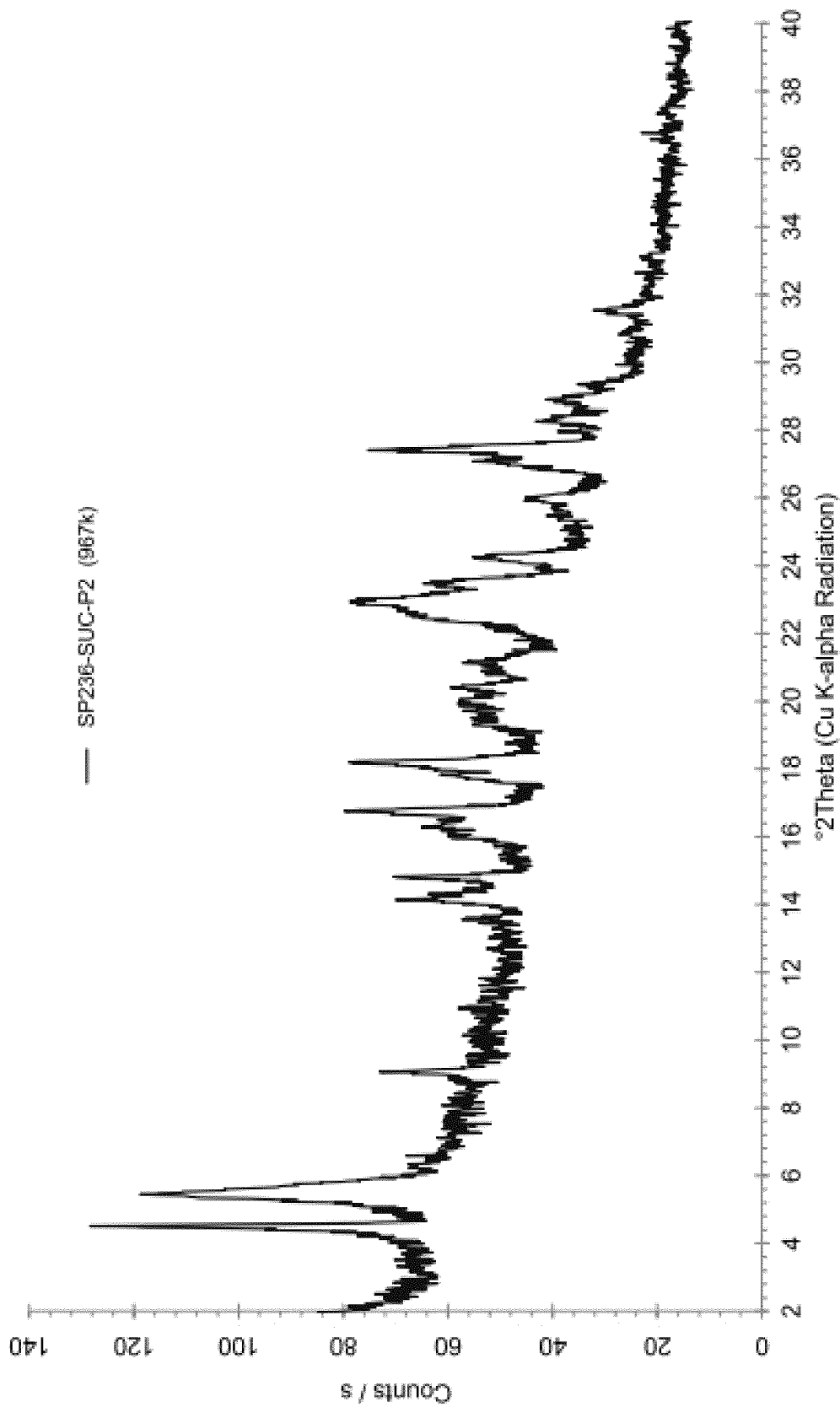
Fig. 6.9

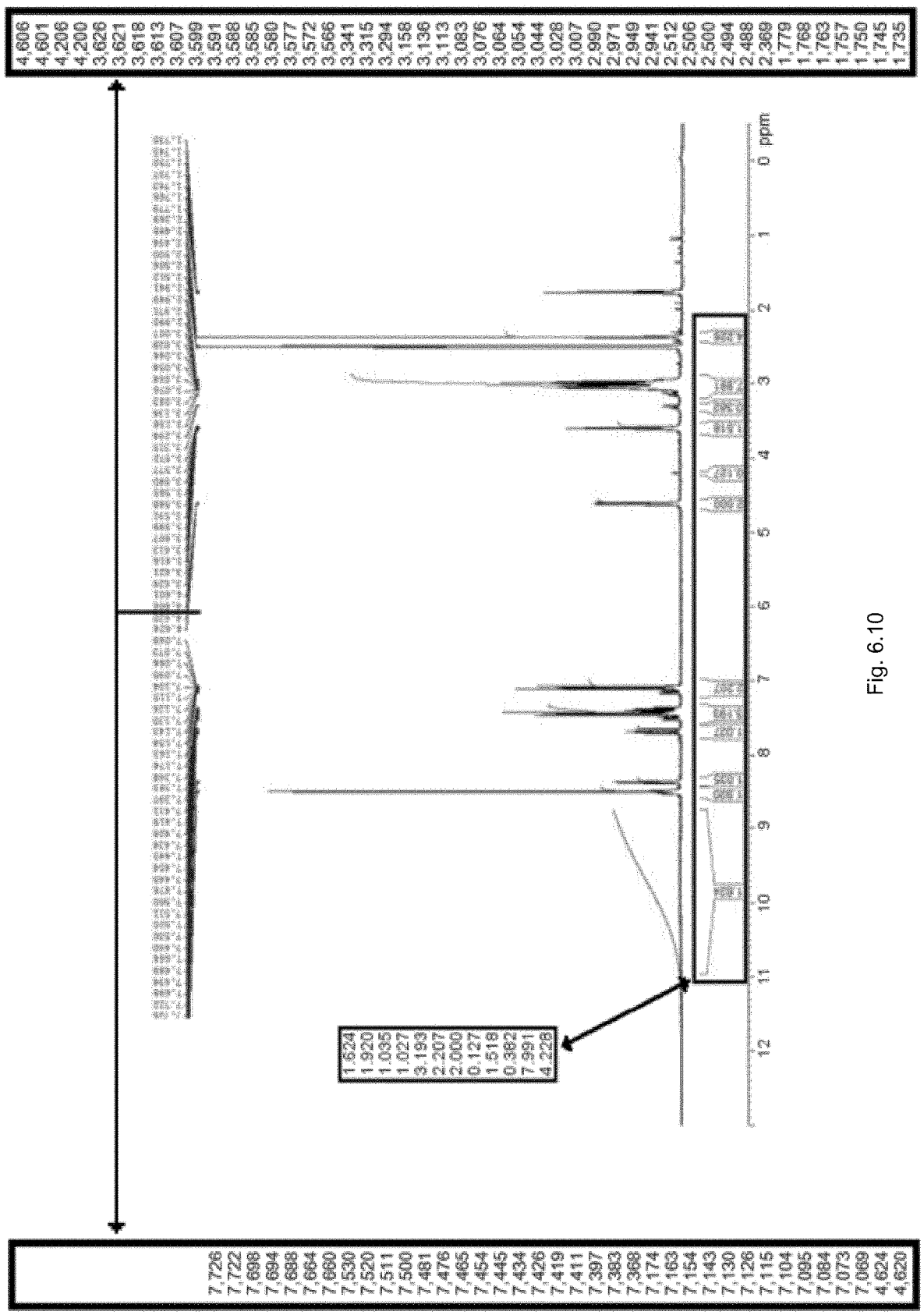
Fig. 6.10

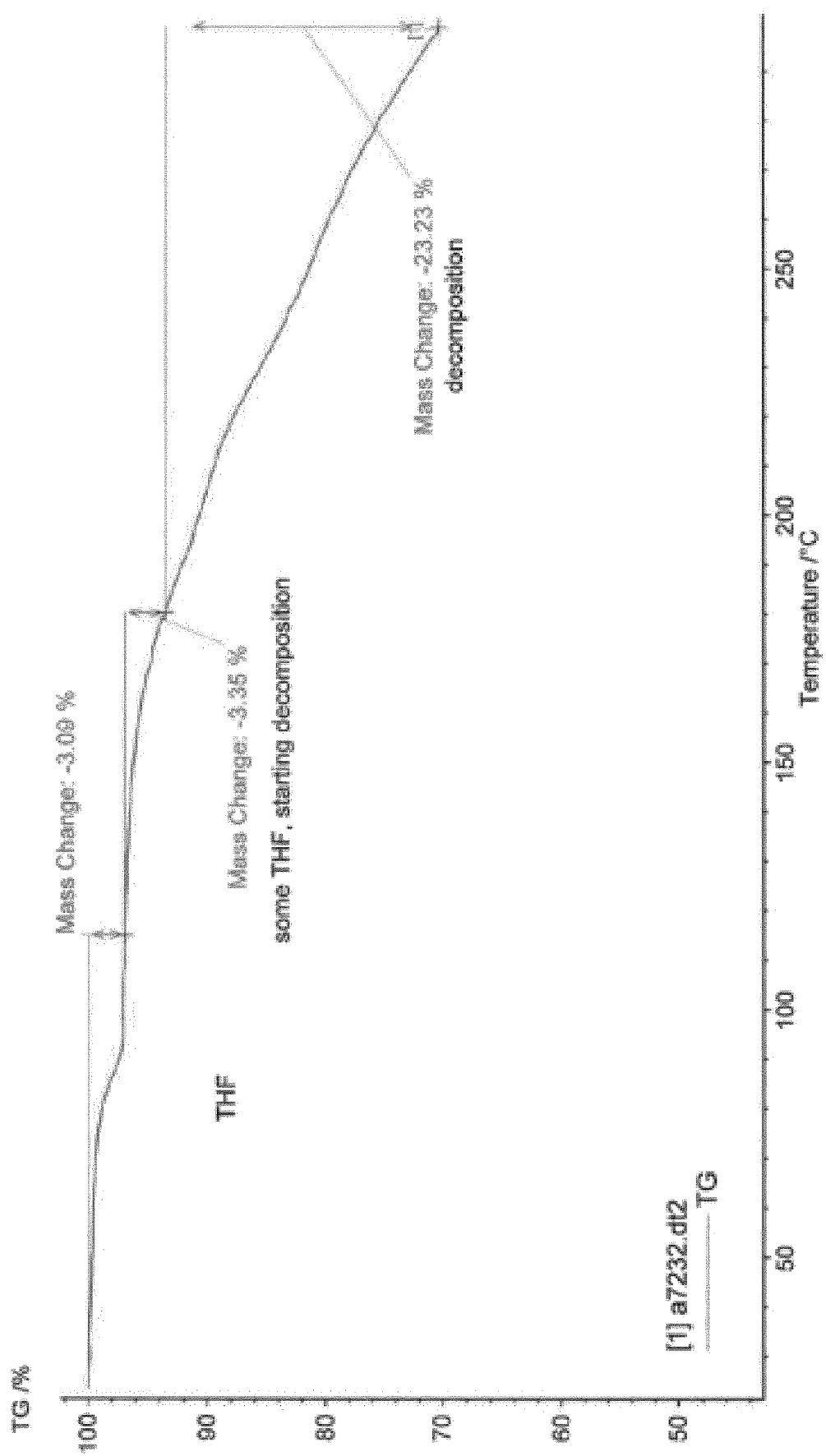
Fig. 6.11

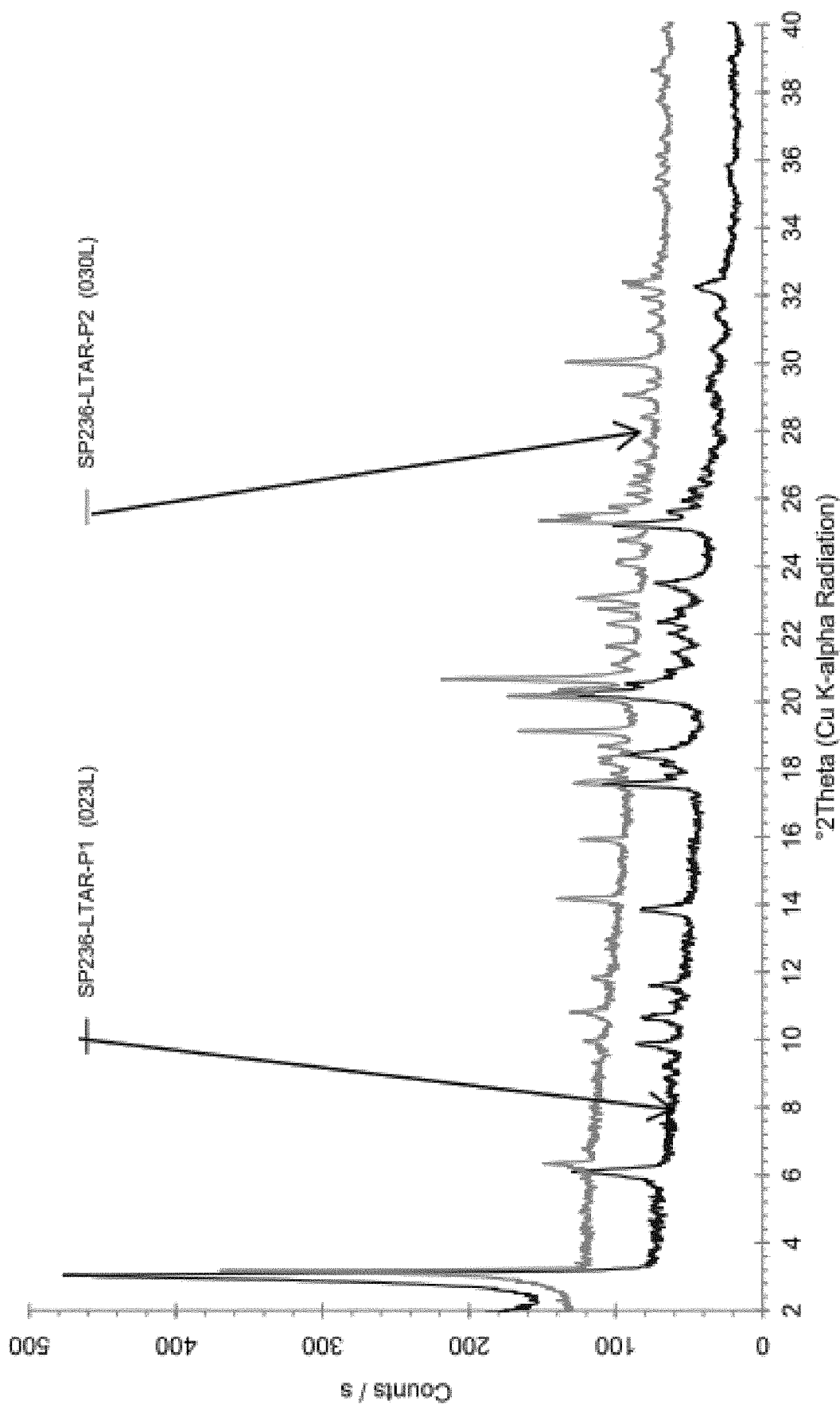
Fig. 6.12

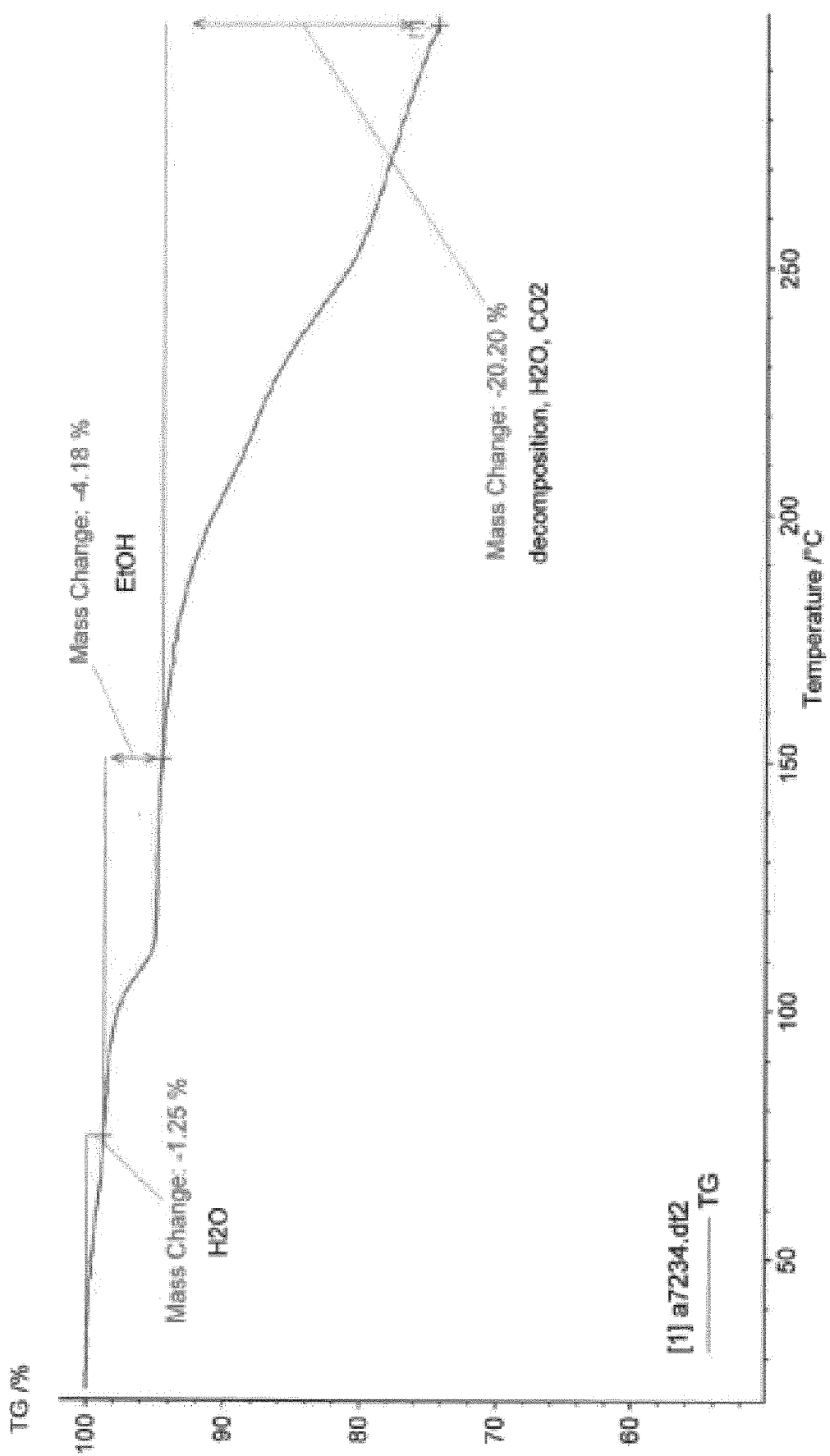
Fig. 6.13

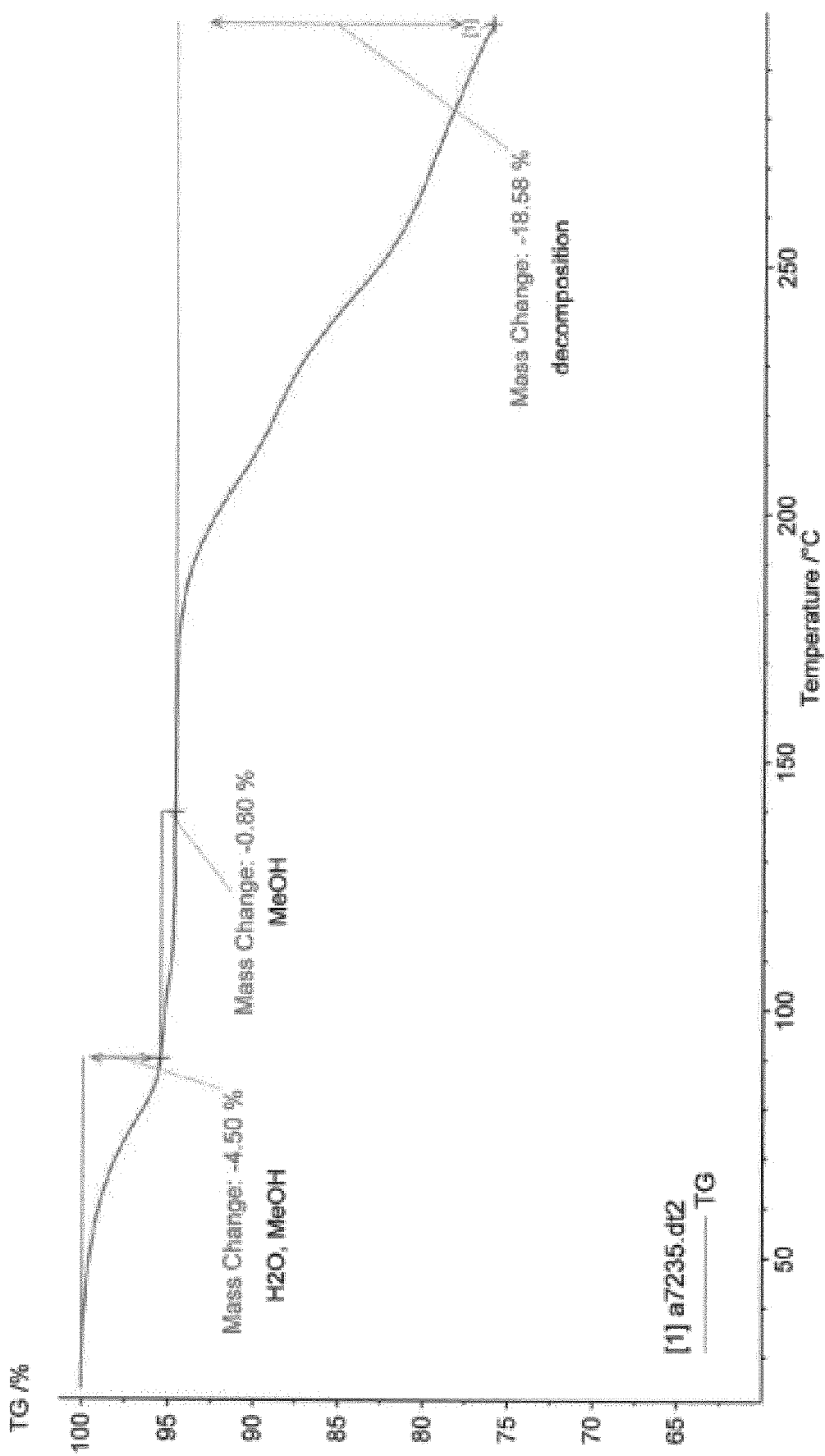
Fig. 6.14

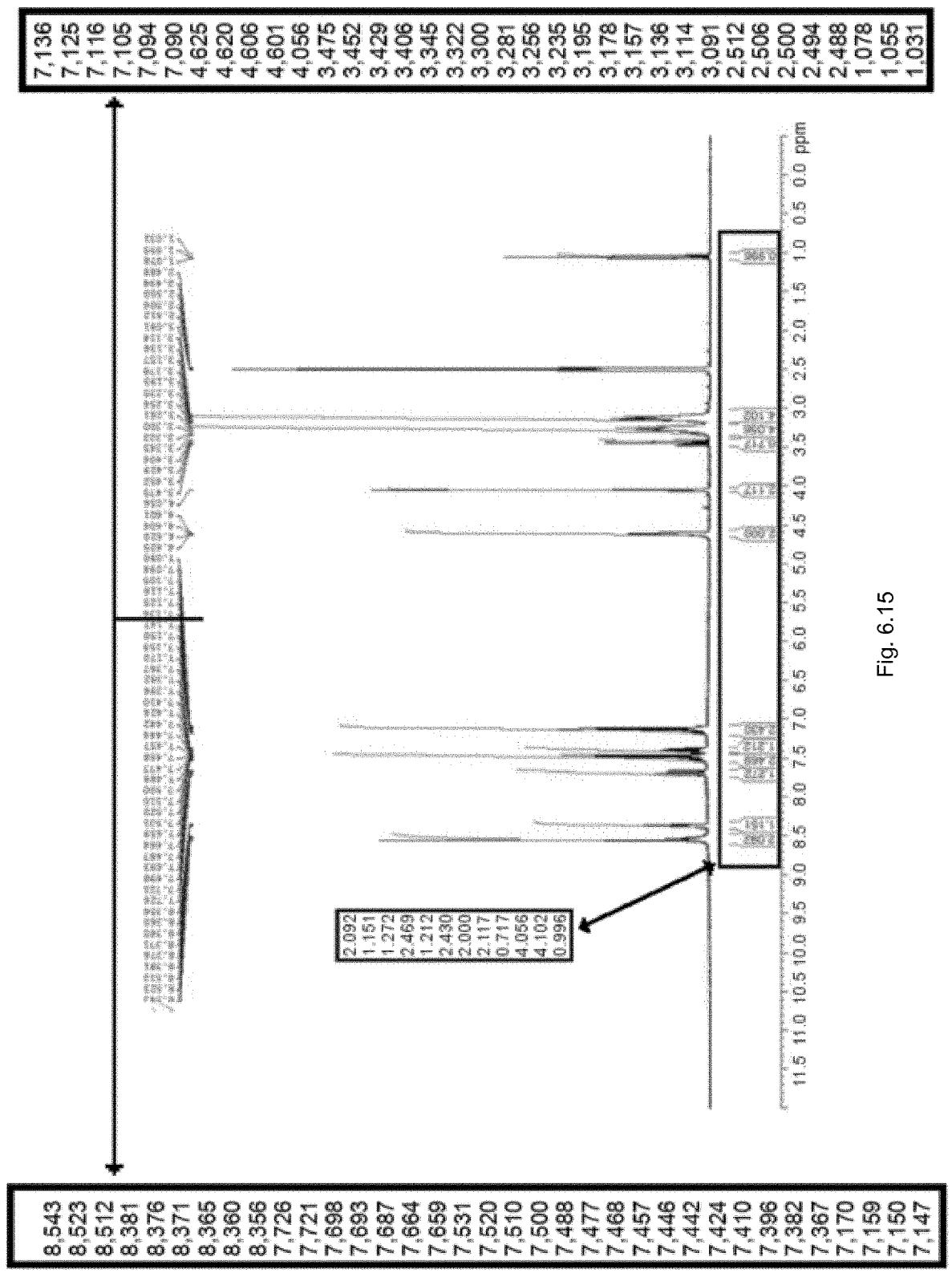
Fig. 6.15

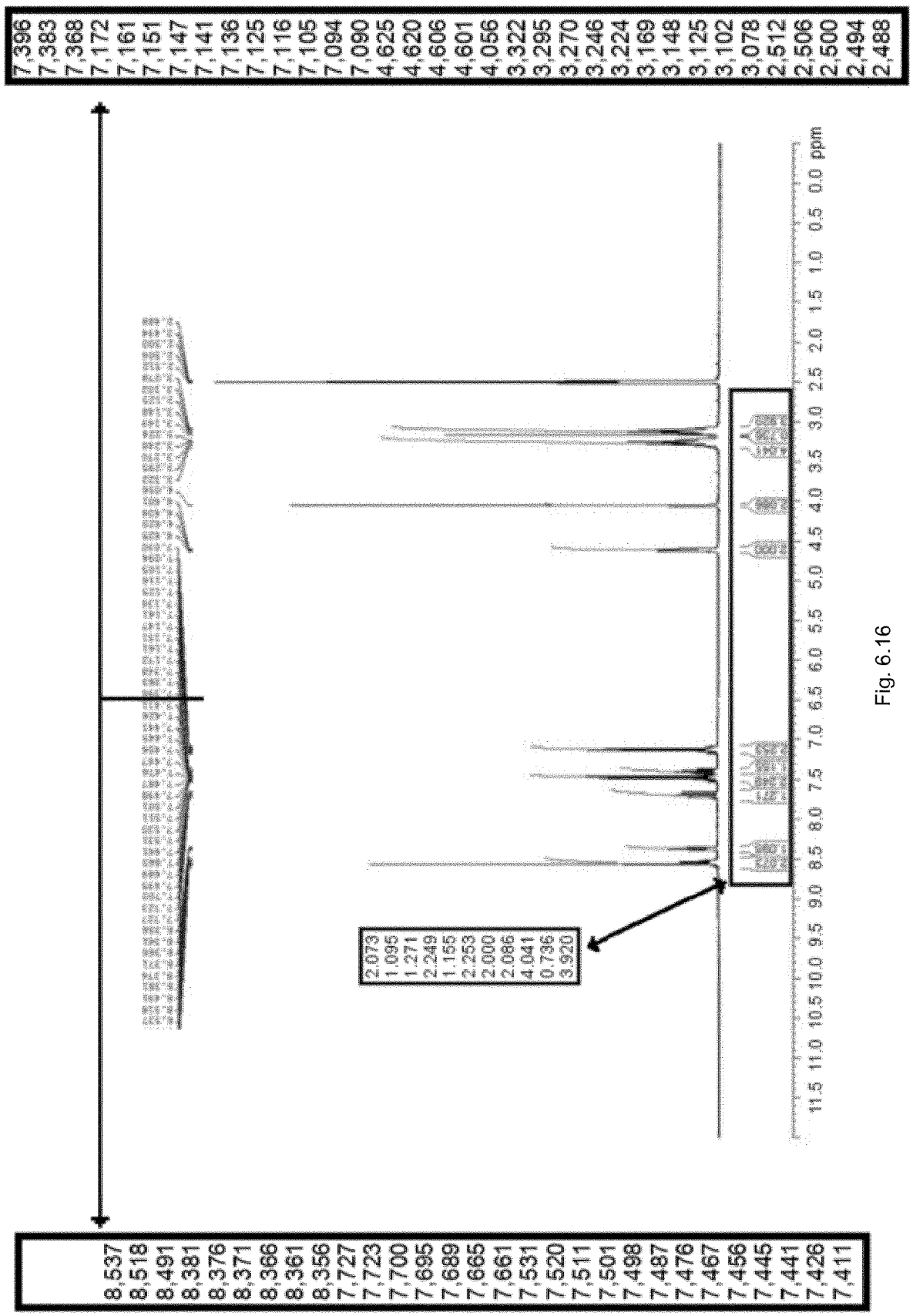
Fig. 6.16

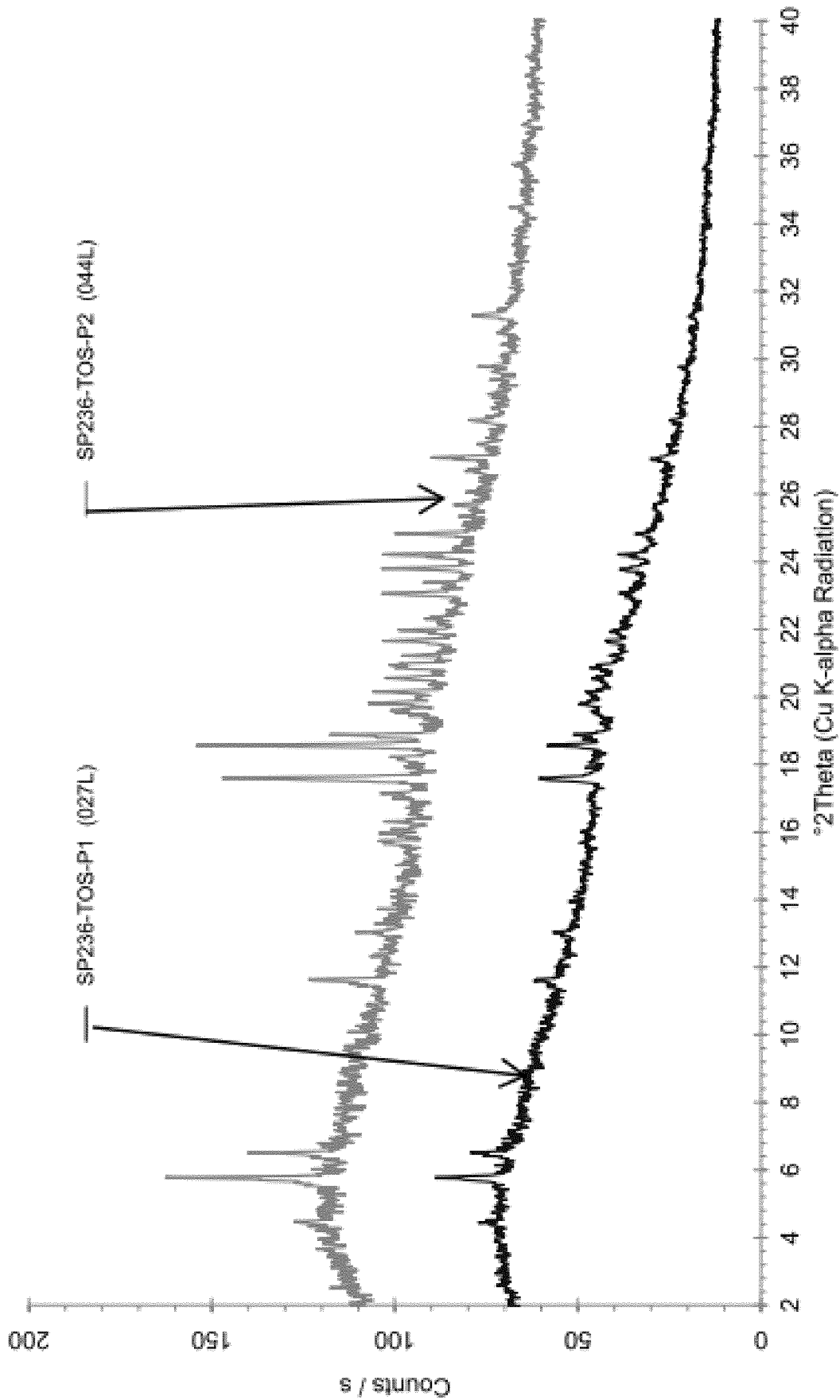
Fig. 6.17

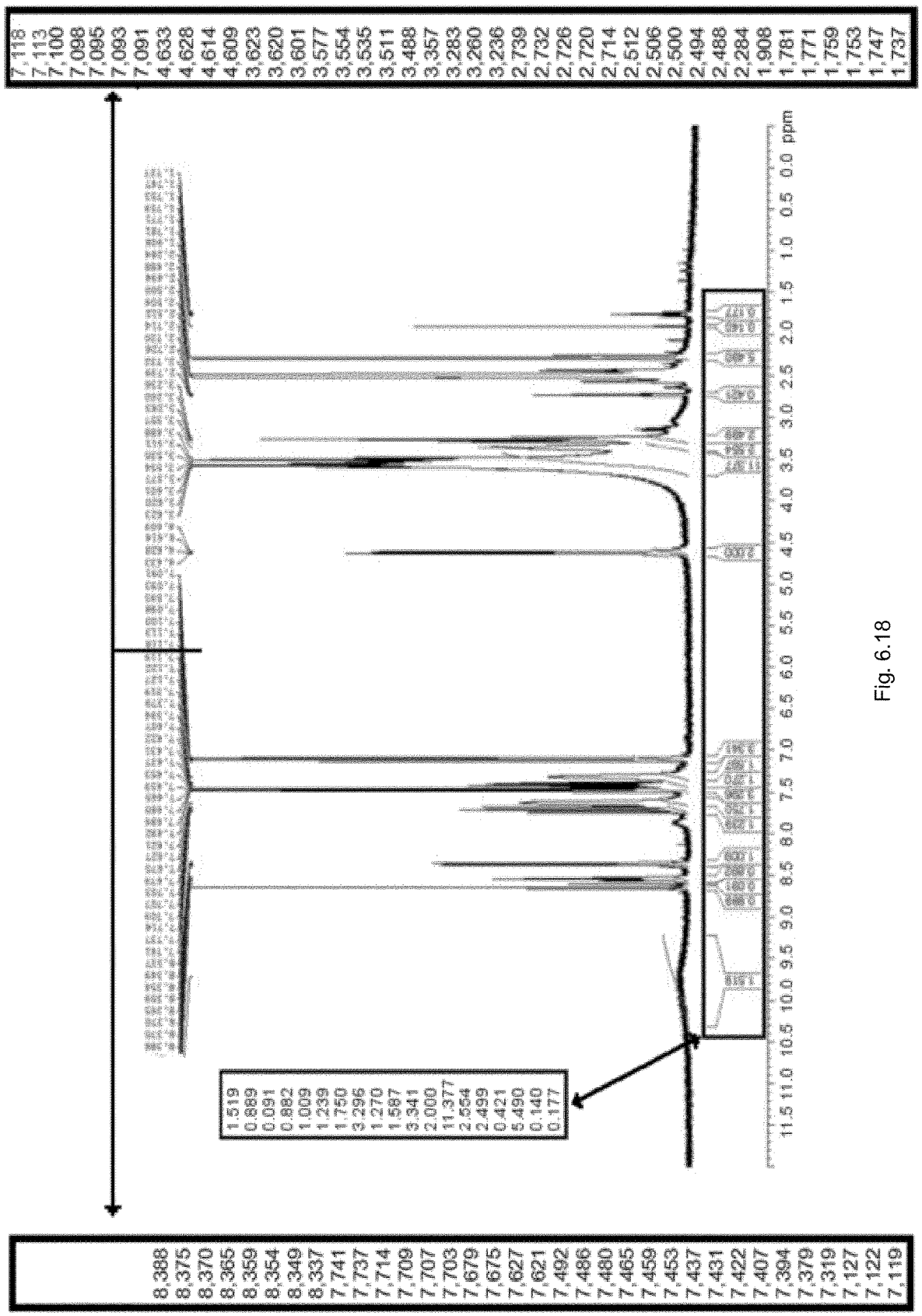
Fig. 6.18

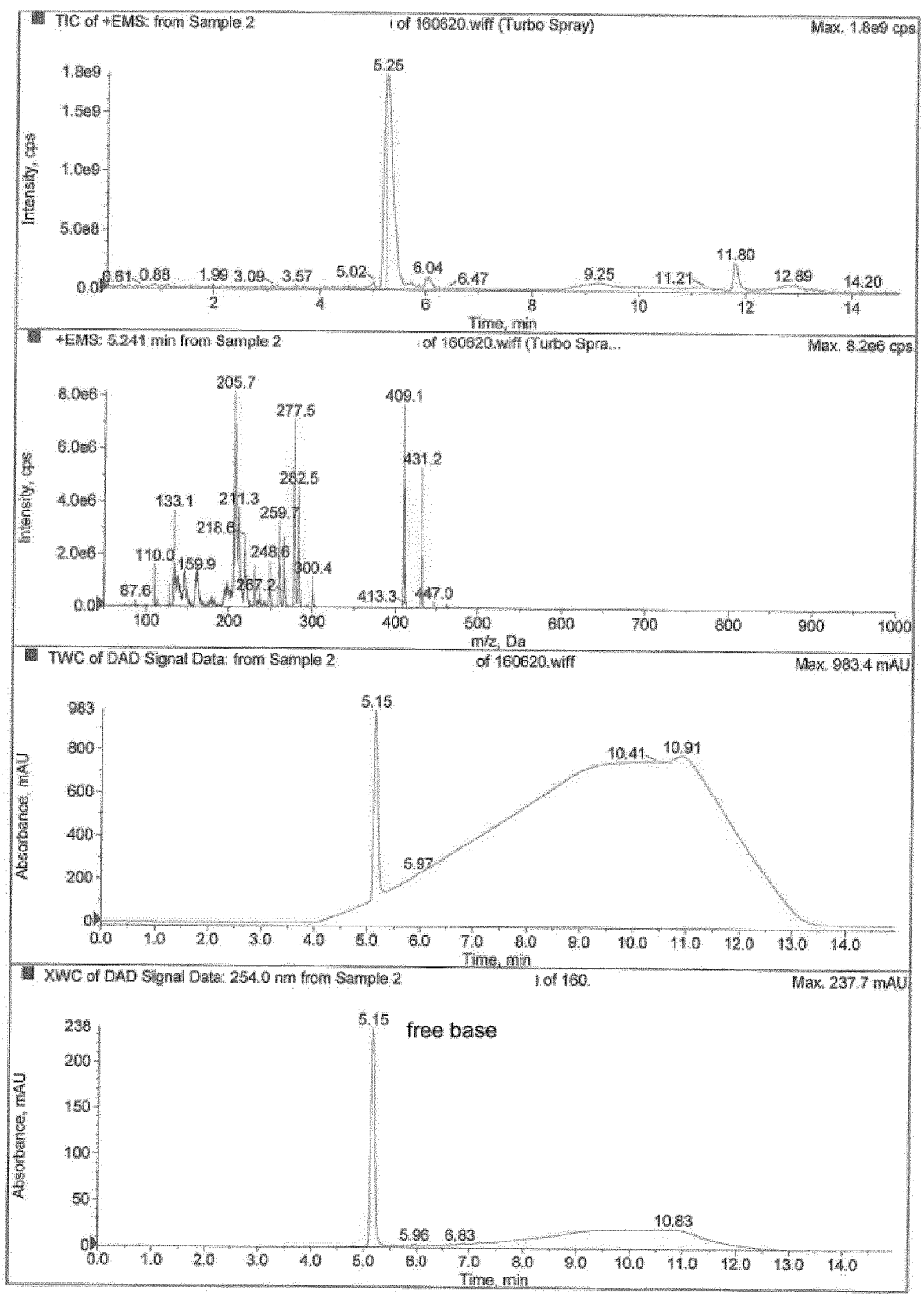
Fig. 7.1

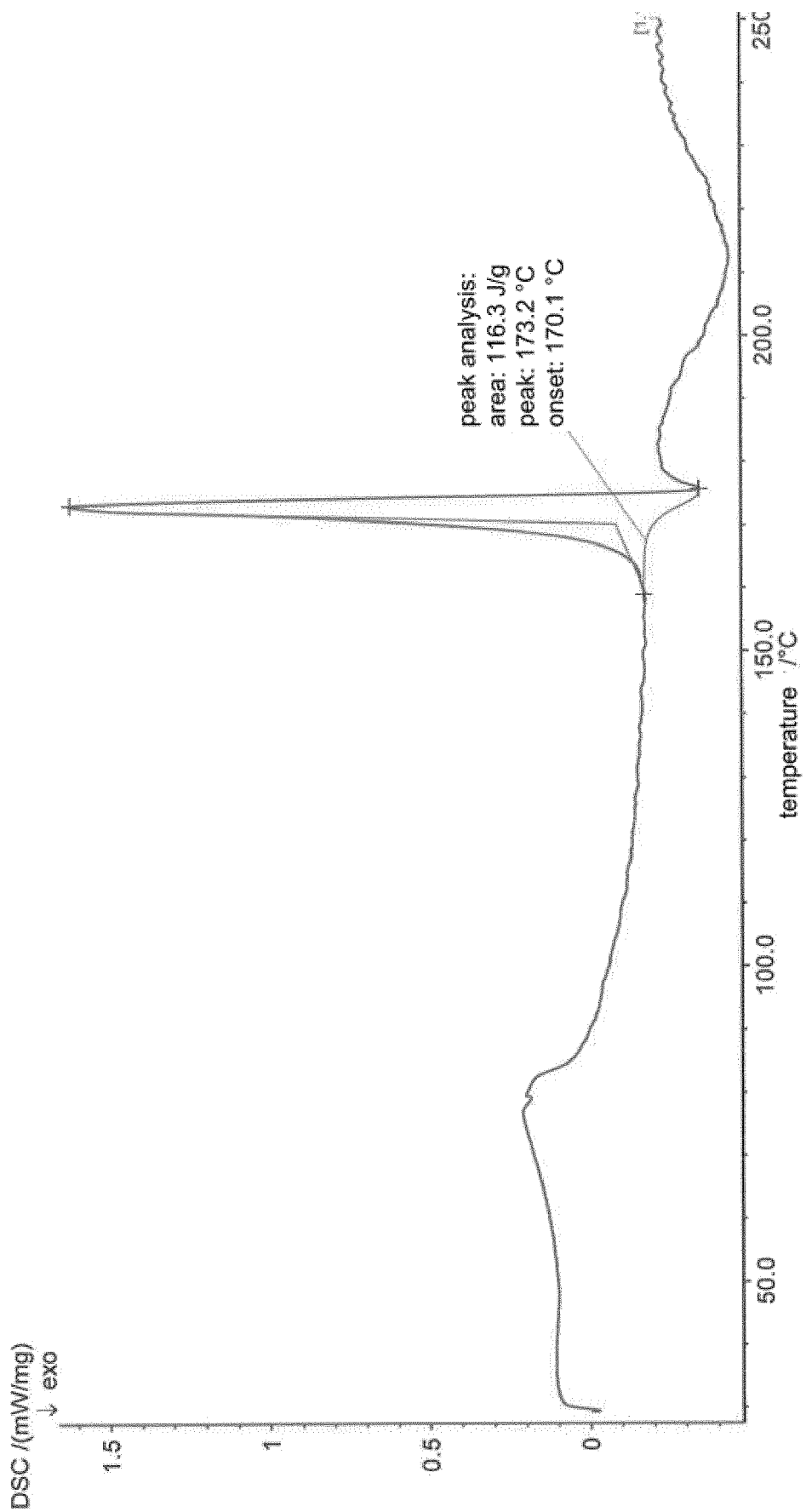
Fig. 7.2

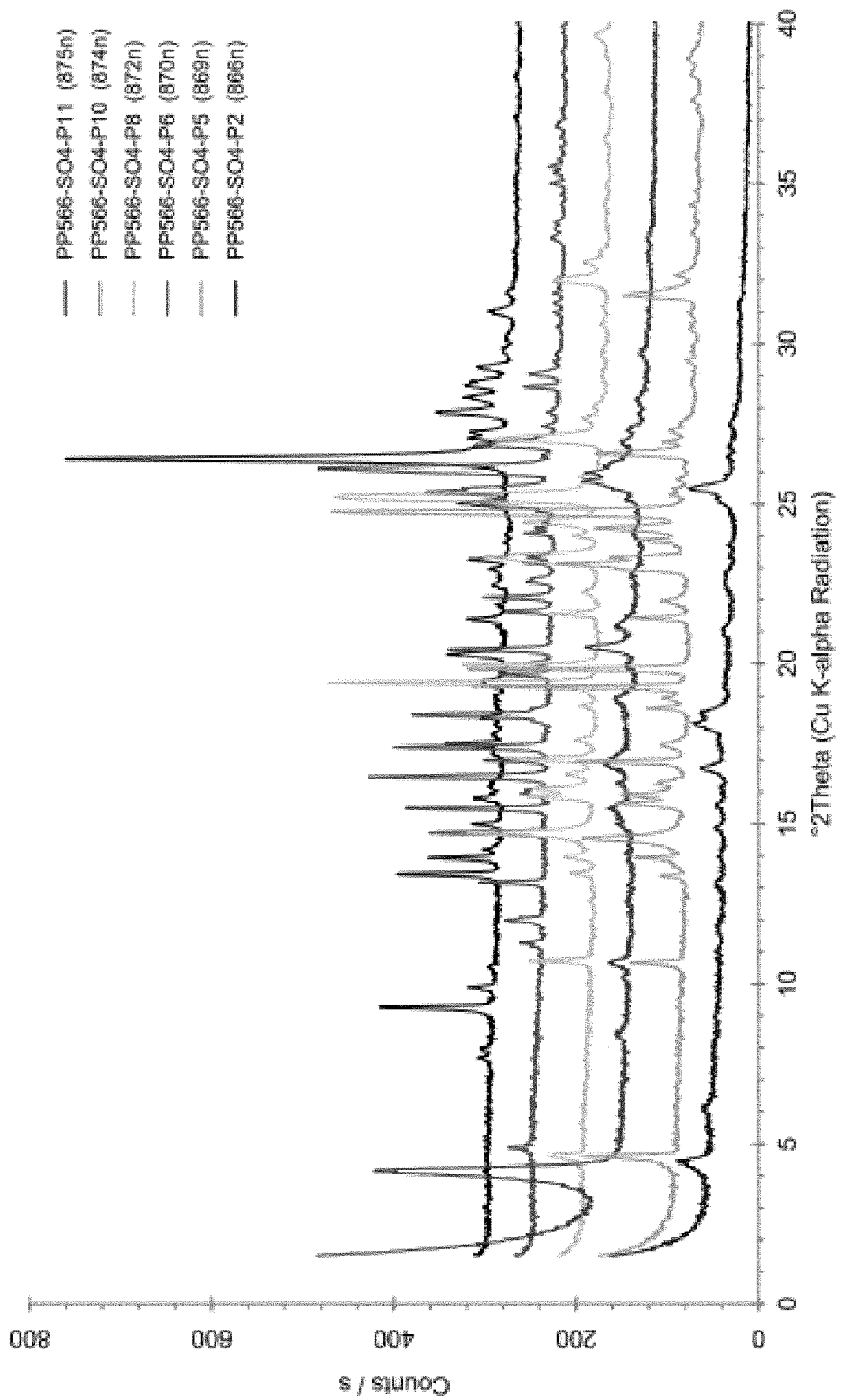
Fig. 8.1

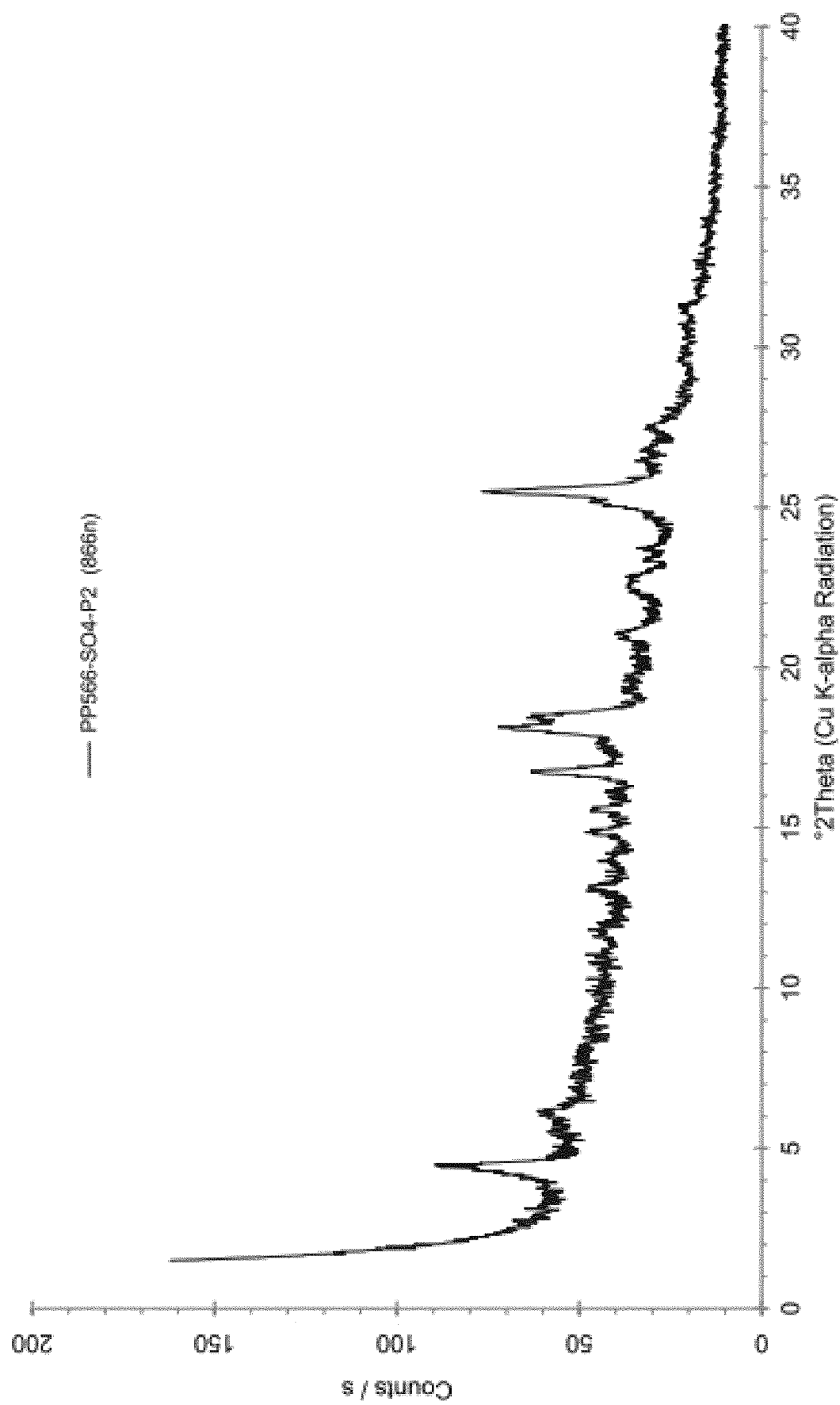
Fig. 8.2

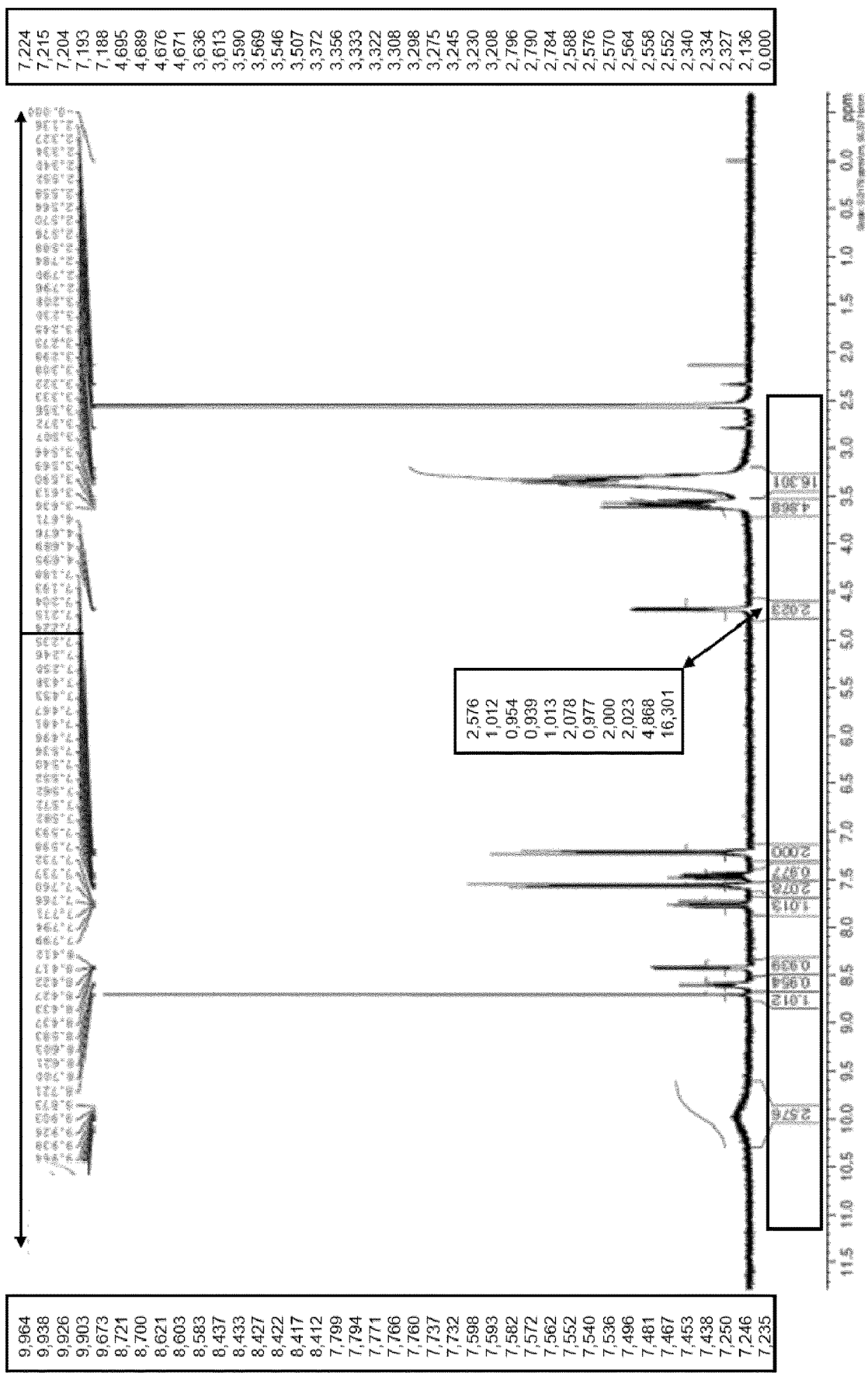
Fig. 8.3

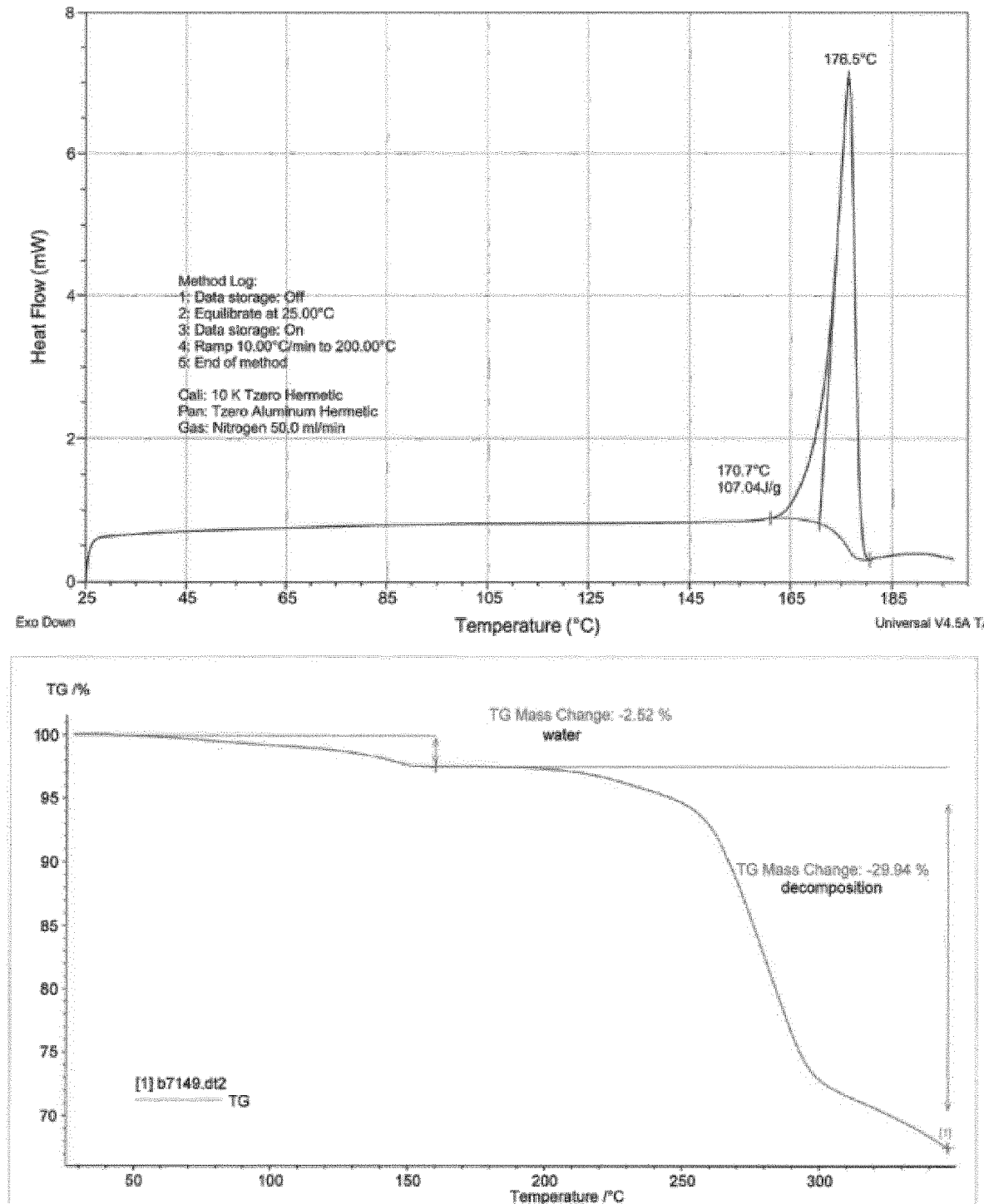
Fig. 8.4

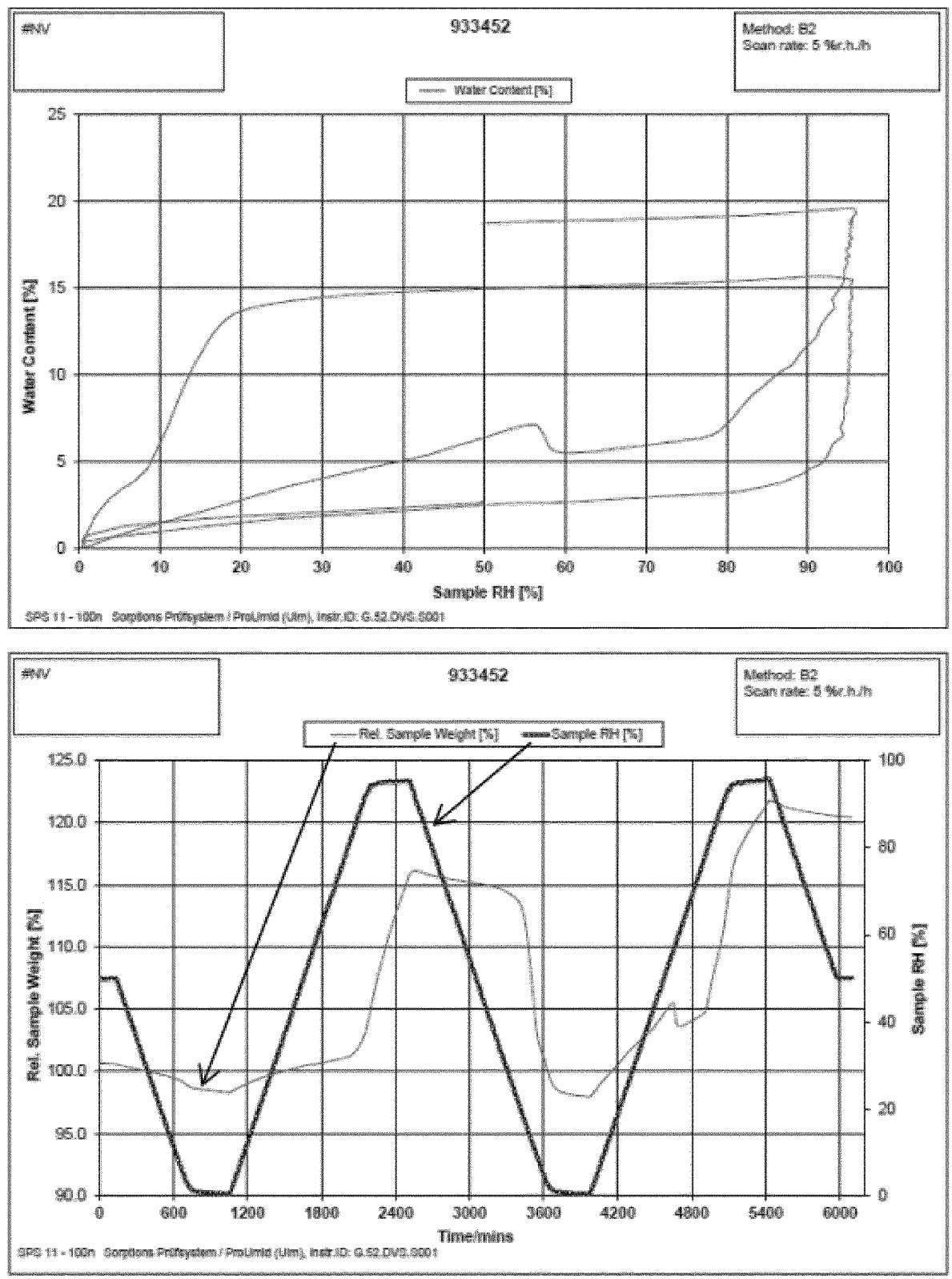
Fig. 8.5

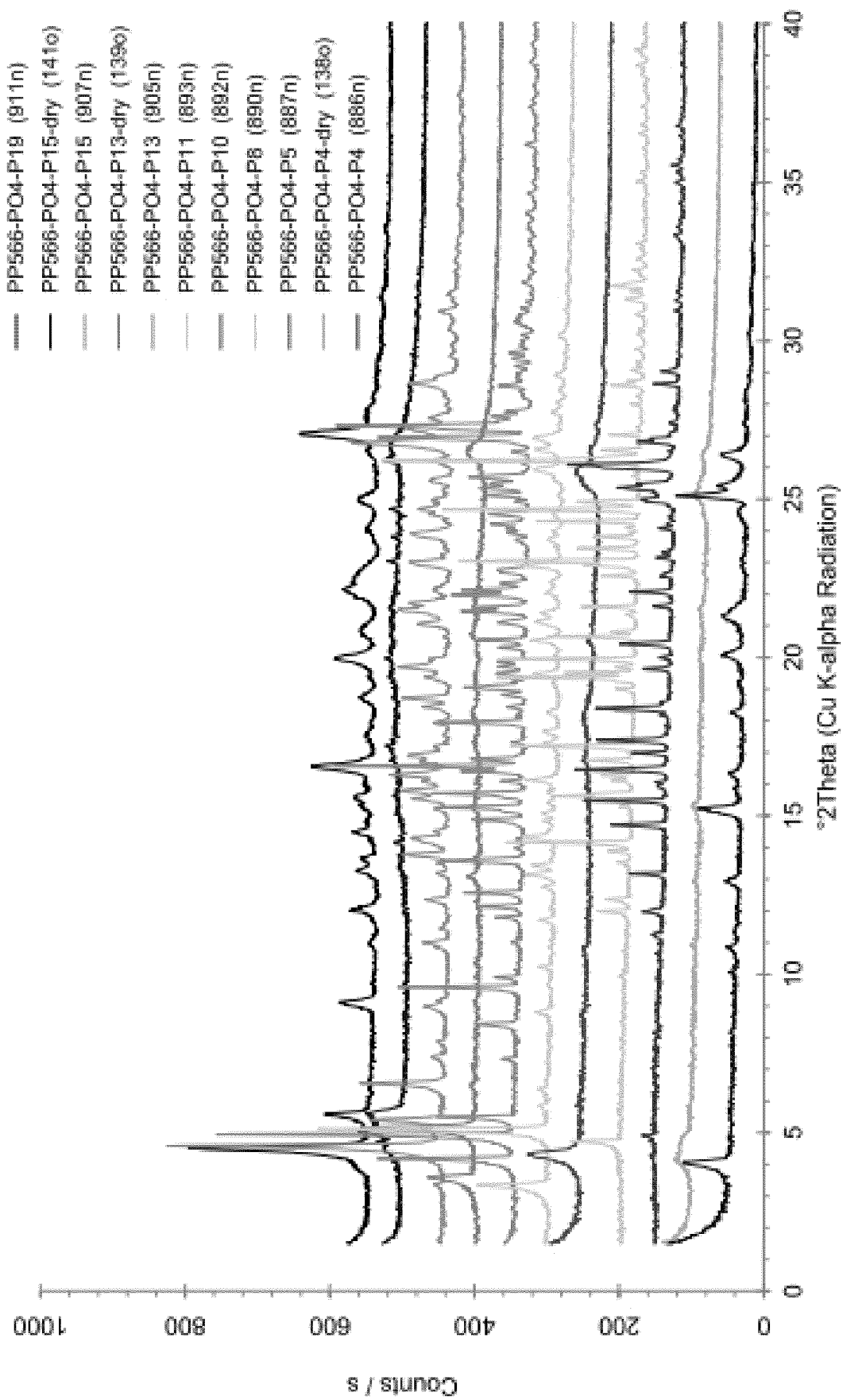
Fig. 9.1

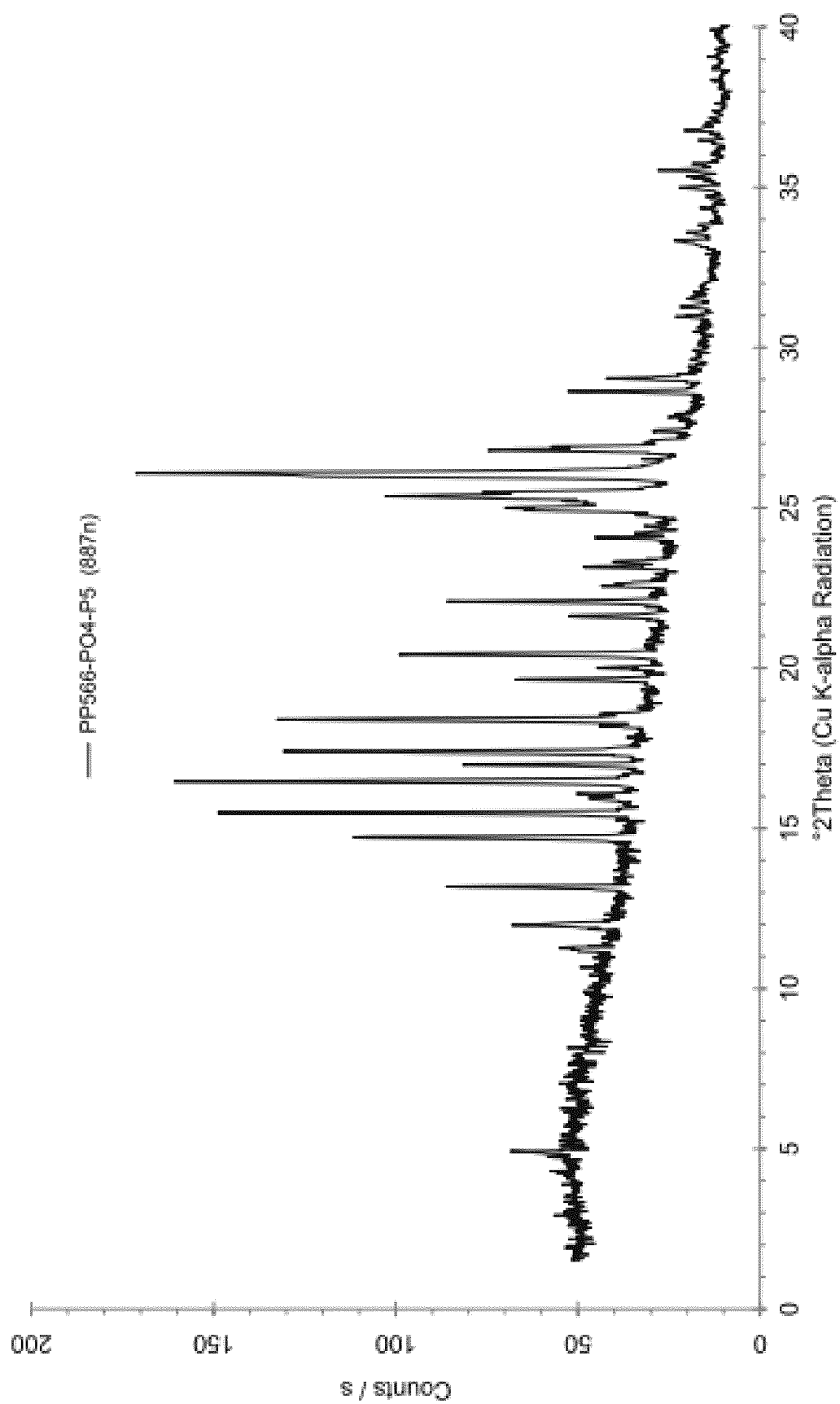
Fig. 9.2

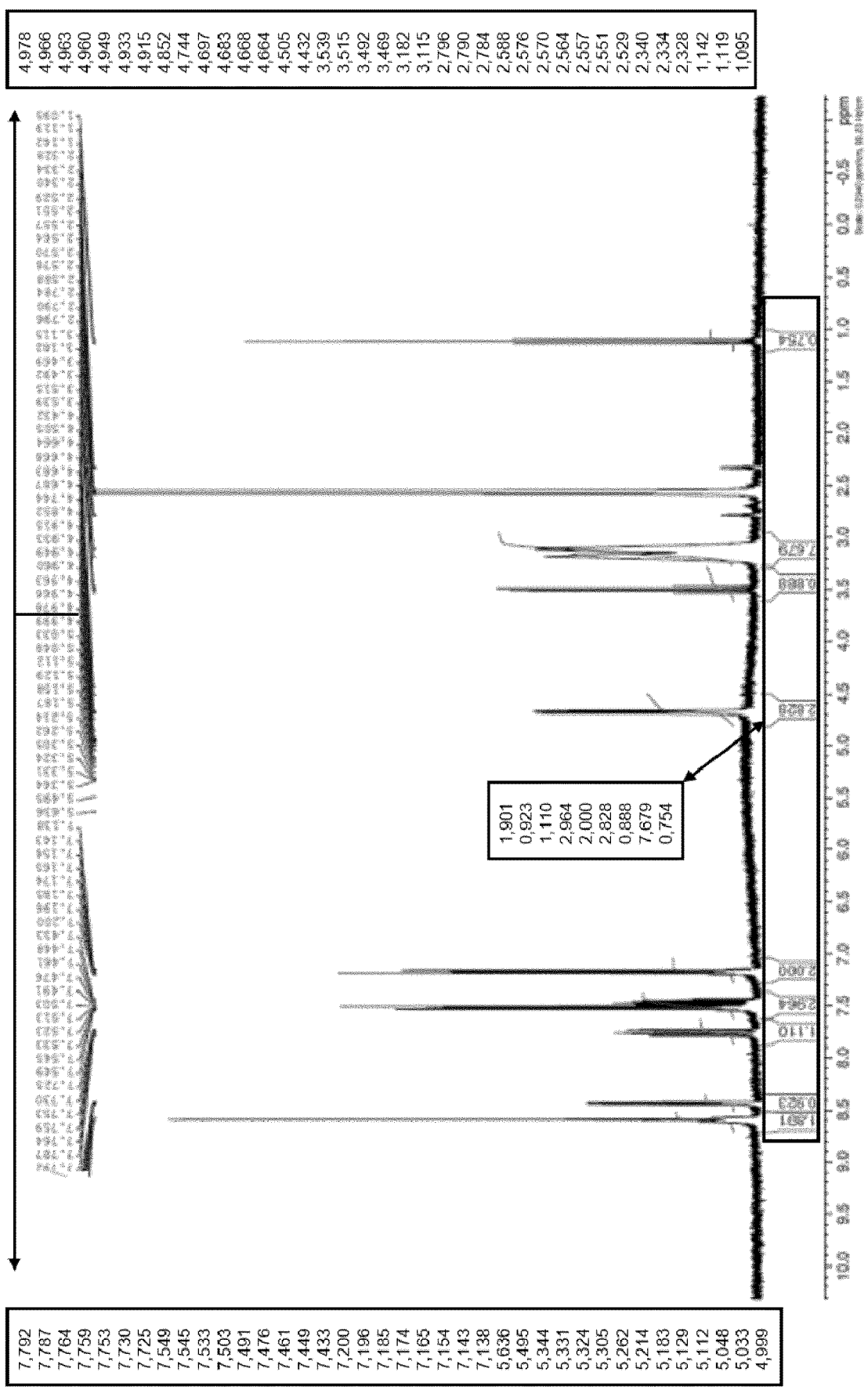
Fig. 9.3

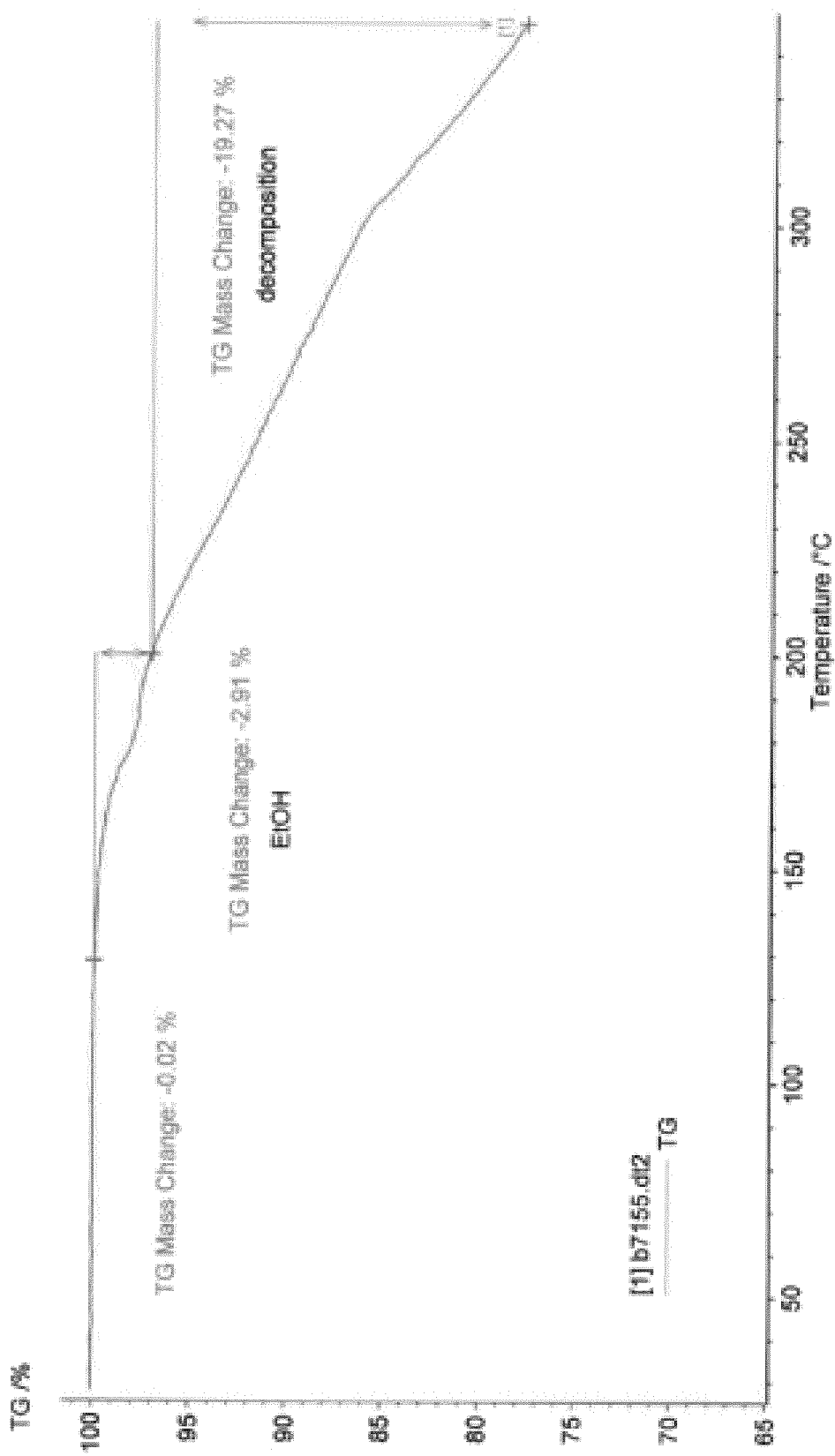
Fig. 9.4

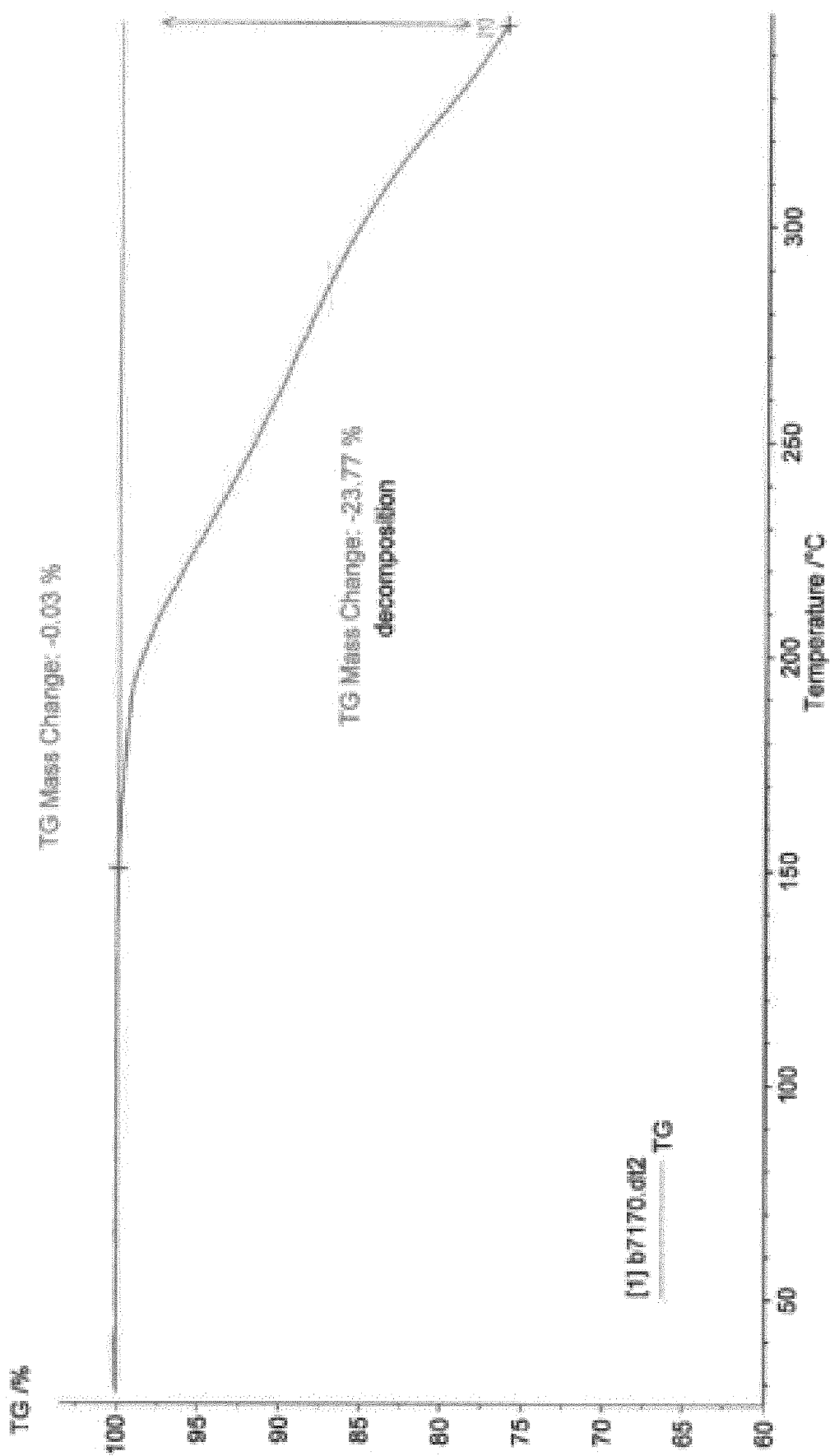
Fig. 9.5

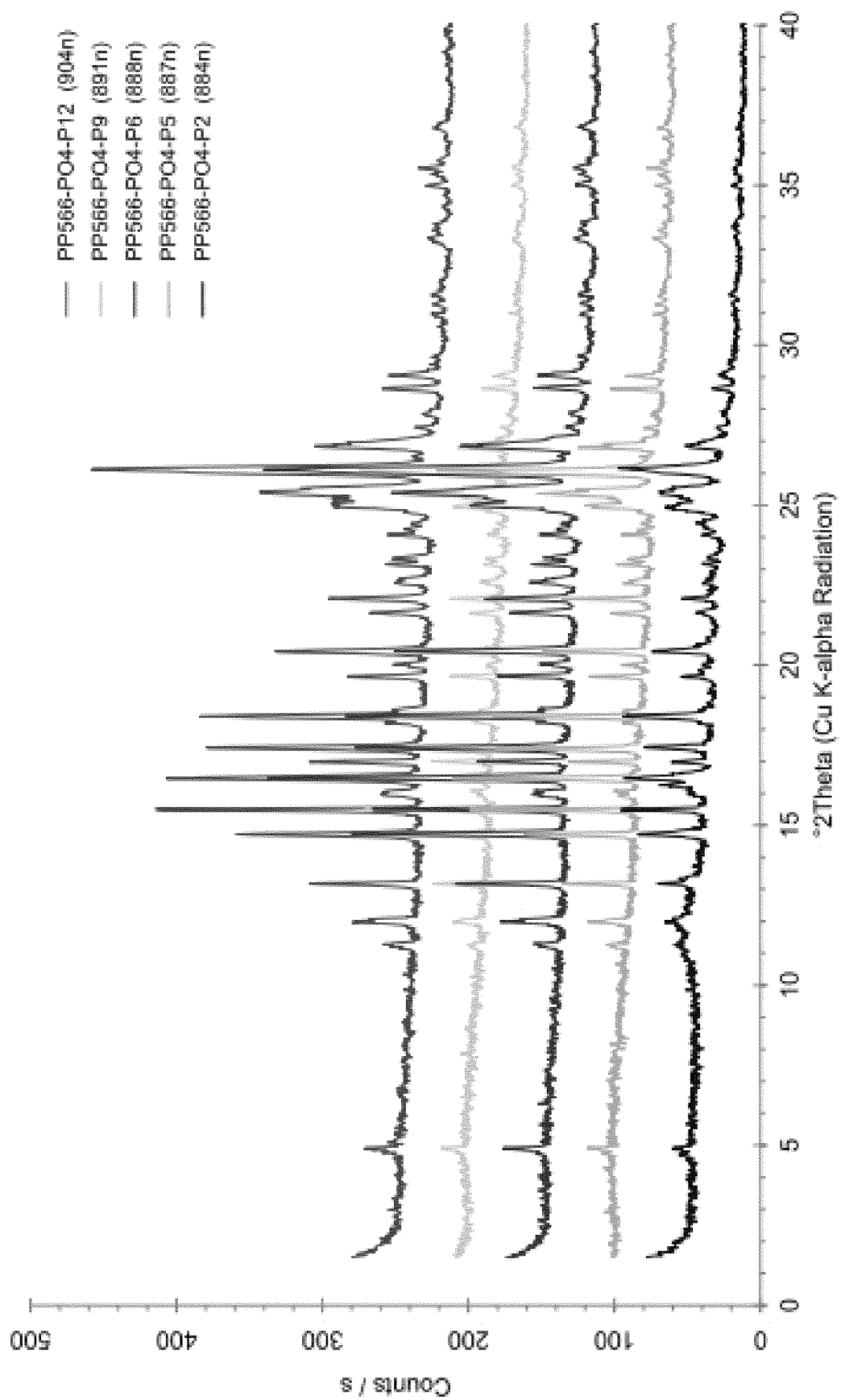
Fig. 9.6

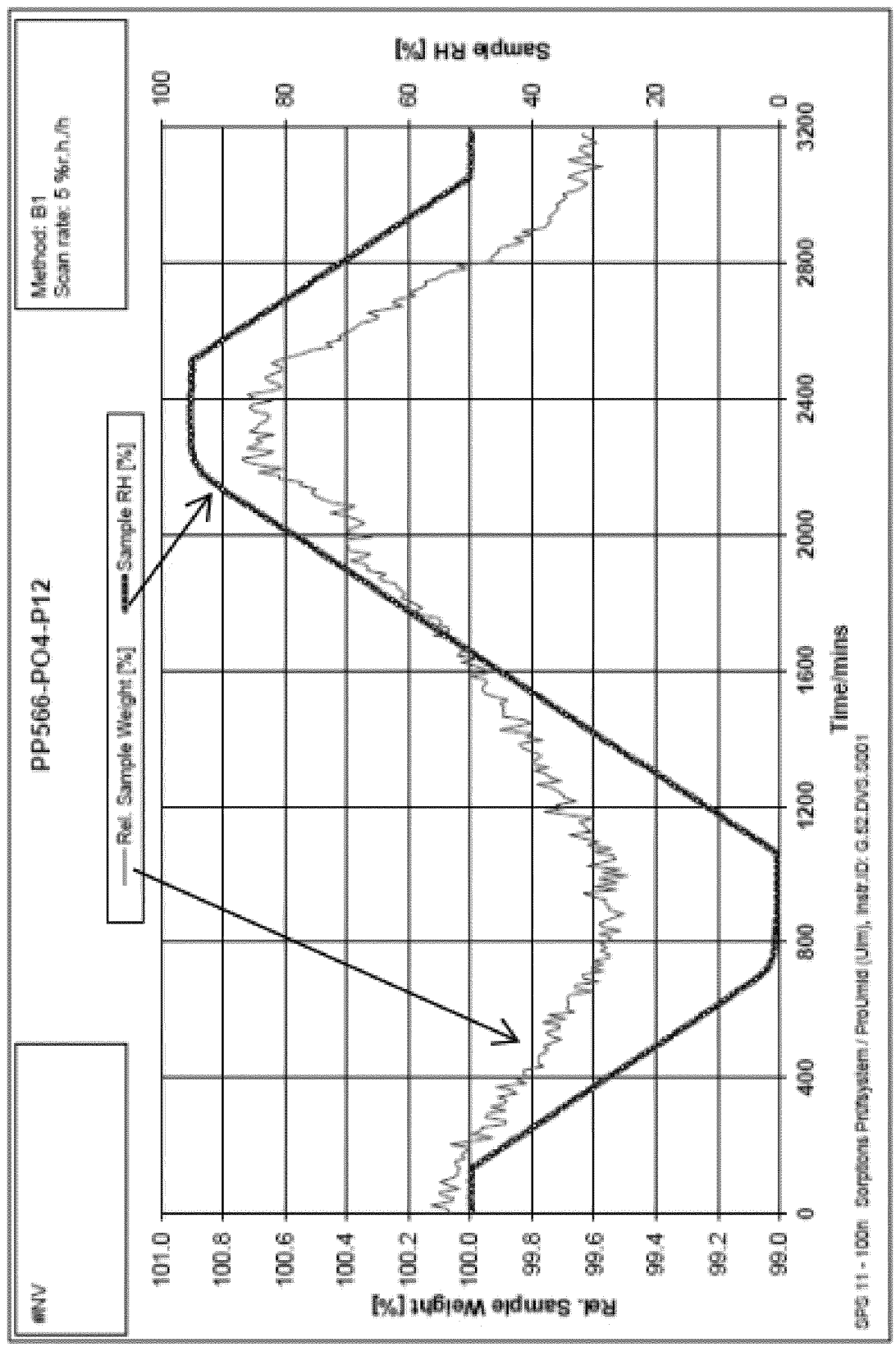
Fig. 9.7

A

B

FERROPORTIN-INHIBITOR SALTS

INTRODUCTION

The invention relates to novel salts of compounds of the general formula (I), pharmaceutical compositions comprising them and the use thereof as medicaments, in particular for the use as ferroportin inhibitors, more particularly for the use in the prophylaxis and/or treatment of diseases caused by a lack of hepcidin or iron metabolism disorders, such as particularly iron overload states such as in particular thalassemia, sickle cell disease and hemochromatosis.

BACKGROUND AND PRIOR ART

Iron is an essential trace element for almost all organisms and is relevant in particular with respect to growth and the formation of blood. The balance of the iron metabolism is in this case primarily regulated on the level of iron recovery from haemoglobin of ageing erythrocytes and the duodenal absorption of dietary iron. The released iron is taken up via the intestine, in particular via specific transport systems (DMT-1, ferroportin), transferred into the blood circulation and thereby conveyed to the appropriate tissues and organs (transferrin, transferrin receptors).

In the human body, the element iron is of great importance, inter alia for oxygen transport, oxygen uptake, cell functions such as mitochondrial electron transport, cognitive functions, etc. and ultimately for the entire energy metabolism.

On average, the human body contains 4 to 5 g iron, with it being present in enzymes, in haemoglobin and myoglobin, as well as depot or reserve iron in the form of ferritin and hemosiderin. Approximately half of this iron, about 2 g, is present as heme iron, bound in the haemoglobin of the erythrocytes. Since these erythrocytes have only a limited lifespan (75-150 days), new ones have to be formed continuously and old ones degraded (over 2 million erythrocytes are being formed per second). This high regeneration capacity is achieved by macrophages phagocytizing the ageing erythrocytes, lysing them and thus recycling the iron thus obtained for the iron metabolism. The majority of the iron required for erythropoiesis, about 25 mg per day, is provided in this way.

The daily iron requirement of a human adult is between 0.5 to 1.5 mg per day, infants and women during pregnancy require 2 to 5 mg of iron per day. The daily iron loss, e.g. by desquamation of skin and epithelial cells, is low. Increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake thus rebalancing the daily iron requirement to the adequate level.

The iron level is regulated by absorption, with the absorption rate of the iron present in food being between 6 and 12%, and up to 25% in the case of iron deficiency. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or released into the blood by the transport protein ferroportin. Hepcidin plays a central role in this process because it is the essential regulating factor of iron absorption. The divalent iron transported into the blood by ferroportin is converted into trivalent iron by oxidases (ceruloplasmin, hephaestin), the trivalent iron then being transported to the relevant places in the organism by transferrin (see for example "Balancing acts: molecular control of mammalian iron metabolism". M. W. Hentze, Cell 117, 2004, 285-297).

Mammalian organisms are unable to actively discharge iron. The iron metabolism is substantially controlled by hepcidin via the cellular release of iron from macrophages, hepatocytes and enterocytes.

Hepcidin is a peptide hormone produced in the liver. The predominant active form has 25 amino acids (see for example: "Hepcidin, a key regulator of iron metabolism and mediator of anaemia of inflammation". T. Ganz, Blood, 102, 2003, 783-8), although two forms which are shortened at the amino end, hepcidin-22 and hepcidin-20, have been found. Hepcidin acts on the absorption of iron via the intestine and via the placenta and on the release of iron from the reticuloendothelial system. In the body, hepcidin is synthesized in the liver from what is known as pro-hepcidin, pro-hepcidin being coded by the gene known as the HAMP gene. The formation of hepcidin is regulated in direct correlation to the organisms iron level, i.e. if the organism is supplied with sufficient iron and oxygen, more hepcidin is formed, if iron and oxygen levels are low, or in case of increased erythropoiesis less hepcidin is formed. In the small intestinal mucosal cells and in the macrophages hepcidin binds with the transport protein ferroportin, which conventionally transports the phagocytotically recycled iron from the interior of the cell into the blood.

The transport protein ferroportin is a transmembrane protein consisting of 571 amino acids which is formed in the liver, spleen, kidneys, heart, intestine and placenta. In particular, ferroportin is localized in the basolateral membrane of intestinal epithelial cells. Ferroportin bound in this way thus acts to export the iron into the blood. In this case, it is most probable that ferroportin transports iron as $Fe^{2+}$. If hepcidin binds to ferroportin, ferroportin is transported into the interior of the cell, where its breakdown takes place so that the release of the phagocytotically recycled iron from the cells is then almost completely blocked. If the ferroportin is inactivated, for example by hepcidin, so that it is unable to export the iron which is stored in the mucosal cells, the stored iron is lost with the natural shedding of cells via the stools. The absorption of iron in the intestine is therefore reduced, when ferroportin is inactivated or inhibited, for example by hepcidin. In addition, ferroportin is markedly localized in the reticuloendothelial system (RES), to which the macrophages also belong. Hepcidin plays an important part here when iron metabolism is impaired by chronic inflammation. In case of inflammation in particular interleukin-6 is increased, triggering an increase in hepcidin levels. As a result, more hepcidin is bound to the ferroportin of the macrophages, thus blocking the release of stored iron, which ultimately leads to anemia of inflammation (ACD or AI).

On the other hand, if the serum iron level decreases, hepcidin production in the hepatocytes of the liver is reduced so that less hepcidin is released and accordingly less ferroportin is inactivated, allowing a larger amount of stored iron to be transported into the serum.

Therefrom it becomes apparent that the hepcidin-ferroportin system directly regulates the iron metabolism and that a disorder of the hepcidin regulation mechanism therefore has a direct effect on iron metabolism in the organism. In principle the hepcidin-ferroportin regulation mechanism acts via the two following opposite principles:

On the one hand, an increase of hepcidin leads to inactivation of ferroportin, thus blocking the release of stored iron from the cells into the serum, thus decreasing the serum iron level. In pathological cases a decreased serum iron level leads to a reduced hemoglobin level, reduced erythrocyte production and thus to iron deficiency anemia.

On the other hand, a decrease of hepcidin results in an increase of active ferroportin, thus allowing an enhanced release of stored iron and an enhanced iron uptake e.g. from the food, thus increasing the serum iron level. In pathological cases an increased iron level leads to iron overload.

Iron overload states and diseases are characterized by excess iron levels. Therein, the problems arise from excess serum iron level which lead to non-transferrin bound iron (NTBI). The NTBI is rapidly taken up unspecifically by the organs, leading to an accumulation of iron in tissue and organs. Iron overload causes many diseases and undesired medical conditions, including cardiac, liver and endocrine damage. Further, iron accumulation in brain has been observed in patients suffering from neurodegenerative diseases such as for example Alzheimer's disease and Parkinson's disease. As a particular detrimental aspect of excess free iron the undesired formation of radicals must be mentioned. In particular iron(II) ions catalyze the formation (inter alia via Fenton reaction) of reactive oxygen species (ROS). These ROS cause damage to DNA, lipids, proteins and carbohydrates which has far-reaching effects in cells, tissue and organs. The formation of ROS is well known and described in the literature to cause the so-called oxidative stress.

A well-established hitherto existing method for treating iron overload is based on the concept to reduce the amount of iron in the serum by increased removal of the iron from the body. The eldest known and still routine treatment method in an otherwise-healthy person consists of regularly scheduled phlebotomies (bloodletting). When first diagnosed, the phlebotomies are usually scheduled fairly frequent, e.g. once a week, until iron levels are brought to within normal range, followed by phlebotomies which are then scheduled once a month or every three months depending upon the patient's rate of iron loading.

For patients unable to tolerate routine blood draws, there are chelating agents available for use. For example, deferoxamine (also known as desferrioxamine B, N'-{5-[acetyl (hydroxy)amino]pentyl}-N-[5-({4-[(5-aminopentyl)(hydroxy)amino]-4-oxobutanoyl} amino)pentyl]-N-hydroxysuccinamide or Desferal®), which is a bacterial siderophore, is an established drug used in chelation therapy. Deferoxamine binds iron in the bloodstream as an chelator and enhances its elimination via urine and faeces. Typical treatment of chronic iron overload requires subcutaneous injection over a period of 8-12 hours daily. Parenterally injectable compositions of desferrioxamine-B salts are described for example in WO 1998/25887.

Two newer drugs, licensed for use in patients receiving regular blood transfusions to treat thalassemia, resulting in the development of iron overload, are deferasirox and deferiprone.

Deferasirox (Exjade®, 4-(3,5-bis(2-hydroxyphenyl)-1H-1,2,4-triazol-1-yl)benzoic acid), being described for example in WO 1997/49395 and deferiprone (Ferriprox®, 3-hydroxy-1,2-dimethylpyridin-4(1H)-one) are similarly acting as an iron chelating agent, thus being suitable as a drug for iron chelation therapy.

Further compounds acting as iron chelator for use in the treatment of iron overload have been described. For example WO 2013/142258 relates to encapsulated particles of diethylenetriaminepentaacetate (DTPA) and a zinc salt. WO 2003/041709 relates to 4-hydroxy-2-alkylquinolines such as 4-hydroxy-2-nonylquinoline as an iron chelator. WO 1998/09626 relates to chelating agents for treating iron overload states on the basis of dithiocarbamate-containing compositions.

WO 2015/077655 relates to desferrithiocin derivatives of the formula (A) or (J)

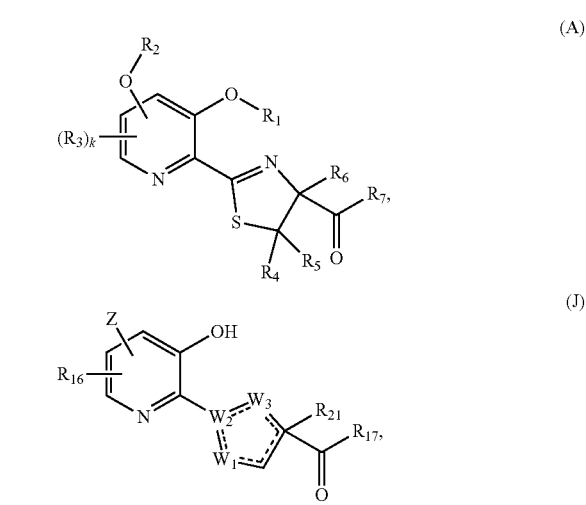

for the use in the treatment of iron overload diseases. According to WO 2015/077655 said desferrithiocin derivatives have been found to act as iron chelating agents.

WO 2005/051411 relates to novel antibiotics or antimycotics on the basis of oxachelin and derivatives thereof according to formula

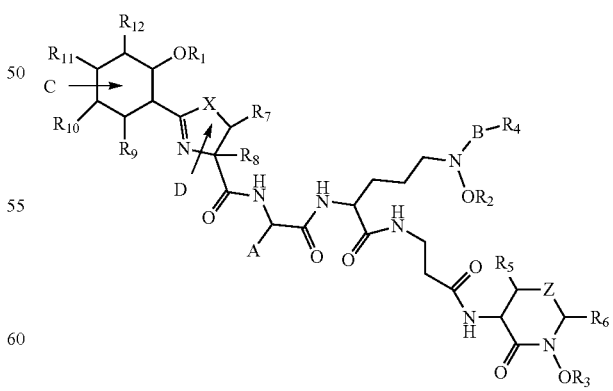

which are described to act as an iron chelator and to be used in the treatment of iron overload diseases.

The disadvantage in the treatment of iron overload by chelation therapy is the removal of the chelated iron from the body when the iron overload has already occurred instead of preventing the occurrence of the disorder. Further, the established drugs for iron chelation therapy are known to exhibit a toxic potential.

Modern approaches can be expected to supersede this method increasingly, in particular with increasing knowledge about the underlying mechanisms and development of appropriate treating methods on the basis of such knowledge. Hepcidin agonists or compounds which have an inhibiting or supporting effect on the biochemical regulatory pathways in the iron metabolism are basically known from the prior art.

Iron overload may occur, for example, if hepcidin expression is prevented, for example due to a genetic defect, such as in the known iron overload disease haemochromatosis. Hemochromatosis is a disease of iron overload caused by mutations in genes that control hepcidin synthesis or in the hepcidin gene itself. Low or absent levels of hepcidin in these patients result in enhanced amounts of active ferroportin, allowing increased absorption of dietary iron, leading to severe iron overload, which causes cardiac, liver and endocrine damages. Hepcidin mimetic peptides, i.e. peptides which similarly bind and inactivate ferroportin, have been shown to effectively reverse the accumulation of tissue iron in the hepcidin knockout mouse, a model of Type 2 (juvenile) hemochromatosis. (Ramos et al., Blood 2012).

In the known iron overload disease beta-thalassemia a mutation in the beta globin gene causes a reduction in hemoglobin production and ineffective erythropoiesis, the inability to produce adequate numbers of red cells because of damage to and death of developing red cells in the bone marrow. This causes upregulation of the rate of erythropoiesis and a reduction in hepcidin level to make more iron available for increased erythropoietic activity. This maladaptive response results in iron overload due to the reduced hepcidin levels, which lead to enhanced amounts of active ferroportin, allowing increased absorption of dietary iron, as described above. Red cells in thalassemia have a shortened half-life because of the toxicity of an imbalanced ratio of alpha- and beta- hemoglobin-subunits. Also in the treatment of beta-thalassemia the use of hepcidin mimetic peptides has been described, the therapeutic rationale being based on the increase of hepcidin activity leading to iron restriction and reduction of iron mediated damage in red cells. Administration of hepcidin mimetic peptides to the th3/+ mouse, a model of non-transfusion dependent beta-thalassemia resulted in relief of ineffective erythropoiesis, increased red cell survival time and improvement of anemia. In this model the prevention of iron overload due to reduction in the absorption of dietary iron turned out as an additional benefit of the hepcidin mimetic therapy (Gardenghi et al, 2010; Casu et al 2013).

The described therapeutic approaches are based on a direct involvement into the disturbed iron metabolism pathway by directly acting via the primary regulator hepcidin by providing a hepcidin mimetic or a hepcidin agonist, i.e. acting in the sense of a kind of hepcidin substitute or supply. The approach is based on the therapeutic rationale to treat iron overload, i.e. excess serum iron level, by inhibiting ferroportin, via the hepcidin-inactivation mechanism, thus blocking excessive iron absorption.

Further known iron overload related diseases are diseases associated with ineffective erythropoiesis such as the myelodysplastic syndromes (also known as MDS or myelodysplasia), polycythemia vera, etc.

Further, mutations in genes involved in sensing the systemic iron stores, such as hepcidin (Hampl), hemochromatosis protein (HFE), hemojuvelin (HJV) and transferrin receptor 2 (TFR2) cause iron overload in mice and men. Accordingly, diseases related to HFE and gene mutations, chronic hemolysis associated diseases, sickle cell diseases, red cell membrane disorders, as well as Glucose-6-phosphate dehydrogenase deficiency (G6PD deficiency), erythrpoietic porphyria and Friedrich's Ataxia can be mentioned. Further, subgroups of iron overload comprise transfusional iron overload, iron intoxication, pulmonary hemosiderosis, osteopenia, insulin resistense, African iron overload, Hallervordan Spatz disease, hyperferritinemia, ceruloplasmin deficiency, neonatal hemochromatosis and red blood cell disorders comprising thalassemia, alpha thalassemia, thalassemia intermedia, sickle cell disease and myelodyplastic syndrome are included.

Further disease and/or disorders and/or diseased conditions associated with elevated iron levels include, but are not limited to, diseases with elevated iron level, comprising ataxia, Friedrich's ataxia, age-related macular degeneration, age-related cataract, age-related retinal diseases and neurodegenrative disease, whereby such neurodegenrative disease comprises Alzheimer's disease, Parkinson's disease, pantothenate kinase-associated neurodegeneration, restless leg syndrome and Huntington's disease, Hepcidin is a host defense peptide, representing a component of the innate immune system that responds to invading organisms.

It has been described that many bacteria are highly dependent on a supply of iron from the host (so-called siderophilic organisms) and have evolved mechanisms to capture iron from the local tissues. The ability to limit the amount of iron available to such organisms by ferroportin-inhibitors may represent effective adjunctive therapy. One such siderophilic organism is *Vibrio vulnificus*, which causes rare but extremely severe infections in coastal communities, often in subjects with undiagnosed iron overload. Studies in animals that have been inoculated with a lethal dose of *Vibrio vulnificus* have demonstrated nearly 100% survival in response to treatment with hepcidin mimetic peptides, inactivating ferroportin, regardless of whether treatment is started before or after the infection is initiated (Arezes et al 2015).

As known hepcidin mimetics the so-called minihepcidins can be mentioned, described for example in WO 2013/086143. Minihepcidins are small-sized synthetic peptide analogues of the hepcidin N-terminus which is crucial for hepcidin interaction with ferroportin. Minihepcidins have been developed on the basis that the first 9 amino acids of hepcidin (DTHFPICIF) have been found to be sufficient for in vitro activity (measured as ferroportin-GFP degradation). Minihepcidins have a modified hepcidin-9 amino acid sequence to exhibit improved resistance to proteolysis and enhanced biophysical interaction with ferroportin. Minihepcidins are described to be useful for the treatment of human iron overload conditions caused by hepcidin deficiency.

WO 2015/069660 describes methods for increasing hepcidin expression for treating iron overload disorders by decreasing non-transferrin bound iron (NTBI) by administering a modified iron binding/releasing transferrin.

All the described compounds which act as hepcidin agonists, hepcidin mimetics or ferroportin inhibitor etc. are relatively high molecular weight compounds, in particular those which are obtainable predominantly by genetic engineering. Various further approaches on the basis of biomolecular interactions and biomolecules have been described. The disadvantage is the complex preparation and high sensitivity of such biomolecular compounds. In particular methods on the basis of ferroportin antibodies are not sufficiently efficient as the antibody-inhibited ferroportin is permanently reproduced by the organism and the inhibition is thus not sufficiently long-lasting to achieve the desired therapeutic effect.

Low molecular weight compounds which play a part in iron metabolism and can have an inhibiting or promoting effect are also known.

For example WO 2008/151288, WO 2008/118790, WO 2008/115999, and WO 2008/109840 describe compounds acting as divalent metal transporter-1 (DMT1) inhibitors and their use for the treatment of iron disorders such as thalassemia or hemochromatosis.

WO 2008/123093 relates to an agent for prevention or treatment of iron overload disorders, comprising 22 beta-methoxyolean-12-ene-3 beta,24(4 beta)-diol.

EP 1074254 and EP1072265 relate to the use of catechic- and flavonoid-structure plant polyphenols for treating iron overload.

WO 2011/029832 relates to thiazol and oxazol compounds which act as hepcidin antagonists and are thus described to be suitable in the use for the treatment of iron deficiency diseases. Therein, hepcidin antagonistic activity is described to inhibit the inhibition of ferroportin by hepcidin, which is the opposite effect as has been found by the inventors of the present invention for the novel thiazol and oxazol compounds as described herein.

The unpublished international applications PCT/EP2016/075305 and PCT/EP2016/075306 describe compounds having activity as ferroportin inhibitors, which overlap with the specific selection of the compounds according to formula (I) of the present invention, and being in the form of the free bases and/or their pharmaceutically acceptable salts in general. The international applications mention a general list of possible acids for pharmaceutically acceptable salts. Further, the international applications mention some specific Example Compounds in the form of 2HCl salts, 3HCl salts or 4HCl salts, wherein only some of said specific examples of HCl-salts are covered from the specific selection of the compounds according to formula (I) of the present invention. Accordingly, the present invention constitutes a novel selection of a very specific group of compounds, defined by formula (I), being in the form of a salt (instead of a free base or mixtures of salts and free bases) and being further defined by the novel selection of a specific ratio of counterions (free base/compound (I):acid).

Chemical compounds and their salts based on the structures of the general formula (I) of the present invention have hitherto not been disclosed in connection with their activity as ferroportin inhibitors or for the use in the prophylaxis and treatment of iron metabolism disorders which are associated with increased iron levels such as iron overload.

US 2004/0138268 A1, US 2011/0224136 A1, CN 103508957, WO 2006/062224 A1, WO 2015/051362 A1, EP 1953145 A1, WO 2009/154739 A2, GB 937878 A, WO 2011/023722 A1, WO 2010/020556 A1, WO 2005/011685 A1, WO 00/56724 A1, WO 2010/036632 A1, WO 2005/014576 A1, WO 2013/067578 A1, WO 2005/116355 A1, EP 1 889 842 A1, US 2013/303508 A1, WO 98/27108 A2, WO 2006/040646 A1, WO2010/078408 A1, or Ashish K. Pathak et al. "Solution-Phase Parallel Synthesis of Acyclic Nucleoside Libraries of Purine, Pyrimidine, and Triazole Acetamides", ACS Combinatorial Science Vol. 16, No. 9, pages 485-493, 2014, Zou Yiquan et al. "Discovery of pyrazole as C-terminus of selective BACE1 inhibitors"; Eur. J. of Medicinal Chemistry 68 (2013) 270-283, Tussing-Humphreys et al. "Rethinking Iron Regulation and Assessment in Iron Deficiency, Anemia of Chronic Disease, and Obesity: Introducing Hepcidin" J. Academy of Nutrition and Dietetics (2012), Vol. 122, No. 3, 391-400, Riordan et al. "Bleomycin analogs. Synthesis and proton NMR spectral assignments of thiazole amides related to bleomycin A2 (1)"; J. Heterocyclic Chem. 18, 1213 (1981), Hideaki Sasaki "Synthesis of a novel bis(2,4'-bithiazole) derivative as a Co(II)-activated DNA cleaving agent"; Chem. Pharm. Bull. 42(8) 1685-1687 (1994), and Ballell et al. "Fueling open-source drug discovery. 177 small-molecule leads against tuberculosis"; ChemMedChem 2013, 8, 313-321 describe compounds for different medical uses and mechanisms of action.

Object

The object of the present invention was to provide, in particular, new therapeutically effective compounds that can be used for an effective therapy for the prophylaxis and treatment of iron metabolism disorders which are associated with increased iron levels, such as in particular iron overload. In a further object, the new compounds should exhibit few side effects and have a very low toxicity and good bioavailability and compatibility. Moreover, these new compounds, in contrast to the known iron chelating compounds, should be suitable to prevent the occurrence of increased iron levels and thus the related disorders, instead of removing excess iron from the body when the iron overload has already occurred. In a further object the new compounds should have a defined structure (stoichiometry) and should be preparable by simple synthesis processes, exhibit less sensitivity and improved long-lasting efficiency as compared to the known biomolecular compounds, such as antibodies.

In a further aspect of the present invention the new compounds should exhibit optimal stability regarding their physical, chemical and physico-chemical characteristics. In particular, for pharmaceutical applications good or improved long-term stability (shelf-life stability) is an important aspect to provide new pharmaceutically active compounds maintaining their physical, chemical and physico-chemical characteristics as well as their pharmacological and physiological activity over a long time. Also the solubility stability (i.e. a stable solubility profile) is important in pharmaceutical applications. In this respect, a further object of the present invention relates to providing new compounds as described herein having good or improved long-term stability, including for example reduced or no solvent release, and/or mass lost under increasing temperatures, being less or not hygroscopic, maintenance of the solid state structure even upon long-term storage under different temperature and/or moisture conditions, resistance of the crystal form to vacuum drying, high reproducibility with high purity and low side- or degradation products in the preparation method, maintenance of the solubility profile even upon long-term storage under different temperature and moisture conditions, as well as combinations thereof.

This goal was achieved by the development of the novel salts of compounds according to the formula (I) as defined herein, which have been found to act as ferroportin inhibitors, thus being suitable for the use in the inhibition of iron transport, and thus being effective in the prophylaxis and treatment of iron metabolism disorders which are associated with increased iron levels, such as in particular iron overload, as well as in the prophylaxis and treatment of diseases caused by a lack of hepcidin, diseases related to or caused by increased iron levels or iron overload and diseases associated with ineffective erythropoiesis.

DESCRIPTION OF THE INVENTION

The inventors have surprisingly found that specific salts of selected compounds having the general structural formula (I) as defined herein, act as ferroportin inhibitors, thus effectively inhibiting iron transport and accordingly being particularly suitable for the use as medicaments, in particular for the use in the treatment and/or prophylaxis of diseases caused by a lack of hepcidin, diseases associated with ineffective erythropoiesis or iron metabolism disorders leading to increased iron levels, such as particularly iron overload states such as in particular thalassemia, sickle cell disease and hemochromatosis. Very particularly the new salt compounds turned out to be suitable for treating thalassemia, sickle cell disease and hemochromatosis. The new salt compounds are also suitable for the treatment of diseases caused by pathologically low hepcidin-levels and for the use in the inhibition of iron transport.

Accordingly, the invention relates to novel salts of compounds of general formula (I)

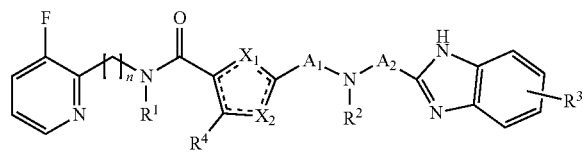

wherein
$X_1$ is N or O; and
$X_2$ is N, S or O;
with the proviso that $X_1$ and $X_2$ are different;
$R^1$ is selected from the group consisting of
　hydrogen and
　optionally substituted alkyl;
n is an integer of 1 to 3;
$A^1$ and $A^2$ are independently selected from the group of alkanediyl;
$R^2$ is
　hydrogen, or
　optionally substituted alkyl;
or
$A^1$ and $R^2$ together with the nitrogen atom to which they are bonded form an optionally substituted 4- to 6-membered ring;
$R^3$ indicates 1, 2 or 3 optional substituents, which may independently be selected from the group consisting of
　halogen,
　cyano,
　optionally substituted alkyl,
　optionally substituted alkoxy, and
　a carboxyl group;
$R^4$ is selected from the group consisting of
　hydrogen,
　halogen,
　$C_1$-$C_3$-alkyl, and
　halogen substituted alkyl;
wherein the salts are selected from salts of the compounds of formula (I) with acids from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid, being characterized by a ratio of compound (I):acid of 1 to 2:1 to 3; and wherein the following 3HCl salts are excluded:

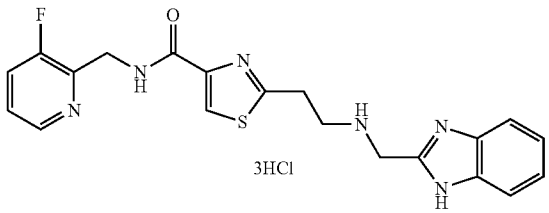

Exp. 40

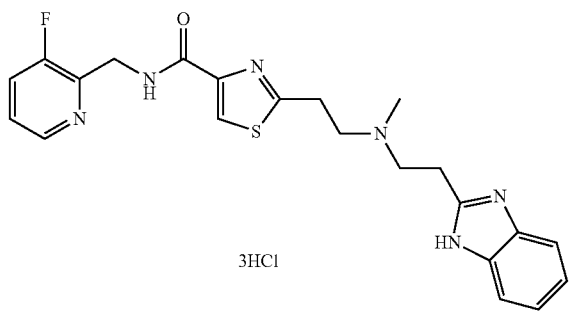

Exp. 94

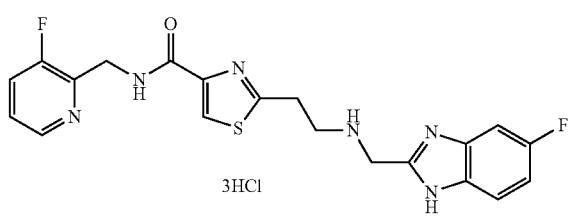

Exp. 112

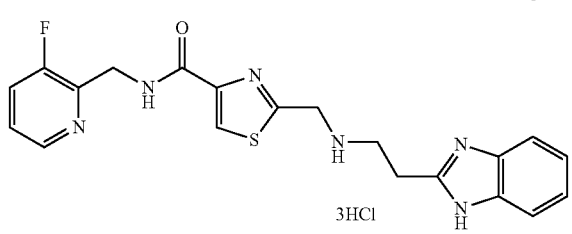

Exp. 114

Exp. 118

-continued

Exp. 119
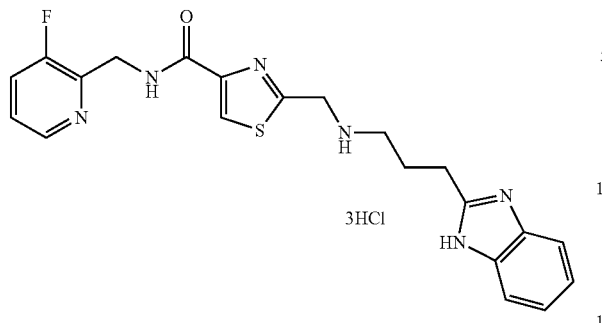
3HCl

Exp.120
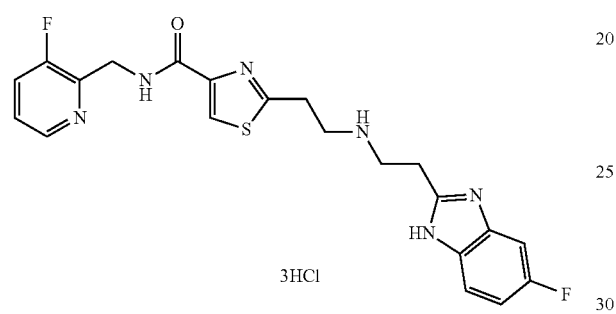
3HCl

Exp. 125
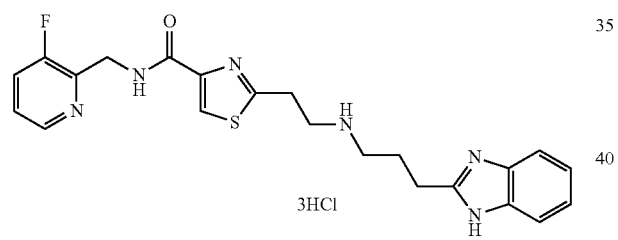
3HCl

Exp. 126
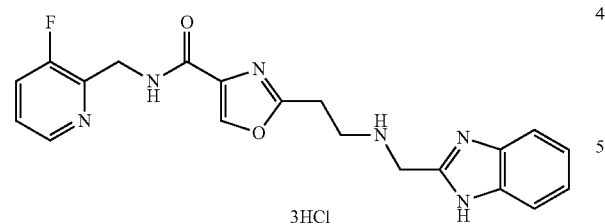
3HCl

Exp. 127
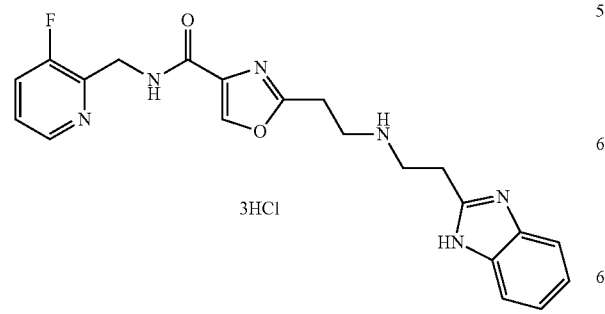
3HCl

-continued

Exp. 134
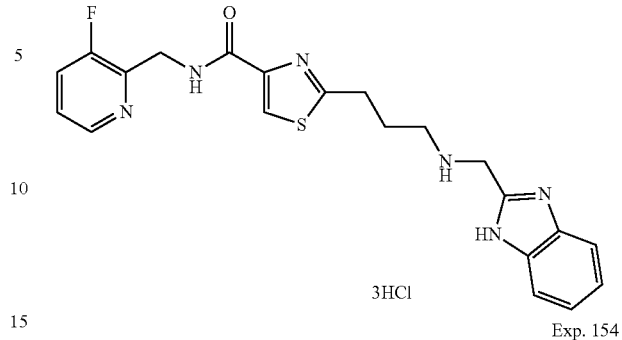
3HCl

Exp. 154

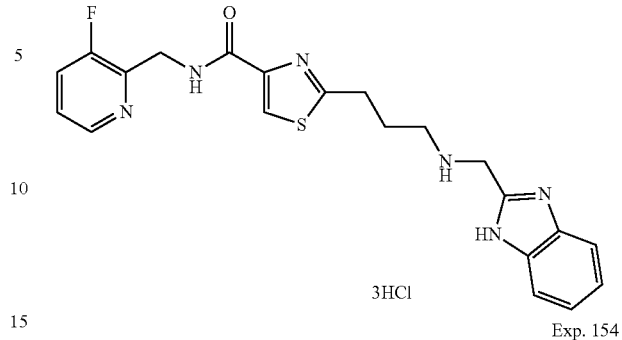

Therein and throughout the invention, the above-mentioned substituent groups are defined as follows: Optionally substituted alkyl preferably includes:

linear or branched alkyl preferably containing 1 to 8, more preferably 1 to 6, particularly preferably 1 to 4, even more preferred 1, 2 or 3 carbon atoms, also being indicated as $C_1$-$C_4$-alkyl or $C_1$-$C_3$-alkyl.

Optionally substituted alkyl further includes cycloalkyl containing preferably 3 to 8, more preferably 5 or 6 carbon atoms.

Examples of alkyl residues containing 1 to 8 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Those containing 1 to 4 carbon atoms ($C_1$-$C_4$-alkyl), such as in particular methyl, ethyl, n-propyl, i-propyl, n-butyl, i-butyl, sec-butyl, and t-butyl are preferred. $C_1$-$C_3$ alkyl, in particular, methyl, ethyl, propyl and i-propyl are more preferred. Most preferred are $C_1$ and $C_2$ alkyl, such as methyl and ethyl.

Cycloalkyl residues containing 3 to 8 carbon atoms preferably include: a cyclopropyl group, a cyclobutyl group, a cyclopentyl group, a cyclohexyl group, a cycloheptyl group and a cyclooctyl group. A cyclopropyl group, a cyclobutyl group, a cyclopentyl group and a cyclohexyl group are preferred. A cyclopropyl group is particularly preferred.

Substituents of the above-defined optionally substituted alkyl preferably include 1, 2 or 3 of the same or different substituents, selected, for example, from the group consisting of: halogen as defined below, such as preferably F, cycloalkyl as defined above, such as preferably cyclopropyl, optionally substituted heteroaryl as defined below, such as preferably a benzimidazolyl group, optionally substituted amino as defined below, such as preferably an amino group or benzyloxycarbonylamino, a carboxyl group, an aminocarbonyl group as defined below, as well as an alkylene group such as in particular a methylene-group, forming for example a methylene-substituted ethyl-group ($CH_3$—(C=$CH_2$)— or *>= wherein * indicates the binding site).

Within the meaning of the present invention, halogen includes fluorine, chlorine, bromine and iodine, preferably fluorine or chlorine, most preferred is fluorine.

Examples of a linear or branched alkyl residue substituted by halogen and containing 1 to 8 carbon atoms include: a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a difluoroethyl group such as a 1,2-difluoroethyl group, a 1,2-dichloroethyl group, a 1,2-dibromoethyl group, a 2,2-difluoroethyl group, a 2,2-dichloroethyl group, a 2,2-dibromoethyl group a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptoyl group, a 7-fluoroheptyl group, a 7-chloroheptyl group, a 7-bromoheptyl group, a perfluoroheptyl group, etc. Fluoroalkyl, difluoroalkyl and trifluoroalkyl are mentioned in particular, and trifluoromethyl and mono- and di-fluoroethyl is preferred. Particularly preferred is trifluoromethyl.

Examples of a cycloalkyl-substituted alkyl group include the above-mentioned alkyl residues containing 1 to 3, preferably 1 cycloalkyl group such as, for example: cyclopropylmethyl, cyclobutylmethyl, cyclopentylmethyl cyclohexylmethyl, 2-cyclopropylethyl, 2-cyclobutylethyl, 2-cyclopentylethyl 2-cyclohexylethyl, 2- or 3-cyclopropylpropyl, 2- or 3-cyclobutylpropyl, 2- or 3-cyclopentylpropyl, 2- or 3-cyclohexylpropyl, etc. Preferred is cyclopropylmethyl.

Examples of a heteroaryl-substituted alkyl group include the above-mentioned alkyl residues containing 1 to 3, preferably 1 (optionally substituted) heteroaryl group, such as, for example a pyridinyl, a pyridazinyl, a pyrimidinyl, a pyrazinyl, a pyrazolyl, an imidazolyl, a benzimidazolyl, a thiophenyl, or an oxazolyl group, such as pyridine-2-yl-methyl, pyridine-3-yl-methyl, pyridine-4-yl-methyl, 2-pyridine-2-yl-ethyl, 2-pyridine-1-yl-ethyl, 2-pyridine-3-yl-ethyl, pyridazine-3-yl-methyl, pyrimidine-2-yl-methyl, pyrimidine-4-yl-methyl, pyrazine-2-yl-methyl, pyrazol-3-yl-methyl, pyrazol-4-yl-methyl, pyrazol-5-yl-methyl, imidazole-2-yl-methyl, imidazole-5-yl-methyl, benzimidazol-2-yl-methyl, thiophen-2-yl-methyl, thiophen-3-yl-methyl, 1,3-oxazole-2-yl-methyl.

Preferred is an alkyl group which is substituted with a benzimidazolyl group, such as benzimidazol-2-yl-methyl and benzimidazol-2-yl-ethyl.

Examples of an amino-substituted alkyl residue include the above-mentioned alkyl residues containing 1 to 3, preferably 1 (optionally substituted) amino group, as defined below, such as, for example, aminoalkyl ($NH_2$-alkyl) or mono- or dialkylamino-alkyl, such as aminomethyl, 2-aminoethyl, 2- or 3-aminopropyl, methylaminomethyl, methylaminoethyl, methylaminopropyl, 2-ethylaminomethyl, 3-ethylaminomethyl, 2-ethylaminoethyl, 3-ethylaminoethyl, etc. with 3-aminopropyl being preferred, or an alkyl group, which may be substituted with an optionally substituted alkyloxycarbonylamino group such as a group according to formula

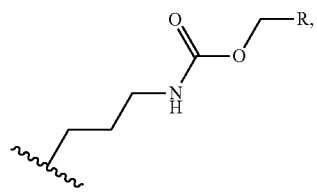

wherein R defines a phenyl group, forming a benzyloxycarbonylaminopropyl group.

Optionally substituted amino according to the invention preferably includes: amino (—$NH_2$), optionally substituted mono- or dialkylamino (alkyl-NH—, (alkyl)$_2$N—), wherein with respect to "alkyl" reference can be made to the definition of optionally substituted alkyl above. Preferred is mono- or dimethylamino, mono- or diethylamino and mono-propylamino. Most preferred is an amino group (—$NH_2$), and monopropylamino.

Further, in the sense of the present invention, a carboxyl group indicates a group [—(C=O)—OH] and an aminocarbonyl group indicates a group [$NH_2$—(C=O)—].

Optionally substituted alkoxy includes an optionally substituted alkyl-O-group, wherein reference may be made to the foregoing definition of the alkyl group. Preferred alkoxy groups are linear or branched alkoxy groups containing up to 6 carbon atoms such as a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, as well as cycloalkyloxy groups such as a cyclopentyloxy group or a cyclohexyloxy group. A methoxy group, an ethoxy group, an n-propyloxy group and an i-propyloxy group are preferred. A methoxy and ethoxy group is more preferred. Particularly preferred is a methoxy group.

Throughout the invention, optionally substituted alkanediyl is preferably a divalent straight-chained or branched alkanediyl radical having from 1 to 6, preferably from 1 to 4, more preferably 1, 2 or 3 carbon atoms, which can optionally carry from 1 to 3, preferably 1 or 2 substituents selected from the group consisting of halogen, hydroxyl (—OH), an oxo group ((=O; forming a carbonyl or acyl group [—(C=O)—]) and an alkyl group as defined above such as preferably methyl. The following may be mentioned as preferred examples: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl, butane-2,3-diyl, butane-1,1-diyl, butane-2,2-diyl, butane-3,3-diyl, pentane-1,5-diyl, etc. Particularly preferred is methylene, ethane-1,2-diyl, ethane-, 1-diyl, propane-1,3-diyl, propane-2,2-diyl, and butane-2,2-diyl. Most preferred are methylene, ethane-1,2-diyl and propane-1,3-diyl.

A preferred substituted alkanediyl radical is a hydroxy-substituted alkanediyl such as a hydroxy-substituted ethanediyl, an oxo-substituted alkanediyl such as an oxo-substituted methylene or ethanediyl radical, forming a carbonyl or an acyl (acetyl) group, a halogen substituted alkanediyl group such as an alkanediyl group being substituted with one or two halogen atoms selected from F and Cl, preferably 2,2-di-fluoro-ethanediyl, or an alkanediyl group which is substituted with a methyl group.

According to the present invention it is further possible that A, having the meaning of a linear or branched alkanediyl group as defined above, and $R^2$, having the meaning of an optionally substituted alkyl group as defined above, together with the nitrogen atom to which they are bonded form an optionally substituted 4- to 6-membered ring, which may be substituted with 1 to 3 substituents as defined above. Accordingly, $A^1$ and $R^2$ may together from a group according to one the following formulae

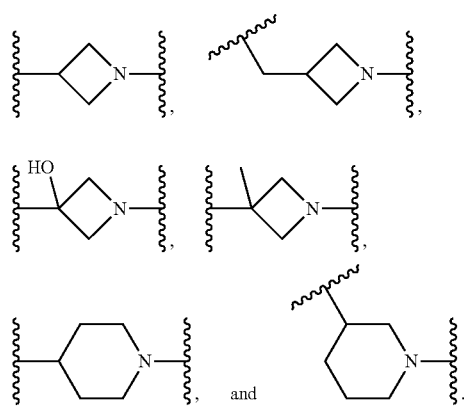

Therein a (substituted or unsubstituted) 4-membered ring-formation is preferred, such as very particularly a group

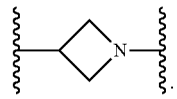 [SMILES: *C1CN(*)C1]

Therein the left-hand binding site indicates the direct binding site to the heterocyclic 5-membered ring between the positions $X^1$ and $X^2$ in formula (I) of the present invention. The right-hand binding site indicates the binding site to the group $A^2$ having the meaning of an alkanediyl group as defined herein.

In the formula (I) as defined herein n has the meaning of an integer of 1 to 3, including 1, 2 or 3 thus indicating a methylene-group, an ethane-1,2-diyl group or a propane-1,3-diyl group. More preferably n is 1 or 2 and even more preferably n is 1, indicating a methylene group.

In the present invention the individual substituents of the formula (I) above may have the following meaning:
A) $X^1$ is N or O; and
   $X^2$ is N, S or O;
   with the proviso that $X^1$ and $X^2$ are different;
   thus forming 5-membered heterocycles according to the formulae

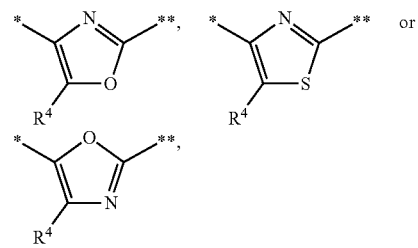

wherein * indicates the binding site to the aminocarbonyl-group and ** indicates the binding site to the $A^1$-group.
B) n is an integer of 1, 2 or 3; preferably n is 1 or 2, more preferably n is 1.
C) $R^1$ is selected from the group consisting of
   hydrogen and
   optionally substituted alkyl (as defined above);
   preferably $R^1$ is hydrogen or methyl, more preferably $R^1$ is hydrogen.
D) $R^2$ is selected from the group consisting of
   hydrogen, and
   optionally substituted alkyl (as defined above);
   preferably $R^2$ is hydrogen or $C_1$-$C_4$-alkyl, more preferably $R^2$ is hydrogen or methyl, even more preferably $R^2$ is hydrogen.
E) $R^3$ indicates 1, 2 or 3 optional substituents, which may independently be selected from the group consisting of
   halogen (as defined above),
   cyano,
   optionally substituted alkyl (as defined above),
   optionally substituted alkoxy (as defined above), and
   a carboxyl group (as defined above);
   preferably $R^3$ indicates 1 or 2 optional substituents, which may independently be selected from the consisting of
   halogen,
   cyano, alkyl (as defined above), which may be substituted with 1, 2 or 3 halogen atoms (as defined above),
optionally substituted alkoxy (as defined above), and
a carboxyl group (as defined above);
more preferably $R^3$ indicates 1 or 2 optional substituents, which may independently be selected from the group consisting of
F and Cl,
cyano,
trifluoromethyl,
methoxy, and
a carboxyl group;
even more preferably $R^3$ is hydrogen, indicating an unsubstituted terminal benzimidazolyl-ring in formula (I)

F) $R^4$ is selected from the group consisting of
hydrogen,
halogen (as defined above),
$C_1$-$C_3$-alkyl, and
halogen substituted alkyl (as defined above);
preferably $R^4$ is selected from the group consisting of
hydrogen
Cl,
methyl, ethyl, iso-propyl, and
trifluoromethyl;
more preferably $R^4$ is selected from the group consisting of
hydrogen,
Cl,
methyl, and
trifluoromethyl;
more preferably $R^4$ is selected from the group consisting of
hydrogen,
Cl, and
methyl,
even more preferably $R^4$ is hydrogen.

G) $A^1$ is alkanediyl,
preferably $A^1$ is methylene or ethane-1,2-diyl, more preferably $A^1$ is ethane-1,2-diyl.

H) $A^2$ is alkanediyl,
preferably $A^2$ is methylene, ethane-1,2-diyl or propane-1,3-diyl,
more preferably $A^2$ is methylene or ethane-1,2-diyl, even more preferably $A^2$ is ethane-1,2-diyl.

I) Or $A^1$ and $R^2$ together with the nitrogen atom to which they are bonded form an optionally substituted 4- to 6-membered ring as defined above;
therein $A^1$ and $R^2$ together with the nitrogen atom to which they are bonded preferably form an optionally substituted 4-membered ring as defined above,
therein $A^1$ and $R^2$ together with the nitrogen atom to which they are bonded more preferably form an unsubstituted 4-membered ring (azetidinyl-ring).

Therein, the substituents of the compounds of the following (I) may in particular have the following meaning:
n has any of the meanings according to B) above and the remaining substituents may have any of the meanings as defined in A) and C) to I).
$R^1$ has any of the meanings according to C) above and the remaining substituents may have any of the meanings as defined in A) and B) and D) to I).
$R^2$ has any of the meanings according to D) above and the remaining substituents may have any of the meanings as defined in A) to C) and E) to H) or I).
$R^3$ has any of the meanings according to E) above and the remaining substituents may have any of the meanings as defined in A) to D) and F) to I).
$R^4$ has any of the meanings according to F) above and the remaining substituents may have any of the meanings as defined in A) to E) and G) to I).
$A^1$ has any of the meanings according to G) above and the remaining substituents may have any of the meanings as defined in A) to F) and H) or I).
$A^2$ has any of the meanings according to H) above and the remaining substituents may have any of the meanings as defined in A) to G) and I).
$R^2$ and $A^1$ have any of the meanings as defined in I) and the remaining substituents may have any of the meanings as defined in A) to C), E), F) and H).

A preferred embodiment of the present invention relates to novel salts of compounds of general formula (I) as defined above, wherein
$X^1$ is N or O; and
$X^2$ is N, S or O;
with the proviso that $X^1$ and $X^2$ are different;
$R^1$ is hydrogen;
n is 1, 2 or 3;
$A^1$ is methylene or ethane-1,2-diyl;
$A^2$ is methylene, ethane-1,2-diyl or propane-1,3-diyl;
$R^2$ is hydrogen or $C_1$-$C_4$-alkyl;
or
$A^1$ and $R^2$ together with the nitrogen atom to which they are bonded form an optionally substituted 4-membered ring;
$R^3$ indicates 1 or 2 optional substituents, which may independently be selected from the group consisting of
halogen,
cyano,
alkyl, which may be substituted with 1, 2 or 3 halogen atoms,
optionally substituted alkoxy, and
a carboxyl group;
$R^4$ is selected from the group consisting of
hydrogen
Cl,
methyl, ethyl, iso-propyl, and
trifluoromethyl;
wherein the salts are selected from salts of the compounds of formula (I) with acids from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid, being characterized by a ratio of compound (I):acid of 1 to 2:1 to 3; and
wherein the 3HCl salts as defined above are excluded.

A further preferred embodiment of the present invention relates to novel salts of compounds of general formula (I) as defined above, wherein
$X^1$ is N or O; and
$X^2$ is N, S or O;
with the proviso that $X^1$ and $X^2$ are different;
$R^1$ is hydrogen;
n is 1 or 2;
$A^1$ is methylene or ethane-1,2-diyl;
$A^2$ is methylene, ethane-1,2-diyl or propane-1,3-diyl;
$R^2$ is hydrogen or methyl;
or
$A^1$ and $R^2$ together with the nitrogen atom to which they are bonded form an unsubstituted 4-membered ring;

$R^3$ indicates 1 or 2 optional substituents, which may independently be selected from the group consisting of
  F and Cl,
  cyano,
  trifluoromethyl,
  methoxy, and
  a carboxyl group;
$R^4$ is selected from the group consisting of
  hydrogen,
  Cl,
  methyl, and
  trifluoromethyl;
wherein the salts are selected from salts of the compounds of formula (I) with acids from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid, being characterized by a ratio of compound (I):acid of 1 to 2:1 to 3; and
wherein the 3HCl salts as defined above are excluded.

A further preferred embodiment of the present invention relates to novel salts of compounds of general formula (I) as defined above, wherein
$X^1$ is N or O; and
$X^2$ is N, S or O;
with the proviso that $X^1$ and $X^2$ are different;
$R^1$ is hydrogen;
n is 1;
$A^1$ is methylene or ethane-1,2-diyl;
$A^2$ is methylene, ethane-1,2-diyl or propane-1,3-diyl;
$R^2$ is hydrogen;
or
$A^1$ and $R^2$ together with the nitrogen atom to which they are bonded form an unsubstituted 4-membered ring;
$R^3$ indicates hydrogen, thus forming an unsubstituted terminal benzimidazolyl-ring;
$R^4$ is selected from the group consisting of
  hydrogen,
  Cl, and
  methyl;
wherein the salts are selected from salts of the compounds of formula (I) with acids from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid, being characterized by a ratio of compound (I):acid of 1 to 2:1 to 3; and
wherein the 3HCl salts as defined above are excluded.

A further preferred embodiment of the present invention relates to novel salts of compounds of general formula (I) as defined above, wherein
$X^1$ is N or O; and
$X^2$ is N, S or O;
with the proviso that $X^1$ and $X^2$ are different;
$R^1$ is hydrogen;
n is 1;
$A^1$ is methylene or ethane-1,2-diyl;
$A^2$ is methylene, ethane-1,2-diyl or propane-1,3-diyl;
$R^2$ is hydrogen;
or
$A^1$ and $R^2$ together with the nitrogen atom to which they are bonded form an unsubstituted 4-membered ring;
$R^3$ indicates hydrogen, thus forming an unsubstituted terminal benzimidazolyl-ring; and
$R^4$ is hydrogen;
wherein the salts are selected from salts of the compounds of formula (I) with acids from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid, being characterized by a ratio of compound (I):acid of 1 to 2:1 to 3; and
wherein the 3HCl salts as defined above are excluded.

A further preferred embodiment of the present invention relates to novel salts of compounds of general formula (I) as defined above, wherein
n=1;
$R^3$=hydrogen;
$R^4$=hydrogen;
$A^1$=ethane-1,2-diyl;
$A^2$=methylene, ethane-1,2-diyl or propane-1,3-diyl;
$R^2$=hydrogen;
or $A^1$ and $R^2$ together with the nitrogen atom to which they are bonded form an optionally substituted 4-membered ring, forming compounds according to formula (II) or (III) below:

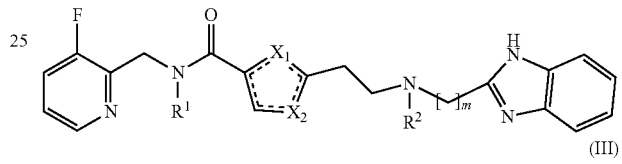

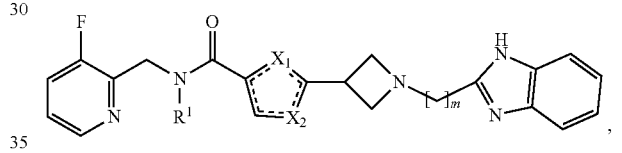

wherein in formula (II) and (III)
m is an integer of 1, 2 or 3 and
$X^1$, $X^2$, and $R^1$ have the meaning as defined above in any embodiment of the invention comprising compounds of formula (I).

In particular, in the formulae (II) and (III) $X^1$ and $X^2$ have the meaning as defined above in A).

In formula (II) $R^1$ and $R^2$ are preferably hydrogen.

In formula (III) $R^1$ is preferably hydrogen and m is preferably 2.

A further preferred embodiment of the present invention relates to novel salts of compounds of general formula (II) as defined above, wherein
  $X^1$ and $X^2$ are selected from N and O and are different;
  $R^1$=hydrogen;
  $R^2$=hydrogen; and
  m=2.

In the following the compounds (I), (II) or (III) forming the salts of the present invention are also referred to as "base" or "free base". The compounds according to formula (I), (II) or (III) in the form the free base have at least one basic group, such as amino groups, to which acidic groups can bind.

According to the present invention the salts of compounds of formula (I), (II) or (III) as defined in any of the embodiments of the present invention above may be selected from salts having a ratio of base (compound (I), (II) or (III)):acid of 1 to 2:1 to 3, wherein with respect to the salt forming acids reference is made to the selection defined above.

The invention also covers mixed salts of a base (compound (I), (II) or (III)) with one or more of the acids indicated above and which may have the same or different ratios base:acid according to the present invention. The acids provide the counter anion for the cationic form of compound (I), (II) or (III).

Accordingly, the selected acids of the present invention provide the following counter anions:

| acid (Abbreviation) | anion(s) |
|---|---|
| benzoic acid (BNZ) | |
| citric acid (CIT) | |
| fumaric acid (FUM) | |
| hydrochloric acid (HCL) HCl | Cl⁻ |
| lactic acid/L-lactic acid (LAC or LLAC) | |
| malic acid/L-malic acid (MLA) | |
| maleic acid (MLE) | |
| methanesulfonic acid (MES) | |
| phosphoric acid (PO4) | PO₄³⁻ |
| succinic acid (SUC) | |
| sulfuric acid (SO4) | SO₄²⁻ |

-continued

| acid (Abbreviation) | anion(s) |
|---|---|
| tartaric acid/L-tartaric acid (TAR or LTAR) | |
| toluenesulfonic acid (TOS) | |

According to the present invention the salts of compounds (I), (II) or (III) are characterized by a selected ratio of base:acid, i.e. compound (I), (II) or (III):the acids as defined above, in the range of 1.0 to 2.0 (mol base):1.0 to 3.0 (mol acid). In a particular embodiment the selected ratio of base:acid is 1.0 to 2.0 (mol base):1.0 to 2.0 (mol acid).

Particular examples comprise the following ratios of base:acid, i.e. compound (I), (II) or (III): the acids as defined above:

1.0 (mol base):1.0 (mol acid);
1.0 (mol base):1.25 (mol acid):
1.0 (mol base):1.35 (mol acid);
1.0 (mol base):1.5 (mol acid);
1.0 (mol base):1.75 (mol acid);
1.0 (mol base):2.0 (mol acid); and
2.0 (mol base):1.0 (mol acid).

Therein, a salt having a ratio of base:acid of 1:1 is also called "mono-salt(s)" or "1:1 salt(s)". For example, a mono-HCl salt is also designated as 1HCl or 1HCl salt.

Therein, a salt having a ratio of base:acid of 1:2 is also called "di-salt(s)" or "1:2 salt(s)". For example, a di-HCl salt is also designated as 2HCl or 2HCl salt.

Therein, a salt having a ratio of base:acid of 1:3 is also called "tri-salt(s)", "triple salts(s)" or "1:3 salt(s)". For example, a tri-HCl salt is also designated as 3HCl or 3HCl salt.

A salt having a ratio of base:acid of 1:1.25 is also called "1:1.25 salt(s)".

A salt having a ratio of base:acid of 1:1.35 is also called "1:1.35 salt(s)".

A salt having a ratio of base:acid of 1:1.5 is also called "1:1.5 salt(s)".

A salt having a ratio of base:acid of 1:1.75 is also called "1:1.75 salt(s)".

A salt having a ratio of base:acid of 2:1 is also called "hemi-salt(s)" or "2:1 salt(s)".

In a further preferred embodiment of the present invention the salts of compounds of formula (I) as defined above are selected from mono-salts (1:1 salts) with one or more of the acids as defined above.

A further embodiment of the present invention relates to the salts of compounds of formula (I), (II) or (III) as defined above wherein the acids are selected from the group consisting of citric acid, hydrochloric acid, maleic acid, phosphoric acid and sulfuric acid.

A further embodiment of the present invention relates to the salts of compounds of formula (I), (II) or (III) as defined above wherein the acids are selected from the group consisting of phosphoric acid and sulfuric acid.

The salts of compounds according to the present invention may be present in amorphous, polymorphous, crystalline and/or semi-crystalline (partly crystalline) form as well as in the form of a solvate of the salt.

Preferably the salts of the present invention are present in crystalline and/or semi-crystalline (partly crystalline) form and/or in the form of solvates thereof.

The preferable crystallinity of the salts or salt solvates of the present invention can be determined by using conventional analytical methods, such as especially by using the various X-ray methods, which permit a clear and simple analysis of the salt compounds. In particular, the grade of crystallinity can be determined or confirmed by using Powder X-ray diffraction (reflection) methods as described for example in the Examples below, or by using Powder X-ray diffraction (transmission) methods as described for example in the Examples below (both being hereinafter also abbreviated as PXRD). For crystalline solids having identical chemical composition, the different resulting crystal gratings are summarized by the term polymorphism.

Preferably the salts of the present invention exhibit a degree of crystallinity of more than 30%, more preferably more than 40%, yet more preferably more than 50% such as at least 55-60%, measured with a PXRD method as described herein.

The salts of the present invention may be present as solvates and/or hydrates, which may be formed by attraction, association, adsorption, adhesion, embedding or complexation of molecules of a solvent in the grystal grating of the salts of the present invention. The solvent molecules which may be embedded in the crystal grating may derive from the solvents used for crystallization as well as from water deriving from the relative humidity.

Solvents used for crystallization comprise acetonitrile, dichloromethane, alcohols, such as especially methanol, ethanol, 2-propanol (iso-propanol), aldehydes, ketones, especially acetone, ethers, e.g. tetrahydrofuran (THF) or dioxane, esters, e.g. ethyl acetate, or alkanes, such as especially pentane, hexane, heptane or cyclohexane and water, and mixtures thereof. Preferred solvents used for crystallization are selected from the group consisting of acetonitrile, dichloromethane, methanol, ethanol, 2-propanol, ethyl acetate, THF, water and mixtures thereof.

Particularly preferred solvents used for crystallization are selected from the group consisting of acetonitrile, methanol, ethanol, 2-propanol, ethyl acetate, THF, water and mixtures thereof. Preferred water/solvent mixtures comprise mixtures of water and acetone, mixtures of water and ethanol and mixtures of water and methanol, wherein mixtures of water and ethanol and mixtures of water and methanol are preferred.

Particularly preferred are solvents used for crystallization, which are selected from the group consisting of acetonitrile, dichloromethane, ethanol, 2-propanol (iso-propanol), acetone and ethyl acetate as well as mixtures thereof with water, such as in particular mixtures of ethanol and water and mixtures of acetone and water. Particularly preferred mixtures are the following mixtures of solvent and water (ratios of solvent mixtures given anywhere herein always refer to vol:vol):

acetone:water=9:1 (vol:vol)
acetone:water=95:1 (vol:vol)
ethanol:water=4:1 (vol:vol)
ethanol:water=3:1 (vol:vol)
ethanol:water=8:2 (vol:vol).

The extent to which a selected solvent or water leads to a solvate or hydrate in crystallisation and in the subsequent process steps or leads directly to the free base is generally unpredictable and depends on the combinations of process conditions and the various interactions between the selected compound (I), the counter anion from the selected acid and the selected solvent and humidity conditions. The salt solvates or hydrates may be preferred, as solvent or water molecules in the crystal structure are bound by strong intermolecular forces and thereby may represent an element of structure formation of these crystals which, in part, may improve stability of the salt. However, solvent and/or water molecules are also existing in certain crystal lattices which are bound by rather weak intermolecular forces. Such molecules are more or less integrated in the crystal structure forming, but to a lower energetic effect. The solvent and/or water content of the solvates is also dependent on the drying and ambient conditions (i.e. relative humidity). in the case of stable solvates or hydrates, there are usually clear stoichiometric ratios between the active compound (i.e. the salt of the present invention) and the solvent or water. In many cases these ratios do not fulfil completely the stoichiometric value, normally it is approached by lower values compared to theory because of certain crystal defects. The ratio of organic molecules to solvent or water molecules for the weaker bound water may vary to a considerable extend, for example, extending over di-, tri- or tetra-hydrates. On the other hand, in amorphous solids, the molecular structure classification of solvent and/or water is not stoichiometric; the classification may however also be stoichiometric only by chance. In some cases, it is not possible to classify the exact stoichiometry of the solvent or water molecules, since layer structures form so that the embedded solvent or water molecules cannot be determined in defined form.

The solvent and/or water content in amorphous solids as well as in crystalline solvates or hydrates can, in general, be determined by conventional methods, such as e.g. by using the well-known Karl-Fischer titration method, by carrying out dynamic vapor sorption (DVS) measurements, by carrying out thermogravimetric measurements (TG-FTIR), as described for example in the Examples below. Also elemental analysis or methods for structural analysis, such as $^1$H NMR spectroscopy or Raman spectroscopy (FT Raman spectroscopy) may give information about the degree of solvate or hydrate formation and/or may be used to confirm or validate the results of the Karl-Fischer (KF), DVS or TG-FTIR measurements.

Examples of solvates and/or hydrates according to the present invention comprise for example, hemi- (0.5), mono-, sesqui- (1.5), di-, tri-, tetra-, penta-, hexa-, hepta-, octa-, nona-deca-, etc. solvates or hydrates, respectively. Further intermediate solvation-degrees are also possible, such as solvation with 2.5, 3.5, 4.5 etc. solvent and/or water molecules.

Preferred examples of solvates and/or hydrates comprise hydrates with about 1.5, 2.5, 3, 4 and 7 water molecules. Further preferred examples of solvates and/or hydrates comprise hydrates with about 0.5, 1.5, 2.5, 3, 4, 6 and 7 water molecules. Anhydrous salts are also preferred. It is further possible, that solvent and/or water residues remain in the salt in non-stoichiometric amounts.

Further, it is possible that mixtures of water and solvent remain in the salt forming so-called mixed hydrate/solvate forms. Examples of such mixed hydrate/solvate forms comprise in particular
acetone/water, preferably with a ratio of 1 to 4:1; such as in particular 4:1;
methanol/water, preferably with a ratio of 3 to 9:1; such as in particular 3:1, 4:1 and 9:1;
ethanol/water, preferably with a ratio of 1 to 4:1; such as in particular 3:1 and 4:1.

Any reference hereinbefore and hereinafter, to the salts according to the invention is to be understood as referring also to the corresponding solvates, such as hydrates, solvates and mixed hydrate/solvate forms, and polymorphous modifications, and also amorphous forms, as appropriate and expedient.

The novel salts of the present invention exhibit good solubility and are stable and are of good quality also during storage and distribution.

The respective stability of the resulting crystalline or amorphous solids in the form of salts, solvates and hydrates (including mixed hydrate/solvate forms), as well as the corresponding salt solvates or salt hydrates, can be determined by conventional experimentation. Improved stability can comprise improved hygroscopic properties, improved melting enthalpy. An essential feature for the quality of a pure active substance both for the physical-chemical procedures such as drying, sieving, grinding, and in the galenic processes which are carried out with pharmaceutical excipients, namely in mixing processes, in granulation, in spray-drying, in tableting, is the water absorption or water loss of this active substance depending on temperature and the relative humidity of the environment in question. With certain formulations, free and bound water is without doubt introduced with excipients and/or water is added to the process mass for reasons associated with the respective formulation process. In this way, the pharmaceutical active substance is exposed to free water over rather long periods of time, depending on the temperature of the different activity (partial vapour pressure). Therefrom it becomes apparent that particularly stable pure compounds are advantageous under pharmaceutical-galenic point of views and their suitability to be formulated in all galenic process stages and different dosage forms.

The salts according to the present invention may exist in isolated and essentially pure form, for example in a degree of purity of ≥65%, preferably ≥70%, more preferably ≥75%, more preferably ≥80%.

In the sense of the present invention the term "salts", as used herein, includes the corresponding solvates, hydrates and mixed hydrate/solvate forms etc. as well as the different polymorphs thereof, such as in particular the specific polymorphs described herein.

The salts of the present invention can be structurally characterized by conventional methods, such as e.g. elemental analysis, thermogravimetric measurements (TG-FTIR), $^1$H NMR spectroscopy and Raman spectroscopy (FT Raman spectroscopy), differential scanning calorimetry (DSC) for determining the melting point, each as described for example in the Examples below, as well as by combinations of said methods, and in particular in combination with the above cited methods for determining the solvate/hydrate degree.

A further embodiment of the present invention relates to a method of preparing the salts as defined herein. The process for preparing the salts can be described as follows:

The salt formation is carried out in a solvent system, in which the two reactants, namely the base compound (I), (II) or (III) and the respective acid, are sufficiently soluble. It is expedient to use a solvent or solvent mixture, in which the resulting salt is only slightly soluble or not soluble at all, in order to achieve crystallization or precipitation. One variant for the salt formation according to the invention would be to use a solvent in which the respective salt is very soluble, and to subsequently add an anti-solvent to this solution, that is a solvent in which the resulting salt has only poor solubility. A further variant for the salt formation comprises concentrating the salt solution, for example by heating, if necessary under reduced pressure, or by slowly evaporating the solvent, e.g. at room temperature, or by seeding with the addition of seeding crystals, or by setting up water activity required for hydrate formation. Therein the solvents as defined above can be used.

To produce hydrates, a dissolving and crystallizing process may be used, or a water-equilibrating crystallization process.

The dissolving and crystallising process can be described by the following steps:
(i) compound (I), (II) or (III) as the free base is dissolved in an organic solvent,
(ii) the selected acid as defined above, preferably as an aqueous solution, is added to the solution obtained in (i),
(iii) the solution is left standing to induce crystallization,
(iv) the crystals are filtered and dried, to obtain the salt.

In the dissolving process (i), the organic solvent employed is advantageously acetonitrile, dichloromethane, methanol, ethanol, 2-propanol, ethyl acetate, THF, water and mixtures thereof, more preferably acetonitrile, methanol, ethanol, 2-propanol, ethyl acetate, THF, water or a mixtures thereof, such as in particular a mixture with water, e.g. a water and ethanol mixture, a water and methanol mixture or a water and acetone mixture. If necessary, the solvent may be heated to above room temperature to, e.g. 25 to 60° C., more preferably 30 to 50° C.

In the process step (ii), the aqueous solution of the acid employed is advantageously a 5 to 30%, more preferably a 5 to 25%, such as a 10%, solution of the respective acid. In particular the ratio of base:acid is 1:1 (mol:mol). In the case of using phosphoric acid or sulfuric acid also a ratio of base to acid of 10:1 (mol:mol) can be used.

In the process step (iii), the solution is advantageously left standing so as to slowly evaporate the solvent. This is preferably conducted by cooling to room temperature or below, more preferably to −10 to 20° C., still more preferably −5 to 10° C., most preferably 0 to 5° C. Alternatively, the concentration of the solution can also take place by heating to above room temperature, e.g. to >25 to 100° C., more preferably 30 to 70° C. It is typically left standing for 8 to 48 h, preferably 17 to 36 h, more preferably 20 to 30 h.

In the process step (iv), the drying is preferably effected at elevated temperatures, more preferably 20 to 50° C., most preferably 30 to 40° C. In any case the drying must be carried out at temperatures below the melting point of the respective salt. The pressure is preferably selected to be 1 to 100 mbar, preferably 10 to 50 mbar, more preferably 20 to 40 mbar, such as 30 mbar. The drying typically takes place until a constant mass is obtained. Depending on the drying conditions, the drying may take from 5 to 48 h, preferably 10 to 24 h such as 15 to 20 h.

It is also possible to accelerate crystallisation by adding a suitable crystallisation initiator, such as e.g. at least one seed crystal.

In a further preferred embodiment of the present invention 3HCl (3HCl) salts of compounds falling under the definition of the general formula (I), (II) or (III) above are excluded.

A particular embodiment of the present invention relates to the salts of compounds of formula (I) as defined in any of the embodiments above, wherein the compounds of formula (I) are selected from the group consisting of:

| Exp No. | Structure |
|---|---|
| 1 | 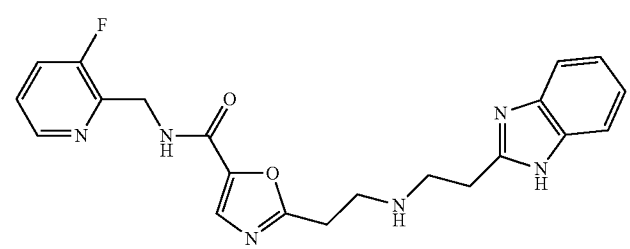 [SMILES: O=C(NCc1ncccc1F)c1cnc(CCNCCc2nc3ccccc3[nH]2)o1] |
| 2 | 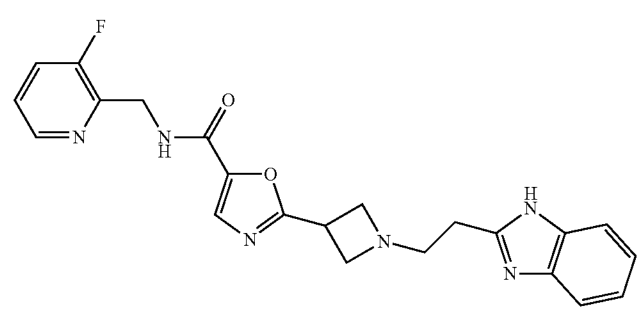 [SMILES: O=C(NCc1ncccc1F)c1cnc(C2CN(CCc3nc4ccccc4[nH]3)C2)o1] |

-continued
| Exp No. | Structure |
|---|---|
| 94 | 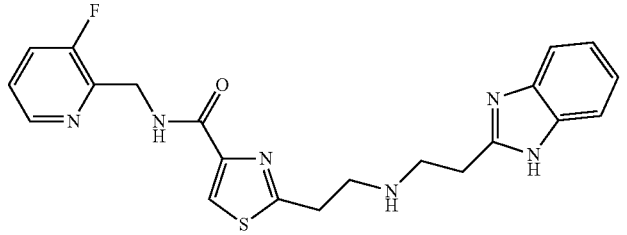 |
| 118 | 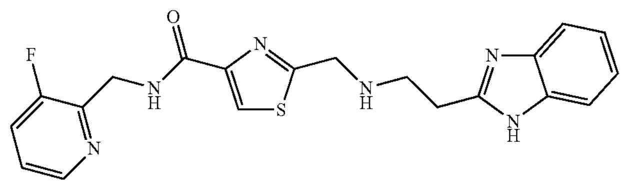 [SMILES: O=C(NCc1ncccc1F)c1csc(CNCCc2nc3ccccc3[nH]2)n1] |
| 126 | 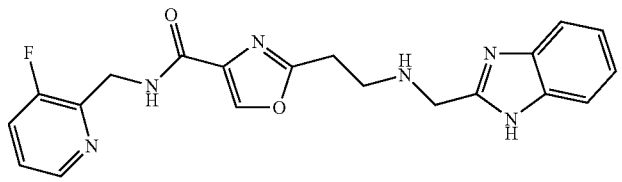 [SMILES: O=C(NCc1ncccc1F)c1coc(CCNCc2nc3ccccc3[nH]2)n1] |
| 127 | 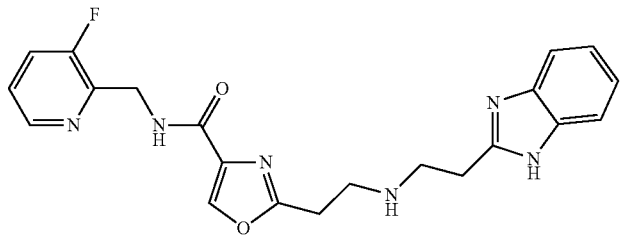 |
| 4 | 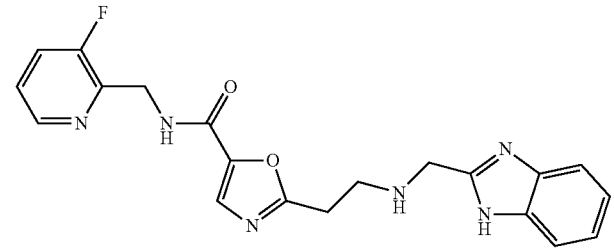 [SMILES: O=C(NCc1ncccc1F)c1cnc(CCNCc2nc3ccccc3[nH]2)o1] |
| 40 | 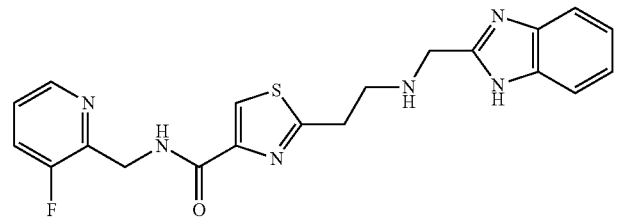 [SMILES: O=C(NCc1ncccc1F)c1csc(CCNCc2nc3ccccc3[nH]2)n1] |

-continued
| Exp No. | Structure |
|---|---|
| 193 | 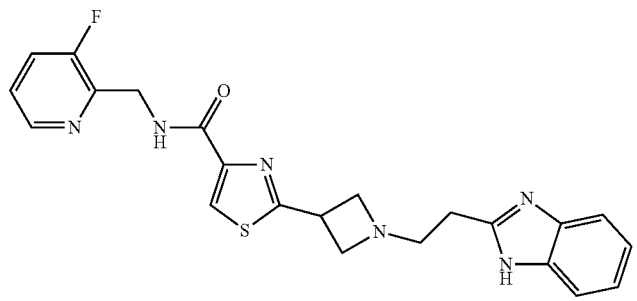 [SMILES: O=C(NCc1ncccc1F)c1csc(C2CN(CCc3nc4ccccc4[nH]3)C2)n1] |
| 206 | 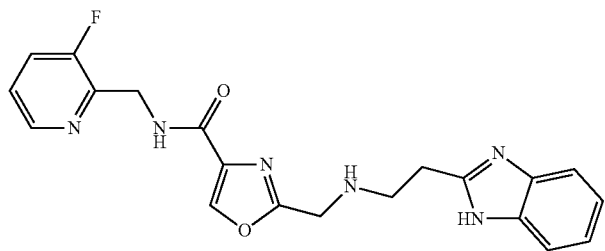 [SMILES: O=C(NCc1ncccc1F)c1coc(CNCCc2nc3ccccc3[nH]2)n1] |
| 208 | 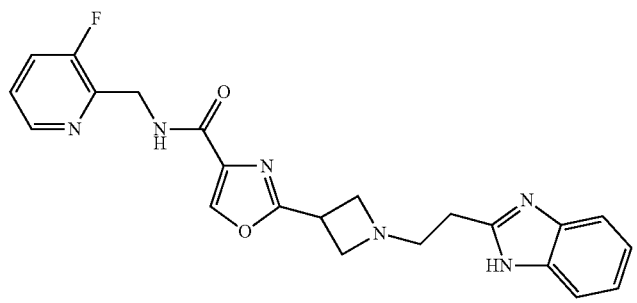 [SMILES: O=C(NCc1ncccc1F)c1coc(C2CN(CCc3nc4ccccc4[nH]3)C2)n1] |
| 233 | 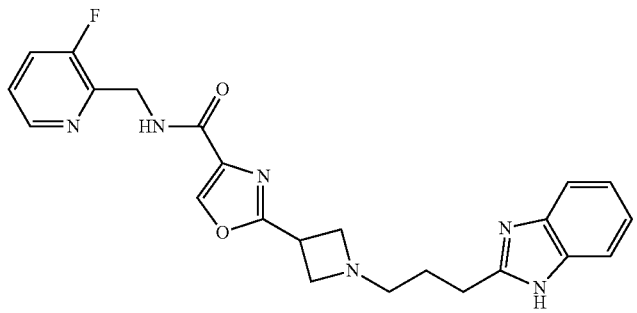 [SMILES: O=C(NCc1ncccc1F)c1coc(C2CN(CCCc3nc4ccccc4[nH]3)C2)n1] |

More preferably the compounds of formula (I) are selected from the group consisting of:
| Exp. No. | Structure |
|---|---|
| 1 | 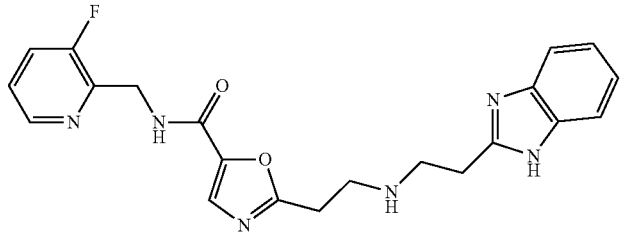 [SMILES: O=C(NCc1ncccc1F)c1cnc(CCNCCc2nc3ccccc3[nH]2)o1] |
| 40 | 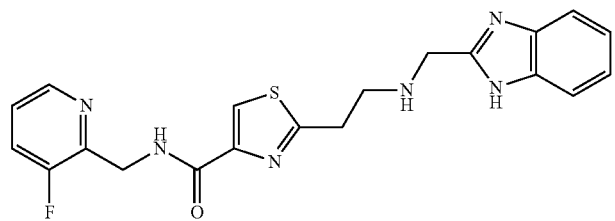 [SMILES: O=C(NCc1ncccc1F)c1csc(CCNCc2nc3ccccc3[nH]2)n1] |
| 94 | 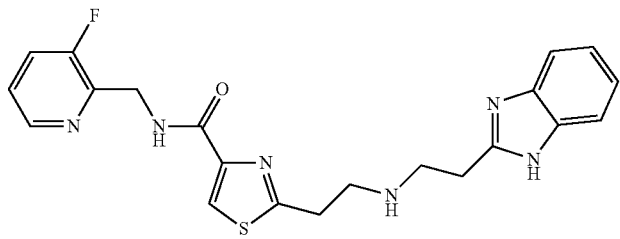 |
| 127 | 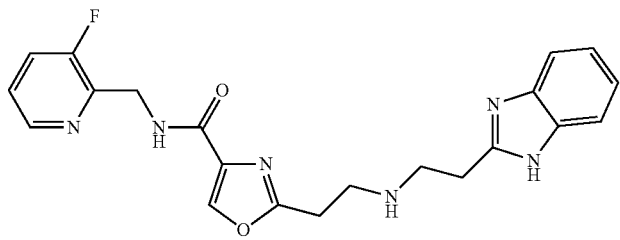 [SMILES: O=C(NCc1ncccc1F)c1coc(CCNCCc2nc3ccccc3[nH]2)n1] |
| 208 | 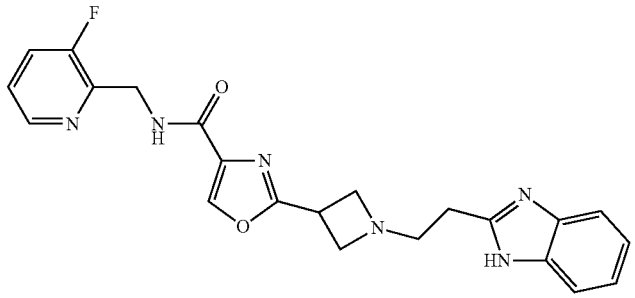 [SMILES: O=C(NCc1ncccc1F)c1coc(C2CN(CCc3nc4ccccc4[nH]3)C2)n1] |

Even more preferably the present invention relates to salts as defined in any of the embodiments above, wherein the compound of formula (I) is

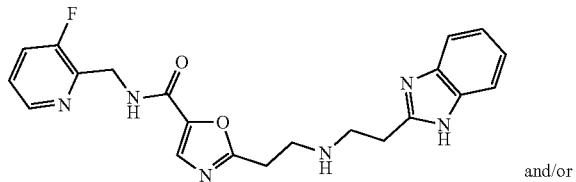

and/or

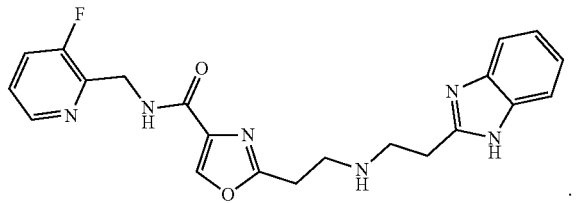

A further particularly preferred embodiment of the present invention relates to the salts of compounds of formula (I) as defined in any of the embodiments above, wherein the acids are selected from the group consisting of phosphoric acid and sulfuric acid.

A further particularly preferred embodiment of the present invention relates to the salts of compounds of formula (I) as defined in any of the embodiments above, wherein the solvents for crystallization are selected from the group consisting of acetonitrile, dichloromethane, ethanol, 2-propanol (iso-propanol), acetone and ethyl acetate as well as mixtures thereof with water, such as in particular mixtures of ethanol and water and mixtures of acetone and water. Particularly preferred mixtures are the following mixtures of solvent and water:

acetone:water=9:1 (vol:vol)
acetone:water=95:1 (vol:vol)
ethanol:water=4:1 (vol:vol)
ethanol:water=3:1 (vol:vol)
ethanol:water=8:2 (vol:vol).

A further particularly preferred embodiment of the present invention relates to the salts of compounds of formula (I) as defined in any of the embodiments above, wherein the acid is phosphoric acid and said phosphate salt is characterized by a ratio of compound (I):acid of 1 to 2:1, preferably by a ratio of compound (I):acid of 1:1 or of 2:1.

More preferably such preferred phosphate salts are obtained by crystallization using a solvent from the group consisting of acetonitrile, ethanol, 2-propanol (iso-propanol), acetone and ethyl acetate as well as mixtures thereof with water, such as in particular mixtures of ethanol and water and mixtures of acetone and water. Therein, a particularly preferred mixture is a mixture of ethanol:water=8:2.

A further particularly preferred embodiment of the present invention relates to the salts of compounds of formula (I) as defined in any of the embodiments above, wherein the acid is sulfuric acid and said sulfate salt is characterized by a ratio of compound (I):acid of 1:1.

More preferably such preferred sulfate salts are obtained by crystallization using a solvent from the group consisting of acetonitrile, dichloromethane, ethanol, 2-propanol (iso-propanol) and acetone as well as mixtures thereof with water, such as in particular mixtures of ethanol and water and mixtures of acetone and water. Therein, a particularly preferred mixture is selected from mixture of acetone:water=9:1 (vol:vol)
acetone:water=95:1 (vol:vol)
ethanol:water=4:1 (vol:vol)
ethanol:water=3:1 (vol:vol).

It is further particularly preferred that the above described preferred phosphate and sulfate salts are salts of the compounds of formula (I) selected from the Example Compounds Nos. 1, 2, 4, 40, 94, 118, 126, 127, 193, 206, 208, 233 as shown in the Table above. More preferably therein the compounds of formula (I) are selected from the Example Compounds Nos. 1, 40, 94, 127, 208. Even more preferably, therein the compounds of formula (I) are selected from the Example Compounds Nos. 1 and 127, with Example Compound No. 127 being most preferred.

Accordingly, the following salts are particularly preferred:

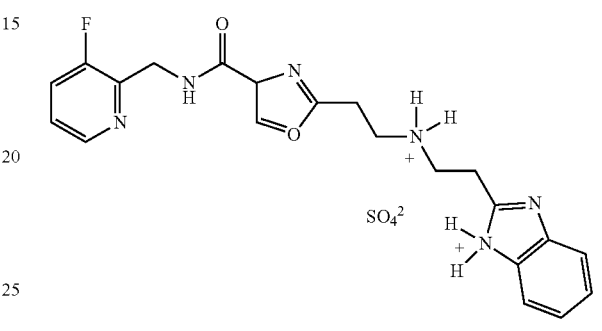

sulfate salt of Example Compound No. 127
(1:1 salt)

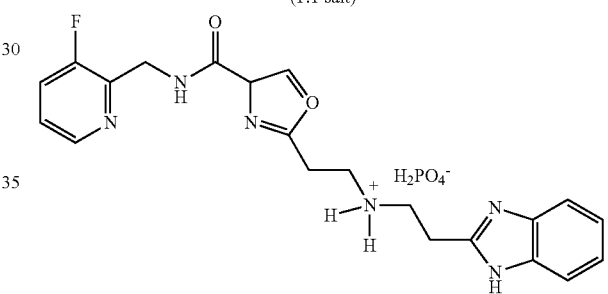

phosphate salt of Example Compound No. 127
(1:1 salt)

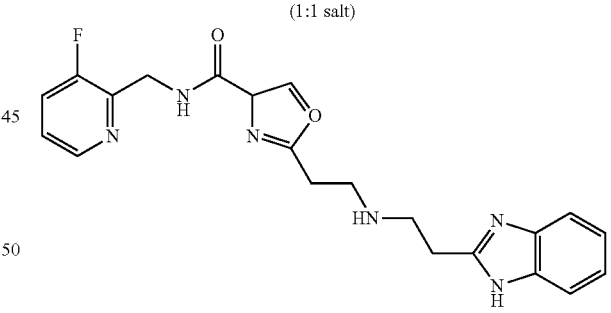

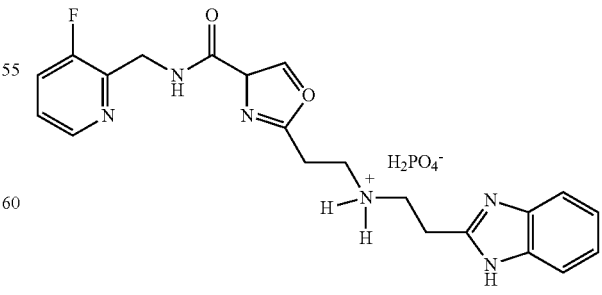

phosphate salt of Example Compound No. 127
(2:1 salt, hemiphosphate)

A further particularly preferred embodiment of the present invention relates to the phosphate salts of compounds according to Example Compound No. 127 with a ratio of compound (I):acid of 1:1, which is characterized by a polymorph form PM2 as defined in detail in the Examples below.

A further particularly preferred embodiment of the present invention relates to the sulfate salts of compounds according to Example Compound No. 127 with a ratio of compound (I):acid of 1:1, which is characterized by a polymorph form PM1 as defined in detail in the Examples below.

It surprisingly turned out that the compounds as described herein turned to have good or even improved long-term stability, including reduced or no solvent release, and/or mass lost under increasing temperatures, they turned out to be less or not hygroscopic, maintained their solid state structure even upon long-term storage under different temperature and/or moisture conditions, the crystal form resists vacuum drying, the compounds exhibit high reproducibility with high purity and low side- or degradation products in the preparation method, and maintained their solubility profile even upon long-term storage under different temperature and moisture conditions. The inventors of the present invention surprisingly found, that in particular the above described preferred sulphate and phosphate salts of Example Compound No. 127 (1:1 salts), in particular the polymorphs PM1 (sulphate salt) and PM2 (phosphate salt) as described herein in detail, achieved said advantageous characteristics. This makes these polymorphs particularly suitable as active ingredients in pharmaceutical preparations for the prophylaxis and treatment as described herein. Said specific preferred polymorphs PM1 (1:1 sulphate salt) and PM2 (1:1 phosphate salt) comprise less water compared to the other polymorphs tested therein, which is advantageous with respect to the desired long-term stability.

Depending on their structure, the salts according to the invention may exist in stereoisomeric forms (enantiomers, diastereomers) in the presence of asymmetric carbon atoms. The invention therefore includes the the enantiomers or diastereomers and the respective mixtures thereof. The pure-enantiomer forms may optionally be obtained by conventional processes of optical resolution, such as by fractional crystallisation of diastereomers thereof by reaction with optically active compounds. Since the compounds according to the invention may occur in tautomeric forms, the present invention covers the use of all tautomeric forms. The salts according to the invention may be present as mixtures of various possible isomeric forms, in particular of stereoisomers such as, for example, E- and Z-, syn and anti, as well as optical isomers. The E- isomers and also the Z-isomers as well as the optical isomers and any mixtures of these isomers are claimed.

The present invention further relates to new polymorphs of the new salt compounds according to formula (I), (II) or (III) as described herein. Polymorphic forms occur where the same compositions of matter crystallise in a different lattice arrangement, resulting in different thermodynamic properties and stabilities specific to the particular polymorph form.

One specific embodiment of the present invention relates to polymorphs of the citric acid salt of Example Compound No. 127, which is characterized by a powder X-ray diffraction pattern (PXRD pattern) comprising characteristic crystalline peaks expressed in degrees 2-theta at 24.5 and 5.3±0.25 degrees, or +0.20 degrees or ±0.10 degrees or ±0.05 degrees. Preferably in such embodiment of a polymorph the PXRD pattern comprises one or more further peaks expressed in degrees 2-theta selected from about 24.3, 21.6, 17.1, 5.9, 25.3, 8.1, 15.1, 20.1, or 12.6±0.25 degrees or ±0.20 degrees or ±0.10 degrees or ±0.05 degrees.

More preferably in such embodiment of a polymorph the PXRD pattern comprises one or more further peaks expressed in degrees 2-theta selected from about 24.3, 21.6, 17.1, 5.9, 25.3, 8.1, 15.1, 20.1, or 12.6.

More preferably in such embodiment of a polymorph the PXRD pattern comprises characteristic crystalline peaks expressed in degrees 2-theta at each of 24.5, 5.3, 24.3, 21.6, and 17.1 and optionally one or more, two or more, three or more at each of 5.9, 25.3, 8.1, 15.1, 20.1, or 12.6±0.20 degrees or ±0.10 degrees or ±0.05 degrees.

Preferably said polymorphs of the citric acid salt of Example Compound No. 127 are in the form of a 1:1 salt.

A further specific embodiment of the present invention relates to polymorphs of the maleic acid salt of Example Compound No. 127, which is characterized by a powder X-ray diffraction pattern (PXRD pattern) comprising characteristic crystalline peaks expressed in degrees 2-theta at 19.0 and 24.5±0.25 degrees or ±0.20 degrees or ±0.10 degrees or ±0.05 degrees. Preferably in such embodiment of a polymorph the PXRD pattern comprises one or more further peaks expressed in degrees 2-theta selected from about 25.1, 17.5, 18.7, 25.7, 18.3, 21.9, 9.6, or 6.1±0.25 degrees or ±0.20 degrees or ±0.10 degrees or ±0.05 degrees.

More preferably in such embodiment of a polymorph the PXRD pattern comprises one or more further peaks expressed in degrees 2-theta selected from about 25.1, 17.5, 18.7, 25.7, 18.3, 21.9, 9.6, or 6.1.

More preferably in such embodiment of a polymorph the PXRD pattern comprises characteristic crystalline peaks expressed in degrees 2-theta at each of 19.0, 24.5, 25.1, 17.5, and 18.7, and optionally one or more, two or more, three or more at each of 25.7, 18.3, 21.9, 9.6, or 6.1±0.20 degrees or ±0.10 degrees or ±0.05 degrees.

Preferably said polymorphs of the maleic acid salt of Example Compound No. 127 are in the form of a 1:1.75 salt.

A further specific embodiment of the present invention relates to polymorphs of the phosphoric acid salt of Example Compound No. 127, which is characterized by a powder X-ray diffraction pattern (PXRD pattern) comprising characteristic crystalline peaks expressed in degrees 2-theta at 27.2 and 4.6±0.25 degrees or ±0.20 degrees or ±0.10 degrees or ±0.05 degrees. Preferably in such embodiment of a polymorph the PXRD pattern comprises one or more further peaks expressed in degrees 2-theta selected from about 16.8, 22.0, 24.5, 5.4, 8.9, 13.1, 12.3, 19.7, or 15.9±0.25 degrees or ±0.20 degrees or ±0.10 degrees or ±0.05 degrees.

More preferably in such embodiment of a polymorph the PXRD pattern comprises one or more further peaks expressed in degrees 2-theta selected from about 16.8, 22.0, 24.5, 5.4, 8.9, 13.1, 12.3, 19.7, or 15.9.

More preferably in such embodiment of a polymorph the PXRD pattern comprises characteristic crystalline peaks expressed in degrees 2-theta at each of 27.2, 4.6, 16.8, 22.0, and 24.5, and optionally one or more, two or more, three or more at each of 5.4, 8.9, 13.1, 12.3, 19.7, or 15.9±0.20 degrees or ±0.10 degrees or ±0.05 degrees.

Preferably said polymorphs of the phosphoric acid salt of Example Compound No. 127 are in the form of a 2:1 salt.

A further specific embodiment of the present invention relates to polymorphs of the phosphoric acid salt of Example Compound No. 127, which is characterized by a powder X-ray diffraction pattern (PXRD pattern) comprising characteristic crystalline peaks expressed in degrees 2-theta at 26.1 and 16.5±0.25 degrees or ±0.20 degrees or ±0.10 degrees or ±0.05 degrees. Preferably in such embodiment of a polymorph the PXRD pattern comprises one or more further peaks expressed in degrees 2-theta selected from about 15.5, 18.4, 17.4, 14.7, 25.4, 20.4, 13.2 or 22.1±0.25 degrees or ±0.20 degrees or ±0.10 degrees or ±0.05 degrees.

More preferably in such embodiment of a polymorph the PXRD pattern comprises one or more further peaks expressed in degrees 2-theta selected from about 15.5, 18.4, 17.4, 14.7, 25.4, 20.4, 13.2 or 22.1.

More preferably in such embodiment of a polymorph the PXRD pattern comprises characteristic crystalline peaks expressed in degrees 2-theta at each of 26.1, 16.5, 15.5, 18.4 and 17.4, and optionally one or more, two or more, three or more at each of 14.7, 25.4, 20.4, 13.2 or 22.1±0.20 degrees or ±0.10 degrees or ±0.05 degrees.

Preferably said polymorphs of the phosphoric acid salt of Example Compound No. 127 are in the form of a 1:1 salt.

A further specific embodiment of the present invention relates to polymorphs of the sulfuric acid salt of Example Compound No. 127, which is characterized by a powder X-ray diffraction pattern (PXRD pattern) comprising characteristic crystalline peaks expressed in degrees 2-theta at 25.4 and 18.1±0.25 degrees or ±0.20 degrees or ±0.10 degrees or ±0.05 degrees. Preferably in such embodiment of a polymorph the PXRD pattern comprises one or more further peaks expressed in degrees 2-theta selected from about 4.5, 25.1, 16.8, 18.5, 18.6, 14.9, 15.6 or 17.6±0.25 degrees or ±0.20 degrees or ±0.10 degrees or ±0.05 degrees.

More preferably in such embodiment of a polymorph the PXRD pattern comprises one or more further peaks expressed in degrees 2-theta selected from about 4.5, 25.1, 16.8, 18.5, 18.6, 14.9, 15.6 or 17.6.

More preferably in such embodiment of a polymorph the PXRD pattern comprises characteristic crystalline peaks expressed in degrees 2-theta at each of 25.4, 18.1, 4.5, 25.1, and 16.8, and optionally one or more, two or more, three or more at each of 18.5, 18.6, 14.9, 15.6 or 17.6±0.20 degrees or ±0.10 degrees or ±0.05 degrees.

Preferably said polymorphs of the sulfuric acid salt of Example Compound No. 127 are in the form of a 1:1 salt.

A further specific embodiment of the present invention relates to polymorphs of the sulfuric acid salt of Example Compound No. 127, which is characterized by a powder X-ray diffraction pattern (PXRD pattern) comprising characteristic crystalline peaks expressed in degrees 2-theta at 25.5 and 4.5±0.25 degrees or ±0.20 degrees or ±0.10 degrees or ±0.05 degrees. Preferably in such embodiment of a polymorph the PXRD pattern comprises one or more further peaks expressed in degrees 2-theta selected from about 18.1, 18.4, 16.8, 6.2, 14.9, 25.2, 15.6, or 13.1±0.25 degrees or ±0.20 degrees or ±0.10 degrees or ±0.05 degrees.

More preferably in such embodiment of a polymorph the PXRD pattern comprises one or more further peaks expressed in degrees 2-theta selected from about 18.1, 18.4, 16.8, 6.2, 14.9, 25.2, 15.6, or 13.1.

More preferably in such embodiment of a polymorph the PXRD pattern comprises characteristic crystalline peaks expressed in degrees 2-theta at each of 25.5, 4.5, 18.1, 18.4 and 16.8, and optionally one or more, two or more, three or more at each of 6.2, 14.9, 25.2, 15.6, or 13.1±0.20 degrees or ±0.10 degrees or ±0.05 degrees.

Preferably said polymorphs of the sulfuric acid salt of Example Compound No. 127 are in the form of a 1:1 salt.

Very particularly, the present invention comprises the polymorphs of the following salts of Example Compound No. 127 as described herein, having the following PXRD peak pattern:

| CITRIC ACID SALT OF EXAMPLE COMPOUND NO. 127 (1:1 SALT) | | |
| --- | --- | --- |
| 2Theta (°) | d value (Å) | Relative Intensity (%) |
| 5.3 | 16.54 | 87 |
| 5.9 | 14.91 | 48 |
| 8.1 | 10.97 | 42 |
| 12.2 | 7.26 | 39 |
| 12.6 | 7.01 | 40 |
| 13.1 | 6.77 | 37 |
| 15.0 | 5.89 | 41 |
| 15.6 | 5.67 | 36 |
| 16.3 | 5.44 | 39 |
| 17.1 | 5.18 | 53 |
| 18.4 | 4.81 | 32 |
| 18.8 | 4.71 | 32 |
| 20.1 | 4.42 | 41 |
| 21.6 | 4.12 | 56 |
| 23.4 | 3.80 | 29 |
| 24.3 | 3.65 | 77 |
| 24.5 | 3.62 | 100 |
| 25.3 | 3.52 | 44 |
| 25.4 | 3.51 | 39 |
| 25.9 | 3.44 | 29 |
| 26.8 | 3.33 | 24 |
| 27.4 | 3.25 | 21 |
| 36.6 | 2.46 | 14 |
| 37.2 | 2.41 | 15 |
| 37.9 | 2.37 | 14 |

| Maleic Acid Salt of Example Compound No. 127 (1:1.75 salt) | | |
| --- | --- | --- |
| 2Theta (°) | d value (Å) | Relative Intensity (%) |
| 6.1 | 14.52 | 42 |
| 9.6 | 9.17 | 43 |
| 11.0 | 8.04 | 35 |
| 12.9 | 6.84 | 39 |
| 15.3 | 5.80 | 34 |
| 16.6 | 5.32 | 31 |
| 17.5 | 5.06 | 47 |
| 17.8 | 4.98 | 31 |
| 18.3 | 4.84 | 46 |
| 18.7 | 4.75 | 47 |
| 19.0 | 4.66 | 100 |
| 19.3 | 4.60 | 40 |
| 19.6 | 4.53 | 33 |
| 20.0 | 4.44 | 32 |
| 20.5 | 4.32 | 28 |
| 21.2 | 4.19 | 29 |
| 21.7 | 4.10 | 29 |
| 21.9 | 4.06 | 44 |
| 22.5 | 3.94 | 25 |
| 23.3 | 3.81 | 28 |
| 23.5 | 3.78 | 24 |
| 24.5 | 3.63 | 70 |
| 24.9 | 3.57 | 36 |
| 25.1 | 3.54 | 50 |
| 25.7 | 3.47 | 47 |
| 26.2 | 3.40 | 24 |
| 26.5 | 3.36 | 21 |
| 27.8 | 3.21 | 26 |
| 28.4 | 3.14 | 19 |
| 29.2 | 3.06 | 19 |
| 30.1 | 2.97 | 18 |
| 30.7 | 2.91 | 15 |
| 31.1 | 2.87 | 14 |
| 32.7 | 2.74 | 12 |
| 34.2 | 2.62 | 12 |
| 35.0 | 2.56 | 13 |
| 35.5 | 2.53 | 16 |
| 38.8 | 2.32 | 12 |

| Phosphoric Acid Salt of Example Compound No. 127 (2:1 salt) |||
| --- | --- | --- |
| 2Theta (°) | d value (Å) | Relative Intensity (%) |
| 4.6 | 19.39 | 94 |
| 5.4 | 16.37 | 38 |
| 7.8 | 11.36 | 24 |
| 8.9 | 9.91 | 38 |
| 9.1 | 9.68 | 26 |
| 10.8 | 8.16 | 24 |
| 11.0 | 8.07 | 25 |
| 11.4 | 7.73 | 24 |
| 12.3 | 7.19 | 31 |
| 13.1 | 6.75 | 35 |
| 13.7 | 6.46 | 27 |
| 13.9 | 6.35 | 24 |
| 14.0 | 6.30 | 25 |
| 14.5 | 6.10 | 23 |
| 14.7 | 6.03 | 27 |
| 15.0 | 5.91 | 23 |
| 15.5 | 5.72 | 25 |
| 15.7 | 5.64 | 28 |
| 15.9 | 5.58 | 30 |
| 16.1 | 5.50 | 27 |
| 16.8 | 5.27 | 75 |
| 17.3 | 5.12 | 23 |
| 17.9 | 4.96 | 21 |
| 18.3 | 4.83 | 24 |
| 19.4 | 4.58 | 27 |
| 19.7 | 4.50 | 31 |
| 19.9 | 4.46 | 25 |
| 20.1 | 4.42 | 24 |
| 20.2 | 4.40 | 22 |
| 20.9 | 4.24 | 21 |
| 21.2 | 4.19 | 24 |
| 21.6 | 4.11 | 22 |
| 21.7 | 4.09 | 23 |
| 22.0 | 4.03 | 44 |
| 22.8 | 3.89 | 20 |
| 23.0 | 3.87 | 17 |
| 23.4 | 3.79 | 21 |
| 24.5 | 3.63 | 39 |
| 24.9 | 3.58 | 23 |
| 25.4 | 3.50 | 17 |
| 25.6 | 3.47 | 14 |
| 26.1 | 3.42 | 13 |
| 26.4 | 3.37 | 16 |
| 27.2 | 3.27 | 100 |
| 27.6 | 3.23 | 22 |
| 28.2 | 3.16 | 29 |
| 28.5 | 3.13 | 15 |
| 29.4 | 3.04 | 12 |
| 29.8 | 3.00 | 13 |
| 30.2 | 2.95 | 14 |
| 30.3 | 2.94 | 15 |
| 30.7 | 2.91 | 10 |
| 30.8 | 2.90 | 11 |
| 31.0 | 2.88 | 11 |
| 31.2 | 2.87 | 11 |
| 31.4 | 2.84 | 11 |
| 32.3 | 2.77 | 9 |
| 32.8 | 2.73 | 11 |
| 33.2 | 2.70 | 9 |
| 34.5 | 2.60 | 8 |

In particular,

| Phosphoric Acid Salt of Example Compound No. 127 (1:1 salt) |||
| --- | --- | --- |
| Angle 2-Theta° | d value Angstrom | Relative Intensity % |
| 4.90 | 18.02 | 40 |
| 6.95 | 12.71 | 30.7 |
| 11.23 | 7.87 | 30.2 |
| 12.00 | 7.37 | 39.8 |
| 13.17 | 6.72 | 50.3 |
| 14.70 | 6.02 | 65.1 |
| 15.49 | 5.72 | 86.8 |
| 15.96 | 5.55 | 27.5 |
| 16.46 | 5.38 | 93.9 |
| 16.98 | 5.22 | 47.6 |
| 17.39 | 5.09 | 76.4 |
| 18.39 | 4.82 | 77.4 |
| 19.65 | 4.51 | 39.2 |
| 20.00 | 4.44 | 26.2 |
| 20.42 | 4.35 | 57.8 |
| 21.62 | 4.11 | 30.6 |
| 22.06 | 4.03 | 50.1 |
| 22.59 | 3.93 | 23.3 |
| 23.14 | 3.84 | 28.3 |
| 23.34 | 3.81 | 23.6 |
| 24.07 | 3.69 | 26.5 |
| 24.97 | 3.56 | 38.5 |
| 25.37 | 3.51 | 60 |
| 26.06 | 3.42 | 100 |
| 26.83 | 3.32 | 42.9 |
| 27.41 | 3.25 | 17.1 |
| 27.85 | 3.20 | 14.7 |
| 28.62 | 3.12 | 30.8 |
| 29.04 | 3.07 | 24.7 |
| 30.97 | 2.89 | 13.5 |
| 31.29 | 2.86 | 12.8 |
| 31.54 | 2.83 | 11.7 |
| 33.31 | 2.69 | 13.2 |
| 33.60 | 2.67 | 11.8 |
| 33.80 | 2.65 | 9.9 |
| 34.35 | 2.61 | 9.6 |
| 35.00 | 2.56 | 12.9 |
| 35.30 | 2.54 | 10.8 |
| 35.54 | 2.52 | 16.4 |
| 35.74 | 2.51 | 10.8 |
| 36.44 | 2.46 | 9.5 |

| Sulfuric Acid Salt of Example Compound No. 127 (1:1 salt) |||
| --- | --- | --- |
| 2Theta (°) | d value (Å) | Relative Intensity (%) |
| 4.5 | 19.61 | 62 |
| 6.1 | 14.38 | 26 |
| 11.1 | 7.99 | 17 |
| 11.8 | 7.49 | 19 |
| 13.1 | 6.75 | 26 |
| 13.9 | 6.35 | 20 |
| 14.1 | 6.26 | 18 |
| 14.9 | 5.96 | 32 |
| 15.6 | 5.68 | 31 |
| 16.1 | 5.50 | 17 |
| 16.8 | 5.27 | 41 |
| 17.6 | 5.04 | 27 |
| 18.1 | 4.89 | 77 |
| 18.5 | 4.80 | 37 |
| 18.6 | 4.77 | 34 |
| 19.3 | 4.59 | 19 |
| 19.7 | 4.51 | 18 |
| 20.1 | 4.42 | 16 |
| 20.4 | 4.34 | 19 |
| 21.1 | 4.22 | 21 |
| 22.5 | 3.95 | 20 |
| 22.7 | 3.91 | 21 |
| 22.9 | 3.88 | 18 |
| 23.4 | 3.79 | 16 |
| 25.1 | 3.54 | 45 |
| 25.4 | 3.50 | 100 |
| 25.9 | 3.43 | 18 |
| 26.4 | 3.37 | 25 |
| 26.8 | 3.32 | 26 |
| 27.5 | 3.24 | 25 |
| 28.1 | 3.17 | 16 |

-continued

Sulfuric Acid Salt of Example Compound No. 127 (1:1 salt)

| 2Theta (°) | d value (Å) | Relative Intensity (%) |
|---|---|---|
| 28.6 | 3.11 | 14 |
| 29.2 | 3.05 | 12 |
| 29.6 | 3.01 | 15 |
| 31.2 | 2.87 | 16 |
| 33.3 | 2.69 | 9 |
| 33.9 | 2.64 | 9 |
| 35.4 | 2.54 | 8 |
| 36.4 | 2.47 | 7 |

In particular,

Sulfuric Acid Salt of Example Compound No. 127 (1:1 salt)

| Angle 2-Theta ° | d value Angstrom | Relative Intensity % |
|---|---|---|
| 4.45 | 19.84 | 100 |
| 6.16 | 14.34 | 69.8 |
| 13.11 | 6.75 | 51.7 |
| 14.86 | 5.96 | 54.9 |
| 15.58 | 5.68 | 52 |
| 16.75 | 5.29 | 71.7 |
| 18.11 | 4.89 | 81.9 |
| 18.44 | 4.81 | 72.9 |
| 20.91 | 4.24 | 44.6 |
| 21.08 | 4.21 | 45.5 |
| 23.38 | 3.80 | 34.7 |
| 23.70 | 3.75 | 38.6 |
| 25.18 | 3.53 | 53.5 |
| 25.48 | 3.49 | 86.9 |
| 26.44 | 3.37 | 39.4 |
| 27.48 | 3.24 | 35.1 |
| 32.66 | 2.74 | 19.2 |
| 36.68 | 2.45 | 15.8 |

It is particularly preferred that according to the present invention ≥70 wt %, preferably ≥75 wt %, ≥85 wt %, ≥90 wt %, ≥95 wt % of the respective novel salts of the present invention (i.e. of the active compound) based on the total weight of said novel salt compound is in the form of such a specific polymorph. Accordingly, a particular embodiment of the present invention relates to the compositions, medicaments or pharmaceutical formulations described below, wherein ≥70 wt %, preferably ≥75 wt %, ≥85 wt %, ≥90 wt %, ≥95 wt % of the respective novel salts as the active compound (based on the total weight of said novel active compound) is in the form of such a specific polymorph.

All the compounds (free base or salts, including solvates, hydrates, mixed hydrate/solvate forms and polymorphs etc.) described in the present application are ferroportin inhibitors. All the new salts described in the present patent application do maintain a ferroportin inhibition activity, and can also improve the ferroportin inhibition activity, and/or improve the pharmacokinetic profile of the compounds, and/or improve the physicochemical properties of the compounds to make it easier to formulate into a galenic form, and/or have the advantage to be isolated in the form of a crystal which improves the physicochemical properties of the compounds to make such compounds easier to formulate into a galenic form or easier to handle/process or to improve its stability. The novel salts according to the present invention are thus suitable for the use as a medicament, such as in particular for the use as ferroportin inhibitors.

As already explained above, ferroportin is the iron transport protein, which is responsible for the uptake of the released iron via the intestine and its transfer into the blood circulation, thereby conveying the iron to the appropriate tissues and organs. Inactivation or inhibition of the ferroportin disables the export of the iron, thereby reducing the absorption of iron in the intestine. Ferroportin inhibition in the sense of the present invention therefore includes the inhibition of iron transport from the cells into the blood circulation and the inhibition of iron absorption in the intestine. Therein, the inhibition of iron transport and/or iron reflux may be effected by different ways of mechanism, comprising for example inhibition of iron transport activity of ferroportin and thus inhibition of iron reflux, triggering internalization, degradation and/or reduction of ferroportin, administering hepcidin agonists, i.e. compounds which compete with hepcidin or by compounds, which inhibit the binding of hepcidin to ferroportin.

Ferroportin inhibition may be determined by measuring the inhibition of ferroportin mediated iron transport activity in an iron response assay (BLAzer-Assay), as described in more detail in the Examples below. Further, ferroportin inhibition may be determined by measuring ferroportin internalization and/or degradation in the Ferroportin Internalization and Degradation Assay (FACS) or by examining the Ferroportin Ubiquitination and Degradation, each as described in more detail in the Examples below. Further, ferroportin inhibition may be determined by measuring the activity as an hepcidin agonist, for example by determining the Hepcidin binding capacity to ferroportin in the Hepcidin Internalization Assay (J774), as described in more detail in the Examples below. Further, ferroportin inhibition may be determined by confirming the inhibition of hepcidin binding to ferroportin, for example in the Biophysical Ferroportin-Hepcidin Binding Assay (Hep Bind FP), as described in more detail in the Examples below. Further, ferroportin inhibition may be determined by determining the activity of a compound regarding its ability to block iron export via ferroportin, for example with a test for measuring inhibition of iron efflux, as described in more detail in the Examples below.

Ferroportin inhibition in the sense of the present invention can thus in particular be defined by exhibiting a ferroportin inhibiting activity in at least one of the aforementioned test methods, shown in particular by:

Inhibition of ferroportin mediated iron transport activity in an iron response assay (Blazer Assay): $IC_{50}$ value [μm] of not more than 100 (≤100), preferably not more than 50 (≤50), more preferably below 50 (<50).

Ferroportin Internalization and Degradation Assay (FACS): $EC_{50}$ value [μm] of not more than 100 (≤100), preferably not more than 50 (≤50), more preferably below 50 (<50).

Ferroportin Ubiquitination and Degradation: visually inspected effect in Western blots of "+ comparable to hepcidin", "+/− intermediate effect" and "+/+/− stronger intermediate effect", preferred is an effect "+" or "+/+/−", most preferred is an effect "+".

Hepcidin Internalization Assay (J774): $IC_{50}$ value of not more than 100 (≤100), preferably not more than 50 (≤50), more preferably below 50 (<50).

Biophysical Ferroportin-Hepcidin Binding Assay: $IC_{50}$ value of not more than 100 (≤100), preferably not more than 50 (≤50), more preferably below 50 (<50).

Inhibition of Iron Efflux: $IC_{50}$ value of not more than 100 (≤100), preferably not more than 50 (≤50), more preferably below 50 (<50).

Ferroportin inhibition may further be determined in in vivo models, as described in more detail in the Examples below. Suitable in vivo models may comprise, for example, examination of hypoferremia in naïve mice via measurement of serum iron reduction; examination of prevention of iron absorption in anemic rats via measurement of serum iron inhibition; examination of correction of hyperferremia in beta2-microglobulin deficient mice via measurement of serum iron reduction; examination of prevention of iron overload in beta2-microglobulin deficient mice via measurement of total iron in spleen or liver; examination of improvement of anemia, ineffective erythropoiesis and iron overload in a mouse model of β-thalassemia intermedia.

The activity of the salts of the present invention as ferroportin inhibitors can in particular be determined by the methods as described in the Examples below.

As further already explained above, ferroportin inhibition may for example be effected by hepcidin, which is thus an essential regulating factor of iron absorption, inhibiting ferroportin and thus blocking iron transport from the cells into the blood circulation and iron absorption. It has further surprisingly been found that several of the salts as defined herein act as hepcidin mimetics or hepcidin agonists, which is also included by ferroportin inhibition in the sense of the present invention.

Accordingly, the salts as defined in the present invention are also suitable for use in the inhibition of iron transport from the cells into the blood circulation and the inhibition of iron absorption in the intestine, as well as for the use as hepcidin mimetics or hepcidin agonists.

Due to the activity of the salts as defined herein as ferroportin inhibitors, the salts of the present invention are further particularly suitable for the use in the inhibition of iron transport mediated by ferroportin and thereby for the use in the prophylaxis and/or treatment of iron metabolism disorders leading to increased iron levels, of diseases related to or caused by increased iron levels, increased iron absorption or iron overload, such as in particular of tissue iron overload, of diseases associated with ineffective erythropoiesis, or of diseases caused by reduced levels of hepcidin. Further, the compounds of the present invention are suitable for the use in an adjunctive therapy by limiting the amount of iron available to pathogenic microorganisms, such as the bacterium *Vibrio vulnificus*, thereby preventing or treating infections caused by said pathogenic microorganisms.

Therein, diseases being associated with, being related to, being caused by or leading to increased iron levels, increased iron absorption, iron overload (e.g. tissue iron overload) or ineffective erythropoiesis comprise thalassemia, hemoglobinopathy, such as hemoglobin E disease (HbE), hemoglobin H disease (HbH), haemochromatosis, hemolytic anemia, such as sickle cell anemia (sickle cell disease) and congenital dyserythropoietic anemia.

The activity of the salts of the present invention in the treatment of sickle cell anemia (sickle cell disease) can be determined by using a mouse model, such as e.g. described by Yulin Zhao et al. in "MEK1/2 inhibitors reverse acute vascular occlusion in mouse models of sickle cell disease"; The FASEB Journal Vol. 30, No. 3, pp 1171-1186, 2016. Said mouse model can be suitably adapted to determine the activity of the salts of the present invention in the treatment of sickle cell anemia. Similarly, the activity of the compounds as described in the above mentioned unpublished international applications PCT/EP2016/075305 and PCT/EP2016/075306, relating to compounds having activity as ferroportin inhibitors in the form of the free bases and/or in the form of pharmaceutically acceptable salts in general, in the treatment of sickle cell anemia can be examined by using said mouse model, probably with suitable adaptions to optimized test conditions, which is within the routine work of a person skilled in the art.

Diseases being associated with, being related to, being caused by or leading to increased iron levels, increased iron absorption, iron overload (e.g. tissue iron overload) further comprise neurodegenerative diseases, such as for example Alzheimer's disease and Parkinson's disease, wherein the compounds are considered to be effective by limiting the deposition or increase of iron in tissue or cells.

The salts of the present invention are further suitable for the use in the prophylaxis and/or treatment of formation of radicals, reactive oxygen species (ROS) and oxidative stress caused by excess iron or iron overload as well as in the prophylaxis and/or treatment of cardiac, liver and endocrine damage caused by excess iron or iron overload, and further in the prophylaxis and/or treatment of inflammation triggered by excess iron or iron overload.

Diseases associated with ineffective erythropoiesis comprise in particular myelodysplastic syndromes (MDS, myelodysplasia) and polycythemia vera as well as congenital dyserythropoietic anemia.

Further diseases, disorders and/or diseased conditions comprise iron overload caused by mutations in genes involved in sensing the systemic iron stores, such as hepcidin (Hampl), hemochromatosis protein (HFE), hemojuvelin (HJV) and transferrin receptor 2 (TFR2), such as in particular diseases related to HFE and HJV gene mutations, chronic hemolysis associated diseases, sickle cell diseases, red cell membrane disorders, Glucose-6-phosphate dehydrogenase deficiency (G6PD deficiency), erythrpoietic porphyria, Friedrich's Ataxia, as well as subgroups of iron overload such as transfusional iron overload, iron intoxication, pulmonary hemosiderosis, osteopenia, insulin resistense, African iron overload, Hallervordan Spatz disease, hyperferritinemia, ceruloplasmin deficiency, neonatal hemochromatosis and red blood cell disorders comprising thalassemia, including alpha thalassemia, beta thalassemia and delta thalassemia, thalassemia intermedia, sickle cell disease and myelodysplastic syndrome.

Further diseases and/or disorders and/or diseased conditions associated with elevated iron levels include, but are not limited to, diseases with elevated iron level, comprising ataxia, Friedrich's ataxia, age-related macular degeneration, age-related cataract, age-related retinal diseases and neurodegenrative disease, such as pantothenate kinase-associated neurodegeneration, restless leg syndrome and Huntington's disease.

The salts of the present invention my further be suitable for the use in the prophylaxis and treatment of diseases caused by a lack of hepcidin.

In view thereof a further object of the present invention relates to a medicament containing one or more of the salts as defined above, such as in particular a medicament for the prophylaxis and treatment in any of the indications, states, disorders or diseases as defined above.

A further object of the present invention relates to pharmaceutical compositions and medicaments comprising one or more of the salts according to the invention as defined above as well as optionally one or more pharmacologically acceptable carriers and/or auxiliary substances and/or solvents. A further object of the present invention relates to pharmaceutical compositions and medicaments comprising one or more of the salts according to the invention as defined above as well as optionally one or more further pharmaceutically effective compound(s). The said pharmaceutical compositions contain, for example up to 99 weight-% or up to 90 weight-% or up to 80 weight-% or up to 70 weight-% of the salts of the invention, the remainder being each formed by pharmacologically acceptable carriers and/or auxiliaries and/or solvents and/or optionally further pharmaceutically active compounds.

Therein, the pharmaceutically acceptable carriers, auxiliary substances or solvents are common pharmaceutical carriers, auxiliary substances or solvents, including various organic or inorganic carrier and/or auxiliary materials as they are customarily used for pharmaceutical purposes, in particular for solid medicament formulations. Examples include excipients, such as saccharose, starch, mannitol, sorbitol, lactose, glucose, cellulose, talcum, calcium phosphate, calcium carbonate; binding agents, such as cellulose, methylcellulose, hydroxypropylcellulose, polypropyl pyrrolidone, gelatine, gum arabic, polyethylene glycol, saccharose, starch; disintegrating agents, such as starch, hydrolyzed starch, carboxymethylcellulose, calcium salt of carboxymethylcellulose, hydroxypropyl starch, sodium glycol starch, sodium bicarbonate, calcium phosphate, calcium citrate; lubricants, such as magnesium stearate, talcum, sodium laurylsulfate; flavorants, such as citric acid, menthol, glycin, orange powder; preserving agents, such as sodium benzoate, sodium bisulfite, paraben (for example methylparaben, ethylparaben, propylparaben, butylparaben); stabilizers, such as citric acid, sodium citrate, acetic acid and multicarboxylic acids from the titriplex series, such as, for example, diethylenetriaminepentaacetic acid (DTPA); suspending agents, such as methycellulose, polyvinyl pyrrolidone, aluminum stearate; dispersing agents; diluting agents, such as water, organic solvents; waxes, fats and oils, such as beeswax, cocoa butter; polyethylene glycol; white petrolatum; etc.

Liquid medicament formulations, such as solutions, suspensions and gels usually contain liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavouring agents, for example as defined above. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected.

Pharmaceutically acceptable preserving agents can be used in order to increase the storage life of the liquid composition. Benzyl alcohol can be suitable, even though a plurality of preserving agents including, for example, paraben, thimerosal, chlorobutanol and benzalkonium chloride can also be used.

The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

A further object of the present invention relates to medicaments or combined preparations containing one or more of the salts as defined above and at least one further pharmaceutically active compound, such as in particular a compound for the prophylaxis and treatment of iron overload and the associated symptoms, preferably an iron-chelating compound, or a compound for the prophylaxis and treatment of any of the states, disorders or diseases as defined above, such as in particular a pharmaceutically active compound for the prophylaxis and treatment of thalassemia, haemochromatosis, sickle cell disease, neurodegenerative diseases (such as Alzheimer's disease or Parkinson's disease) and the associated symptoms.

A further object of the present invention relates to the use of the salts as defined above per se, in a combination therapy (fixed dose or free dose combinations for sequential use) with one or two other active ingredients (drugs). Such combination therapy comprises co-administration of the salts of the present invention with the at least one additional pharmaceutically active compound (drug). Combination therapy in a fixed dose combination therapy comprises co-administration of the salts of the present invention with the at least one additional pharmaceutically active compound in a fixed-dose formulation. Combination therapy in a free dose combination therapy comprises co-administration of the salts of the present invention and the at least one additional pharmaceutically active compound in free doses of the respective compounds, either by simultaneous administration of the individual compounds or by sequential use of the individual compounds distributed over a time period. The at least one additional pharmaceutically active compound (drug) comprises in particular drugs for reducing iron overload (e.g. Tmprss6-ASO) or iron chelators, in particular curcumin, SSP-004184, Deferitrin, deferasirox, deferoxamine and/or deferiprone, or antioxidants such as n-acetyl cysteine, anti-diabetics such as GLP-1 receptor agonists, antibiotics such as vancomycin (Van) or tobramycin, drugs for the treatment of malaria, anticancer agents, antifungal drugs, drugs for the treatment of neurodegenerative diseases such as Alzheimer's disease and Parkinson's disease (e.g. dopamine agonists such as Levodopa), anti-viral drugs such as interferon-α or ribavirin, or immunosuppressents (cyclosporine A or cyclosporine A derivatives), iron supplements, vitamin supplements, red cell production stimulators (e.g. erythropoietin, Epo), anti-inflammatory biologies, anti-thrombolytics, statins, vasopressors and inotropic compounds.

A further object of the present invention relates to the use of the above combinations for the prophylaxis and/or treatment of diseases caused by a lack of hepcidin or iron metabolism disorders, such as particularly iron overload states such as in particular thalassemia, sickle cell disease and hemochromatosis and other disorders as described in the present application.

A further object of the present invention relates to the use of the salts as defined herein per se or the hereinabove described combination therapies, in combination with Blood transfusion.

Potential synergistic or additive effects of the salts of the present invention with other therapeutic agents (second agents) can be evaluated by combination studies in mouse models of thalassemia intermedia ($Hbb^{th3/+}$ or $Hbb^{th1/th1}$, Jackson Laboratories) or thalassemia major ($C57\text{-}FLC^{th3/th3}$, thereby evaluating the salts of the present invention per se (i.e. the salts alone) or in combination with additional compound(s) for effects on anemia, hematopoiesis, iron overload, production of reactive oxygen species (ROS), splenomegaly and other biomarkers in the thalassemia models. In addition to the combination therapies already listed in the previous paragraph, combination therapies according to the present invention do also comprise the salts of the present invention in combination with one of the following second agents:

Modified activin receptor type IIA or IIB fusion proteins (such as described by Suragani R N, et al. "Modified activin receptor IIB ligand trap mitigates ineffective erythropoiesis and disease complications in murine β-thalassemia." Blood. 2014 Jun. 19; 123(25):3864-72 and by Dussiot M, et al. "An activin receptor IIA ligand trap corrects ineffective erythropoiesis in β-thalassemia." Nat Med. 2014 April; 20(4):398-407), acting as ligand traps to members of the transforming growth factor beta (TGFβ) superfamily, such as RAP-011 or RAP-536 (murine analogues of ACE-011, Sotatercept or ACE-536, Luspatercept (described in the patent application WO2010019261 or claimed in the U.S. Pat. No. 8,361,957), respectively, Acceleron/Celgene) or other antagonists of TGFβ superfamily members (antibodies, fragments of antibodies, non-antibody scaffold drugs or cells producing activin receptor ligand traps).

JAK1/2 or JAK2 inhibitors, including but not limited to Ruxotilinib (Novartis—claimed in the U.S. Pat. Nos. 7,598,257 and 8,415,362) or Fedratinib (Sanofi), such as described in Casu C, et al. "Short-term administration of JAK2 inhibitors reduces splenomegaly in mouse models of ß-thalassemia intermedia and major."; Haematologica, 2017.

pan-HDAC inhibitor, such as Panobinostat (LC Laboratories, USA, and claimed by the U.S. Pat. Nos. 6,552,065 and 6,833,384) or HDAC3 inhibitor RGFP966 (Selleckchem—such as described by Pasricha S R et al. "Hepcidin is regulated by promoter-associated histone acetylation and HDAC3." Nat Commun. 2017 Sep. 1; 8(1):403).

Antagonists of matriptase-2 (also known as Tmprss6), such as lipid nanoparticle (LNP)-formulated Tmprss6 siRNA or antisense oligonucleotides (ASOs) targeting mouse Tmprss6 (such as described by Guo S et al "Reducing TMPRSS6 ameliorates hemochromatosis and β-thalassemia in mice." J. Clin Invest. 2013 April; 123(4):1531-41 or by Schmidt P J, et al. "An RNAi therapeutic targeting Tmprss6 decreases iron overload in Hfe(−/−) mice and ameliorates anemia and iron overload in murine β-thalassemia intermedia." Blood. 2013 Feb. 14; 121(7):1200-8).

Exogenous apotransferrin (such as described by Li H, et al. "Transferrin therapy ameliorates disease in beta-thalassemic mice." Nat Med. 2010 February; 16(2): 177-82).

Hepcidin-inducing steroids (HISs) as epitiostanol, progesterone, and mifepristone or antagonists of progesterone receptor membrane component-1 (PGRMC1), Ref. 7.

Erythroferrone antagonists, such as antibodies or ligand traps

Recombinant erythropoietin (epo). Erythropoietins available for use as therapeutic agents according to this invention are produced by recombinant DNA technology in cell culture, and include Epogen/Procrit (epoetin alfa) and Aranesp (darbepoetin alfa) or Myrcera (epoetin beta and methoxy polyethylene glycol).

glycine transporter 1 (GlyT1) inhibitors such as bitopertin (Roche AG).

The salts of the present invention can be dosed orally either as a single agent twice daily at 10, 30 and 60 mg/kg or in combination with one of the compounds listed above (second agents). More specifically, the second agent will be dosed as a single treatment or co-administered with the salts of the present invention as follows:

RAP-011 or RAP-536 can be injected subcutaneously twice weekly at 1, 10 or 30 mg/kg for up to 8 weeks.

JAK1/2 inhibitors can be dosed orally twice daily in the absence or presence of the salts of the present invention.

Ruxotilinib (60 or 180 mg/kg) or Fedratinib (40 or 120 mg/kg) can be administered orally once daily for 2 weeks, in the absence or presence of the salts of the present invention.

Panobinostat or RGFP966 can be dosed once daily at 10 or 20 mg/kg in the absence or presence of the salts of the present invention.

Apotransferrin is injected intraperitoneally at 100 or 300 mg/kg daily for 8 weeks Mifepristone (30 or 100 mg/kg) can be injected intraperitoneally, daily for 2 weeks Antibodies or ligand traps specific to erythroferron can be administered twice weekly by subcutaneous injection Erythropoietin can be injected intraperitoneally at 200 IU daily for 2 weeks glycine transporter 1 (GlyT1) inhibitors such as bitopertin (Roche AG) can also be administered via suitable routes.

The salts, medicaments and or combined preparations according to the present invention may be administered orally, parentally, as well as intravenously.

For this purpose, the salts according to the invention are preferably provided in medicaments or pharmaceutical compositions in the form of pills, tablets, such as enteric-coated tablets, film tablets and layer tablets, sustained release formulations for oral administration, depot formulations, dragees, granulates, emulsions, dispersions, microcapsules, microformulations, nanoformulations, liposomal formulations, capsules, such as enteric-coated capsules, powders, microcrystalline formulations, epipastics, drops, ampoules, solutions, suspensions, infusion solutions or injection solutions or in the form of a preparation suitable for inhalation.

In a preferred embodiment of the invention the salts are administered in the form of a tablet or capsule, as defined above. These may be present, for example, as acid resistant forms or with pH dependent coatings.

The salts of the present invention as the active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

Accordingly, a further object of the present invention relates to salts, medicaments, compositions and combined preparations as defined above for the preparation of a medicament, particularly for the prophylaxis and treatment of any indication, state, disorder or disease as defined above, in particular for oral or parenteral administration.

A further object of the present invention relates to a method for the prophylaxis and treatment as defined above, such as in particular for the prophylaxis and/or treatment of iron metabolism disorders being associated with or leading to increased iron levels and in particular iron overload, diseases related to or caused by increased iron levels or iron overload, iron storage diseases being associated with or leading to increased iron levels, and diseases being associated with ineffective erythropoiesis, the method comprising administering, to a patient (human or animal) in need thereof, a salt, a medicament, a composition or a combined preparation as defined above.

Therein, diseases being associated with, being related to, being caused by or leading to increased iron levels or iron overload are as defined above.

A further object of the present invention relates to the use of the salts as defined above for the preparation of a medicament, particularly for the prophylaxis and treatment and of any indication, state, disorder or disease as defined above.

DESCRIPTION OF THE FIGURES

FIG. 1: Formula (I) of the present invention

FIG. 2: Visualized example of applied DVS measurement program

FIG. 3.1: Structure of the Example Compound No. 127 in the form of the free base indicating the calculated pKa-values FIG. 3.2: $^1$H NMR of SP236-FB-P1 in DMSO-d6

FIG. 3.3: Overview of FT-Raman spectrum of SP236-FB-P1 from 50 to 3500 cm$^{-1}$ FIG. 3.4: Fingerprint region of FT-Raman spectrum of SP236-FB-P1 from 50 to 1800 cm$^{-1}$

FIG. 5.1: Comparison of PXRD patterns of SP236-CIT-P1, SP236-CIT-P1(2), SP236-CIT-P2, and SP236-CIT-P3

FIG. 5.2: TG-FTIR thermogram of SP236-CIT-P2

FIG. 5.3: DSC thermogram of SP236-CIT-P3

FIG. 5.4: Comparison of the FT-Raman spectra of SP236-CIT-P3 and SP236-FB-P1 from 50 to 3500 cm$^{-1}$ FIG. 5.5: Comparison of the FT-Raman spectra of SP236-CIT-P3 and SP236-FB-P1 from 50 to 1800 cm$^{-1}$ FIG. 5.6: $^1$H NMR of SP236-CIT-P2 in DMSO-d6

FIG. 5.7: Plot of the sample mass (%) and relative humidity (%) vs. time for SP236-CIT-P3 showing the sample mass (left y-axis) and the r.h. set by the measurement program (right y-axis)

FIG. 5.8: Water vapor sorption isotherm plot for SP236-CIT-P3

FIG. 5.9: Comparison of PXRD patterns of SP236-MLE-P1, SP236-MLE-P2, and SP236-MLE-P3

FIG. 5.10: TG-FTIR thermogram of SP236-MLE-P1

FIG. 5.11: DSC thermogram of SP236-MLE-P3

FIG. 5.12: Comparison of the FT-Raman spectra of SP236-MLE-P3 and SP236-FB-P1 from 50 to 3500 cm$^{-1}$ FIG. 5.13: Comparison of the FT-Raman spectra of SP236-MLE-P3 and SP236-FB-P1 from 50 to 1800 cm$^{-1}$ FIG. 5.14: $^1$H NMR of SP236-MLE-P1 in DMSO-d6

FIG. 5.15: Plot of the sample mass (%) and relative humidity (%) vs. time for SP236-MLE-P3 showing the sample mass (left y-axis) and the r.h. set by the measurement program (right y-axis)

FIG. 5.16: Water vapor sorption isotherm plot for SP236-MLE-P3

FIG. 5.17: Comparison of PXRD patterns of SP236-PO4-P1 and SP236-PO4-P2

FIG. 5.18: TG-FTIR thermogram of SP236-PO4-P2

FIG. 5.19: $^1$H NMR of SP236-PO4-P2 in DMSO-d6

FIG. 5.20: $^{31}$P NMR of SP236-PO4-P2 in DMSO-d6

FIG. 5.21: Comparison of PXRD patterns of SP236-PO4-P2, SP236-PO4-P5, SP236-PO4-P6, SP236-PO4-P7, and SP236-PO4-P8

FIG. 5.22: Comparison of the FT-Raman spectra of SP236-PO4-P8 and SP236-FB-P1 from 50 to 3500 cm$^{-1}$ FIG. 5.23: Comparison of the FT-Raman spectra of SP236-PO4-P8 and SP236-FB-P1 from 50 to 1800 cm$^{-1}$ FIG. 5.24: TG-FTIR thermogram of SP236-PO4-P8

FIG. 5.25: DSC thermogram of SP236-PO4-P6

FIG. 5.26: DSC thermogram of SP236-PO4-P8

FIG. 5.27 Plot of the sample mass (%) and relative humidity (%) vs. time for SP236-PO4-P8 showing the sample mass (left y-axis) and the r.h. set by the measurement program (right y-axis)

FIG. 5.28: Water vapor sorption isotherm plot for SP236-PO4-P8

FIG. 5.29: Comparison of PXRD patterns of SP236-SO4-P1 and SP236-SO4-P3

FIG. 5.30: $^1$H NMR of SP236-SO4-P3 in DMSO-d6

FIG. 5.31: Comparison of PXRD patterns of SP236-SO4-P4, SP236-SO4-P5, and SP236-SO4-P6

FIG. 5.32: TG-FTIR thermogram of SP236-SO4-P4

FIG. 5.33: Plot of the sample mass (%) and relative humidity (%) vs. time for SP236-SO4-P6 showing the sample mass (left y-axis) and the r.h. set by the measurement program (right y-axis)

FIG. 5.34: Water vapor sorption isotherm plot for SP236-SO4-P6

FIG. 5.35: DSC thermogram of SP236-SO4-P6

FIG. 5.36: $^1$H NMR of SP236-SO4-P4 in DMSO-d6

FIG. 5.37: Comparison of the FT-Raman spectra of SP236-SO4-P6 and SP236-FB-P1 from 50 to 3500 cm$^{-1}$ FIG. 5.38: Comparison of the FT-Raman spectra of SP236-SO4-P6 and SP236-FB-P1 from 50 to 1800 cm$^{-1}$ FIG. 5.39: Zoomed-in HPLC trace for SP236-FB-P1

FIG. 5.40: Zoomed-in HPLC trace for SP236-CIT-P3

FIG. 5.41: Zoomed-in HPLC trace for SP236-MLE-P3

FIG. 5.42: Zoomed-in HPLC trace for SP236-PO4-P8

FIG. 5.43: Zoomed-in HPLC trace for SP236-SO4-P6

FIG. 6.1: PXRD pattern of SP236-BNZ-P2

FIG. 6.2: TG-FTIR thermogram of SP236-BNZ-P2

FIG. 6.3: $^1$H NMR of SP236-BNZ-P2 in DMSO-d6

FIG. 6.4: Comparison of PXRD patterns of SP236-FUM-P1 and SP236-FUM-P2

FIG. 6.5: TG-FTIR thermogram of SP236-FUM-P2

FIG. 6.6: $^1$H NMR of SP236-FUM-P2 in DMSO-d6

FIG. 6.7: Comparison of PXRD patterns of SP236-MLA-P1 and SP236-MLA-P2

FIG. 6.8: $^1$H NMR of SP236-MLA-P1 in DMSO-d6

FIG. 6.9: PXRD pattern of SP236-SUC-P2

FIG. 6.10: $^1$H NMR of SP236-SUC-P2 in DMSO-d6

FIG. 6.11: TG-FTIR thermogram of SP236-SUC-P2

FIG. 6.12: Comparison of PXRD patterns of SP236-LTAR-P1 and SP236-LTAR-P2

FIG. 6.13: TG-FTIR thermogram of SP236-LTAR-P1

FIG. 6.14: TG-FTIR thermogram of SP236-LTAR-P2

FIG. 6.15: $^1$H NMR of SP236-LTAR-P1 in DMSO-d6

FIG. 6.16: $^1$H NMR of SP236-LTAR-P2 in DMSO-d6

FIG. 6.17: Comparison of PXRD patterns of SP236-TOS-P1 and SP236-TOS-P2

FIG. 6.18: H NMR of SP236-TOS-P2 in DMSO-d6

FIG. 7.1: HPLC analysis of the HCl-mono salt of Example Compound No. 127 according to preparation Example 7.2

FIG. 7.2: DSC thermogram of the HCl-mono salt of Example Compound No. 127 according to preparation Example 7.2

FIG. 8.1: PXRD pattern summary of polymorphs PM1 to PM6 of PP566-SO4-P1 (from bottom to top: PP566-SO4-P2 (PM1), P5 (PM2), P6 (PM3), P8 (PM4), P10 (PM5) and P11 (PM6))

FIG. 8.2: PXRD pattern of polymorph PM1 (PP566-SO4-P2)

FIG. 8.3: $^1$H NMR of polymorph PM1 (PP566-SO4-P2)

FIG. 8.4: DSC thermogram of PM1 (PP566-SO4-P2)

FIG. 8.5: DVS behaviour of PM1 of PP566-SO4-P1

FIG. 9.1: PXRD pattern summary of polymorphs PM1 to PM11 of PP566-PO4-P1 (from bottom to top PP566-PO4-P4(PM1), P4-DRY(PM9), P5(PM2), P8(PM3), P10(PM4), P11(PM5), P13(PM6), P13-DRY(PM10), P15(PM7), P15-DRY (PM11) and P19(PM8))

FIG. 9.2: PXRD pattern of polymorph PM2 (PP566-PO4-P5)

FIG. 9.3: $^1$H NMR of polymorph PM2 (PP566-PO4-P5)

FIG. 9.4: TG-FTIR thermogram of PM2 (PP566-PO4-P5)

FIG. 9.5: TG-FTIR thermogram of PM2 (PP566-PO4-P12)

FIG. 9.6: PXRD pattern summary of polymorphs PM2 samples PP566-PO4-P2, P5, P6, P9, P12 (from bottom to top: PP566-PO4-P2, P5, P6, P9 and P12)

FIG. 9.7: DVS behaviour of PP566-PO4-P2 (PP566-PO4-P12)

EXAMPLES

Figure 4:
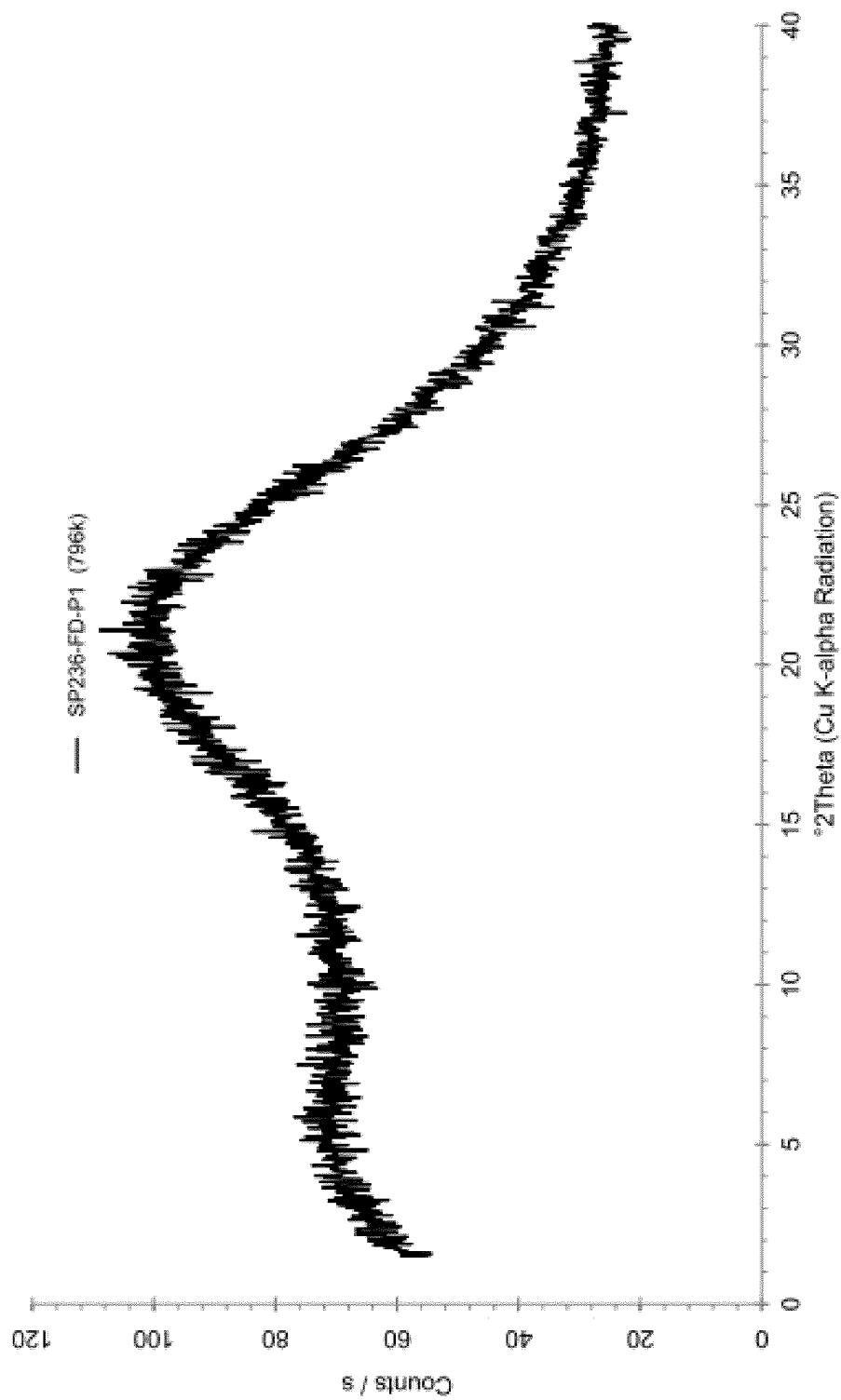
FIG. 4: PXRD pattern of SP236-FB-P1

The invention is illustrated in more detail by the following examples. The examples are merely explanatory, and the person skilled in the art can extend the specific examples to further claimed salts, such as in particular to further salts as described herein being formed with compounds according to formula (I) as shown in FIG. 1.

In the following, the samples are indicated by an identification code in the form SP236-XYZ-Pw, wherein XYZ specifies the salt/co-crystal former (i.e. the kind of acid) and Pw indicates the specific sample/experiment (w=1, 2, ... n).

As the starting compound the free base of Example Compound No. 127 has been used.

I. Preparation of Various Salts of Example Compound No. 127

1. Abbreviations

DCM dichloromethane
DMSO dimethyl sulfoxide
DSC differential scanning calorimetry
DVS dynamic vapor sorption
EtoAc ethyl acetate
EtOH ethanol
FT Raman Fourier-transform Raman spectroscopy
$^1$H-NMR proton nuclear magnetic resonance
i-PrOH isopropanol
MeCN acetonitrile
MeOH methanol
n-BuOH 1-butanol
r.h./RH relative humidity
r.t./RT room temperature (22-25° C.)
$T_g$ glass transition temperature
TG-FTIR thermogravimetry coupled to Fourier transform infrared spectroscopy
THF tetrahydrofurane
PXRD powder X-ray diffraction 2. General Experimental Details

DSC:

Differential scanning calorimetry was carried out with a TA Instruments Q2000 instrument (closed or open, gold or aluminum sample pans, with or without a pinhole were used) Generally, the heating rate was 10 K/min. The melting point is understood as the peak onset in most cases.

Dynamic Vapor Sorption:

DVS measurements were performed with an SPS11-100n "Sorptions Prufsystem" from ProUmid (formerly "Projekt Messtechnik"), August-Nagel-Str. 23, 89079 Ulm (Germany) or with a DVS-1 instrument from Surface Measurement Systems. About 5-20 mg of sample were put into an aluminum sample pan. Humidity change rates of 5% per hour were used. An example applied measurement program is visualized in the FIG. 2. Presentations showing the effective water content are adjusted based on the mass loss observed in the TGA. A double cycle was carried out in some cases.

In the Polymorph Evaluation Tests the sample was placed on an aluminum holder on top of a microbalance and allowed to equilibrate at 50% RH before starting the pre-defined humidity programs:

(1) 2 h at 50% RH
(2) 50-0% RH (5%/h); 5 h at 0% RH
(3) 0-95% RH (5%/h); 5 h at 95% RH
(4) 95-50% RH (5%/h); 2 h at 50% RH

Classification of Hygroscopicity

The hygroscopicity was classified based on the mass gain at 85% RH relative to the initial mass as follows: deliquescent (sufficient water adsorbed to form a liquid), very hygroscopic (mass increase of ≥15%), hygroscopic (mass increase <15% but ≥2%), slightly hygroscopic (mass increase <2% but ≥0.2%), or non-hygroscopic (mass increase <0.2%).

Elemental Analysis:

Elemental analysis has been performed on a 'vario EL cube' analyzer manufactured by Elementar. The analyzer uses combustion to convert elements to simple gasses, e.g.

CO$_2$, H$_2$O, N$_2$. The product gasses are separated by selective trap columns and measured as a function of thermal conductivity. Oxygen is converted to carbon monoxide by pyrolysis and subsequently can be also measured as a function of thermal conductivity.

$^1$H-NMR:

Bruker DPX300 spectrometer; proton frequency of 300.13 MHz; 30° excitation pulse; recycle delay of 1 s; accumulation of 16 scans; deuterated DMSO as the solvent; solvent peak used for referencing; chemical shifts reported on the TMS scale.

HPLC:

An Agilent Series 1100 HPLC system with Agilent 1260 Infinity degasser operation with Chromeleon Version 6.8 software.

Karl-Fischer Titration:

Karl-Fischer titration can be carried out in accordance well-known methods such as e.g. according to ISO 760-1978: Determination of water—Karl Fischer method (General method).

pKa-Measurement:

Sirius T3 titration instrument. Photometric or potentiometric analysis was applied with the use of co-solvents for samples with low aqueous solubility.

Powder X-Ray Diffraction (Reflection):

Measurements with a Bruker D8 Advance powder X-ray diffractometer were performed in reflection (Bragg-Brentano) geometry. 2θ values usually are accurate within an error of ±0.1-0.2°. The samples were generally prepared without any special treatment other than the application of slight pressure to get a flat surface. Silicon single crystal sample holder for polymorph screening of 0.5 mm depth. Normally samples were measured uncovered. The tube voltage was 40 kV and current was 40 mA. The PXRD diffractometer is equipped with a LynxEye detector. A variable divergence slight was used with a 3° window. The step size was 0.02° 2θ with a step time of 37 seconds. The samples were rotated at 0.5 rps during the measurement. The sample preparation and measurement was done in an ambient air atmosphere.

Powder X-Ray Diffraction (Transmission):

Stoe Stadi P equipped with a Mythen1K Detector; Cu-Kα radiation; standard measurement conditions: transmission; 40 kV and 40 mA tube power; curved Ge monochromator; 0.02° 2θ step size, 12 s or 48 s step time, 1.5-50.5° 2θ scanning range; detector mode: step scan; 1° 2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

In the Polymorph Evaluation Tests each sample (25-40 mg of powder) was placed between two cellulose acetate foils that were spaced with a metal washer (0.4-mm thick, 12-mm inner diameter). This sandwich element was transferred to a special sample holder for highly potent substances (SCell), which again was sealed with acetate foils. No special treatment was used in preparing the samples. An ambient air atmosphere was used for all measurements, and each sample was rotated during the measurement.

Raman Spectroscopy:

FT-Raman spectra were recorded on a Bruker MultiRAM FT-Raman system with a near infrared Nd:YAG laser operating at 1064 nm and a liquid nitrogen-cooled germanium detector. 64 scans with a resolution of 2 cm$^{-1}$ were accumulated in the range from 3500 to −50 cm$^{-1}$; however, only data above 100 cm$^{-1}$ are evaluated due to filter cutoff effects. Nominal laser powers are typically 100 or 300 mW.

Solubility:

Approximate solubilities were determined by incremental addition of solvent to about 10 mg the compound. If the substance was not dissolved by addition of a total of at least 10 mL solvent, the solubility is indicated as <1 mg/mL. Due to the experimental error inherent in this method, the solubility values are intended to be regarded as rough estimates and are to be used solely for the design of crystallization experiments.

TG-FTIR:

Thermogravimetric measurements were carried out with a Netzsch Thermo-Microbalance TG 209 coupled to a Bruker FTIR Spectrometer Vector 22 (sample pans with a pinhole, N$_2$ atmosphere, heating rate 10 K/min).

Approximate Solubility:

Approximate solubilities were determined by incremental addition of solvent to about 10 mg of the compound. If the substance was not dissolved by addition of a total of at least 10 mL solvent, the solubility was indicated as <1 mg/mL. Due to the experimental error inherent in this method, the solubility values were regarded as rough estimates and were only used for the design of crystallization experiments.

3. Characterization of Starting Material

Starting Compound (Free Base/FB):
Example Compound No. 127 (SP236-FB-P1)
pKa Calculation of the Starting Compound:

Theoretical pKa values were calculated using the ACD/pKa DB Vers. 10.00, Release 10.00 software. The values obtained are presented along with the structure of the starting compound (free base) in FIG. 3.1.

$^1$H NMR Spectroscopy of the Starting Compound:

The NMR spectrum of SP236-FB-P1 was recorded in DMSO-d$_6$ as presented in FIG. 3.2. The spectrum contains at least one broad signal at a chemical shift ~δ12 ppm, however the spectrum appears to agree with the chemical structure provided. Residual ethanol and dichloromethane are also observed in the NMR spectrum.

Raman Spectroscopy:

The FT-Raman spectrum of SP236-FB-P1 was recorded in the region of 50 to 3500 cm$^{-1}$ as presented in FIG. 3.3, with a zoomed-in view of the fingerprint region from 50 to 1800 cm$^{-1}$ as presented in FIG. 3.4.

Powder X-Ray Diffraction:

The PXRD pattern of SP236-FB-P1 was recorded in transmission mode as presented in FIG. 4, which confirmed that the sample (in the form of the free base) is amorphous in nature.

Approximate Solubility of the Starting Compound:

The approximate solubility of SP236-FB-P1 was determined in a number of different solvents and solvent mixtures to help guide the salt/co-crystal experiments. The results are as follows:

| Solvent | Solubility [mg/ml] | Solvent Mixture | Solubility [mg/ml] |
|---|---|---|---|
| Acetonitrile | S >200 | | |
| Dioxane | S >100 | | |
| DMSO | S >100 | | |
| Ethanol | 8 >100 | | |
| Ethyl acetate | S >100 | Ethyl acetate-cyclohexane 3:1 | 5 < S < 7 |
| Heptane | S <1 | Methanol-water 1:1 | S >100 |
| Methanol | S >200 | | |

-continued

| Solvent | Solubility [mg/ml] | Solvent Mixture | Solubility [mg/ml] |
|---|---|---|---|
| 2-Propanol | 80 < S < 120 | 2-propanol-water 1:3 | 39 < S < 47 |
| THF | S >200 | THF-heptane 3:1 | S >200 |
| Water | S ~15 | | |

4. Crystallization Experiments

Crystallization Conditions:

In all experiments, a free base:acid ratio of 1:1 (mol:mol) was used; in the case of $PO_4$ and $SO_4$, two experiments were also performed with a free base:acid ratio of 10:1. Many of the experiments have resulted in crystalline products as indicated by their PXRD patterns, which are discussed in more detail below. Those experiments which only resulted in amorphous products are not presented in further detail (i.e. LLAC and MES).

Selected Acids and Crystallization Solvents:

| Acid | Abbreviation | Solvent Used | Result |
|---|---|---|---|
| Benzoic acid | BNZ | 2-propanol | amorphous |
| | | ethyl acetate | Crystalline PXRD |
| Citric acid | CIT | ethanol | Crystalline PXRD |
| | | methanol | Crystalline PXRD |
| Fumaric acid | FUM | THF | Semi-crystalline PXRD |
| | | 2-propanol | Crystalline PXRD |
| Lactic acid, L- | LLAC | 2-propanol | amorphous |
| | | methanol | amorphous |
| Malic acid, L- | MLA | 2-propanol | Semi-crystalline PXRD |
| | | THF | Mostly amorphous |
| Maleic acid | MLE | 2-propanol | Crystalline PXRD |
| | | THF | Crystalline PXRD |
| Methanesulfonic acid | MES | THF | amorphous |
| | | acetonitrile | amorphous |
| Phosphoric acid | PO4 | acetonitrile (10:1 ratio) | Crystalline PXRD |
| | | 2-propanol (10:1 ratio) | Crystalline PXRD |
| | | acetonitrile (1:1 ratio) | amorphous |
| | | 2-propanol (1:1 ratio) | amorphous |
| Succinic acid | SUC | ethanol | amorphous |
| | | THF | Semi-crystalline PXRD |
| Sulfuric acid | SO4 | 2-propanol (10:1 ratio) | Crystalline PXRD |
| | | acetonitrile (10:1 ratio) | No solid obtained |
| | | 2-propanol (1:1 ratio) | Crystalline PXRD |
| | | acetonitrile (1:1 ratio) | Crystalline PXRD |
| Tartaric acid, L- | LTAR | ethanol | Crystalline PXRD |
| | | methanol | Crystalline PXRD |
| Toluenesulfonic acid | TOS | 2-propanol | Semi-crystalline PXRD |
| | | THF | Crystalline PXRD |

In the following the preparation and characterization of selected salts according to the conditions described above is further described in more detail:

5. Selected Salts of Example Compound No. 127

5.1 Citric Acid Salt of Example Compound No. 127

The crystallization experiment using citric acid in ethanol first resulted in an amorphous material that crystallized upon heating at 30° C. with intermittent sonication (SP236-CIT-P1(2)). The PXRD pattern matches with crystalline material obtained from the experiment in methanol (FIG. 5.1, SP236-CIT-P2). The preparation of this crystalline form could also be reproduced on the ~600 mg scale in experiment SP236-CIT-P3. Sample –P2 contains ~0.9% of water and methanol, which it loses ~150° C. (FIG. 5.2). Another 8.1% of water is lost when heating to 200° C. DSC of sample SP236-CIT-P3 indicates the salt melts with an onset temperature of 153° C. (FIG. 5.3). The FT-Raman spectrum of SP236-CIT-P3 is compared with that of the free base in FIG. 5.4 and FIG. 5.5 and clear differences can be seen between the two spectra. The $^1$H NMR spectrum of SP236-CIT-P2 recorded in DMSO-d 6 has an additional signal ~δ2.6 ppm that integrates to 3.8 and suggests a 1:1 free base:acid salt (FIG. 5.6). Assuming this ratio is correct, the 8.1% water observed by TG-FTIR suggests a trihydrate of the 1:1 salt. Interestingly, DVS shows a decrease in the relative sample weight from the start of the measurement and the sample eventually becomes anhydrous at 0% relative humidity (FIG. 5.7 and FIG. 5.8). It then starts adsorbing water as soon as the relative humidity is increased and the difference between the relative sample mass at 0 and 95% relative humidity is ~8%, corresponding well to the results of TG-FTIR. The elemental analysis results also match well with a 1:1 salt, however the water content determination by Karl-Fischer titration suggests an anhydrous sample:

| Element/Species | Theoretical 1:1 Salt | SP236-CIT-P3 Found |
|---|---|---|
| C | 54.0 | 53.0 |
| H | 4.9 | 5.1 |
| N | 14.0 | 13.7 |
| O | 24.0 | 24.2 |
| $H_2O$ | — | 0.5 (Karl Fischer) |

5.2 Maleic Acid Salt of Example Compound No. 127

The screening crystallization experiments using maleic acid in 2-propanol and THF resulted in crystalline solids whose PXRD patterns match very well with one another (FIG. 5.9). Scale up of this synthesis on a roughly 500 mg scale in 2-propanol resulted in the same crystalline form for sample SP236-MLE-P3. TG-FTIR indicates the sample is essentially anhydrous but undergoes a large mass loss and decomposition starting ~170° C. (FIG. 5.10). DSC of sample SP236-MLE-P3 in a sealed gold pan suggests a melting point of ~161° C. (FIG. 5.11). The FT-Raman spectrum of SP236-MLE-P3 was recorded and shows several differences from that of the free base (FIG. 5.12 and FIG. 5.13). The $^1$H NMR spectrum of SP236-MLE-P1 has a signal attributed to maleic acid at 66.1 with an integral of 3.5, which suggests a free base:acid ratio of 1:1.75 (FIG. 5.14). DVS shows a mass loss of ~1% when the relative humidity is reduced to 0% and then an adsorption of water as soon as the relative humidity is increased again (FIG. 5.15 and FIG. 5.16). A maximum increase in mass of ~6.5% is achieved at 95% relative humidity, which corresponds to ~2.5 waters per mole salt (assuming at 1:1.75 ratio of free base:MLE). Elemental analysis of SP236-MLE-P3 fits well with a 1:1.75 salt and the water content of 0.4% by Karl-Fischer titration agrees with the results from TG-FTIR:

| Element | Theoretical Free Base:MLE | | | SP236-MLE-P3 Found |
|---|---|---|---|---|
| | 1:1 | 1:1.75 | 1:2 | |
| C | 57.2 | 55.0 | 54.4 | 54.7 |
| H | 4.8 | 4.6 | 4.6 | 4.8 |
| N | 16.0 | 13.7 | 13.1 | 13.6 |
| O | 18.3 | 23.5 | 25.0 | 23.8 |
| H$_2$O | | | | 0.4 (Karl Fischer) |

5.3 Phosphoric Acid Salt of Example Compound No. 127

The screening crystallization experiments using phosphoric acid with acetonitrile (SP236-PO4-P1) and 2-propanol (SP236-PO4-P2) as solvents resulted in two different crystalline solids by PXRD (FIG. 5.17). It is important to note that these two experiments had a free base:acid molar ratio of 10:1. TG-FTIR of sample –P2 indicates a mass loss of 1.0% at 130° C. due to loss of 2-propanol with decomposition starting above 200° C. (FIG. 5.18). This sample was also investigated by $^1$H and 31P NMR, the latter of which shows evidence of the phosphate ion (FIG. 5.19 and FIG. 5.20). Two experiments were performed in the same way but with a 1:1 molar ratio of free base:acid. These experiments only gave amorphous solids and were not investigated further. Several more experiments were performed to further investigate this system and better understand the synthesis. In SP236-PO4-P5, experiment –P2 was repeated in order to confirm its reproducibility. The PXRD pattern of sample –P5 matches that of –P2 (FIG. 5.21) and phosphorus analysis suggests that sample –P5 is a hemiphosphate (i.e. a 2:1 free base:phosphate salt (Table 5.3). In experiment SP236-PO4-P6, aqueous phosphoric acid was added stepwise in 0.1 molar equivalent steps until a 2:1 ratio of free base:acid was achieved. The PXRD pattern confirms the same crystalline form was obtained as in –P2 and –P5 (FIG. 5.21) and the result of 2.83 mass percent phosphorus again suggests a hemiphosphate. Experiment SP236-PO4-P7 was performed similarly to –P6, however phosphoric acid was added until a 1:1 ratio of free base:acid was reached in order to try and obtain a monophosphate salt. PXRD analysis of the resultant solid again indicates the hemiphosphate was obtained (FIG. 5.21). The scale up of this synthesis on a ~600 mg scale in experiment SP236-PO4-P8 was also successful in producing the same crystalline form. The FT-Raman spectrum of this sample is compared to that of the free base in FIG. 5.22 and FIG. 5.23 and shows substantial differences. Surprisingly, TG-FTIR of SP236-PO4-P8 shows significantly more water and 2-propanol is present within the sample despite having the same PXRD pattern (FIG. 5.24). Therefore, it appears this phosphate salt has isomorphic solvated/hydrated and non-solvated/hydrated forms. DSC of samples SP236-PO4-P6 and –P8 in sealed gold pans show fairly reproducible melting points with onsets of 79 and 80° C. (FIG. 5.25 and FIG. 5.26). These values correspond well to the boiling point of 2-propanol and suggest the simultaneous release of solvent and melting of the solid. DSC measurements should most probably be investigated in open pans as well. DVS of sample SP236-PO4-P8 shows an immediate mass loss as the relative humidity is decreased from 50 to 0% that is not complete during the first cycle. A greater mass loss is observed during the second cycle of DVS and the difference between the highest and lowest relative sample masses of ~12.5% agrees well with the mass loss observed by TG-FTIR. A water content of 12.5% corresponds to ~7 molecules of water per 2:1 salt. The elemental analysis of samples SP236-PO4-P5 and –P8 are somewhat consistent, although the carbon content varies quite a lot:

| Element/Species | Theoretical Free Base:PO4 | | Found | |
|---|---|---|---|---|
| | 2:1 | 2:1·4H$_2$O | SP236-PO4-P5 | SP236-PO4-P8 |
| C | 55.1 | 51.1 | 52.1 | 50.7 |
| H | 5.0 | 5.4 | 5.7 | 5.9 |
| N | 18.4 | 17.0 | 16.4 | 15.9 |
| O | 14.0 | 19.5 | — | 20.2 |
| P | 3.4 | 3.1 | 2.96 | 2.92 |
| H$_2$O | — | 7.3 | — | 8.0 |

Also important to note is the water content of 8 mass percent determined by Karl-Fischer titration. This value is significantly lower than the 12 mass percent water assumed to be adsorbed in the DVS but could suggest some 2-propanol still remains.

5.4 Sulfuric Acid Salt of Example Compound No. 127

The first screening experiments performed with sulfuric acid were done with a 10:1 molar ratio of free base:acid. The crystallization in 2-propanol (SP236-SO4-P1) resulted in a crystalline solid that was reproduced on a larger scale (–P3) whereas the experiment in acetonitrile (–P2) failed to give any solids (FIG. 5.29). The $^1$H NMR spectrum of the crystalline solid does not indicate the molecule has decomposed at all (FIG. 5.30). Two additional experiments were performed in a similar way however a free base:acid molar ratio of 1:1 was used this time. These results are of more interest since the initially desired ratio of starting materials was used. The crystallization experiments in both solvents resulted in very similar crystalline forms by PXRD and the experiment in 2-propanol could be reproduced on ~600 mg scale (FIG. 5.31). TG-FTIR indicates sample –P4 contains ~5.5 mass percent water that it loses during two different step-losses of 4% and 1.5% and starts to decompose above 200° C. (FIG. 5.32). A water content of 4% corresponds to ~1 water per salt, whereas 1.5 mass percent water suggests 0.5 waters per salt (assuming a 1:1 free base:sulfate salt). DVS indicates a constant mass loss as the relative humidity is decreased from 50 to 0% followed by an immediate mass gain once the relative humidity is increased again (FIG. 5.33 and FIG. 5.34). The difference between the minimum and maximum relative sample weights in the DVS is between ~5 and 5.5%, which agrees well with the results from TG-FTIR and suggests a total of 1.5 waters per salt (assuming a 1:1 salt). A melting onset temperature of 173° C. was determined for sample SP236-SO4-P6 by performing DSC in a sealed gold pan (FIG. 5.35). The $^1$H NMR spectrum of SP236-SO4-P4 does not indicate any decomposition of the molecule (FIG. 5.36) and FT-Raman spectroscopy of the sulfate salt shows significant differences when compared to that of the free base (FIG. 5.37 and FIG. 5.38). The elemental analysis results presented in Table 5.4 agree fairly well with a 1.5 waters, although the oxygen content and water determination by Karl Fischer titration are somewhat conflicting:

|  | Theoretical 1:1 Salts | | | Found | |
| --- | --- | --- | --- | --- | --- |
| Species | Anhydrous | +1.5 H$_2$O | +2.5 H$_2$O | SP236-SO4-P4 | SP236-SO4-P6 |
| C | 49.79 | 47.27 | 45.73 | 47.0 | 45.5 |
| H | 4.58 | 4.91 | 5.12 | 4.6 | 4.6 |
| N | 16.60 | 15.76 | 15.24 | 15.7 | 15.2 |
| O | 19.0 | 22.5 | 24.66 | — | 19.0 |
| S | 6.33 | 6.01 | 5.81 | 6.1 | 5.7 |
| H$_2$O | — | 5.06 | | 5.56 (TG-FTIR) | 8.0 (KF) |

5.5 Overview of Aqueous Solubility and HPLC Purity for Selected Salts

The aqueous solubility and HPLC purity of each of the selected salts was determined and the results are presented in following table:

| Sample | Solubility (mg/mL) | pH of Saturated Solution | Purity (Rel. Area %) |
| --- | --- | --- | --- |
| SP236-CIT-P3 | 23.6 | 4.3 | 88.2 |
| SP236-MLE-P3 | 14.2 | 4.2 | 82.2 |
| SP236-PO4-P8 | 29.8 | 7.0 | 93.1 |
| SP236-SO4-P6 | 8.2 | 3.2 | 77.9 |

The measured solubilities in water range from ~8 mg/mL for the sulfate salt to ~30 mg/mL for the phosphate salt. It must be noted, however, that SP236-PO4-P8 is a 2:1 free base:phosphate salt and therefore delivers two molecules of free base. The pH of the saturated solution for this sample is also significantly higher than those of the other salts (pH ~7 versus pH 3.2-4.3). The purity of each salt was also determined by using the relative area percent of the main peak compared to those of all other peaks detected and ranges from 78% for SP238-SO4-P6 to 93% for SP236-PO4-P8, Zoomed-in HPLC traces for the tested samples are shown in FIGS. 5.39 (SP236-FB-P1), 5.40 (SP236-CIT-P3), 5.41 (SP236-MLE-P3), 5.42 (SP236-PO4-P8) and 5.43 (SP236-SO4-P6).

6. Screening Experiments with Other Salt Formers 6.1 Benzoic Acid

Two crystallization experiments have been performed using benzoic acid. No solid was obtained when using 2-propanol as the solvent (SP236-BNZ-P1), however crystalline solid was obtained in the experiment using ethyl acetate (SP236-BNZ-P2, FIG. 6.1). The sample still contains ~0.6% of ethyl acetate that is seen by TG-FTIR and starts to decompose and lose benzoic acid above ~200° C. (FIG. 6.2). The $^1$H NMR spectrum indicates an additional 5 aromatic protons and suggests a 1:1 free base:BNZ salt (FIG. 6.3).

6.2 Fumaric Acid

A white precipitate formed in the crystallization experiment with fumaric acid using THF as the solvent system (SP236-FUM-P1), however this solid was found to only be partially crystalline in nature by PXRD. The experiment using 2-propanol appears to have given a much more crystalline sample after tempering the reaction between 25 and 30° C. (FIG. 6.4, SP236-FUM-P2). TG-FTIR of the latter sample indicates a loss of ~2.6% 2-propanol at ~140° C. (FIG. 6.5) and the $^1$H NMR spectrum suggests a free base:acid ratio of 1:1.35 based on the signal at δ6.6 ppm.

6.3 L-Malic Acid

The crystallization experiment with L-malic acid in 2-propanol originally resulted in an oily solid that crystallized upon tempering between 25 and 30° C. (SP236-MLA-P1, FIG. 6.7). A similar experiment in THF gave only amorphous solids (SP236-MLA-P2). The 1H NMR spectrum of the former sample has signals attributed to L-malic acid at δ2.4 and 3.9 that indicate a free base:acid ratio of 1:1 (FIG. 6.8).

6.4 Succinic Acid

The crystallization experiment with succinic acid using THF as the solvent resulted in a partially crystalline solid that shows evidence of succinate in a 1:1 ratio with the free base by $^1$H NMR (SP236-SUC-P2, FIG. 6.9 and FIG. 6.10). TG-FTIR indicates a 3.1% mass loss at 110° C. due to loss of THF with decomposition starting above 150° C. (FIG. 6.11). The experiment using ethanol as the solvent (SP236-SUC-P1) gave only a viscous solid that was not investigated further.

6.5 L-Tartaric Acid

Crystallization experiments with L-tartaric acid were performed using ethanol (–P1) and methanol (–P2) as solvents. The PXRD patterns of the obtained solids indicate both samples are crystalline and may be structurally similar (FIG. 6.12). The products of these two crystallizations contain similar mass percentages of solvent/water (i.e. ~5.3%, see FIG. 6.13 and FIG. 6.14) and their 1H NMR spectra indicate a free base:LTAR ratio of 1:1 based on the signal at ~δ4 ppm (see FIG. 6.15 and FIG. 6.16).

6.6 Toluenesulfonic Acid

Crystallization experiments with toluenesulfonic acid were performed in 2-propanol (–P1) and THF (–P2). PXRD indicates the solid forms obtained may be similar, however the experiment using THF produced a much more crystalline sample (FIG. 6.17). Unfortunately the yields of these crystallizations were quite low and only a small amount of a fine, highly electrostatic solid was recovered. The $^1$H NMR spectrum of sample –P2 could be measured and suggests a free base:TOS ratio of 1:1.5 with ~10 molar percent THF remaining in the sample (FIG. 6.18).

7. Preparation of a HCl-Monosalt of Example Compound No. 127

7.1 Salt Formation Starting from the Free Base

The mono-HCl salt exhibits a much higher solubility in ethanol than the 3HCl-salt (which has been disclaimed from the scope of the present invention).

Accordingly, yields of the mono-salt are lower. For increasing the yield ethanol-water mixtures can be used as crystallization solvent.

For the preparation of the mono-HCl salt from the free base 1.4 g (3.4 mmol) of Example Compound No. 127 in the form of the free base are dissolved in 86 ml of ethanol and heated to 50° C. 0.61 g (1.05 eq.) of HCl 32% are added dropwise and the solution is cooled to 0-5° C. within a period of 2 h. The resulting suspension is filtered and washed with 10 ml of 2-propanol. The moist product is dried for at least 10 h in a vacuum (<100 mbar) at 45° C.

The yield is 0.51 g (34% of the theoretically calculated yield) in the form of a white solid.

7.2 Salt Formation Starting from the 3HCl-Salt of Example Compound No. 127

Since the mono-HCl salt exhibits a reduced solubility in water, it precipitates at a pH≥5.

For the preparation of the mono-HCl salt from the 3HCl salt 5 g (9.7 mmol) of Example Compound No. 127 in the form of the 3HCl salt are dissolved in 50 ml of water at 20-25° C. The pH is then adjusted to pH 5-6 with NaOH 30% and the suspension is stirred for 10 minutes. The suspension is filtered and washed with 10 ml of 2-propanol. The moist product is dried for at least 10 h in a vacuum (<100 mbar) at 45° C.

The yield is 3.7 g (85% of the theoretically calculated yield) in the form of a white solid.

The mono-salt product has been characterized by conventional titrimetic determination of the Cl⁻ content according to the internal method of the applicant INS0053241PV-DE03v.2:

$$Cl\ \%\ [m/m] = \frac{V \cdot f \cdot 0.03545}{E}$$

V=volume $AgNO_3$ 0.01 M
f=$AgNO_3$ standard 0.01 M 1.004
E=initial weight [g]

| Sample No. | E | V | Cl % | average |
|---|---|---|---|---|
| Sample 1-1 | 31.34 mg | 6.9877 ml | 7.94% m/m Cl | 7.94% m/m |
| Sample 1-2 | 30.21 mg | 6.7354 ml | 7.94% m/m Cl | |
| Sample 2-1 | 31.98 mg | 7.1941 ml | 8.01% m/m Cl | 7.99% m/m |
| Sample 2-2 | 29.55 mg | 6.6148 ml | 7.97% m/m Cl | |

The theoretically calculated value is 7.97%, which confirms the mono-salt formation.

| Elemental analysis: | | | | |
|---|---|---|---|---|
| Sample No. | C [%] | H [%] | N [%] | Prot [%] |
| theoretically calculated mono-salt | 56.69 | 4.98 | 18.89 | |
| Sample 1-1 | 55.47 | 5.589 | 18.36 | 0.000 |
| Sample 1-2 | 55.71 | 5.684 | 18.40 | 0.000 |
| average | 55.59 | 5.636 | 18.38 | 0.000 |
| standard deviation, abs. | 0.17 | 0.068 | 0.03 | 0.000 |
| standard deviation, rel. [%] | 0.3 | 1.199 | 0.16 | 0.000 |
| Delta [%] | 0.23 | 0.096 | 0.04 | 0.000 |

Crystallization occurred at pH 5-5.5.

It is assumed that the delta results from residual water.

FIG. 7.1 shows the confirmation of the mono-salt by HPLC analysis FIG. 7.2 shows the confirmation of the mono-salt by DSC measurement.

II. Evaluation of Polymorphs of selected Salts of Example Compound No. 127

In the following, the samples are indicated by an identification code in the form PP566-XYZ-Pw, wherein XYZ specifies the salt/co-crystal former (i.e. the kind of acid), which is either SO4 for sulphate salts or P04 for phosphate salts, and Pw indicates the specific sample/experiment (w=1, 2, . . . n).

The polymorphs are numbered as PMx, i.e. PM1, PM2, PM3 . . . etc.

1. Polymorphs of Sulfuric Acid Salts of Example Compound No. 127

The following experiment describes the evaluation of various polymorphs of sulfuric acid salts of Example Compound No. 127 and determines the stable form (or hydrate) of the sulphate salt of Example Compound No. 127 in the solid state. All polymorphs of sulfuric acid evaluated herein were 1:1 salts of the compound No. 127.

1.1 Characterization of the Starting Material (PP566-SO4-P1)

Powder X-Ray Diffraction:

The PXRD pattern of PP566-SO4-P1 was recorded in reflection mode (not shown), which confirmed that the sample is amorphous in nature.

TG-FTIR Analysis:

TG-FTIR indicates that the amorphous sulphate salt PP566-SO4-P1 contains appr. 5% wt and starts to decompose around 160° C. (not shown).

DSC Analysis:

PP566-SO4-P1 presents first a small endothermic event at 53° C., associated with a ΔH of 4.7 J/g. At 78° C. a sharp exothermic event can be observed, associated with a ΔH of 52 J/g, likely crystallization. An additional small thermic event is visible at 59° C. This signal is assumed to correspond to the glass transition of the amorphous fraction, which has, however, not been finally confirmed yet. At 164° C., a broad endothermic event takes place, possibly attributable to melting of the new crystalline phase along with decomposition of the compound.

$^1$H NMR Spectroscopy:

The chemical integrity of the compound PP566-SO4-P1 was verified by $^1$H-NMR. The spectrum presents a broad feature, centred at 10 ppm, assigned to hydrogen bonds formers or possibly to not completely deprotonated acid (likely $HSO_4$) (spectrum not shown).

DVS Studies:

The behaviour of the substance in the DVS was analysed. The compound picks up water very quickly at 50% r.h. (ca. 4.5% wt) and reaches a plateau, suggesting the formation of a crystalline hydrate. At 0% r.h. the sample loses around 5% wt of the original weight (9% of the weight at 50% r.h.), however does not reach a plateau, suggesting that some water could be still present in the compound and the substance might reach eventually an anhydrous state. However this hypothetical state is extremely unstable as already at 5% r.h. it starts to pick up water, gaining more than 10% wt at 55% r.h. where it undergoes to a sharp decrease of ca. 3% wt, suggesting a recrystallization induced by humidity, where a less hydrated structure is generated. This process continues until ca. 65% r.h. where the compound reaches a minimum, then the substance slowly picks up water until 80% r.h. (order of 2% wt); however when a critical r.h. is reached, in few minutes the sample picks up more than 13% wt and reaches a plateau which looks to be very stable, even when the relative humidity is lowered to 50%, suggesting the formation of a higher hydrate which is stable at more than 50% (not shown).

A PXRD has been taken after the DVS cycle, which shows crystalline material (pattern not shown herein).

1.2 Evaluation of Polymorphs

The polymorphism landscape of the compound PP566-SO4-P1 was investigated by suspending the material in a variety of solvents and solvent mixtures in order to investigate a broad variety of physical conditions and water activities. At least 6 crystalline forms (PM1 to PM6) were identified so far, but more can be hypothesized. The solid forms were tested by vacuum drying at 45° C. The summary of the results are presented in the following Table:

| Sample | Solvent/Conditions | Result |
| --- | --- | --- |
| PP566-SO4-P1 | starting compound | amorphous |
| PP566-SO4-P2 | MeCN | PM1 |
| PP566-SO4-P3 | dioxane | amorphous |
| PP566-SO4-P4 | DCM | PM1 |
| PP566-SO4-P5 | EtOH | PM2 |
| PP566-SO4-P5-DRY | vacuum drying 45° C./30 mbar | PM2 |
| PP566-SO4-P6 | EtOAc | PM3 |
| PP566-SO4-P6-DRY | vacuum drying 45° C./30 mbar | PM3 |
| PP566-SO4-P7 | heptane | amorphous |
| PP566-SO4-P8 | MeOH | PM4 |
| PP566-SO4-P9 | i-PrOH | PM1 |
| PP566-SO4-P9-DRY | vacuum drying 45° C./30 mbar | PM1 |
| PP566-SO4-P10 | THF | PM5 |
| PP566-SO4-P10-DRY | vacuum drying 45° C./30 mbar | PM5 |
| PP566-SO4-P11 | water | PM6 |
| PP566-SO4-P12 | acetone | PM1 |
| PP566-SO4-P13 | MeOH:water 3:1 $a_w = 0.6$ | PM4 |
| PP566-SO4-P14 | MeOH:water 8:2 $a_w = 0.4$ | PM4 |
| PP566-SO4-P15 | MeOH:water 9:1 $a_w = 0.3$ | PM4 |
| PP566-SO4-P16 | MeOH:water 95:5 $a_w = 0.2$ | PM4 |
| PP566-SO4-P16-DRY | vacuum drying 45° C./30 mbar | PM4 |
| PP566-SO4-P17 | acetone:water 8:2 $a_w = 0.8$ | PM6 |
| PP566-SO4-P17-DRY | vacuum drying 45° C./30 mbar | amorphous |
| PP566-SO4-P18 | acetone:water 9:1 $a_w = 0.7$ | PM1 |
| PP566-SO4-P19 | acetone:water 95:5 $a_w = 0.5$ | PM1 |
| PP566-SO4-P1 after DVS | water vapor—down/up | PM6 |
| PP566-SO4-P20 | EtOH:water 4:1, 50° C. $a_w = 0.6$ | PM1 |
| PP566-SO4-P21 | EtOH:water 3:1, 50° C. $a_w = 0.7$ | PM1 |
| PP566-SO4-P22 | EtOH:water 4:1, 5° C. $a_w = 0.6$ | PM1 |
| PP566-SO4-P23 | EtOH:water 3:1, 5° C. $a_w = 0.7$ | PM1 |

A summary of the PXRDs of the obtained forms PM1 to PM6 is depicted in FIG. 8.1.

1.3 Polymorph Form PM1

The PM1 polymorph form is obtained from MeCN, i-PrOH, DCM, acetone, acetone:water 95:5 and acetone:water 9:1. PXRD shows broad peaks, suggesting poor crystallinity (FIG. 8.2), but ¹H-NMR shows that the chemical integrity is maintained (FIG. 8.3). TG-FTIR for sample PP566-SO4-P2 shows loss of water of 2.5% wt which begins at ca. 50° C. until 150° C., suggesting a hemihydrate (FIG. 8.4). The fact that form PM1 was obtained from a sample in acetone—water 9:1 suggests that PM1 is stable at water activities up to 0.7. Surprisingly form PM1 was obtained in experiments with water-free solvents. In these cases the water presumably comes from the starting material which has about 5% of water as can be seen in the respective TG-FTIR (not shown herein). Form PM1 is resistant to vacuum drying and the crystallinity is kept even after overnight drying at 45° C. and p<30 mbar (experiment PP566-SO4-P9-DRY). This form was also reproducibly and independently obtained in an independent experiment. This form was further investigated by DVS, TG-FTIR, DSC, and NMR.

DVS was carried out in a two cycles humidity ramp (FIG. 8.5). Also in the case of form PM1 (like the amorphous starting material, not shown herein), the material shows an extremely complex behaviour in the thermogram. Few % wt are lost when the humidity is lowered at 0% RH, and the thermogram reaches a minimum, when the RH is increased, the sample comes back close to the original weight, and slowly takes water up (2-3% wt), however, when 80% RH is reached the material rapidly absorbs ca. 15% wt of water, without reaching a plateau, presumably the mass uptake would continue if the material was kept longer at 95% RH. The hydration level looks to be stable when the humidity comes back to 50% and then close to 0%, sharply loses 18% wt. During the second cycle the uptake is quicker, and is similar to the one observed in the amorphous phase (not shown herein), suddenly a sharp decrease suggests recrystallization. The material goes then to a quick mass uptake to almost 20% wt, which is stable until the end of the cycle at 50% wt. This behaviour gives some insights to the mechanism of formation of the hydrates and suggest that when the salt reaches a high hydration level and exposed then to drying conditions, the lattice collapses and undergoes to amorphous phase; which is supported by the behaviour which was observed for form PM6 (see below). The PM1 form looks to be stable also when suspended in mixtures EtOH:water 4:1 and 3:1 at 5° C. and 50° C.

In conclusion the PM1 form remains stable under strict humidity controlled conditions (about 50% and in any case below 70% RH), which was confirmed by exposing 10 mg of PM1 to 53% RH for 10 days followed by PXRD (experiment PP566-SO4-P24). The polymorph form remained PM1.

| theoretical and experimental hydrates | |
| --- | --- |
| Hydration | Water Content (%) |
| Hemihydrate | 1.8 |
| Monohydrate | 3.7 |
| Found | 2.5 |

1.4 Polymorph Form PM2

The PM2 polymorph form is highly crystalline and was only obtained from EtOH. ¹H-NMR and TG-FTIR suggest a mono EtOH solvate (not shown herein). Interestingly only traces of water are present in the TG-FTIR, suggesting that EtOH (ca.8.3% wt) replaced the water in the crystal lattice, and favours a highly ordered system. This is consistent with the sharp loss of solvent between 120 and 150° C., well above the boiling point of ethanol. This form is also resistant to vacuum drying and the PXRD is unchanged after overnight drying at 30 mbar at 45° C. as confirmed by experiment PP566-SO4-P5-DRY.

1.5 Polymorph Form PM3

The PM3 polymorph form was obtained from a slurry in EtOAc and turned out to be poorly crystalline. The PM3 form shares few similarities in terms of line width with form PM1, but the peak position in the PXRD is essentially different (not shown herein). ¹H-NMR confirms the chemical integrity of the compound (not shown herein) and TG-FTIR confirms the solvated nature of the form showing release of EtOAc up to 150° C. (not shown herein). This form is also resistant to vacuum drying and the PXRD remained unchanged after overnight drying at 30 mbar at 45° C. as confirmed by experiment PP566-SO4-P6-DRY.

1.6 Polymorph Form PM4

The PM4 polymorph form is a highly crystalline form which was obtained from a slurry experiment in MeOH and from several MeOH:water mixtures. The solvated nature of the form is suggested by both ¹H-NMR and TG-FTIR (not shown herein). Despite some water is present, the most of it is lost around 100° C., and therefore a mixed hydrate/solvate is unlikely. On the other hand MeOH release starts around 110° C., above the boiling point of this solvent of more than 35° C., and ends around 170° C., suggesting that MeOH is tightly bound to the crystal lattice. The form PM4 is stable until a water activity of at least 0.6, as demonstrated in the experiments PP566-SO4-P13 to P16.

1.7 Polymorph Form PM5

The PM5 polymorph form was obtained from suspension equilibration in THF and shows a good degree of crystallinity with sharp reflections (not shown herein) The compound is a THF solvate with a minor amount of water which is not quantifiable. The $^1$H-NMR shows that the chemical integrity of the salt compound is maintained and THF is also visible at 1.76 ppm but the resonance at 3.63 ppm overlaps with other signals (FIG. 9.16). The amount of THF was estimated approximatively in the TG-FTIR as the signal overlaps with water, and is less than 3.9% wt. The solvated nature of the phase is confirmed by the fact that THF can be observed in the thermogram up to 160° C., suggesting that it is tightly bound to the crystal lattice (FIG. 9.17). This can be confirmed by the fact that it is also resistant to vacuum drying and the PXRD is unchanged after overnight drying at 30 mbar at 45° C. as confirmed by experiment PP566-SO4-P10-DRY.

1.8 Polymorph Form PM6

The PM6 polymorph form is the most hydrated form which was obtained in the present experiments, and is obtained from suspension equilibration from water. The form shows a high degree of crystallinity (not shown herein) and looks to be stable for a reasonable time even when the r.h. is lowered at 50%.

Similar as for the other polymorph forms evaluated herein, the chemical integrity of the salt compound is not modified ($^1$H-NMR, not shown herein). The water which is contained in the lattice is 19.6% wt, close to a hexahydrate, and is release up to ca. 150° C. (not shown herein), consistent with the value observed in the DVS (ca. 19% wt). This form undergoes to transformation to the amorphous phase once it is dried under vacuum overnight as confirmed by experiment PP566-SO4-P17-DRY.

2. Polymorphs of Phosphoric Acid Salts of Example Compound No. 127

The following experiment describes the evaluation of various polymorphs of phosphoric acid salts of Example Compound No. 127 and determines the stable form (or hydrate) of the phosphate salt of Example Compound No. 127 in the solid state. The polymorphs PM1 and PM3 to PM11 of phosphoric acid evaluated herein are 2:1 salts of the compound No. 127. The polymorph PM2 of phosphoric acid evaluated herein is a 1:1 salt of the compound No. 127.

2.1 Characterization of the Starting Material (PP566-PO4-P1)

Powder X-ray Diffraction:

The PXRD pattern of PP566-PO4-P1 was recorded in reflection mode, which confirmed that the sample is partially crystalline or mesomorphic (not shown herein).

TG-FTIR Analysis:

TG-FTIR indicates that the phosphate complex contains ca. 1.3% wt of i-PrOH. PP566-PO4-P1 starts to decompose around 120° C. (not shown herein).

DSC Analysis:

PP566-PO4-P1 presents complex thermal behavior. A glass transition is observed at ca. 47° C., associated with a change in heat capacity of ca. 0.8 J/g° C., followed by a endothermic thermal event at about 57° C. The sample is partially crystalline or consists of mesomorphic (glassy liquid crystalline) material (not shown herein).

$^1$H NMR Spectroscopy:

The chemical integrity of the compound PP566-PO4-P1 was verified by $^1$H-NMR. A minor amount of isopropanol can be observed in the phosphate spectrum, consistent with TG-FTIR. The spectrum present a broad feature, centred at 5.7 ppm, assigned to hydrogen bonds formers or possibly to not completely deprotonated acids ($H_2PO_4^-$, $HPO_4^{2-}$).

DVS Studies:

The behaviour of the substance in the DVS was analysed. The compound PP566-PO4-P1 suggests the formation of several hydrates. The sample picks up water within minutes and then shows a plateau at 50% r.h. followed by the formation of a possible anhydrous phase at 0% r.h., very sensitive to water (starts to uptake mass around 5% r.h.). Eventually a plateau is reached at 95% r.h. but this superior hydration state is not stable at lower r.h. and loses water reaching a new plateau at 50% r.h. (but not the same of the initial plateau observed at the beginning of the experiment). The final water content at 50% r.h. is about 10%.

A PXRD has been taken after the DVS cycle, which shows the presence of the hydrate form PM5 (not shown herein).

Elemental Analyses:

The starting material was submitted for CHNF analyses and the phosphorous content was determined by ICP-OES. The stoichiometry falls close to the ratio of Example Compound No. 127:PO$_4$ of 2:1.

| Summary of the elemental analysis results. | | | | | |
|---|---|---|---|---|---|
| Complex | C (%) | H (%) | N (%) | F (%) | P (%) |
| 1:1 (Theor.) | 50.1 | 4.2 | 16.7 | 3.6 | 6.1 |
| 2:1 (Theor.) | 55.1 | 4.6 | 18.3 | 3.9 | 3.4 |
| Found | 54.0 | 5.0 | 18.0 | 4.0 | 3.4 |

2.2 Evaluation of Polymorphs

The polymorphism landscape of the compound PP566-PO4-P1 was investigated by suspending the material in a variety of solvents and solvent mixtures in order to investigate a broad variety of physical conditions and water activities. At least 11 crystalline forms (PM1 to PM11) were identified so far, but more can be hypothesized. The summary of the results are presented in the following Table:

| Sample | Solvent/Conditions | Result |
|---|---|---|
| PP566-PO4-P1 | starting compound | mesomorphic material |
| PP566-PO4-P2 | MeCN | mixture PM2 + unknown peaks |
| PP566-PO4-P3 | dioxane | amorphous |
| PP566-PO4-P4 | DCM | new phase PM1 |
| PP566-PO4-P4-DRY | vacuum drying 45° C./30 mbar | new phase PM9 |
| PP566-PO4-P5 | EtOH | new phase PM2 |
| PP566-PO4-P5-DRY | vacuum drying 45° C./30 mbar | new phase PM2 |

| Sample | Solvent/Conditions | Result |
| --- | --- | --- |
| PP566-PO4-P6 | EtOAc | new phase PM2 |
| PP566-PO4-P7 | heptane | mesomorphic material |
| PP566-PO4-P8 | MeOH | new phase PM3 |
| PP566-PO4-P8-DRY | vacuum drying 45° C./30 mbar | new phase PM3 |
| PP566-PO4-P9 | i-PrOH | new phase PM2 |
| PP566-PO4-P10 | THF | new phase PM4 |
| PP566-PO4-P11 | water | new phase PM5 |
| PP566-PO4-P12 | acetone | new phase PM2 |
| PP566-PO4-P13 | MeOH:water 3:1 $a_w = 0.6$ | new phase PM6 |
| PP566-PO4-P13-DRY | vacuum drying 45° C./30 mbar | new phase PM10 |
| PP566-PO4-P14 | MeOH:water 8:2 $a_w = 0.4$ | new phase PM6 |
| PP566-PO4-P15 | MeOH:water 9:1 $a_w = 0.3$ | new phase PM7 |
| PP566-PO4-P15-DRY | vacuum drying 45° C./30 mbar | new phase PM11 |
| PP566-PO4-P16 | MeOH:water 95:5 $a_w = 0.2$ | mixture PM7 + PM3 |
| PP566-PO4-P17 | acetone:water 8:2 $a_w = 0.8$ | mixture PM8 + PM5 |
| PP566-PO4-P18 | acetone:water 9:1 $a_w = 0.7$ | mixture PM8 + PM5 |
| PP566-PO4-P19 | acetone:water 95:5 $a_w = 0.5$ | new phase PM8 |
| PP566-PO4-P19-DRY | vacuum drying 45° C./30 mbar | new phase PM8 |
| PP566-PO4-P1 after DVS | water vapor—down/up | new phase PM5 |
| PP566-PO4-P20 | EtOH:water 8:2, 50° C. $a_w = 0.6$ | amorphous |
| PP566-PO4-P21 | EtOH:water 3:1, 50° C. $a_w = 0.7$ | amorphous |
| PP566-PO4-P22 | EtOH:water 8:2, 5° C. $a_w = 0.6$ | new phase PM2 |
| PP566-PO4-P23 | EtOH:water 3:1, 5° C. $a_w = 0.7$ | amorphous |
| PP566-PO4-P24 | acetone | new phase PM2 |

A summary of the PXRDs of the obtained forms PM1 to PM11 is depicted in FIG. 9.1.

2.3 Polymorph Form PM1

The PM1 polymorph form is obtained from DCM and shows moderate crystallinity (not shown herein), $^1$H-NMR shows that the chemical integrity is maintained (not shown herein). The signal in the $^1$H-NMR at 5.57 ppm indicates the presence of DCM. TG-FTIR shows loss of DCM of 14.2% wt which begins at ca. 30° C., presumably for physisorbed DCM; however the mass loss continues up to 150° C., suggesting a solvate. (not shown herein). This form evolves to a less crystalline form when exposed to vacuum drying for 12 h at 45° C.

2.4 Polymorph Form PM2

The PM2 polymorph form is highly crystalline and was only obtained from EtOH, but also from several other solvents suggesting that it could be an anhydrous phase (FIG. 9.2 and FIG. 9.6). Even though $^1$H-NMR and TG-FTIR of the experiment PP566-PO4-P5 suggest that it could be a hemi EtOH solvate (FIGS. 9.3 and 9.4 respectively), as ethanol is released up to 170° C., TG-FTIR was recorded on another sample where the form PM2 was obtained (experiment PP566-PO4-P12, slurry from acetone) and the thermogram shows no solvent release, nor mass loss up to the decomposition temperature at about 150° C. This suggests that the structure of this compound can accommodate different solvents in the crystal lattice and maintain the same solid state structure. The crystal form is resistant to vacuum drying overnight at 45° C. DVS was run also for this form. The material takes up appr. 0.7% wt at 95% r.h. reaching a plateau, and returns to slightly lower weight after the cycle (FIG. 9.7). The material is only slightly hygroscopic.

The material was also submitted for elemental analyses and the result is consistent with a 1:1 salt:

| Elemental analyses results for PP566-PO4-P24 | | | | | |
| --- | --- | --- | --- | --- | --- |
| Complex | C (%) | H (%) | N (%) | F (%) | P (%) |
| 1:1 (Theor.) | 50.1 | 4.2 | 16.7 | 3.6 | 6.1 |
| 2:1 (Theor.) | 55.1 | 4.6 | 18.3 | 3.9 | 3.4 |
| Found | 49.1 | 4.6 | 16.1 | 3.6 | 5.9 |

2.5 Polymorph Form PM3

The PM3 polymorph form is a highly crystalline form which was obtained from a slurry experiment in MeOH and in a mixture with form PM7 (see below) in MeOH:water 95:5 mixture. The solvated nature of the form is suggested by both $^1$H-NMR and TG-FTIR (not shown herein). MeOH release starts around 90° C., above the boiling point of this solvent of more than 35° C., and ends around 120° C. in a sharp step, suggesting that MeOH is tightly bound to the crystal lattice. It is interesting to note that the formation of this phase has a very narrow water activity range, and evolves in a mixed solvate:hydrate form (Form PM7) slightly below $a_w=0.2$, and there is no trace of this form at $a_w=0.3$.

2.6 Polymorph Form PM4

The PM4 polymorph form was obtained from suspension equilibration in THF and shows a low degree of crystallinity with broad reflections (not shown herein). The compound is a THF solvate. The $^1$H-NMR shows that the chemical integrity of the API is maintained and THF is also visible at 1.76 ppm and at 3.63 ppm (not shown herein). The amount of THF can be estimated by TG-FTIR, and is about 2.8% wt. The solvated nature of the phase is confirmed by the fact that THF can be observed in the thermogram up to 180° C. along with decomposition, suggesting that it is tightly bound to the crystal lattice (not shown herein).

2.7 Polymorph Form PM5

The PM5 polymorph form is the most hydrated form which was obtained in the present experiments. It is obtained from suspension equilibration from water and storing the material at 95% r.h (see DVS of the starting material). The form shows a high degree of crystallinity (not shown herein). As the other obtained forms the chemical integrity of the API is not modified ($^1$H-NMR, not shown herein). The water which is contained in the lattice could not be quantified by TG-TFIR, as not enough material could be recovered in experiment PP566-PO4-P11, but can be deduced from DVS (not shown herein) which is about 11% wt.

2.8 Polymorph Form PM6

The PM6 polymorph form is a hydrate, lower than PM5, obtained from a mixture of MeOH:water 3:1 and 4:1. The form shows a high degree of crystallinity (not shown herein). As the other obtained forms the chemical integrity of the compound is not modified ($^1$H-NMR, not shown herein). Water is released during the TG-FTIR experiment in two steps (not shown herein). No trace of methanol could be observed, neither in the TG-FTIR nor in the NMR spectrum. This form is obtained at a moderate water activity (about 0.4 to 0.6).

2.9 Polymorph Form PM7

The PM7 polymorph form is a mixed hydrate solvate, obtained from a mixture methanol:water 9:1 ($a_w$=0.3) and is a pure crystalline phase (not shown herein) in which both methanol and water are bound to the lattice. The form is obtained at relatively low water activity. The TG-FTIR shows mass release of both solvents in two separate steps (not shown herein).

2.10 Polymorph Form PM8

The PM8 polymorph form is supposed to be a mixed solvate/hydrate and is generated when the water activity is between 0.5 and 0.7 (not shown herein). Interestingly an acetone solvate is not observed when the compound is stirred in pure acetone at RT (experiment PP566-PO4-P12).

2.11 Polymorph Form PM9

The PM9 polymorph form was obtained after exposing the material PP566-PO4-P4 to 30 mbar and 45° C. for ca. 12 h. This form is presumed to be the desolvated form from PM1, the DCM solvate. The form is poorly crystalline and shows broad peaks in the diffractogram (not shown herein).

2.12 Polymorph Form PM10

The PM10 polymorph form was obtained after exposing the material PP566-PO4-P13 to 30 mbar and 45° C. for ca. 12 h (not shown herein). Interestingly, the form shares some similarities with the hydrate form PM5 rather than PM6 (not shown herein), but less crystalline and a slight shift to higher 2theta suggesting a slightly smaller unit cell (leading to the assumption that it could be a lower hydrate). This is confirmed by TG-FTIR (not shown herein).

2.13 Polymorph Form PM11

The PM11 polymorph form was obtained after exposing the material PP566-PO4-P15 to 30 mbar and 45° C. for appr. 12 h (not shown herein). The form is poorly crystalline, TG-FTIR indicates the presence of water (not shown herein).

III. Pharmacological Assays

The following pharmacological assays have been carried out with selected Example Compounds in the form of the corresponding free base and/or in the form of the HCl triple salt. As the compound according to formula (I) mainly constitutes the active principle, comparable activity results are to be expected for the corresponding salts according to the present invention. The following experimental results support that the new salts (including their solvates, hydrates and polymorphs etc.) according to the presents patent application maintain a ferroportin inhibition activity, and can also improve the ferroportin inhibition activity, and/or improve the pharmacokinetic profile of the compounds, and/or improve the physicochemical properties of the compounds to make it easier to formulate into a galenic form, and/or have the advantage to be isolated in the form of a crystal which improves the physicochemical properties of the compounds to make such compounds easier to formulate into a galenic form or easier to handle/process or to improve its stability.

In particular, in the following tests the Example Compounds have been tested in the form of the triple salt (3HCl) and/or in the form of the free base as follows:

| Example Compound No. | Base | 3HCl Salt |
|---|---|---|
| 1 | + | + |
| 2 | + | − |
| 4 | + | − |
| 40 | + | + |
| 94 | + | + |
| 118 | − | + |
| 126 | + | + |
| 127 | + | + |
| 193 | + | − |
| 206 | + | − |
| 233 | + | − |
| 234 | + | − |
| 208 | + | − |
| 225 | + | + |

1. Hepcidin Internalization Assay (J774)

This cellular assay allows quantification of the binding of hepcidin to ferroportin (Fpn) through microscopic detection of internalization of a fluorescently labeled hepcidin into J774 cells. J774 is a mouse macrophage cell line which was shown to express Fpn endogenously upon incubation with iron (Knutson et al, 2005). Binding of hepcidin to Fpn triggers internalization and degradation of both hepcidin and Fpn. However, the TMR (6-carboxytetramethylrhodamine) fluorophore attached to hepcidin remains associated with the cell after degradation of the hepcidin peptide backbone. Therefore, microscopic detection of cell-associated TMR fluorescence is a measure of hepcidin binding to Fpn and internalization of hepcidin and Fpn. If TMR-hepcidin is prevented from binding to Fpn, cellular TMR fluorescence remains low (Durrenberger et al, 2013). The effect of small molecular weight Fpn inhibitor compounds in this assay was evaluated in vitro as described below.

J774 cells, harvested from ca. 80% confluent cultures, are plated at 8×10$^5$ cells/ml in complete medium (DMEM, 10% FBS, 1% Penicillin-Streptomycin) containing 200 µM Fe(II-I)NTA (nitrilotriacetic acid), 100 µl per well of 96 well MicroClear plates (Greiner; Cat. 655090) and grown at 37° C. with 5% $CO_2$. After overnight incubation, cells are washed 3 times with pre-warmed DMEM w/o phenol red, 30 µl/well of DMEM w/o phenol red is added after the final wash and 10 µl/well of dilution series of test compounds are added in triplicates. J774 cells are pre-incubated with test compounds at 37° C. with 5% $CO_2$ for 15 min. before TMR-hepcidin is added at 25 nM final concentration. Cells are incubated in a total volume of 50 µl at 37° C. with 5% $CO_2$ for 2 hours, then Hoechst 33342 dye is added to a final concentration of 0.5 µg/ml to stain nuclei and further incubated for 10 min. at 37° C. with 5% $CO_2$. Cells are washed 3 times with PBS and fixed in 100 µl of 4% paraformaldehyde in PBS for 15 min. at room temperature. After removal of the paraformaldehyde solution, cells are washed 3 times with PBS leaving 100 µl per well and the plates are sealed with foil plate seal. TMR (530-550 nm excitation/575-625 nm emission/400 ms exposure time) and Hoechst 33342 (360-370 nm excitation/420-460 nm emission/10 ms exposure time) fluorescence images are acquired using a ScanR plate imager (Olympus) with a 20× high NA objective. Four pictures are acquired per well and fluorescence channel covering ca. 1500 cells per well. The acquired image data is analysed with the ScanR image analysis software. Image analysis include detection of nuclei (Hoechst 33342 fluorescence), identification of cell-associated regions, application of a virtual channel and thresholding for rolling-ball-type background reduction, followed by application of the Sum(Mean) algorithm to measure the TMR fluorescence associated with cells as a quantitative measure for internalized TMR-hepcidin. $IC_{50}$ values are calculated with the Sum(Mean) raw data using "log(inhibitor) vs. response" curve fitting of Prism 5 software (GraphPad Software Inc., version 5.02). For each data set the fit of the "log(inhibitor) vs. response (three parameters)" model is compared to the fit of the "log(inhibitor) vs. response—Variable slope (four parameters)" model and the $IC_{50}$ data of the preferred model is used. $IC_{50}$ data of the Fpn inhibitors that were tested in the hepcidin internalization assay are listed in Table 1. The $IC_{50}$ of unlabeled hepcidin in this assay is 0.015±0.011 µM.

Table 1 Average (AVE) $IC_{50}$ data of Fpn inhibitors tested in the hepcidin internalization assay is shown for multiple measurements

TABLE 1

| Exp. Comp. No. | J774 IC50 (uM) |
|---|---|
| 1 | 0.012 |
| 2 | 0.035 |
| 4 | 0.155 |
| 40 | 0.049 |
| 94 | 0.012 |
| 118 | 0.103 |
| 126 | 0.096 |
| 127 | 0.009 |
| 193 | 0.287 |
| 206 | 0.18 |
| 208 | 0.012 |
| 233 | 16 |

2. Biophysical Ferroportin-Hepcidin Binding Assay

This biophysical assay was developed to confirm inhibition of hepcidin binding to ferroportin (Fpn) more directly. Incubation of TMR-hepcidin with purified human Fpn isolated from *Pichia pastoris* yeast cells expressing human Fpn with a C-terminal FLAG affinity tag (Bonaccorsi di Patti, 2014) leads to increased fluorescence polarization (FP) of the TMR-hepcidin ligand. Small molecular weight Fpn inhibitors are tested for inhibition of binding of TMR-hepcidin to Fpn, as detected by dose-dependent decrease of the TMR FP signal, as described in detail below.

A mixture of 1.3 µM human Fpn and 30 nM TMR-hepcidin in FP assay buffer containing 50 mM Tris-HCl pH 7.3, 200 mM NaCl, 0.02% DDM, 0.1% BSA is plated into a 384 well black low volume round bottom plate (Corning, Cat. 3677) at 16 µl per well. 8 µl of serial dilutions of test compounds are added in duplicates to reach final Fpn and TMR-hepcidin concentrations of 1 µM and 20 nM, respectively. Plates are incubated for 90 minutes at room temperature and parallel (S) and perpendicular (P) fluorescence is measured in a Synergy H1 fluorescence reader (BioTek). FP values are calculated in mP according to the following formula.

$$mP = \frac{F_{parallel} - F_{perpendicular}}{F_{parallel} + F_{perpendicular}} \times 1000$$

$IC_{50}$ values are determined with the calculated mP values as described for the hepcidin internalization assay and are listed in Table 2. The $IC_{50}$ of unlabeled hepcidin in this assay is 0.37±0.067 µM.

Table 2 Average (AVE) $IC_{50}$ data of Fpn inhibitors tested in the biophysical hepcidin-ferroportin binding assay is shown for multiple measurements.

TABLE 2

| Exp. Comp. No. | FP IC50 (uM) |
|---|---|
| 1 | 0.016 |
| 2 | 0.017 |
| 40 | 0.068 |
| 94 | 0.044 |
| 118 | 0.25 |
| 126 | 0.12 |
| 127 | 0.023 |
| 193 | 0.074 |
| 206 | 0.036 |
| 208 | 0.019 |
| 233 | 6.776 |

3. Inhibition of Ferroportin Mediated Iron Export Activity in an Iron Response Assay Intracellular iron levels are indirectly measured in this assay by monitoring the activity of a beta-lactamase (BLA) reporter gene fused to the human ferritin promoter and the associated iron regulatory element (IRE) contained within the 5' untranslated region of the ferritin mRNA. Expression of ferroportin (Fpn) in such a cell line leads to iron efflux and lower iron levels as reflected by lower activity of the reporter gene. On the other hand, inhibition of Fpn-mediated iron efflux results in elevated cellular iron levels which is detected as increased reporter gene activity. Small molecular weight Fpn inhibitor compounds are tested for dose-dependent effects in this in vitro iron response assay as described below.

The HEK-293 cell line #354 is generated by stable integration of (i) a human Fpn-GFP fusion construct inserted in a derivative of the doxycycline-inducible pTRE-Tight-BI plasmid (Clontech, Cat. 631068) and (ii) a human ferritin promoter-BLA reporter gene into a derivative of the HEK-293 Tet-ON Advanced cell line (Clontech). To generate the ferritin-BLA reporter gene construct, a 1.4 kb fragment of the human ferritin H promoter is amplified by PCR from human genomic DNA (forward primer 5'-CAGGTTTGT-GAGCATCCTGAA-3'; reverse primer 5'-GGCGGCGA-CTAAGGAGAGG-3') and inserted in front of the BLA gene present in the pcDNA™6.2/cGeneBLAzer™-DEST plasmid (Invitrogen, Cat. 12578-043) thereby replacing the original CMV promoter and placing the IRE that regulates translation of the ferritin gene ca. 170 bp upstream of the start codon of the reporter gene. #354 cells are harvested from ca. 80% confluent cultures, seeded at $1.8 \times 10^5$ cells/ml in DMEM/F12 GlutaMAX™ medium (Invitrogen, Cat. 31331-028) containing 10% FBS (Clontech, Cat. 631106), 1% Penicillin-Streptomycin, 200 µg/ml Hygromycin B (Invitrogen, Cat. 10687-010), Blasticidin 5 µg/ml, (Invitrogen, Cat. R210-01), 4 µg/ml doxycycline (Clontech, Cat. 631311), 50 µl per well of 384 well PDL-coated plates and grown at 37° C. with 5% $CO_2$. After overnight incubation, 10 µl/well of dilution series of the test compounds are added in quadruplicates and plates are further incubated overnight at 37° C. with 5% $CO_2$. Cells are washed 3 times with HBSS leaving 25 µl per well. BLA activity was detected by adding 5 µl/well of the GeneBlazer reagent CCF4-AM (Invitrogen, Cat. K1085) to the cells. After incubation of the plates in the dark at 18° C. for 60 min., blue and green fluorescence signals are measured in a Safire2 fluorescence plate reader (Tecan) with excitation at 410 nm and emissions at 458 nm (blue) and 522 nm (green). The ratio of blue/green fluorescence as a measure for BLA activity is calculated and $EC_{50}$ values are determined with the calculated blue/green fluorescence ratios as described for the hepcidin internalization assay. The $EC_{50}$ data of the tested Fpn inhibitors is listed in Table 3. The $EC_{50}$ of hepcidin in this assay is 0.096±0.063 µM (n=37).

Table 3 Average (AVE) $EC_{50}$ data of Fpn inhibitors tested in the iron response assay is shown for multiple measurements.

TABLE 3

| Exp. Comp. No. | BLAzer EC50 (uM) |
|---|---|
| 1 | 0.93 |
| 2 | 1.03 |
| 4 | 1.259 |
| 40 | 1.45 |
| 94 | 0.53 |
| 118 | 2.69 |
| 126 | 1.26 |
| 127 | 0.42 |
| 193 | 3.64 |
| 206 | 3.26 |
| 208 | 0.50 |

4. Ferroportin Internalization and Degradation Assay

HEK-293 cell line #354 (described in example 3) is used to measure the capacity of the compounds to induce internalization and degradation of ferroportin (Fpn) by fluorescence activated cell sorting (FACS). Growing HEK-293 #354 cells in doxycycline containing media induce expression of human Fpn-GFP fusion protein on the cell surface. Data from 10 independent experiments show that cultivation of HEK #354 cells for 48 h in the presence of 4 µg/ml doxycycline induce in average 42.6%±6.4% Fpn-GFP-positive cells. Small molecular weight Fpn inhibitor compounds are tested for dose-dependent effects on the Fpn-GFP mean fluorescence intensity (MFI) on HEK-293 cell line #354, as described below.

HEK #354 cells are harvested from ca. 80% confluent cultures, seeded at $0.6 \times 10^6$ cells/ml in DMEM/F12 GlutaMAX™ medium (Invitrogen, Cat. 31331-028) containing 10% FBS (Clontech, Cat. 631106), 1% Penicillin-Streptomycin (Invitrogen, Cat. 15140-122), 200 µg/ml Hygromycin B (Invitrogen, Cat. 10687-010), Blasticidin 5 µg/ml, (Invitrogen, Cat. R210-01), 4 µg/ml doxycycline (Clontech, Cat. 631311), 50 µl per well of 384 well plates (Greiner; Cat. 781091) and grown at 37° C. with 5% $CO_2$. After overnight incubation, 10 µl/well of dilution series of the test compounds are added in quadruplicates and plates are further incubated overnight at 37° C. with 5% $CO_2$. Cells are washed once with FACS buffer (PBS containing 1% FBS, 2 mM EDTA and 0.05% $NaN_3$), harvested in FACS buffer with 0.5 µg/ml propidium iodide (Sigma, Cat. P4864) and analyzed in a flow cytometer (CANTO™ II, BD Biosciences) equipped with high throughput sampler. Live HEK #354 cells are gated as propidium iodide negative population and analyzed for expression of Fpn-GFP. MFI of Fpn-GFP of ≥2000 live cells for each compound dilution is calculated using FlowJo (Tree Star's, Oregon) and the potency of the Fpn-inhibitors to induce internalization and degradation of Fpn-GFP is calculated as described for the hepcidin internalization assay. $EC_{50}$ data of the Fpn inhibitors that were tested in the ferroportin internalization and degradation assay by FACS are listed in Table 4. The average $EC_{50}$ value of hepcidin in this assay is 0.004±0.002 µM.

Table 4 Average (AVE) $EC_{50}$ data of Fpn inhibitors tested in the ferroportin internalization and degradation assays shown for multiple measurements.

TABLE 4

| Exp. Comp. No. | EC50 (uM) |
|---|---|
| 1 | 0.22 |
| 2 | 0.63 |
| 4 | 1.198 |
| 40 | 0.81 |
| 94 | 0.22 |
| 118 | 4.908 |
| 126 | 0.757 |
| 127 | 0.081 |
| 193 | 3.946 |
| 193-B | 1.391 |
| 206 | 2.072 |
| 208 | 0.15 |

5. Ferroportin Ubiquitination and Degradation

Exposure of cells expressing ferroportin (Fpn) to hepcidin is known to trigger ubiquitination and subsequent internalization and degradation of Fpn (Qiao, 2012). The potential of Fpn inhibitors to induce Fpn ubiquitination and degradation is investigated with an immunoprecipation assay using the J774 mouse macrophage cell line which expresses Fpn upon treatment with iron.

J774 cells (DSMZ, Cat. ACC170) are seeded at $0.8 \times 10^6$ cells/ml in 15 ml of medium (DMEM Gibco Cat. 11971-025, 10% heat inactivated FBS Gibco Cat. 10500-064, 1% Penicillin-Streptomycin Gibco Cat. 15140-122) containing 200 µM Fe(III)-NTA into 10 cm tissue culture dishes (Greiner Cat. 664160) and grown overnight at 37° C. with 5% $CO_2$. Cells are incubated with synthetic human hepcidin (Bachem, Cat. H-5926) or Fpn inhibitor compounds for 10 min or 120 min. Cells are washed and lysed with ice-cold lysis buffer (Pierce, Life Technoligies, Cat. 87787) including 1×HALT protease inhibitor cocktail (Life technologies, Cat. 78429) and 10 mM iodoacetamide (Sigma, Cat. 16125) to stabilize ubiquitinated proteins. Immunoprecipitation is done using the Pierce Classic IP Kit (Life Technologies, Cat. 26146) following the manufacturer's protocol. Briefly, 2 mg protein in 1.25 ml IP lysis buffer is incubated by mixing for 1 h at 4° C. with control agarose beads to pre-clear the lysate and reduce nonspecific signal. Unbound lysate is then incubated overnight with 12 µg per reaction of the affinity purified anti-Fpn antibody F308 that was raised against a GST fusion protein of mouse Fpn amino acids 224-308. Immune complexes are captured by pipetting 14 µl settled Pierce Protein A/G Plus Agarose beads (Life Technologies, Cat. 20423) per reaction and the slurry is incubated for 1.5 h at 4° C. with gentle end-over-end mixing. The beads are washed and immune complexes are eluted directly with 75 µl SDS NuPAGE LDS sample buffer (Life Technologies, Cat. NP0007) containing DTT (Life Technologies, Cat. NP0009).

After immunoprecipitation samples are analyzed by Western blotting using a rabbit anti-mouse MTP1 antiserum (Alpha Diagnostic International, Cat. MTP11-A) and a mouse anti-mono- and polyubiquitinylated conjugates monoclonal antibody (Enzo Lifesciences, Cat. BML-PW8810) for detection of ferroportin and ubiquitin, respectively. Mouse monoclonal anti-rabbit IgG light chain (Abcam, Cat. ab99697) and anti-mouse IgG H&L (Abcam, Cat. ab6789) HRP conjugates are used as secondary antibodies.

Figure 10:
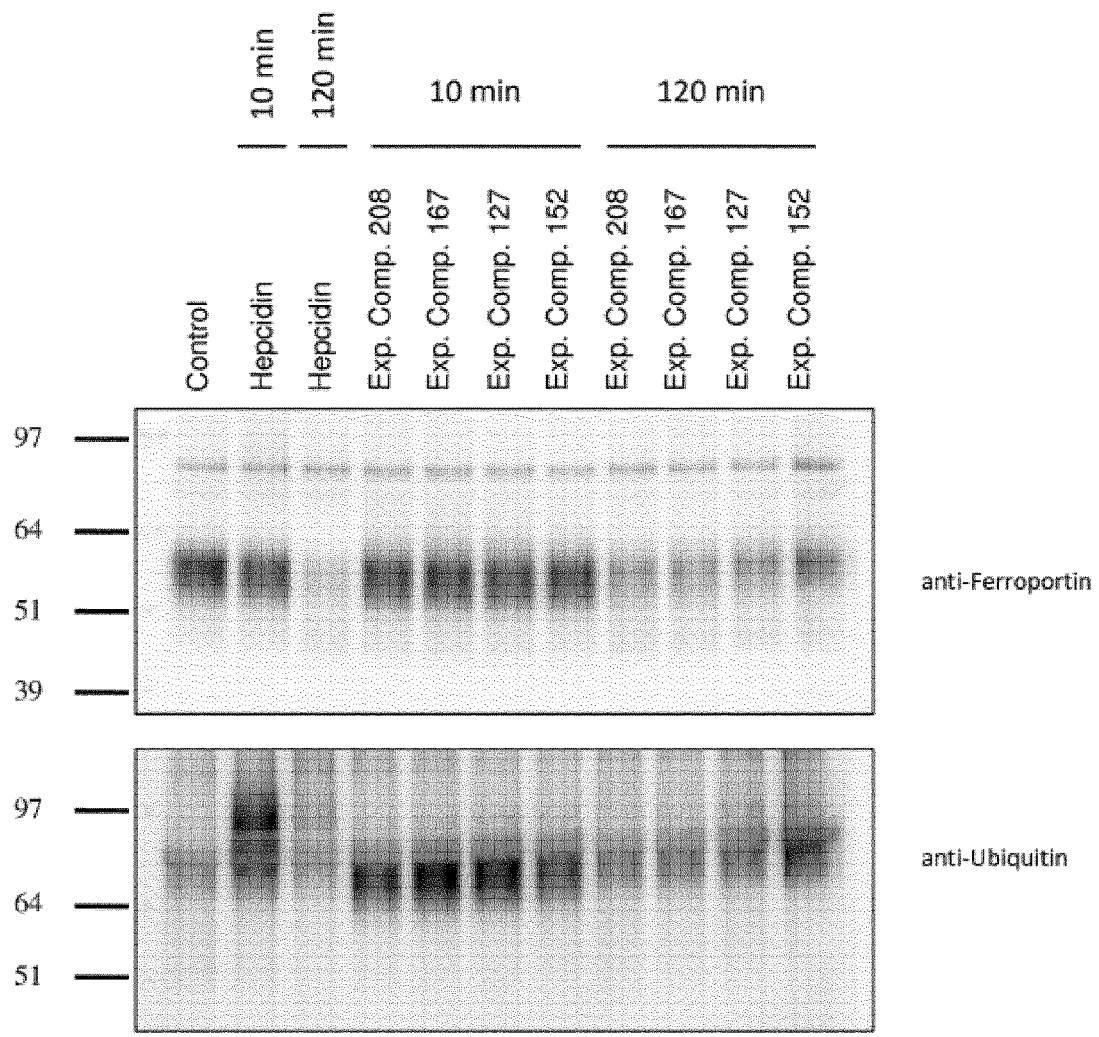
FIG. 10: Immunoblotting of immunoprecipitates with the anti-Fpn antibody MTP1

A selection of eleven Fpn inhibitors were tested in this assay and compared to hepcidin. As shown in FIG. 10 and Table 5, treatment of cells with Fpn inhibitors lead to rapid ubiquitination within 10 minutes (FIG. 10 upper panel) and degradation after 2 hours of Fpn (FIG. 10 lower panel). The degree of Fpn degradation by the Fpn inhibitors was comparable to the effect of hepcidin. However, hepcidin treatment resulted in ubiquitinated Fpn with higher molecular weight compared to Fpn inhibitor treatment, suggesting poly-ubiquitination versus mono-ubiquitination by hepcidin versus Fpn inhibitors, respectively.

Table 5 Summary of Fpn inhibitors tested in the Fpn ubiquitination and degradation assay. The effects of treatment with Fpn inhibitors on Fpn degradation and Fpn ubiquitination were scored by visual inspection of Western blots (+ comparable to hepcidin; − no effect; +/− intermediate effect).

TABLE 5

| Exp. Comp. No. | Concentration (uM) | Fpn Ubiquitination (10 min.) | Fpn Degradation (120 min.) |
|---|---|---|---|
| 1 | 0.12 | + | + |
| 40 | 1.9 | + | + |
| 94 | 0.3 | + | + |
| 126 | 0.8 | +/− | + |
| 127 | 0.1 | + | + |
| 208 | 0.2 | + | + |
| hepcidin | 0.15 | + | + |

FIG. 10 Fpn inhibitor trigger ubiquitination and degradation of Fpn expressed in a mouse macrophage cell line. J774 cells were incubated overnight with Fe(III)-NTA to induce expression of Fpn. Cells were then treated with ca. 10-fold $IC_{50}$ concentrations, as determined in the hepcidin internalization assay (see Table 1), of hepcidin (Hepcidin, 150 nM) or Fpn inhibitors Example Compound No. 208 (210 nM), Example Compound No. 167 (1.5 µM), Example Compound No. 127 (120 nM), Example Compound No. 152 (40 nM) for 10 or 120 min before harvesting and immunoprecipitation with the anti-Fpn antibody F308. Mock treated cells were harvested after 120 min (Control).

Immunoblotting of immunoprecipitates with the anti-Fpn antibody MTP1 revealed disappearance of ferroportin 120 min after treatment with the Fpn inhibitors, to a similar extent as in the sample treated with hepcidin (upper panel). Rapid ubiquitination of Fpn was observed 10 min after treatment of cells with Fpn inhibitors and hepcidin. Protein molecular weight standards are indicated on the left in kD.

6. Inhibition of Iron Efflux by Ferroportin Inhibitors

The activity of hepcidin and ferroportin inhibitor compounds regarding their ability to block iron export via ferroportin is tested on T47D cells (ECACC, Cat. 85102201) as described below.

Cells are plated in 24-well plates (Greiner, Cat. 662160) containing 350'000 cells/well and incubated overnight with 100 µM $^{58}$Fe ($^{58}$Fe(II)-Sulfate, Vifor Pharma Batch No. ROR 3085) in 500 µM L-Ascorbic Acid (Sigma Aldrich, Cat. 795437) containing growth medium. Cells are washed once with 500 µl iron uptake buffer (IUB; PIPES 40 mM, Cat. P1851, Glucose Monohydrate 10 mM, Cat. 49158, Sodium Chloride 260 mM, Cat. 71379, Potassium Chloride 20 mM, Cat. P9541, Magnesium Sulfate 2 mM, Cat. 63138, Sigma Aldrich), then once with removal buffer (2 min incubation, BPDS 100 µM, Cat. 11890 and $Na_2S_2O_4$ 500 µM, Cat. 157953, Sigma Aldrich, in IUB) and again twice with IUB. A serial dilution of hepdicin (Bachem) or ferroportin inhibitors (4 µM-0.0064 µM, 5 fold dilution) is added in a total volume of 0.6 ml per well. Cells are incubated at 37° C. with 5% $CO_2$ for 20 h. Supernatants are collected and $^{58}$Fe was measured using inductively coupled plasma mass spectrometry (ICP-MS, Thermo Scientific, Element 2). Pellets are harvested for protein concentration measurements. Results are plotted as ng $^{58}$Fe in supernatant per mg protein in cell lysates. Example Compound No. 127 inhibited iron efflux with similar potency as the endogenous Fpn ligand hepcidin (FIG. 11).

Figure 11:
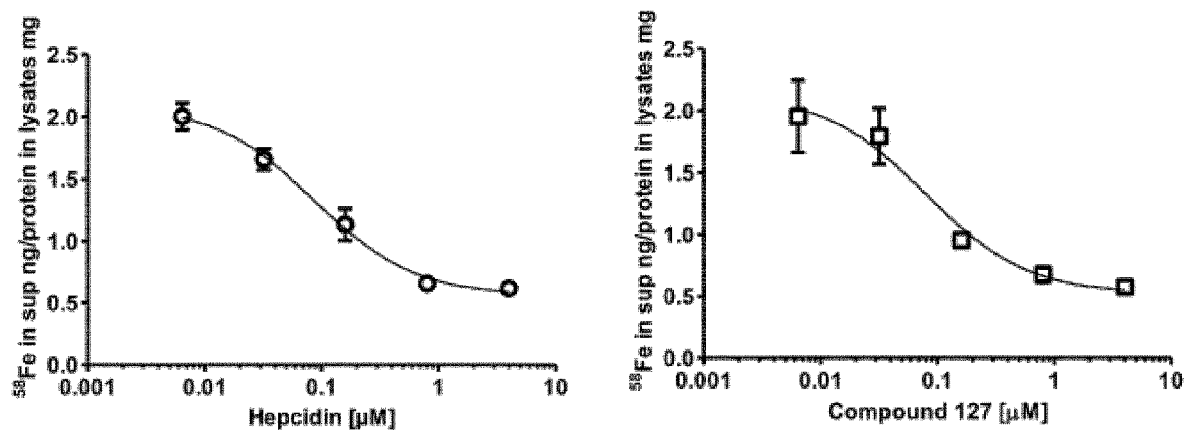
FIG. 11: Iron efflux inhibition of Hepcidin (IC50: 0.086 µM) and Example Compound No. 127 (IC50: 0.080 µM)

FIG. 11 Representative iron efflux inhibition of Hepcidin ($IC_{50}$: 0.086 µM) and Example Compound No. 127 ($IC_{50}$: 0.080 µM).

7. Hypoferremia in Naïve Mice

Figure 12A:
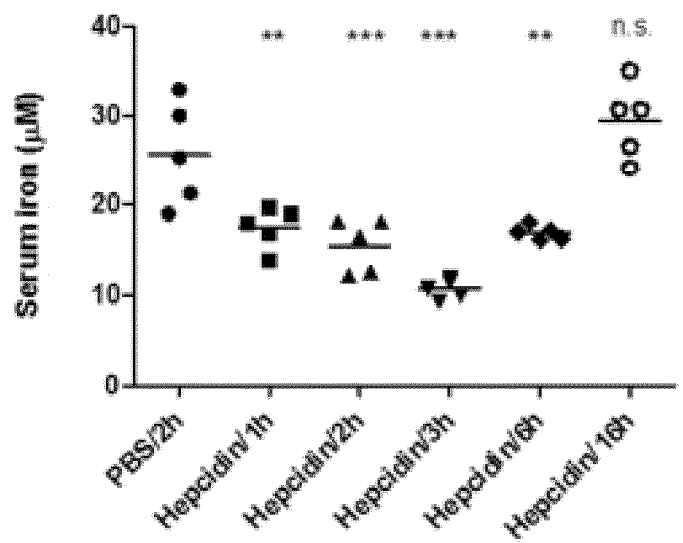
FIG. 12 A/B: Serum iron reduction induced by hepcidin and ferroportin inhibitor according to Example Compound 94 (Example Compound No. 94); with FIG. 12A: Kinetic of serum iron in naïve C57BL/6 mice injected with synthetic hepcidin (5 mg/kg) intraperitoneally (i.p.) for the indicated time; and with FIG. 12B: Serum iron levels in naïve C57BL/6 mice treated with the indicated amounts of either hepcidin (i.p.) or Example Compound 94 (Example Compound No. 94). (p.o.) for 3 h

Injection of synthetic hepcidin in wild-type (WT) naïve mice results in a reduction of serum iron levels (40-50% from the vehicle control) with a maximal effect at 3-4 hours post treatment (Rivera, 2005; FIG. 12A). This data suggest that the injected hepcidin binds to and triggers the internalization of ferroportin (Fpn) on duodenal enterocytes and splenocytes, causing a rapid drop in serum iron. Similarly, orally administered small molecular weight Fpn inhibitors decrease the levels of serum iron of WT C57BL/6 mice in a dose-dependent manner with an efficacy comparable to hepcidin. This data validated the use of WT mice as a simple and reliable model for testing the acute efficacy of Fpn inhibitors in vivo.

Female C57BL/6 mice (Janvier, France) at age of 9 weeks are fed a standard diet (Harlan Provimi Kliba 3436) and treated per os (p.o.) with compounds or the corresponding amount of vehicle at a volume of 10 ml/kg body weight. Fpn inhibitors are formulated in 0.5% methylcellulose/water or 20% cremophor EL/water and dosed p.o. in mice at 10, 30 or 100 mg/kg body weight. Three hours later, mice are pre-terminally anesthetized in isoflurane chambers and blood is collected by retro-orbital bleeding. Mice are sacrificed by cervical dislocation and spleens, livers and duodena were harvested and used for biomarker analysis. All experiments are conducted in compliance with the license approved by the responsible veterinarian authorities. Serum is isolated by centrifugation of blood into gel-containing microtainers and serum iron is determined by the MULTIGENT Iron assay (Abbott Diagnostics, 6K95). Eight mice per group are used and one-way ANOVA with Bonferroni's multiple comparison test is performed to analyze the statistical differences between the experimental groups. The efficacy of selected Fpn inhibitors in WT C57BL/6 mice is shown in Table 6.

Figure 12B:
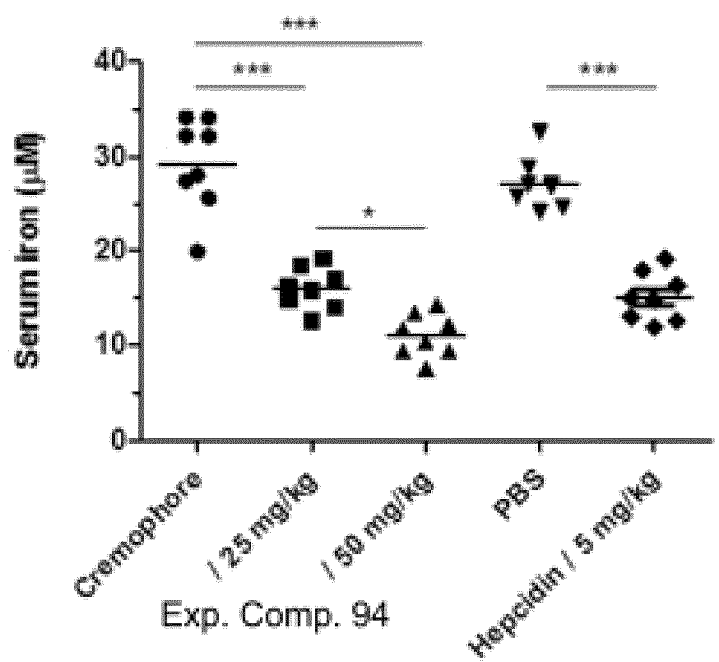

FIG. 12 Serum iron reduction induced by hepcidin and ferroportin inhibitor according to Example Compound 94 (Example Compound No. 94).

A Kinetic of serum iron in naïve C57BL/6 mice injected with synthetic hepcidin (5 mg/kg) intraperitoneally (i.p.) for the indicated time. *-***—indicate statistically significant serum iron reduction compared to PBS-treated mice.

B Serum iron levels in naïve C57BL/6 mice treated with the indicated amounts of either hepcidin (i.p.) or Example Compound 94 (Example Compound No. 94). (p.o.) for 3 h.

Table 6 Efficacy of Fpn inhibitors tested in the naïve mouse hypoferremia model. Serum iron reduction induced by selected ferroportin inhibitors dosed p.o. in naïve WT C57BL/6 mice at 10, 30 and 100 mg/kg. Relative serum iron reduction at 3 h after dosing was calculated by subtracting the average of serum iron values of animals dosed with the Fpn inhibitor from that of vehicle-treated animals. The difference in average serum iron values between vehicle and compound treated groups was then divided by the average of serum iron of the vehicle control group and listed as percentage.

TABLE 6

| Exp. Comp. No. | Serum Iron Reduction at 3 h (%) | | |
|---|---|---|---|
| | Dose 10 mg/kg | Dose 30 mg/kg | Dose 100 mg/kg |
| 1 | 0 | 28 | 51 |
| 2 | 9 | 26 | 50 |
| 40 | 10 | 30 | 50 |
| 94 | 30 | 50 | 80 |
| 118 | 8 | 24 | 49 |
| 126 | 7 | 23 | 62 |
| 127 | 17 | 47 | 54 |
| 193 | 13 | 11 | 31 |
| 208 | 50 | 65 | 73 |

8. Prevention of Iron Absorption in Anemic Rats

To assess the in vivo efficacy of ferroportin (Fpn) inhibitors to block iron absorption, a series of Fpn inhibitors is tested in an anemic rat model for iron absorption. Wistar rats (3-4 weeks old, n=5, Janvier Labs) are fed a low iron diet (Provimi-Kliba, Cat. 2039) until their hemoglobin (Hb) values reach 7-8 g/dl one day before dosing of the Fpn inhibitor compounds. One hour before oral application of 0.5 mg/kg of ferrous sulfate, test compounds formulated in methyl cellulose or Cremophor are dosed orally. Blood samples are taken by tail vein puncture one hour before administration of iron (−1 h), immediately after dosing of the Fpn inhibitors (0 h) and one hour (1 h), three hours (3 h) and occasionally up to 6 hours (6 h) after dosing of the test compounds. Serum iron levels are measured (Abbott Diagnostics, Cat. 6K95) and inhibition of the rise of serum iron three hours after dosing of the test compound is calculated as a measure for efficacy of the Fpn inhibitors in blocking iron absorption (Table 7). As shown in FIG. 4, oral administration of the Fpn inhibitor Example Compound No. 55 at 3 mg/kg, 10 mg/kg or 30 mg/kg reduced serum iron levels by 54%, 72% and 89%, respectively, three hours after iron dosing when compared to serum iron levels of vehicle-control animals before iron dosing and corrected for the baseline serum iron levels in vehicle-treated animals that did not receive a dose of iron.

Table 7 Fpn inhibitors tested in the anemic rat model for inhibition of iron absorption. Relative inhibition values (%) of serum iron levels are shown, corrected for average baseline serum iron levels of the control group which did not receive a dose of oral iron, compared to control groups treated with vehicle before iron dosing. Average values of groups (n=5) treated with the indicated doses of Fpn inhibitor are shown. Statistically significant (2-way ANOVA with Bonferroni post test) differences observed between compound-treated and vehicle-treated groups are indicated (* $p<0.001$;  $p<0.01$, * $p<0.05$).

TABLE 7

| Exp. Comp. No. | Serum Iron Inhibition (%) at 3 h | | | | |
|---|---|---|---|---|---|
| | Dose 1 mg/kg | Dose 3 mg/kg | Dose 10 mg/kg | Dose 30 mg/kg | Dose 100 mg/kg |
| 1 | nd | 2.1 | 42.6** | 64.9*** | nd |
| 2 | nd | −3 | 29** | 57*** | nd |
| 40 | nd | nd | 32** | 53*** | 97*** |
| 94 | 59*** | 0 | 70*** | nd | nd |
| 127 | nd | −8 | 47*** | 79*** | nd |
| 208 | nd | 59*** | 86*** | 109*** | nd |

9. Correction of Hyperferremia in Beta2-Microglobulin Deficient Mice

Mutations in genes involved in sensing the systemic iron stores, such as hepcidin (Hampl), hemochromatosis protein (HFE), hemojuvelin (HJV) and transferrin receptor 2 (TFR2) cause iron overload in mice and men. HFE, HJV and TFR2 molecules on hepatocytes are necessary for signaling of appropriate hepcidin production and their deficiency results in pathophysiologically low hepcidin levels and excessive iron absorption. HFE mutations is the most frequent cause of hereditary hemochromatosis (HH) in Caucasian adults. HFE is a MHC class I-like membrane molecule that associates with beta 2-microglobulin and participates in hepcidin transcriptional regulation through the bone morphogenetic protein receptor (BMPR) pathway. HFE−/− mice have decreased hepcidin levels, develop hyperferremia and high hepatic iron levels, which makes them a suitable animal model for studying iron overload in humans (Zhou, 1998). Mice deficient in beta 2-microglobulin (b2m−/−) develop hyperferremia and hemochromatosis similarly to HFE−/− animals, as beta 2-microglobulin is necessary for the cell-surface expression and function of HFE (Rothenberg and Voland, 1996). Due to the unavailability of HFE−/− mice, b2m−/− mice are used as a model of iron overload. A pilot study confirmed that HFE−/− and b2m−/− mice have similar iron metabolism-related parameters.

Female and male homozygous b2m−/− mice are supplied from Jackson Laboratories (B6.129P2-B2mtm1Unc/J, Stock Number: 002087) at age of 6 to 7 weeks and fed standard diet (Harlan Provimi Kliba 3436) ad libitum. Age and gender matched WT C57BL/6 mice are supplied by Charles River. To study the acute effects of ferroportin (Fpn) inhibitors in iron overload b2m−/− mice are treated with compounds or the corresponding amount of vehicle at a volume of 10 ml/kg body weight. Fpn inhibitor compounds are formulated in 0.5% methylcellulose/water or 20% cremophor EL/water and dosed p.o. in mice at 50 mg/kg body weight. WT controls received only vehicle. Three hours later, mice are pre-terminally anesthetized in isoflurane chambers and blood is collected by retro-orbital bleeding. Mice are sacrificed by cervical dislocation and spleens, livers and duodena are harvested and used for biomarker analysis. All experiments are performed in compliance with license approved by the responsible veterinarian authorities. Serum is isolated by centrifugation of blood into gel-containing microtainers (BD Biosciences) and serum iron is determined by the MULTIGENT Iron assay (Abbott Diagnostics, Cat. 6K95). Four to nine mice per group are used and one-way ANOVA with Bonferroni's multiple comparison test is applied to analyze the statistical differences between the experimental groups.

To investigate the effects of Fpn inhibitors Example Compound No. 40 and Example Compound No. 94 in conditions of iron overload b2m−/− mice or WT controls were dosed with Fpn inhibitors or vehicle for 3 h. Due to their genetic deficiency, b2m−/− mice treated with vehicle showed significantly higher serum iron levels compared to WT mice (FIG. 13, group average of 60 µM in A and 56 µM in B). Treatment of b2m−/− mice with Example Compound No. 40 or Example Compound No. 94 at 50 mg/kg for 3 h corrected the elevated serum iron to the levels observed in WT controls. These data demonstrated the acute efficacy of small molecular weight ferroportin inhibitors in a disease relevant model. Serum iron correction was observed in further studies as summarized in Table 8.

Figure 13:
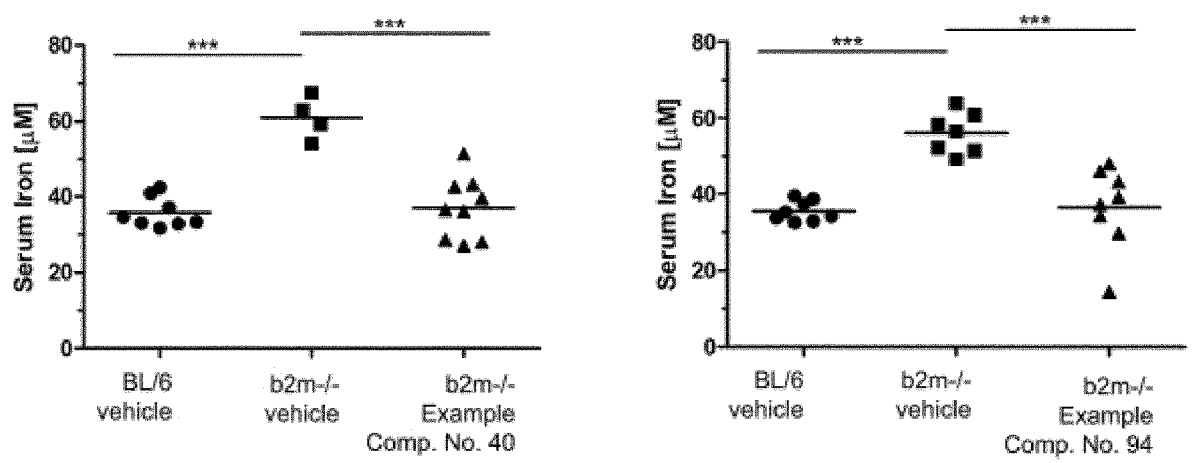
FIG. 13: Complete correction of the elevated serum iron levels in b2m−/− mice by treatment with the ferroportin inhibitors Example Compound No. 40/methylcellulose (A.) and Example Compound No. 94/cremophor EL (B.) for 3 h.

FIG. 13 Complete correction of the elevated serum iron levels in b2m−/− mice by treatment with the ferroportin inhibitors Example Compound No. 40/methylcellulose (A.) and Example Compound No. 94/cremophor EL (B.) for 3 h.

Table 8 Fpn inhibitors tested in the beta2-microglobulin deficient mouse model for lowering elevated serum iron levels Blood is collected 1 (#) or 3 (##) hours after oral administration of the indicated doses of Fpn inhibitors to beta2-microglobulin deficient mice and serum iron concentrations are measured. Relative reduction (%) of serum iron levels are shown, which were calculated by subtracting the average of serum iron values of animals dosed with the Fpn inhibitor from that of vehicle-treated animals. The difference in average serum iron values between vehicle and compound treated groups was then divided by the average of serum iron of the vehicle control group and listed as percentage. Values are listed separately for female (♀) and male (♂) animals, because a marked sex-dependent difference in efficacy was noted. Statistically significant (2-way ANOVA with Bonferroni post test) differences observed between compound-treated and vehicle-treated groups are indicated (* $p<0.001$;  $p<0.01$, $p<0.05$).

TABLE 8

| Exp. Comp. No. | | Serum Iron Reduction (%) | |
|---|---|---|---|
| | | Dose 20 mg/kg | Dose 60 mg/kg |
| 1 | ♀ | 31** | 52** |
| | ♂ | 31** | 59** |
| 2 | ♀ | 27 | 57** |
| | ♂ | 29 | 66** |
| 40[#] | ♀ | 0 | 13 |
| | ♂ | 35** | 32** |
| 40[#] | ♀ | nd | 10 |
| | ♂ | nd | 58** |
| 94[##] | ♀ | nd | 47 |
| | ♂ | nd | 67 |
| 127 | ♀ | 47*** | 74*** |
| | ♂ | 21 | 83** |
| 208[##] | ♀ | 9 | 49*** |
| | ♂ | 44 | 67** |

10. Prevention of Iron Overload in Beta2-Microglobulin Deficient Mice

As a result of decreased hepcidin levels and increased iron absorption in the gut beta2-microglobulin deficient (b2m-/-) mice on a standard diet accumulate excessive amounts of iron in liver, heart and pancreas. A pilot study showed that liver iron loading in b2m-/- starts at age of 3-4 weeks and that liver iron levels reaches up to 4 fold the liver iron content of wild-type (WT) mice at age of 6 weeks. In addition, feeding 3 week old b2m-/- mice a diet with low iron content (LID) immediately after weaning prevents liver iron loading by age of 6-7 weeks. The efficacy of the Fpn inhibitors to prevent liver iron accumulation in b2m-/- mice is investigated. Three weeks old b2-/- mice fed LID are dosed with either Fpn inhibitor or vehicle (methylcellulose; 10 ml/kg). Mice have access to drinking water supplemented with 1 mM $^{58}$Fe(II)-sulfate and 10 mM ascorbic acid. Dosing of Fpn inhibitor or vehicle followed by exposure to iron-containing water is repeated for 14 days. Mice are euthanized and the liver and spleen iron contents are analyzed by ICP-OES (all iron isotopes) and liver tissue is also analyzed for $^{58}$Fe concentration (ICP-MS). The data summarized in Table 9 illustrates that oral dosing of Fpn inhibitors for two weeks prevented liver iron loading in b2m-/- mice and increased spleen iron concentrations, indicating inhibition of ferroportin both in the intestine and in the spleen.

These data demonstrated the efficacy of a small molecular weight ferroportin inhibitor to prevent liver iron loading in b2-/- mice, which provides a proof of concept in a disease-relevant model.

Table 9 Fpn inhibitors tested in the beta2-microglobulin deficient mouse model for inhibition of liver iron overload.

Livers and spleens are collected after 14 day treatment (p.o.; b.i.d) of beta2-microglobulin deficient mice with the indicated doses of Fpn inhibitors. Total liver and spleen tissue iron concentrations are measured using ICP-OES and $^{58}$Fe liver concentrations are determined with ICP-MS. Relative changes (%) of tissue iron levels are calculated by normalizing the difference between the averages of tissue iron values of animals dosed with the Fpn inhibitors and those of vehicle-treated animals with the average of vehicle controls. Values are listed separately for female (?) and male (6) animals, because a marked sex-dependent difference in efficacy was noted. Statistically significant (2-way ANOVA with Bonferroni post test) differences observed between compound-treated and vehicle-treated groups are indicated (* $p<0.001$;  $p<0.01$, * $p<0.05$). nd, not determined; na, not available.

TABLE 9

| Exp. Comp. No. | | Total Spleen Iron Increase (%) | | Total Liver Iron Reduction (%) | | $^{58}$Fe Liver Iron Reduction (%) | |
|---|---|---|---|---|---|---|---|
| | | \multicolumn{6}{c}{Dose (mg/kg)} | | | | | |
| | | 20 | 60 | 20 | 60 | 20 | 60 |
| 1 | ♀ | 21 | 65 | -1 | 15 | 4 | 59 |
| | ♂ | 28 | 49 | 16 | 25 | -8 | 22 |
| 2 | ♀ | 13 | 1 | 26 | 45 | 60** | 77*** |
| | ♂ | 18 | -20 | 10 | 28 | 24 | 70 |
| 40 | ♀ | 50* | 85*** | 32 | 67* | 44 | 80* |
| | ♂ | 25 | 24 | 31 | 69*** | 53* | 81*** |
| 40 | ♀ | nd | 9 | nd | 66 | nd | 67 |
| | ♂ | nd | 36 | nd | 85** | nd | 95** |
| 94 | ♀ | nd | 65 | nd | 57 | nd | na |
| | ♂ | nd | 41 | nd | 79 | nd | na |
| 127 | ♀ | 71* | 51 | -38 | 2 | 34 | 63*** |
| | ♂ | -7 | -16 | 50** | 65*** | 71*** | 73*** |
| 208 | ♀ | 56** | 150*** | 15 | 8 | 71* | 87** |
| | ♂ | 21 | 43 | 41 | 84** | 58 | 94** |

11. Improvement of Anemia, Ineffective Erythropoiesis and Iron Overload in a Mouse Model of β-Thalassemia Intermedia β-thalassemia is inherited anemia caused by mutations in the β-globin gene of hemoglobin resulting in abnormal red blood cells with decreased life span. The most severe form, thalassemia major, requires blood transfusions which result in secondary iron overload. Patients with thalassemia intermedia have a moderate transfusion-independent anemia but still develop iron overload due to inefficient erythropoiesis and chronic repression of hepcidin production.

As can be shown in the previous examples, oral ferroportin (Fpn) inhibitors similarly to hepcidin blocked ferroportin mediate export of iron from cells in vitro and upon dosing in wild-type mice transiently reduced serum iron. Based on these findings and published studies (Schmidt P J, et al, Blood 2013, Guo S, et al, JCI, 2013 and Casu C. et al, Blood, 2016) Fpn inhibitors are examined with respect to its capacity to prevent iron loading and improve erythropoiesis in thalassemia intermedia by restricting iron absorption and reutilization from senescent erythrocytes. The efficacy of Fpn inhibitors is investigated using a mouse model of transfusion-independent β-thalassemia. Mice with heterozygous deletion of β 1 and β 2 globin genes (called Hbb th3/+ mice) develop transfusion-independent anemia, ineffective erythropoiesis, splenomegaly and secondary iron overload in spleen, liver and kidneys. Heterozygous Hbb th3/+ mice are supplied from Jackson Laboratories (B6; 129P-Hbb-b1tm1Unc Hbb-b2tm1Unc/J, Stock Number: 002683) at age of 8-18 weeks and during experiments fed a low iron diet (Harlan Provimi Kliba 2039, 13.4 ppm Fe) ad libitum. Hbb th3/+ mice are dosed twice daily with either compound at 20 or 60 mg/kg or with methylcellulose (10 ml/kg, Sigma, Cat. 274429) as a vehicle. Between both doses mice have access to drinking water supplemented with 1 mM $^{58}$Fe(II)-sulfate (Vifor Pharma, Batch No. ROR 3096) and 10 mM ascorbic acid (Sigma, Cat. 795437) for 6 h. The concentration of $^{58}$Fe(II)-Sulfate supplied in the drinking water is adjusted to substitute for intake of standard rodent diet with iron content of 250 ppm. Water without $^{58}$Fe(II)-Sulfate and ascorbic acid is provided during the remaining 18 h. Dosing of Fpn inhibitors or vehicle followed by exposure to iron-containing water is repeated for 20 to 46 days in individual experiments.

As previously shown in wild-type and b2m−/− mice, Fpn inhibitors dosed for 3 h in Hbb th3/+ mice reduce efficiently serum iron levels also in this mouse strain (Table 10), demonstrating the ability of these small molecules to cause iron restriction.

Hbb th3/+ mice are anemic with hemoglobin levels in the range of 70-80 g/L. Oral administration of Fpn inhibitors in Hbb th3/+ mice for two weeks increase significantly hemoglobin levels compared to vehicle treated mice (Table 10). The change of hemoglobin levels in compound-dosed compared to vehicle-treated group reaches 19-22 g/L by the study end. Additional hematologic parameters are measured in terminal blood using automated blood cell analyzer. Treating Hbb th3/+ mice with Fpn inhibitors increases red blood cell counts, hematocrit and decreased reticulocyte concentration and red cell distribution width (RDW), indicating improved erythropoiesis. In addition, Hbb th3/+ mice receiving Fpn inhibitors have significantly lower leucocyte counts in blood compared to the vehicle group, further demonstrating the beneficial effect of Fpn inhibitors in correcting pathologically altered parameters in the disease model. Therefore, Fpn inhibitors improve significantly anemia and correct blood composition in the mouse model of thalassemia intermedia.

The inefficient erythropoiesis of Hbb th3/+ mice causes excessive proliferation of erythroid precursors in spleen, leading to splenomegaly. Treatment of Hbb th3/+ mice with Fpn inhibitors results in significant reduction in spleen weight, therefore highlighting the potential of Fpn inhibitors to revert splenomegaly (Table 10).

The effect of Fpn inhibitors on erythropoiesis is studied by analyzing the percentage of differentiating erythroid precursors in bone marrow and spleen using flow cytometry and Ter119 (eBioscience, Cat. 17-5921) and CD44 (BioLegend, Cat. 103028) markers. Bone marrow or spleen cells isolated from Hbb th3/+ mice treated with Fpn inhibitors contain significantly reduced percentage of the early erythroid precursors proerythroblasts, basophilic, and polychromatic erythroblast and increased percentage of mature erythrocytes compared to vehicle-treated Hbb th3/+ mice (Table 10). These data demonstrate that Fpn inhibitors ameliorate the inefficient erythropoiesis in Hbb th3/+ mice and are in agreement with the improved hematological parameters in blood.

Serum erythropoietin levels in Hbb th3/+ mice and patients with thalassemia are upregulated due to a feedback response to anemia, hypoxia and inefficient erythropoiesis (Guo et al. JCI, 2013). Hbb th3/+ mice treated with Fpn inhibitors produce significantly less serum erythropoietin (DuoSet ELISA R&D Systems, Cat. DY959) compared to the vehicle group, most likely as a consequence of partially corrected anemia and improved erythropoiesis (Table 10).

Elevated erythropoietin levels in Hbb th3/+ mice induce overexpression of erythroferrone, an erythroid regulator hormone known to suppress hepcidin (Kautz L. et al, Nat. Genet., 2014). In agreement with reduced serum erythropoietin, erythroferrone mRNA expression is significantly reduced in spleens of Fpn inhibitor-treated Hbb th3/+ mice compared to those administered with vehicle alone (Table 10). Erythroferrone is produced by erythrocyte precursors proliferating massively in spleens of Hbb th3/+ mice as a consequence of extramedullar erythropoiesis. Therefore, the effect of Fpn inhibitors on erythroferrone expression in spleen is mediated by the improved erythropoiesis.

Increased iron demand due to inefficient erythropoiesis and chronically low hepcidin levels in patients with thalassemia causes organ iron loading and associated morbidities, such as hepatocellular carcinoma and heart failure (Rivella S. Haematologica, 2015). Hbb th3/+ mice absorb excessive amounts of iron as a consequence of inadequately low hepcidin levels relative to the high iron content in liver, spleen and kidney and increased ferroportin expression in duodenum (Gardenghi S., Blood, 2007). Total liver iron and $^{58}$Fe content in organs of Hbb th3/+ mice treated with either vehicle or Fpn inhibitors are analyzed by inductively coupled plasma optical emission spectrometry (ICP-OES) and inductively coupled plasma mass spectrometry (ICP-MS), respectively. $^{58}$Fe concentrations in livers and spleens of Hbb th3/+ mice dosed with Fpn inhibitors are significantly lower compared to those of vehicle treated mice, indicating that Fpn inhibitors prevent organ iron accumulation (Table 10).

As Fpn inhibitors are systemically available, they are able to block iron export in all ferroportin expressing tissues, including duodenum, spleen and liver. Accordingly, Fpn inhibitors are expected to prevent iron absorption from duodenum, however, they could not remove pre-existing iron in liver and spleen. Indeed, total liver iron in mice treated with Fpn inhibitor or vehicle remains unchanged (not shown). Importantly, Fpn inhibitors reduce significantly $^{58}$Fe concentration in spleens and livers of Hbb th3/+ mice, demonstrating the ability of these small molecules to prevent iron loading.

Additionally, reactive oxygen species (ROS) are detected in bone marrow cells using a fluorescent indicator, CM-H$_2$DCFDA (Thermo Fisher Scientific, Cat. C6827). Flow cytometric analysis show that Fpn inhibitors decrease significantly ROS in mature erythroid cells compared to vehicle treated Hbb th3/+ mice (Table 10).

These data demonstrate the disease-modifying capacity of orally administered small molecular weight ferroportin inhibitors in improving anemia and ineffective erythropoiesis, as well in reducing splenomegaly and preventing further liver and spleen iron loading in a disease model of β-thalassemia intermedia.

Vascular occlusion crises (VOC) are the major cause of morbidity and mortality in sickle cell disease (SCD) patients. Hypoxia, dehydration, inflammation or hemolysis all contribute to increased adherence of sickle cell red blood cells (SSRBCs), neutrophils and platelets to activated endothelium in the small vessels promoting coagulation, vessel obstruction, painful crises and irreversible damage of multiple organs. High leukocyte counts, particularly activated neutrophils, have been correlated with early death, silent brain infarcts, hemorrhagic strokes, and acute chest syndrome in SCD patients (Platt O S, NEJM, 1994). Hemolysis in SCD arises from damaged sickle RBC membranes, causing chronic anemia and the release of Hb into the circulation, which promotes inflammation by depleting NO, generating oxidative stress and releasing heme. SSRBC shed microvesicles which trigger reactive oxygen species (ROS) production by endothelial cells, promote leukocyte

TABLE 10

| Parameter | Exp. Comp. No. 1 | Exp. Comp. No. 2 | Exp. Comp. No. 40 | Exp. Comp. No. 127 |
| --- | --- | --- | --- | --- |
| Decrease in serum iron by 20/60 mg/kg compound | 49/66% | 50/69% | 28/58% | 68/81% |
| Correction of anemia at day 20-48 by 20/60 mg/kg | 6/20 g/d | 3/11 g/L | 6/13 g/L | 12/20 g/L |
| Increase in blood erythrocyte counts by 20/60 mg/kg compound | 4/8% | 0/33% | 2/22% | 0/36% |
| Decrease in blood reticulocyte counts by 20/60 mg/kg compound | 8/39% | 0/11% | 19/43% | 16/61% |
| Increase in hematocrit by 20/60 mg/kg compound | 0/4% | 0/15% | 0/1% | 3/20% |
| Decrease in RDW by 20/60 mg/kg compound | 3/16% | 0/15% | NA/NA | 19/25% |
| Decrease in leukocyte counts by 20/60 mg/kg compound | 32/44% | 29/55% | 0/36% | 46/66% |
| Decreased in ROS in bone marrow erythrocytes | 20/45% | 13/65% | NA/NA | NA/75% |
| Decrease in relative spleen weight by 20/60 mg/kg | 23/59% | 16/47% | 23/48% | 40/61% |
| Decrease in $^{58}$Fe spleen iron content by 20/60 mg/kg compound | 14/48% | 13/40% | 19/51% | 43/68% |
| Prevention of liver $^{58}$Fe loading by 20/60 mg/kg | 12/40% | 14/47% | 20/48% | 39/59% |
| Decrease in serum erythropoietin by 20/60 mg/kg compound | 64/78% | 4/27% | 6/37% | 32/33% |
| Decrease in spleen erythroferrone mRNA by 20/60 mg/kg compound | 82/292% | 461/639% | NA/NA | 1012/3031% |

Table 10 Efficacy of Ferroportin inhibitors in a mouse model of thalassemia intermedia (Hbb th3/+ mice). The indicated Fpn inhibitors were dosed twice daily for 20 days (Example Compound 1 and 2), 27 days (Example Compound 127) or 46 days (Example Compound 40). Data are expressed as difference to the vehicle control group for hemoglobin and as % change to the vehicle control group for all other parameter shown 12. Determination of the in the Treatment of Sickle Cell Anemia in a Mouse Model Using the mouse model as described by Yulin Zhao et al. in "MEK1/2 inhibitors reverse acute vascular occlusion in mouse models of sickle cell disease"; The FASEB Journal Vol. 30, No. 3, pp 1171-1186, 2016, the activity of the salts of the present invention in the treatment of sickle cell anemia has been determined as follows:

Ferroportin inhibitors prevent acute vascular occlusion and organ damage in a mouse model of sickle cell disease adhesion, and induce endothelial apoptosis in a phosphatidylserine-dependent manner, contributing to acute VOC in SCD (Camus M, Blood, 2012). Chronic iron restriction by administration of Ferroportin inhibitors decreased the formation of ROS into RBC of β-thalassemic mice, as has been shown for example for the compounds as described in the above mentioned unpublished international applications PCT/EP2016/075305 and PCT/EP2016/075306, (The Jackson Laboratories, Yang B, et al, PNAS. 1995). Based on this data, it can be hypothesized that Ferroportin inhibitors may alleviate VOC in SCD by decreasing hemolysis and ROS formation in SSRBC and consecutively preventing leukocyte adhesion to endothelium.

To test this hypothesis vehicle or Ferroportin inhibitors are dosed orally at 30 or 100 mg/kg twice daily (BID) for 4 weeks in the Townes mouse model of SCD (Ryan T, Science, 1990). These mice have been genetically engineered to exclusively express human hemoglobin (hα/hα::βS/βS, The Jackson Laboratories). Townes mice have anemia, elevated reticulocyte counts, splenomegaly, vascular inflammation and are prone to VOC in response to hypoxia, inflammation and hemolysis. To investigate the effect of Ferroportin inhibitors on leucocyte and SSRBC adhesion to inflamed endothelium Townes mice treated with vehicle or Ferroportin inhibitor for 25 days are anesthetized and a window chamber is surgically implanted into the dorsal skin fold under sterile conditions, as previously described (Kalambur V S et al., Am J Hematol. 2004; Zennadi, R et al, Blood, 2007). Three days after the surgery mice are injected with 0.5 µg TNFα (R&D Systems) to induce inflammation leading to VOC. Ninety minutes after TNFα administration, leukocytes and RBCs are labeled in vivo by intravenous injection of rhodamine-conjugated Ly6G (Sigma) and phycoerythrin-conjugated anti-TER119 mAb (BioLegend), respectively. The adherence of leucocytes and RBS to the endothelium of microvessels is monitored in the following 90 minutes by fluorescent intravital microscopy, as previously described (Zhao et al, FASEB J, 2016). Briefly, anesthetized animals with window chambers are maintained at 37° C., blood flow and cell adhesion events are recorded using a digital video camera C2400 (Hamamatsu Photonics KK, Hamamatsu City, Japan) connected to fluorescent microscope (Axoplan microscope, Carl Zeiss). Twenty to thirty segments of microcapillaries are examined per mouse and cell adherence is quantified on still images by measuring the fluorescence intensity of adherent fluorescence-labeled cells using ImageJ software. Results are expressed as fluorescence units per million cells.

13. Single Dose Intravenous and Oral Pharmacokinetic Study of Example Compound No. 127 as a $H_2SO_4$ or HCl Mono-Salt in Male Sprague Dawley Rats To determine the pharmacokinetics (PK) of Example Compound No. 127 as a $H_2SO_4$ (MW 604.6 g/mol) or HCl (MW 444.9 g/mol) mono-salt a single dose of these salt compounds was administered in male Sprague Dawley rats (n=3 per route) intravenously (1 mg/kg) or per oral (30 mg/kg). The doses used were corrected to the weight of the compound as a base (MW 408.43 g/mol).

Rats were maintained in ventilated cages at a temperature of 22 to 25° C., humidity of 40-70% RH, and a 12-hour light/12-hour dark cycle and provided with a standard rodent diet and water ad libitum. Before the PK study rats were fasted overnight and were fed 4 h after the dosing. The protocol was reviewed and approved by the Institutional Animal Ethics Committee of the CRO (GVK Biosciences Pvt. Ltd. Hyderabad, India).

Example Compound No. 127 $H_2SO_4$ mono salt or Example Compound No. 127 HCl mono salt formulated in PBS containing 5% DMSO and 10% Solutol was dosed intravenously into the tail vein of rats using 27-gauze needle at 5 ml/kg and a concentration of 0.2 mg/ml.

For oral administration of 30 mg/kg the salt compounds were formulated at a concentration of 6 mg/ml in a solution of 0.5% methylcellulose containing 5% DMSO and were orally dosed at 5 ml/kg.

Blood samples of 0.20-0.30 mL were collected from the cannulated jugular vein of rats in lithium heparin pre-filled tubes at the following time points: 5, 15, 30 min, 1 hr, 2 hr, 4 hr, 8 hr and 24 hr after dosing. Plasma was prepared by centrifugation at 2500×g for 15 minutes at 4° C. Plasma concentrations of the compounds were measured by liquid chromatography tandem mass spectrometry (LC-MS/MS) and standard PK parameters, such as C0, Cmax, Tmax, Cl, Vd, AUClast, T½, MRT, % F were determined by non-compartmental model with Phoenix software version 6.4.

The results show a good/improved pharmacokinetic profile.

III. Evaluation of Combination Therapies

Regarding the aforesaid possible combination therapies of the salts as described herein, having an activity as ferroportin inhibitors, with other active ingredients, such combination therapies can be studied in a mouse model of beta-thalassemia intermedia.

Potential synergistic or additive effects of the salts of the present invention with other therapeutic agents (second agents) are being evaluated by combination studies in the mouse models of thalassemia intermedia ($Hbb^{th3/+}$ or $Hbb^{th1/th1}$, Jackson Laboratories) or thalassemia major (C57-$FLC^{th3/th3}$, such as described in Casu C, et al. "Short-term administration of JAK2 inhibitors reduces splenomegaly in mouse models of ß-thalassemia intermedia and major."; Haematologica, 2017. the salts of the present invention per se (i.e. the salts alone) or in combination with additional compound(s) is tested for effects on anemia, hematopoiesis, iron overload, production of reactive oxygen species (ROS), splenomegaly and other biomarkers in the thalassemia models. Mice from both genders at age of 12 weeks are treated with the salts of the present invention per se or in combination with one of the following second agents:

Modified activin receptor type IIA or IIB fusion proteins (such as described by Suragani R N, et al. "Modified activin receptor IIB ligand trap mitigates ineffective erythropoiesis and disease complications in murine β-thalassemia." Blood. 2014 Jun. 19; 123(25):3864-72 and by Dussiot M, et al. "An activin receptor IIA ligand trap corrects ineffective erythropoiesis in β-thalassemia." Nat Med. 2014 April; 20(4):398-407), acting as ligand traps to members of the transforming growth factor beta (TGFβ) superfamily, such as RAP-011 or RAP-536 (murine analogues of ACE-011, Sotatercept or ACE-536, Luspatercept (described in the patent application WO2010019261 or claimed in the U.S. Pat. No. 8,361,957), respectively, Acceleron/Celgene) or other antagonists of TGFβ superfamily members (antibodies, fragments of antibodies, non-antibody scaffold drugs or cells producing activin receptor ligand traps).

JAK1/2 or JAK2 inhibitors, including but not limited to Ruxotilinib (Novartis—claimed in the U.S. Pat. Nos. 7,598,257 and 8,415,362) or Fedratinib (Sanofi), such as described in Casu C, et al. "Short-term administration of JAK2 inhibitors reduces splenomegaly in mouse models of ß-thalassemia intermedia and major."; Haematologica, 2017.

pan-HDAC inhibitor, such as Panobinostat (LC Laboratories, USA, and claimed by the U.S. Pat. Nos. 6,552, 065 and 6,833,384) or HDAC3 inhibitor RGFP966 (Selleckchem—such as described by Pasricha S R et al. "Hepcidin is regulated by promoter-associated histone acetylation and HDAC3." Nat Commun. 2017 Sep. 1; 8(1):403).

Antagonists of matriptase-2 (also known as Tmprss6), such as lipid nanoparticle (LNP)-formulated Tmprss6 siRNA or antisense oligonucleotides (ASOs) targeting mouse Tmprss6 (such as described by Guo S et al "Reducing TMPRSS6 ameliorates hemochromatosis and β-thalassemia in mice." J. Clin Invest. 2013 April; 123(4):1531-41 or by Schmidt P J, et al. "An RNAi therapeutic targeting Tmprss6 decreases iron overload in Hfe(−/−) mice and ameliorates anemia and iron overload in murine β-thalassemia intermedia." Blood. 2013 Feb. 14; 121(7):1200-8).

Exogenous apotransferrin (such as described by Li H, et al. "Transferrin therapy ameliorates disease in beta-thalassemic mice." Nat Med. 2010 February; 16(2): 177-82).

Hepcidin-inducing steroids (HISs) as epitiostanol, progesterone, and mifepristone or antagonists of progesterone receptor membrane component-1 (PGRMC1), Ref. 7.

Erythroferrone antagonists, such as antibodies or ligand traps

Recombinant erythropoietin (epo). Erythropoietins available for use as therapeutic agents according to this invention are produced by recombinant DNA technology in cell culture, and include Epogen/Procrit (epoetin alfa) and Aranesp (darbepoetin alfa) or Myrcera (epoetin beta and methoxy polyethylene glycol).

glycine transporter 1 (GlyT1) inhibitors such as bitopertin (Roche AG).

The salts of the present invention are dosed orally in thalassemic mice either as a single agent twice daily at 10, 30 and 60 mg/kg or in combination with one of the compounds listed above (second agents). A control group of thalassemic mice is receiving a second agent alone. Age and gender matched vehicle treated thalassemic and wild-type (WT) mice are used as controls. In some experiments the salts of the present invention could be also dosed into the drinking water to facilitate co-administration of other orally administered drugs.

More specifically, the second agent will be dosed as a single treatment or co-administered with the salts of the present invention as follows:

RAP-011 or RAP-536 can be injected subcutaneously twice weekly at 1, 10 or 30 mg/kg for up to 8 weeks.

JAK1/2 inhibitors can be dosed orally twice daily in the absence or presence of the salts of the present invention formulated into the drinking water.

Ruxotilinib (60 or 180 mg/kg) or Fedratinib (40 or 120 mg/kg) can be administered orally once daily for 2 weeks, in the absence or presence of the salts of the present invention formulated into the drinking water.

Panobinostat or RGFP966 can be dosed once daily at 10 or 20 mg/kg in the absence or presence of the salts of the present invention formulated into the drinking water.

Apotransferrin is injected intraperitoneally at 100 or 300 mg/kg daily for 8 weeks Mifepristone (30 or 100 mg/kg) can be injected intraperitoneally, daily for 2 weeks Antibodies or ligand traps specific to erythroferron can be administered twice weekly by subcutaneous injection Erythropoietin can be injected intraperitoneally at 200 IU daily for 2 weeks glycine transporter 1 (GlyT1) inhibitors such as bitopertin (Roche AG) can also be administered by suitable administration routes.

Mice are monitored for hemoglobin changes weekly and blood and organs are collected in the end of the study. Spleen weight is normalized to body weight and evaluated as an effect of treatment on the extramedullary erythropoiesis. Liver, spleen, kidney and heart iron concentrations are measured by inductively coupled plasma (ICP) with optical emission spectrometer (OES). Complete blood counts are measured using automated counter. Erythropoiesis in the bone marrow and spleen is analyzed by labeling cells with CD71, CD44 and Ter119 antibodies and detection of erythroid cells by flow cytometry. Membrane bound alpha globin fraction on red blood cells (RBC) is quantified by HPLC. Presence of reactive oxygen species (ROS) in RBC is measured by staining using the fluorescent indicator chloromethyl-2',7'-dichlorodihydrofluorescein diacetate. Serum iron is measured by colorimetric assay using Ferene-S-based reagent (Abbott). Serum erythropoietin is quantified by ELISA (R&D, duo set). Serum hepcidin is measured by ELISA (Intrinsic Lifesciences). Liver hepcidin, bone marrow and spleen erythroferron gene expression is quantified by qRT-PCR.

The invention claimed is:

1. Salts of compounds according to formula (I)

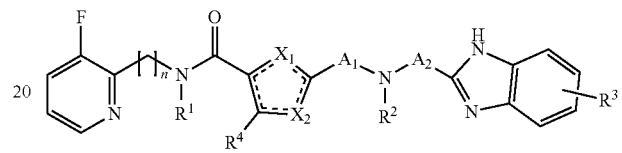

wherein $X^1$ is N or O; and $X^2$ is N, S or O;

with the proviso that $X^1$ and $X^2$ are different;

$R^1$ is selected from the group consisting of hydrogen and optionally substituted alkyl;

n is an integer of 1 to 3;

$A^1$ and $A^2$ are independently selected from the group of alkanediyl $R^2$ is hydrogen, or optionally substituted alkyl;

or $A^1$ and $R^2$ together with the nitrogen atom to which they are bonded form an optionally substituted 4- to 6-membered ring;

$R^3$ indicates 1, 2 or 3 optional substituents, which may independently be selected from the group consisting of halogen cyano, optionally substituted alkyl, optionally substituted alkoxy, and a carboxyl group;

$R^4$ is hydrogen, halogen, $C_1$-$C_3$-alkyl, and halogen substituted alkyl;

wherein the salts are selected from salts of the compounds of formula (I) with acids from the group consisting of benzoic acid, citric acid, fumaric acid, hydrochloric acid, lactic acid, malic acid, maleic acid, methanesulfonic acid, phosphoric acid, succinic acid, sulfuric acid, tartaric acid and toluenesulfonic acid, being characterized by a ratio of compound (I):acid of 1 to 2:1 to 3; and solvates, hydrates and polymorphs of the salts; and wherein the following 3HCl salts are excluded:
Exp. 40
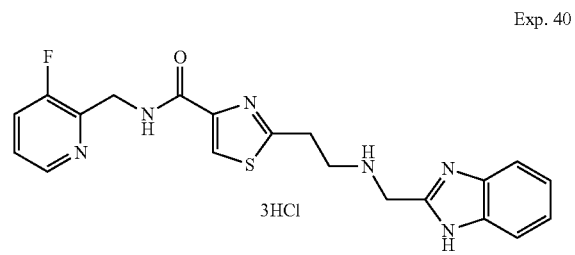
3HCl
Exp. 94
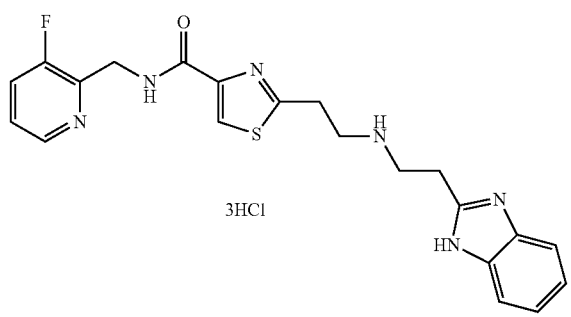
3HCl
Exp. 112
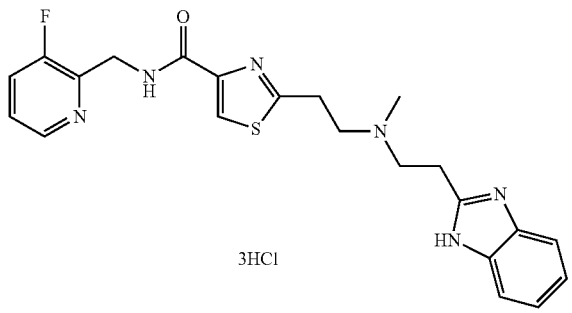
3HCl
Exp. 114
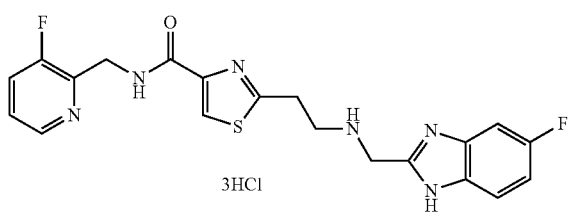
3HCl
Exp. 118
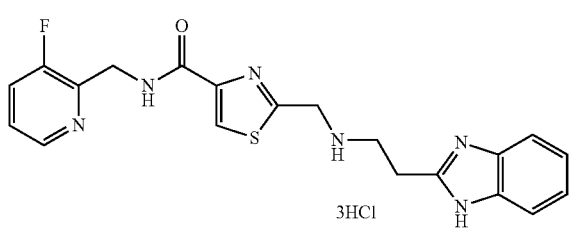
3HCl
-continued
Exp. 119
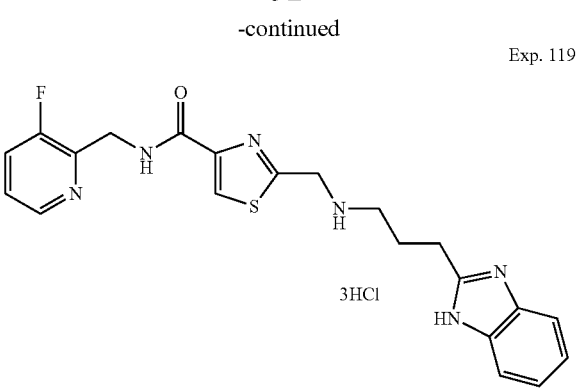
3HCl
Exp. 120
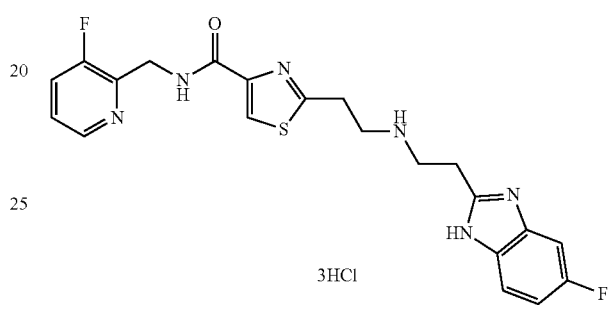
3HCl
Exp. 125
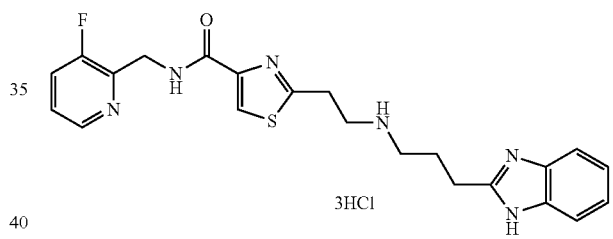
3HCl
Exp. 126
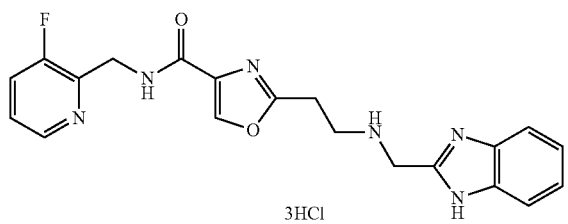
3HCl
Exp. 127
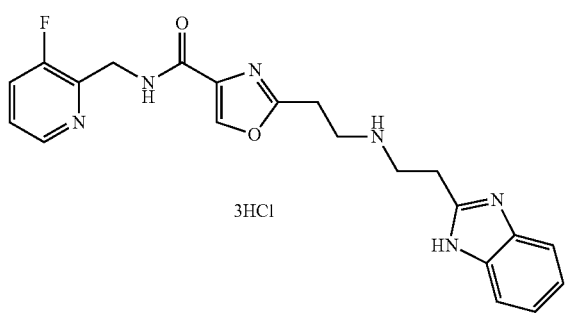
3HCl 93
-continued Exp. 134

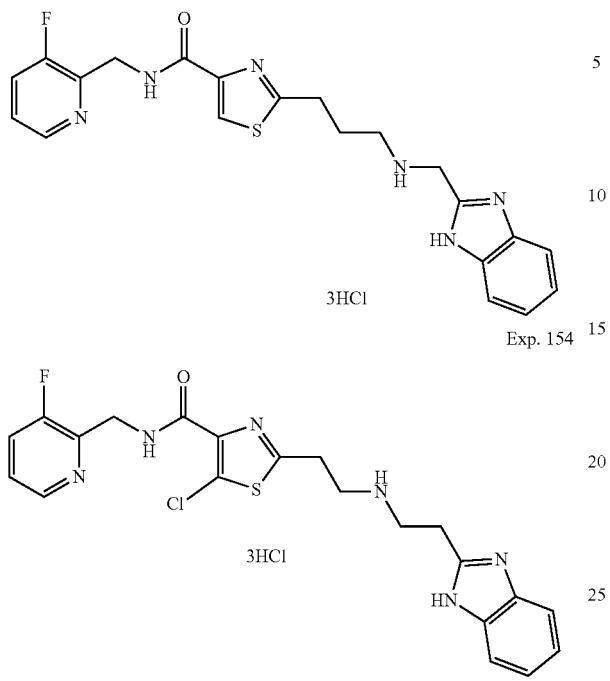

Exp. 154

3HCl

2. The salts of compounds of formula (I) according to claim 1, wherein
n=1;
R²=hydrogen;
R³=hydrogen;
R⁴=hydrogen;
A¹=methylene or ethane-1,2-diyl;
A²=methylene, ethane-1,2-diyl or propane-1,3-diyl;
or A¹ and R² together with the nitrogen atom to which they are bonded form an optionally substituted 4-membered ring, forming compounds according to formula (II) or (III):

(II)

(III)

wherein in formula (II) and (III)
m is an integer of 1, 2 or 3 and
X¹, X², and R¹ have the meaning as defined in claim 1,
and solvates, hydrates and polymorphs thereof.

3. The salts of compounds of formula (I) according to claim 1, wherein the salts are selected from mono-salts, solvates, hydrates and polymorphs thereof.

4. The salts of compounds of formula (I) according to claim 1, wherein the acids are selected from the group consisting of citric acid, hydrochloric acid, maleic acid, and sulfuric acid, and solvates, hydrates and polymorphs thereof.

5. The salts of compounds of formula (I) according to claim 1, wherein the acids are selected from the group consisting of phosphoric acid and sulfuric acid, and solvates, hydrates and polymorphs thereof.

6. The salts of compounds of formula (I) according to claim 1, wherein the acid is selected from phosphoric acid forming salts in a ratio of compound of formula (I) : PO₄ of 2:1, and solvates, hydrates and polymorphs thereof.

7. The salts of compounds of formula (I) according to claim 1, wherein 3HCl salts are excluded, and solvates, hydrates and polymorphs thereof.

8. The salts of compounds of formula (I) according to claim 1, wherein the compounds of formula (I) are selected from the group consisting of:

| Exp No. | Structure |
|---|---|
| 1 | 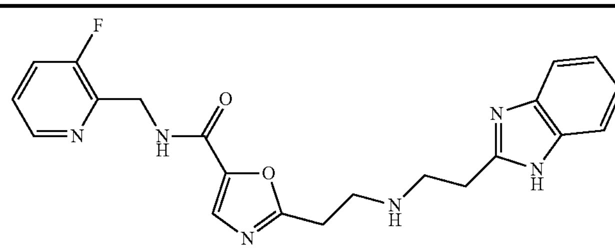 |
| 2 | 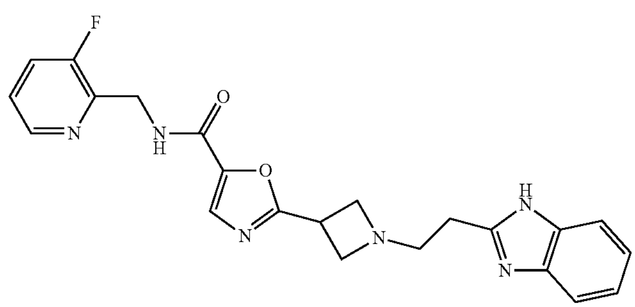 [SMILES: O=C(NCc1ncccc1F)c1cnc(C2CN(CCc3nc4ccccc4[nH]3)C2)o1] |

-continued

| Exp No. | Structure |
|---|---|
| 4 | 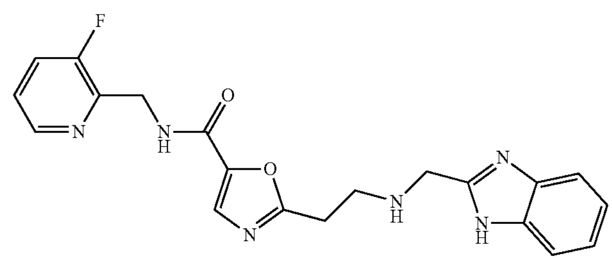 [SMILES: O=C(NCc1ncccc1F)c1cnc(CCNCc2nc3ccccc3[nH]2)o1] |
| 126 | 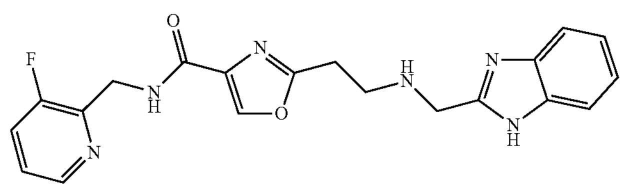 [SMILES: O=C(NCc1ncccc1F)c1coc(CCNCc2nc3ccccc3[nH]2)n1] |
| 127 | 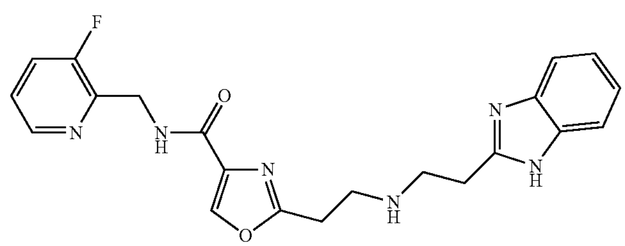 [SMILES: O=C(NCc1ncccc1F)c1coc(CCNCCc2nc3ccccc3[nH]2)n1] |
| 193 | 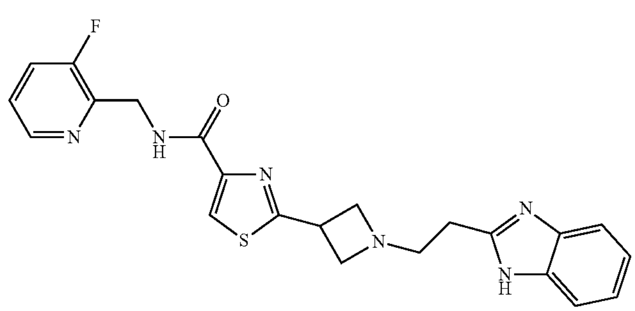 [SMILES: O=C(NCc1ncccc1F)c1csc(C2CN(CCc3nc4ccccc4[nH]3)C2)n1] |
| 40 | 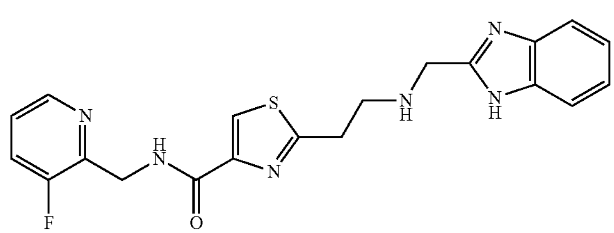 [SMILES: O=C(NCc1ncccc1F)c1csc(CCNCc2nc3ccccc3[nH]2)n1] |
| 94 | 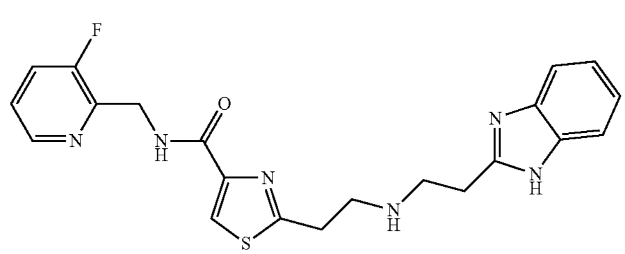 |

| Exp No. | Structure |
|---|---|
| 118 | *[chemical structure: 3-fluoropyridin-2-ylmethyl-NH-C(O)-thiazole-CH2-NH-CH2CH2-benzimidazole]* |
| 206 | *[chemical structure: 3-fluoropyridin-2-ylmethyl-NH-C(O)-oxazole-CH2-NH-CH2CH2-benzimidazole]* |
| 208 | *[chemical structure: 3-fluoropyridin-2-ylmethyl-NH-C(O)-oxazole-azetidine-CH2CH2-benzimidazole]* |
| 233 | *[chemical structure: 3-fluoropyridin-2-ylmethyl-NH-C(O)-oxazole-azetidine-CH2CH2CH2-benzimidazole]* | and solvates, hydrates and polymorphs thereof.

9. The salts of compounds of formula (I) according to claim 8, which are selected from the group consisting of:

| Exp. No. | Structure |
|---|---|
| 1 | *[chemical structure: 3-fluoropyridin-2-ylmethyl-NH-C(O)-oxazole-CH2CH2-NH-CH2CH2-benzimidazole]* |

-continued
| Exp. No. | Structure |
|---|---|
| 40 | 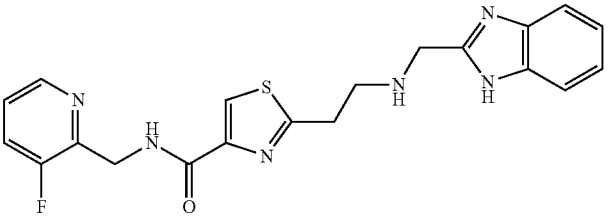 [SMILES: O=C(NCc1ncccc1F)c1csc(CCNCc2nc3ccccc3[nH]2)n1] |
| 94 | 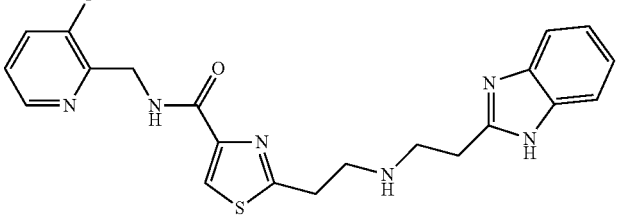 |
| 127 | 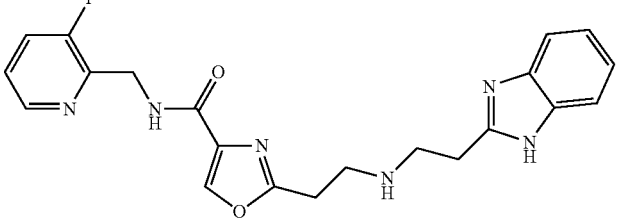 |
| 208 | 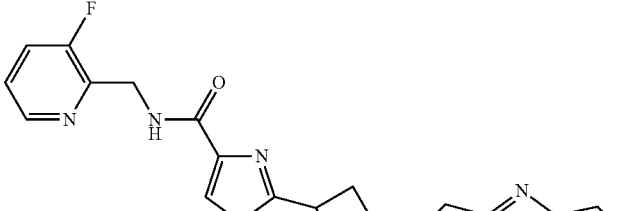 |
and solvates, hydrates and polymorphs thereof.
10. The salts of compounds of formula (I) according to claim 8, which are selected from the group consisting of:
and solvates, hydrates and polymorphs thereof.
11. The salts of compounds of formula (I) according to claim 1, which is a 1:1 sulfate salt having the formula:
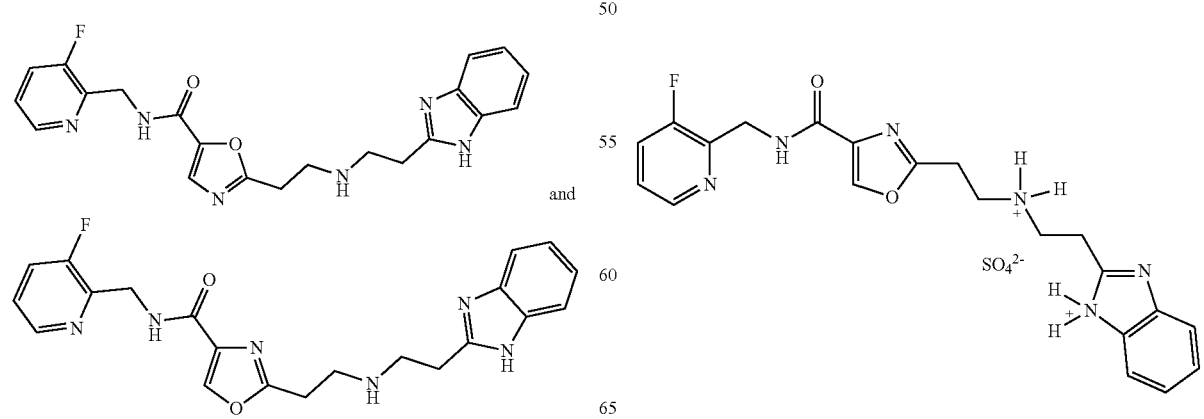
and polymorphs thereof.

12. The salts of compounds of formula (I) according to claim 1, which is a 1:1 phosphate salt having the formula;

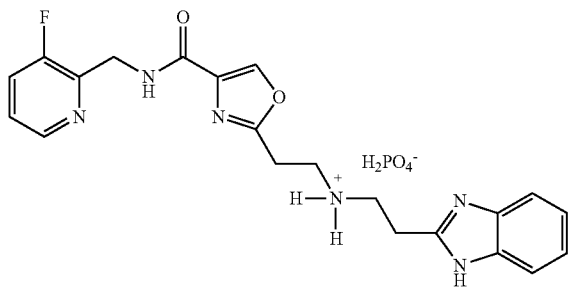

and polymorphs thereof.

13. A method of preventing or treating increased iron levels, increased iron absorption or iron overload in a patient in need thereof, the method comprising administering the salts according to claim 1, or solvates, hydrates and polymorphs thereof to the patient in need thereof.

14. A method of inhibiting ferroportin and/or inhibiting iron transport mediated by ferroportin in a patient in need thereof, the method comprising administering the salts according to claim 1, or solvates, hydrates and polymorphs thereof to the patient in need thereof.

15. A method of preventing or treating disorders related to or caused by increased iron levels or increased iron absorption selected from the group consisting of: diseases associated with ineffective erythropoiesis selected from the group consisting of myelodysplastic syndromes, polycythemia vera and congenital dyserythropoietic anemia; an adjunctive therapy by limiting the amount of iron available to pathogenic microorganisms including the bacterium Vibrio vulnificus, thereby treating infections caused by said pathogenic microorganisms; neurodegenerative diseases selected from the group consisting of Alzheimer's disease and Parkinson's disease by limiting the deposition or increase of iron in tissue or cells; formation of radicals, reactive oxygen species and oxidative stress; cardiac, liver and endocrine damage caused by iron overload; inflammation triggered by excess iron, the method comprising administering the salts according to claim 1, or solvates, hydrates and polymorphs thereof, to a patient in need thereof.

16. A method of preventing or treating disorders related to or caused by increased iron levels or increased iron absorption, the method comprising administering the salts according to claim 1, or solvates, hydrates and polymorphs thereof, to a patient in need thereof, wherein the diseases are selected from thalassemia, hemoglobinopathy, hemoglobin E disease, hemoglobin H disease, haemochromatosis, hemolytic anemia, thalassemia, including alpha-thalassemia, beta-thalassemia and delta-thalassemia, sickle cell anemia (sickle cell disease) and congenital dyserythropoietic anemia.

17. A medicament for preventing or treating increased iron levels, increased iron absorption or iron overload, the medicament comprising the salts according to claim 1, or , solvates, hydrates and polymorphs thereof.

18. The medicament according to claim 17, which is in the form of a formulation for oral or parenteral administration.

19. A method of preventing or treating increased iron levels, increased iron absorption or iron overload in a patient in need thereof in a combination therapy, the method comprising:

co-administration of the salts according to claim 1, or solvates, hydrates and polymorphs thereof, with at least one additional pharmaceutically active compound, wherein the co-administration of the combination therapy is carried out in a fixed dose combination therapy by co-administration of the salts, including the solvates, the hydrates and the polymorphs thereof, with at least one additional pharmaceutically active compound in a fixed-dose formulation; or in a free dose combination therapy by co-administration of the salts, including the solvates, the hydrates and the polymorphs thereof, with the at least one additional pharmaceutically active compound in free doses of the respective components, either by simultaneous administration of the individual components or by sequential use of the individual components distributed over a time period, and wherein the at least one additional pharmaceutically active compounds are selected active compounds for reducing iron overload selected from Tmprss6-ASO, iron chelators, curcum in, SSP-004184, Deferitrin, deferasirox, deferoxamine and/or deferiprone and/or the at least one additional pharmaceutically active compounds are selected from antioxidants; anti-diabetics; antibiotics; drugs for the treatment of malaria; anticancer agents; antifungal drugs; drugs for the treatment of neurodegenerative diseases; anti-viral drugs; immunosuppressants; iron supplements; vitamin supplements; red cell production stimulators; anti-inflammatory biologies; anti-thrombolytics;

statins; vasopressors; and inotropic compounds.

20. A method of preventing or treating increased iron levels, increased iron absorption or iron overload in a patient in need thereof, the method comprising administering the salts according to claim 8, or solvates, hydrates and polymorphs thereof, to the patient in need thereof.

21. A method of inhibiting ferroportin and/or inhibiting iron transport mediated by ferroportin in a patient in need thereof, the method comprising administering the salts according to claim 8, or solvates, hydrates and polymorphs thereof to the patient in need thereof.

22. A method of preventing or treating disorders related to or caused by increased iron levels or increased iron absorption selected from the group consisting of:

diseases associated with ineffective erythropoiesis selected from the group consisting of myelodysplastic syndromes, polycythemia vera and congenital dyserythropoietic anemia; an adjunctive therapy by limiting the amount of iron available to pathogenic microorganisms including the bacterium Vibrio vulnificus, thereby treating infections caused by said pathogenic microorganisms; neurodegenerative diseases selected from the group consisting of Alzheimer's disease and Parkinson's disease by limiting the deposition or increase of iron in tissue or cells; formation of radicals, reactive oxygen species and oxidative stress; cardiac, liver and endocrine damage caused by iron overload; inflammation triggered by excess iron, the method comprising administering the salts according to claim 8, or solvates, hydrates and polymorphs thereof, to a patient in need thereof.

23. A method of preventing or treating disorders related to or caused by increased iron levels or increased iron absorption, the method comprising administering the salts according to claim 8, or solvates, hydrates and polymorphs thereof, to a patient in need thereof, wherein the diseases are selected from thalassemia, hemoglobinopathy, hemoglobin E disease, hemoglobin H disease, haemochromatosis, hemolytic anemia, thalassemia, including alpha-thalassemia, beta-thalassemia and delta-thalassemia, sickle cell anemia (sickle cell disease) and congenital dyserythropoietic anemia.

24. A medicament for preventing or treating increased iron levels, increased iron absorption or iron overload, the medicament comprising the salts according to claim 8, or solvates, hydrates and polymorphs thereof.

25. The medicament according to claim 24, which is in the form of a formulation for oral or parenteral administration.

26. A method of preventing or treating increased iron levels, increased iron absorption or iron overload in a patient in need thereof in a combination therapy the method comprising:
   co-administration of the salts according to claim 8, or solvates, hydrates and polymorphs thereof, with at least one additional pharmaceutically active compound,
   wherein the co-administration of the combination therapy is carried out in a fixed dose combination therapy by co-administration of the salts, including the solvates, the hydrates and the polymorphs thereof, with at least one additional pharmaceutically active compound in a fixed-dose formulation; or
   in a free dose combination therapy by co-administration of the salts, including the solvates, the hydrates and the polymorphs thereof, with the at least one additional pharmaceutically active compound in free doses of the respective components, either by simultaneous administration of the individual components or by sequential use of the individual components distributed over a time period, and
   wherein the at least one additional pharmaceutically active compounds are selected from active compounds for reducing iron overload selected from Tmprss6-ASO, iron chelators, curcumin, SSP-004184, Deferitrin, deferasirox, deferoxamine and/or deferiprone and/or the at least one additional pharmaceutically active compounds are selected from antioxidants; anti-diabetics; antibiotics; drugs for the treatment of malaria; anticancer agents; antifungal drugs; drugs for the treatment of neurodegenerative diseases; anti-viral drugs; immunosuppressants; iron supplements; vitamin supplements; red cell production stimulators; anti-inflammatory biologies; anti-thrombolytics; statins; vasopressors; and inotropic compounds.

* * * * *